United States Patent
LaVon et al.

(10) Patent No.: US 11,737,928 B2
(45) Date of Patent: *Aug. 29, 2023

(54) LAMINATE(S) COMPRISING BEAMED ELASTICS AND ABSORBENT ARTICLE(S) COMPRISING SAID LAMINATE(S)

(71) Applicant: The Procter & Gamble Company, Cincinnati, OH (US)

(72) Inventors: Gary Dean LaVon, Liberty Township, OH (US); Uwe Schneider, Cincinnati, OH (US); Bret Darren Seitz, West Chester, OH (US); Sarah Marie Wade, Springfield Township, OH (US); Joseph Allen Eckstein, Sunman, IN (US)

(73) Assignee: The Procter & Gamble Company, Cincinnati, OH (US)

( * ) Notice: Subject to any disclaimer, the term of this patent is extended or adjusted under 35 U.S.C. 154(b) by 75 days.

This patent is subject to a terminal disclaimer.

(21) Appl. No.: 17/315,945

(22) Filed: May 10, 2021

(65) Prior Publication Data

US 2021/0330513 A1    Oct. 28, 2021

Related U.S. Application Data

(63) Continuation of application No. 15/846,341, filed on Dec. 19, 2017, now Pat. No. 11,000,420.

(Continued)

(51) Int. Cl.
*A61F 13/15* (2006.01)
*A61F 13/49* (2006.01)
(Continued)

(52) U.S. Cl.
CPC .... *A61F 13/15593* (2013.01); *A61F 13/4902* (2013.01); *A61F 13/49061* (2013.01);
(Continued)

(58) Field of Classification Search
CPC .......... A61F 13/15593; A61F 13/15585; A61F 13/15601; A61F 13/15699;
(Continued)

(56) References Cited

U.S. PATENT DOCUMENTS 3,113,225 A    12/1963 Claus
3,434,189 A    3/1969 Buck et al.
(Continued)

FOREIGN PATENT DOCUMENTS

CA    2158790 A1    3/1996
CN    1649730 A    8/2005
(Continued)

OTHER PUBLICATIONS

Extended EP Search Report and Written Opinion for 21168628.2 dated Jul. 16, 2021, 6pages.

(Continued)

*Primary Examiner* — Jacqueline F Stephens
(74) *Attorney, Agent, or Firm* — Charles R. Matson

(57) ABSTRACT

The present disclosure relates to one or a combination of an absorbent article's chassis, inner leg cuffs, outer leg cuffs, ear panels, side panels, waistbands, and belts that may comprise one or more pluralities of tightly spaced (less than 4 mm, less than 3 mm, less than 2 mm, and less than 1 mm) and/or very fine (less than 300, less than 200, less than 100 dtex) and/or low strain (less than 300%, less than 200%, less than 100%) elastics to deliver low pressure less than 1 psi (according to the conditions defined by the Pressure-Under-Strand method below) under the elastics, while providing adequate modulus of (between about 2 gf/mm and 15 gf/mm) to make the article easy to apply and to comfortably maintain the article in place on the wearer, even with a loaded core (holding at least 50 mls of liquid), to provide for the advantages described above.

1 Claim, 118 Drawing Sheets

Related U.S. Application Data

(60) Provisional application No. 62/581,278, filed on Nov. 3, 2017, provisional application No. 62/553,171, filed on Sep. 1, 2017, provisional application No. 62/553,538, filed on Sep. 1, 2017, provisional application No. 62/553,149, filed on Sep. 1, 2017, provisional application No. 62/483,965, filed on Apr. 11, 2017, provisional application No. 62/436,589, filed on Dec. 20, 2016.

(51) Int. Cl.

| | | |
|---|---|---|
| B32B 27/12 | (2006.01) | |
| D01F 6/04 | (2006.01) | |
| A61F 13/53 | (2006.01) | |
| D01D 5/08 | (2006.01) | |
| B29C 65/08 | (2006.01) | |
| B29C 65/48 | (2006.01) | |
| B29L 31/48 | (2006.01) | |
| B05C 1/08 | (2006.01) | |
| B32B 37/14 | (2006.01) | |
| B65H 39/16 | (2006.01) | |
| B65H 51/30 | (2006.01) | |
| B29C 65/00 | (2006.01) | |
| B29C 65/74 | (2006.01) | |
| B29K 701/12 | (2006.01) | |
| A61F 13/64 | (2006.01) | |
| A61F 13/84 | (2006.01) | |
| B32B 5/04 | (2006.01) | |
| B32B 37/00 | (2006.01) | |
| B32B 37/12 | (2006.01) | |
| D04H 3/12 | (2006.01) | |
| A61F 13/56 | (2006.01) | |
| B32B 37/22 | (2006.01) | |
| A61F 13/513 | (2006.01) | |

(52) U.S. Cl.
CPC ... *A61F 13/15601* (2013.01); *A61F 13/15699* (2013.01); *A61F 13/15739* (2013.01); *A61F 13/15764* (2013.01); *A61F 13/49012* (2013.01); *A61F 13/49015* (2013.01); *A61F 13/49017* (2013.01); *A61F 13/49019* (2013.01); *A61F 13/53* (2013.01); *A61F 13/5622* (2013.01); *A61F 13/64* (2013.01); *A61F 2013/1552* (2013.01); *A61F 2013/1591* (2013.01); *A61F 2013/15292* (2013.01); *A61F 2013/15373* (2013.01); *A61F 2013/15406* (2013.01); *A61F 2013/15447* (2013.01); *A61F 2013/15552* (2013.01); *A61F 2013/15869* (2013.01); *A61F 2013/15918* (2013.01); *A61F 2013/15959* (2013.01); *A61F 2013/49022* (2013.01); *A61F 2013/49025* (2013.01); *A61F 2013/49026* (2013.01); *A61F 2013/49074* (2013.01); *A61F 2013/49092* (2013.01); *A61F 2013/49093* (2013.01); *A61F 2013/51322* (2013.01); *A61F 2013/53043* (2013.01); *A61F 2013/530343* (2013.01); *A61F 2013/8497* (2013.01); *B05C 1/0808* (2013.01); *B29C 65/08* (2013.01); *B29C 65/086* (2013.01); *B29C 65/48* (2013.01); *B29C 65/74* (2013.01); *B29C 66/01* (2013.01); *B29C 66/344* (2013.01); *B29C 66/8141* (2013.01); *B29C 66/83411* (2013.01); *B29K 2701/12* (2013.01); *B29K 2995/0046* (2013.01); *B29L 2031/4878* (2013.01); *B32B 5/04* (2013.01); *B32B 27/12* (2013.01); *B32B 37/0053* (2013.01); *B32B 37/12* (2013.01); *B32B 37/144* (2013.01); *B32B 37/22* (2013.01); *B32B 2305/20* (2013.01); *B32B 2307/51* (2013.01); *B32B 2307/726* (2013.01); *B32B 2555/02* (2013.01); *B65H 39/16* (2013.01); *B65H 51/30* (2013.01); *C08J 2300/26* (2013.01); *D01D 5/08* (2013.01); *D01F 6/04* (2013.01); *D04H 3/12* (2013.01)

(58) Field of Classification Search
CPC .......... A61F 13/15739; A61F 13/15764; A61F 13/49011; A61F 13/49012; A61F 13/49014; A61F 13/49015; A61F 13/49017; A61F 13/4019; A61F 13/4902; A61F 13/49061; A61F 13/491; A61F 13/493; A61F 13/496; A61F 13/511; A61F 13/51464; A61F 13/51478; A61F 13/55115; A61F 13/64; A61F 13/53; A61F 2013/15292; A61F 2013/15373; A61F 2013/15406; A61F 2013/15447; A61F 2013/15552; A61F 2013/15869; A61F 2013/1591; A61F 2013/15918; A61F 2013/15959; A61F 2013/49022; A61F 2013/49025; A61F 2013/49026; A61F 2013/49031; A61F 2013/49074; A61F 2013/49092; A61F 2013/49093; A61F 2013/51322; A61F 2013/530343; A61F 2013/8497
See application file for complete search history.

(56) References Cited

U.S. PATENT DOCUMENTS

| | | |
|---|---|---|
| 3,508,722 A | 4/1970 | Kohl |
| 3,562,041 A | 2/1971 | Robertson |
| 3,575,782 A | 4/1971 | Hansen |
| 3,733,238 A | 5/1973 | Long |
| 3,860,003 A | 1/1975 | Buell |
| 3,871,378 A | 3/1975 | Duncan et al. |
| 4,251,587 A | 2/1981 | Mimura et al. |
| 4,333,979 A | 6/1982 | Sciaraffa |
| 4,525,905 A | 7/1985 | Bogucki-land |
| 4,610,678 A | 9/1986 | Weisman |
| 4,640,859 A | 2/1987 | Hansen |
| 4,657,539 A | 4/1987 | Hasse |
| 4,673,402 A | 6/1987 | Weisman |
| 4,695,278 A | 9/1987 | Lawson |
| 4,704,115 A | 11/1987 | Buell |
| 4,741,941 A | 5/1988 | Englebert |
| 4,776,911 A | 10/1988 | Uda et al. |
| 4,795,454 A | 1/1989 | Dragoo |
| 4,834,735 A | 5/1989 | Alemany |
| 4,854,984 A | 8/1989 | Ball |
| 4,888,231 A | 12/1989 | Angstadt |
| 4,909,803 A | 3/1990 | Aziz |
| 4,940,464 A | 7/1990 | Van Gompel |
| 4,984,584 A | 1/1991 | Hansen |
| 5,003,676 A | 4/1991 | Mcfalls |
| 5,060,881 A | 10/1991 | Bogucki-land |
| 5,092,861 A | 3/1992 | Nomura |
| 5,110,403 A | 5/1992 | Ehlert |
| 5,167,897 A | 12/1992 | Weber |
| 5,246,433 A | 9/1993 | Hasse |
| 5,334,289 A | 8/1994 | Trokhan |
| 5,342,341 A | 8/1994 | Igaue |
| 5,360,420 A | 11/1994 | Cook |
| 5,393,360 A | 2/1995 | Bridges |
| 5,413,849 A | 5/1995 | Austin |
| 5,514,523 A | 5/1996 | Trokhan |
| 5,531,729 A | 7/1996 | Coles |
| 5,558,658 A | 9/1996 | Menard et al. |
| 5,562,646 A | 10/1996 | Goldman |
| 5,569,234 A | 10/1996 | Buell |
| 5,575,874 A | 11/1996 | Griesbach, III |

(56) References Cited

U.S. PATENT DOCUMENTS

| | | |
|---|---|---|
| 5,599,335 A | 2/1997 | Goldman |
| 5,599,420 A | 2/1997 | Yeo |
| 5,628,097 A | 5/1997 | Benson |
| 5,643,588 A | 7/1997 | Roe |
| 5,643,653 A | 7/1997 | Griesbach, III |
| 5,669,894 A | 9/1997 | Goldman |
| 5,674,216 A | 10/1997 | Buell |
| 5,702,551 A | 12/1997 | Huber |
| 5,775,380 A | 7/1998 | Roelstraete |
| 5,827,259 A | 10/1998 | Laux |
| 5,858,504 A | 1/1999 | Fitting |
| 5,887,322 A | 3/1999 | Hartzheim |
| 5,895,623 A | 4/1999 | Trokhan |
| 5,897,545 A | 4/1999 | Kline |
| 5,916,661 A | 6/1999 | Benson |
| 5,957,908 A | 9/1999 | Kline |
| 5,968,025 A | 10/1999 | Roe |
| 5,993,433 A | 11/1999 | St. Louis |
| 5,997,521 A | 12/1999 | Robles et al. |
| 6,036,796 A | 3/2000 | Halbert |
| 6,043,168 A | 3/2000 | Colman |
| 6,107,537 A | 8/2000 | Elder |
| 6,107,539 A | 8/2000 | Palumbo |
| 6,118,041 A | 9/2000 | Roe |
| 6,120,487 A | 9/2000 | Ashton |
| 6,120,489 A | 9/2000 | Johnson |
| 6,139,941 A | 10/2000 | Jankevics |
| 6,153,209 A | 11/2000 | Vega |
| 6,248,195 B1 | 6/2001 | Schmitz |
| 6,248,197 B1 | 6/2001 | Nakanishi et al. |
| 6,291,039 B1 | 9/2001 | Combe |
| 6,319,239 B1 | 11/2001 | Daniels |
| 6,361,638 B2 | 3/2002 | Takai |
| 6,383,431 B1 | 5/2002 | Dobrin |
| 6,395,957 B1 | 5/2002 | Chen |
| 6,410,129 B2 | 6/2002 | Zhang |
| 6,426,444 B2 | 7/2002 | Roe |
| 6,475,600 B1 | 11/2002 | Morman et al. |
| 6,478,785 B1 | 11/2002 | Ashton et al. |
| 6,482,191 B1 | 11/2002 | Roe et al. |
| 6,508,641 B1 | 1/2003 | Kubik |
| 6,545,197 B1 | 4/2003 | Muller |
| 6,554,815 B1 | 4/2003 | Umebayashi |
| 6,586,652 B1 | 7/2003 | Roe |
| 6,617,016 B2 | 9/2003 | Zhang |
| 6,627,787 B1 | 9/2003 | Roe |
| 6,632,504 B1 | 10/2003 | Gillespie |
| 6,645,330 B2 | 11/2003 | Pargass |
| 6,673,418 B1 | 1/2004 | Deolivera |
| 6,676,054 B2 | 1/2004 | Heaney |
| 6,702,798 B2 | 3/2004 | Christoffel |
| 6,790,798 B1 | 9/2004 | Suzuki |
| 6,821,301 B2 | 11/2004 | Azuse |
| 6,825,393 B2 | 11/2004 | Roe |
| 6,861,571 B1 | 3/2005 | Roe |
| 7,008,685 B2 | 3/2006 | Groitzsch |
| 7,118,558 B2 | 10/2006 | Wu |
| 7,465,367 B2 | 12/2008 | Day |
| 7,569,039 B2 | 8/2009 | Matsuda |
| 7,582,348 B2 | 9/2009 | Ando |
| 7,642,398 B2 | 1/2010 | Jaerpenberg |
| 7,708,849 B2 | 5/2010 | Mccabe |
| 7,777,094 B2 | 8/2010 | Mori |
| 7,861,756 B2 | 1/2011 | Jenquin |
| 7,878,447 B2 | 2/2011 | Hartzheim |
| 7,901,390 B1 | 3/2011 | Ashton et al. |
| 7,901,393 B2 | 3/2011 | Matsuda |
| 7,905,446 B2 | 3/2011 | Hartzheim |
| 7,954,213 B2 | 6/2011 | Mizutani |
| 8,093,161 B2 | 1/2012 | Bansal |
| 8,143,177 B2 | 3/2012 | Noda |
| 8,186,296 B2 | 5/2012 | Brown |
| 8,226,625 B2 | 7/2012 | Turner |
| 8,308,706 B2 | 11/2012 | Fukae |
| 8,377,554 B2 | 2/2013 | Martin |
| 8,388,594 B2 | 3/2013 | Turner |
| 8,440,043 B1 | 5/2013 | Schneider |
| 8,585,666 B2 | 11/2013 | Weisman |
| 8,647,319 B2 | 2/2014 | Een |
| 8,729,332 B2 | 5/2014 | Takahashi |
| 8,778,127 B2 | 7/2014 | Schneider |
| 8,853,108 B2 | 10/2014 | Ahoniemi |
| 8,906,275 B2 | 12/2014 | Davis |
| 8,939,957 B2 | 1/2015 | Raycheck |
| 9,005,392 B2 | 4/2015 | Schneider |
| 9,039,855 B2 | 5/2015 | Schneider |
| 9,050,213 B2 | 6/2015 | Lavon |
| 9,156,648 B2 | 10/2015 | Yamamoto |
| 9,168,182 B2 | 10/2015 | Hargett |
| 9,198,804 B2 | 12/2015 | Nakamura |
| 9,226,861 B2 | 1/2016 | Lavon |
| 9,248,054 B2 | 2/2016 | Brown |
| 9,265,672 B2 | 2/2016 | Brown |
| 9,295,590 B2 | 3/2016 | Brown |
| 9,370,775 B2 | 6/2016 | Harvey |
| 9,440,043 B2 | 9/2016 | Arora |
| 9,453,303 B2 | 9/2016 | Aberg |
| 9,539,735 B2 | 1/2017 | Ferguson |
| 9,732,454 B2 | 8/2017 | Davis |
| 9,758,339 B2 | 9/2017 | Yanez, Jr. |
| 9,795,520 B2 | 10/2017 | Kaneko |
| 9,877,876 B2 | 1/2018 | Huang |
| 10,190,244 B2 | 1/2019 | Ashraf |
| 10,596,045 B2 | 3/2020 | Koshijima |
| 10,792,194 B2 | 10/2020 | Hohm |
| 2001/0030014 A1 | 10/2001 | Kwok |
| 2002/0026660 A1 | 3/2002 | Goda |
| 2002/0046802 A1 | 4/2002 | Tachibana |
| 2002/0072723 A1 | 6/2002 | Ronn |
| 2002/0099347 A1 | 7/2002 | Chen et al. |
| 2002/0103469 A1 | 8/2002 | Chen |
| 2002/0134067 A1 | 9/2002 | Heaney |
| 2002/0153271 A1 | 10/2002 | Mcmanus |
| 2002/0177829 A1 | 11/2002 | Fell |
| 2003/0044585 A1 | 3/2003 | Taylor |
| 2003/0070780 A1 | 4/2003 | Chen |
| 2003/0087056 A1 | 5/2003 | Ducker |
| 2003/0093045 A1 | 5/2003 | Erdman |
| 2003/0119404 A1 | 6/2003 | Belau |
| 2003/0125687 A1 | 7/2003 | Gubernick |
| 2003/0144643 A1 | 7/2003 | Jarpenberg |
| 2003/0203162 A1 | 10/2003 | Fenwick |
| 2003/0233082 A1 | 12/2003 | Kline |
| 2004/0006323 A1 | 1/2004 | Hall |
| 2004/0030317 A1 | 2/2004 | Torigoshi |
| 2004/0059309 A1 | 3/2004 | Nortman |
| 2004/0097895 A1 | 5/2004 | Busam |
| 2004/0127881 A1 | 7/2004 | Stevens et al. |
| 2004/0133180 A1 | 7/2004 | Mori |
| 2004/0158212 A1 | 8/2004 | Ponomarenko |
| 2004/0158217 A1 | 8/2004 | Wu |
| 2004/0219584 A1 | 11/2004 | Xu et al. |
| 2004/0219854 A1 | 11/2004 | Groitzsch |
| 2004/0230171 A1 | 11/2004 | Ando |
| 2005/0013975 A1 | 1/2005 | Brock |
| 2005/0107764 A1 | 5/2005 | Matsuda |
| 2005/0148971 A1 | 7/2005 | Kuroda |
| 2005/0230037 A1 | 10/2005 | Jenquin |
| 2005/0244640 A1 | 11/2005 | Riswick et al. |
| 2005/0267431 A1 | 12/2005 | Sasaki |
| 2006/0047260 A1 | 3/2006 | Ashton |
| 2006/0069373 A1 | 3/2006 | Schlinz |
| 2006/0087053 A1 | 4/2006 | Odonnell |
| 2006/0105075 A1 | 5/2006 | Otsubo |
| 2006/0189954 A1 | 8/2006 | Kudo |
| 2006/0228969 A1 | 10/2006 | Erdman |
| 2006/0270302 A1 | 11/2006 | Ando |
| 2007/0026753 A1 | 2/2007 | Neely |
| 2007/0045143 A1 | 3/2007 | Clough |
| 2007/0045144 A1 | 3/2007 | Wheeler |
| 2007/0131335 A1 | 6/2007 | Zhou |
| 2007/0141311 A1 | 6/2007 | Mleziva |
| 2007/0179466 A1 | 8/2007 | Tremblay |
| 2007/0196650 A1 | 8/2007 | Yamamoto et al. |

(56) References Cited

U.S. PATENT DOCUMENTS

| | | |
|---|---|---|
| 2008/0134487 A1 | 6/2008 | Hartono |
| 2008/0149292 A1 | 6/2008 | Scherb |
| 2008/0161768 A1 | 7/2008 | Baba |
| 2008/0287897 A1 | 11/2008 | Guzman Reyes |
| 2009/0177176 A1 | 7/2009 | Saito |
| 2009/0204093 A1 | 8/2009 | Vasic |
| 2009/0312730 A1 | 12/2009 | Lavon |
| 2010/0022151 A1 | 1/2010 | Malowaniec |
| 2010/0036346 A1 | 2/2010 | Hammons |
| 2010/0048072 A1 | 2/2010 | Kauschke |
| 2010/0075103 A1 | 3/2010 | Miyamoto |
| 2010/0076394 A1 | 3/2010 | Hayase |
| 2010/0248575 A1 | 9/2010 | Malz |
| 2010/0307668 A1 | 12/2010 | Lange |
| 2011/0092943 A1 | 4/2011 | Bishop |
| 2011/0118689 A1 | 5/2011 | Een |
| 2011/0120897 A1 | 5/2011 | Takahashi |
| 2011/0250378 A1 | 10/2011 | Eaton |
| 2012/0004633 A1 | 1/2012 | R. Marcelo |
| 2012/0061015 A1 | 3/2012 | Lavon |
| 2012/0061016 A1 | 3/2012 | Lavon |
| 2012/0071852 A1 | 3/2012 | Tsang et al. |
| 2012/0095429 A1 | 4/2012 | Kobayashi |
| 2012/0271267 A1 | 10/2012 | Love |
| 2012/0277713 A1 | 11/2012 | Raycheck |
| 2012/0323206 A1 | 12/2012 | Mcmorrow |
| 2012/0330264 A1 | 12/2012 | Lawson |
| 2013/0032656 A1 | 2/2013 | Yamamoto |
| 2013/0072887 A1 | 3/2013 | Lavon |
| 2013/0102982 A1 | 4/2013 | Nakano |
| 2013/0112584 A1 | 5/2013 | Gaspari |
| 2013/0139960 A1 | 6/2013 | Maruyama |
| 2013/0171421 A1 | 7/2013 | Weisman |
| 2013/0199696 A1 | 8/2013 | Schneider |
| 2013/0199707 A1 | 8/2013 | Schneider |
| 2013/0211356 A1 | 8/2013 | Nishikawa |
| 2013/0211363 A1 | 8/2013 | Lavon |
| 2013/0255861 A1 | 10/2013 | Schneider |
| 2013/0255862 A1 | 10/2013 | Schneider |
| 2013/0255863 A1 | 10/2013 | Lavon |
| 2013/0255864 A1 | 10/2013 | Schneider |
| 2013/0255865 A1 | 10/2013 | Brown |
| 2013/0261589 A1 | 10/2013 | Fujkawa |
| 2013/0306226 A1 | 11/2013 | Zink |
| 2014/0000794 A1 | 1/2014 | Hamilton |
| 2014/0005621 A1 | 1/2014 | Roe |
| 2014/0018759 A1 | 1/2014 | Jayasinghe |
| 2014/0041797 A1 | 2/2014 | Schneider |
| 2014/0107605 A1 | 4/2014 | Schroer, Jr. |
| 2014/0127460 A1 | 5/2014 | Xu |
| 2014/0136893 A1 | 5/2014 | Xie et al. |
| 2014/0148773 A1 | 5/2014 | Brown |
| 2014/0234575 A1 | 8/2014 | Mitsuno |
| 2014/0235127 A1 | 8/2014 | Dejesus |
| 2014/0257231 A1 | 9/2014 | Wang |
| 2014/0276517 A1 | 9/2014 | Chester |
| 2014/0288521 A1 | 9/2014 | Wade |
| 2014/0296815 A1 | 10/2014 | Takken |
| 2014/0302286 A1 | 10/2014 | Okuda |
| 2014/0305570 A1 | 10/2014 | Matsunaga |
| 2014/0324009 A1 | 10/2014 | Lee |
| 2014/0343525 A1 | 11/2014 | Kimberly-Clark |
| 2014/0377506 A1 | 12/2014 | Eckstein |
| 2014/0377513 A1 | 12/2014 | Galie |
| 2015/0083309 A1 | 3/2015 | Long |
| 2015/0088088 A1 | 3/2015 | Wade |
| 2015/0126956 A1 | 5/2015 | Raycheck |
| 2015/0136893 A1 | 5/2015 | Koskol |
| 2015/0164708 A1 | 6/2015 | Hashimoto |
| 2015/0167207 A1 | 6/2015 | Bongartz et al. |
| 2015/0173967 A1 | 6/2015 | Kreuzer |
| 2015/0230995 A1 | 8/2015 | Kaneko |
| 2015/0245958 A1 | 9/2015 | Chmielewski |
| 2015/0257941 A1 | 9/2015 | Eckstein |
| 2015/0282999 A1 | 10/2015 | Arizti |
| 2015/0297419 A1 | 10/2015 | Nelson |
| 2015/0320612 A1 | 11/2015 | Seitz |
| 2015/0320613 A1 | 11/2015 | Seitz |
| 2015/0320619 A1 | 11/2015 | Seitz |
| 2015/0320620 A1 | 11/2015 | Seitz |
| 2015/0320622 A1 | 11/2015 | Seitz |
| 2015/0328056 A1 | 11/2015 | Een |
| 2015/0351972 A1 | 12/2015 | Bing-wo |
| 2016/0058624 A1 | 3/2016 | Hohm |
| 2016/0058627 A1 | 3/2016 | Barnes |
| 2016/0067119 A1 | 3/2016 | Weisman |
| 2016/0100989 A1 | 4/2016 | Seitz |
| 2016/0100997 A1 | 4/2016 | Seitz |
| 2016/0106633 A1 | 4/2016 | Nagata |
| 2016/0129661 A1 | 5/2016 | Arora |
| 2016/0136009 A1 | 5/2016 | Weisman |
| 2016/0228305 A1 | 8/2016 | Gualtieri |
| 2016/0270977 A1 | 9/2016 | Surushe et al. |
| 2016/0331600 A1 | 11/2016 | Polidori |
| 2017/0014281 A1 | 1/2017 | Xie |
| 2017/0027774 A1 | 2/2017 | Ashraf |
| 2017/0029993 A1 | 2/2017 | Ashraf |
| 2017/0029994 A1 | 2/2017 | Ashraf |
| 2017/0056256 A1 | 3/2017 | Smith |
| 2017/0065461 A1 | 3/2017 | Schneider |
| 2017/0079852 A1 | 3/2017 | Fujima |
| 2017/0119595 A1 | 5/2017 | Carla |
| 2017/0191198 A1 | 7/2017 | Ashraf |
| 2017/0258650 A1 | 9/2017 | Rosati |
| 2017/0281417 A1 | 10/2017 | Ishikawa |
| 2017/0319403 A1 | 11/2017 | Bewick-sonntag |
| 2017/0348163 A1 | 12/2017 | Lakso |
| 2018/0092784 A1 | 4/2018 | Wade |
| 2018/0140473 A1 | 5/2018 | Koshijima |
| 2018/0168874 A1 | 6/2018 | Lavon |
| 2018/0168875 A1 | 6/2018 | Lavon |
| 2018/0168876 A1 | 6/2018 | Lavon |
| 2018/0168877 A1 | 6/2018 | Schneider |
| 2018/0168878 A1 | 6/2018 | Schneider |
| 2018/0168879 A1 | 6/2018 | Schneider |
| 2018/0168880 A1 | 6/2018 | Schneider |
| 2018/0168885 A1 | 6/2018 | Zink, II |
| 2018/0168887 A1 | 6/2018 | Lavon |
| 2018/0168888 A1 | 6/2018 | Zink |
| 2018/0168889 A1 | 6/2018 | Lavon |
| 2018/0168890 A1 | 6/2018 | Lavon |
| 2018/0168891 A1 | 6/2018 | Wise |
| 2018/0168892 A1 | 6/2018 | Lavon |
| 2018/0168893 A1 | 6/2018 | Ashraf |
| 2018/0169964 A1 | 6/2018 | Schneider |
| 2018/0170026 A1 | 6/2018 | Schneider |
| 2018/0170027 A1 | 6/2018 | Schneider |
| 2018/0214318 A1 | 8/2018 | Ashraf |
| 2018/0214321 A1 | 8/2018 | Ashraf |
| 2018/0216269 A1 | 8/2018 | Ashraf |
| 2018/0216270 A1 | 8/2018 | Ashraf |
| 2018/0216271 A1 | 8/2018 | Ashraf |
| 2018/0333311 A1 | 11/2018 | Maki |
| 2019/0003079 A1 | 1/2019 | Ashraf |
| 2019/0003080 A1 | 1/2019 | Ashraf |
| 2019/0070041 A1 | 3/2019 | Schneider |
| 2019/0070042 A1 | 3/2019 | Beck |
| 2019/0112737 A1 | 4/2019 | Ashraf |
| 2019/0246196 A1 | 8/2019 | Han |
| 2019/0254881 A1 | 8/2019 | Ishikawa |
| 2019/0298586 A1 | 10/2019 | Ashraf |
| 2019/0298587 A1 | 10/2019 | Ashraf |
| 2019/0374392 A1 | 12/2019 | Ninomiya |
| 2019/0374404 A1 | 12/2019 | Ninomiya |
| 2020/0155370 A1 | 5/2020 | Ohtsubo |
| 2020/0155371 A1 | 5/2020 | Ohtsubo |
| 2020/0206040 A1 | 7/2020 | Andrews |
| 2020/0214901 A1 | 7/2020 | Andrews |
| 2020/0298545 A1 | 9/2020 | Andrews |

FOREIGN PATENT DOCUMENTS

| | | |
|---|---|---|
| CN | 1685099 A | 10/2005 |
| CN | 1276196 C | 9/2006 |

(56) References Cited

FOREIGN PATENT DOCUMENTS

| | | |
|---|---|---|
| CN | 101010053 A | 8/2007 |
| CN | 101448477 A | 6/2009 |
| CN | 101646558 A | 2/2010 |
| CN | 101746057 | 6/2010 |
| CN | 101754735 A | 6/2010 |
| CN | 102076295 A | 5/2011 |
| CN | 103391762 A | 11/2013 |
| CN | 104203178 A | 12/2014 |
| CN | 105188629 A | 12/2015 |
| CN | 105997351 A | 10/2016 |
| EP | 0989218 A1 | 3/2000 |
| EP | 1305248 | 5/2003 |
| EP | 1452157 | 9/2004 |
| EP | 1473148 A1 | 11/2004 |
| EP | 1393701 31 | 7/2013 |
| EP | 3056176 | 8/2016 |
| EP | 3092997 B1 | 8/2017 |
| EP | 3251642 A1 | 12/2017 |
| EP | 3257488 A1 | 12/2017 |
| EP | 3563817 | 11/2019 |
| JP | 3213543 B2 | 9/1991 |
| JP | H03213543 A | 9/1991 |
| JP | H0430847 A | 2/1992 |
| JP | H06254117 A | 9/1994 |
| JP | 8071107 | 3/1996 |
| JP | H08071107 | 3/1996 |
| JP | H08132576 A | 5/1996 |
| JP | H09290002 A | 11/1997 |
| JP | 2000026015 A | 1/2000 |
| JP | 2000160460 A | 6/2000 |
| JP | 3086141 B2 | 9/2000 |
| JP | 2002035029 | 2/2002 |
| JP | 2002178428 | 6/2002 |
| JP | 2002248127 A | 9/2002 |
| JP | 2003521949 A | 7/2003 |
| JP | 2004081365 A | 3/2004 |
| JP | 2004229857 A | 8/2004 |
| JP | 2004237410 A | 8/2004 |
| JP | 2004254862 A | 9/2004 |
| JP | 2004298362 A | 10/2004 |
| JP | 2005320636 A | 11/2005 |
| JP | 2006149747 A | 6/2006 |
| JP | 2006149749 A | 6/2006 |
| JP | 2006204673 | 12/2006 |
| JP | 2007190397 A | 8/2007 |
| JP | 2008029749 A | 2/2008 |
| JP | 2008055198 A | 3/2008 |
| JP | 2008104853 A | 5/2008 |
| JP | 2008105425 A | 5/2008 |
| JP | 2008148942 A | 7/2008 |
| JP | 2008154998 A | 7/2008 |
| JP | 2008179128 A | 8/2008 |
| JP | 2008194493 A | 8/2008 |
| JP | 2008229006 A | 10/2008 |
| JP | 2008229007 A | 10/2008 |
| JP | 2008253290 | 10/2008 |
| JP | 2008260131 A | 10/2008 |
| JP | 2008264480 A | 11/2008 |
| JP | 2008272250 A | 11/2008 |
| JP | 2008272253 A | 11/2008 |
| JP | 2008296585 A | 12/2008 |
| JP | 2009000161 A | 1/2009 |
| JP | 2009039341 A | 2/2009 |
| JP | 2009056156 A | 3/2009 |
| JP | 2009106667 A | 5/2009 |
| JP | 2009172231 A | 8/2009 |
| JP | 2009240804 A | 10/2009 |
| JP | 2009241607 A | 10/2009 |
| JP | 2010131833 | 6/2010 |
| JP | 2011015707 A | 1/2011 |
| JP | 2011111165 A | 6/2011 |
| JP | 2011178124 A | 9/2011 |
| JP | 2011225000 A | 11/2011 |
| JP | 2012050882 A | 3/2012 |
| JP | 2012050883 A | 3/2012 |
| JP | 2012115358 A | 6/2012 |
| JP | 2012521498 A | 9/2012 |
| JP | 5124187 B2 | 11/2012 |
| JP | 5124188 B2 | 11/2012 |
| JP | 2013138795 A | 7/2013 |
| JP | 2014097257 A | 5/2014 |
| JP | 2014111222 A | 6/2014 |
| JP | 2014188042 A | 10/2014 |
| JP | 2015510831 A | 4/2015 |
| JP | 2015521499 A | 7/2015 |
| JP | 2016013687 A | 1/2016 |
| JP | 2016016536 A | 2/2016 |
| JP | 5942819 B2 | 6/2016 |
| JP | 2016193199 | 11/2016 |
| JP | 6149635 B2 | 6/2017 |
| JP | 2019081304 A | 5/2019 |
| JP | 2019166804 A | 10/2019 |
| JP | 2019181807 A | 10/2019 |
| JP | 2020054741 A | 4/2020 |
| JP | 2020054742 A | 4/2020 |
| JP | 2020054744 A | 4/2020 |
| JP | 2020054745 A | 4/2020 |
| RU | 2580492 C2 | 4/2016 |
| WO | 9925296 A1 | 5/1999 |
| WO | 2003015681 | 2/2003 |
| WO | 03059603 A1 | 7/2003 |
| WO | 2008123348 A1 | 10/2008 |
| WO | 2013084977 A1 | 6/2013 |
| WO | 2014084168 A1 | 6/2014 |
| WO | 2014098683 A1 | 6/2014 |
| WO | 2014196669 A2 | 9/2014 |
| WO | 2016047320 A1 | 3/2016 |
| WO | 2016056092 A1 | 4/2016 |
| WO | 2016056093 A1 | 4/2016 |
| WO | 2016063346 A1 | 4/2016 |
| WO | 2016067387 A1 | 5/2016 |
| WO | 2016071981 A1 | 5/2016 |
| WO | 2016075974 A1 | 5/2016 |
| WO | 2016098416 A1 | 6/2016 |
| WO | 2016104412 A1 | 6/2016 |
| WO | 2016104422 A1 | 6/2016 |
| WO | 2016104752 A1 | 6/2016 |
| WO | 2016158499 A1 | 10/2016 |
| WO | 2016158746 A1 | 10/2016 |
| WO | 2016208502 A1 | 12/2016 |
| WO | 2016208513 A1 | 12/2016 |
| WO | 2017105997 A1 | 6/2017 |
| WO | 2018061288 A1 | 4/2018 |
| WO | 2018084145 A1 | 5/2018 |
| WO | 2018154680 A1 | 8/2018 |
| WO | 2018154682 A1 | 8/2018 |
| WO | 2018167836 A1 | 9/2018 |
| WO | 2019046363 A1 | 3/2019 |
| WO | 2019111203 A1 | 6/2019 |
| WO | 2019150802 A1 | 8/2019 |
| WO | 2020006996 A1 | 1/2020 |

OTHER PUBLICATIONS

PCT International Search Report, PCT/US2017/067229, dated Mar. 27, 2018, 14 pages.
3D Nonwovens Developments for textured nonwovens; Sep. 19, 2017, pp. 1-2.
All Office Actions, U.S. Appl. No. 15/831,448.
All Office Actions, U.S. Appl. No. 15/832,929.
All Office Actions, U.S. Appl. No. 15/833,057.
All Office Actions, U.S. Appl. No. 15/838,405.
All Office Actions, U.S. Appl. No. 15/839,896.
All Office Actions, U.S. Appl. No. 15/846,382.
All Office Actions, U.S. Appl. No. 16/115,617.
All Office Actions, U.S. Appl. No. 15/831,464.
All Office Actions, U.S. Appl. No. 15/846,745.
All Office Actions, U.S. Appl. No. 17/205,418.
All Office Actions, U.S. Appl. No. 17/218,366.
All Office Actions, U.S. Appl. No. 15/846,341.
All Office Actions, U.S. Appl. No. 15/846,360.
All Office Actions, U.S. Appl. No. 15/846,371.

(56) References Cited

OTHER PUBLICATIONS

All Office Actions, U.S. Appl. No. 15/846,391.
All Office Actions, U.S. Appl. No. 15/846,409.
All Office Actions, U.S. Appl. No. 15/846,433.
All Office Actions, U.S. Appl. No. 16/117,579.
American Cancer Society—What Cancer Patients Their Families and Caregivers Need to Know About COVID 19—is Impacting Our Patient Services.
ASTM—Standard Tables of Body Measurements for Adult Females Misses Figure Type Size Range 00-20.
ASTM—Standard Tables of Body Measurements for Children Infant Size—Preemie to 24 Months.
International Search Report and Written Opinion; Application Ser. No. PCT/US2017/067230, dated Mar. 7, 2018, 12 pages.
U.S. Unpublished U.S. Appl. No. 17/218,366, filed Mar. 18, 2021, to LaVon Gary Dean et al.
U.S. Unpublished U.S. Appl. No. 17/218,366, filed Mar. 31, 2021, to LaVon Gary Dean et al.
Extended EP Search Report and Search Opinion for 23154101.2 dated Mar. 14, 2023, 10 pages.

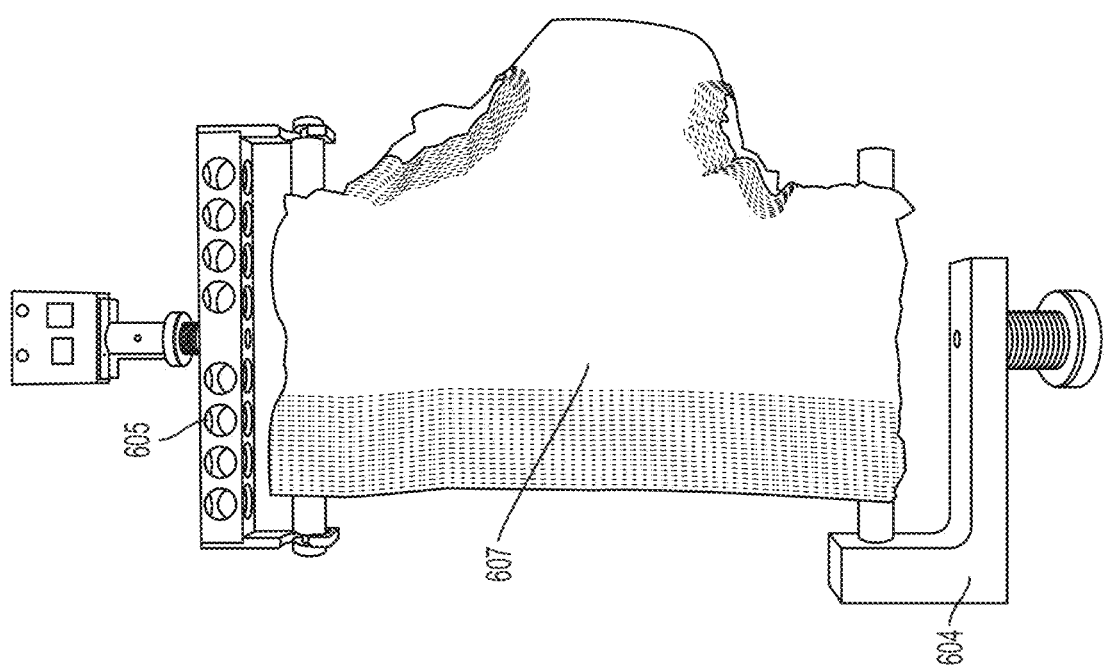

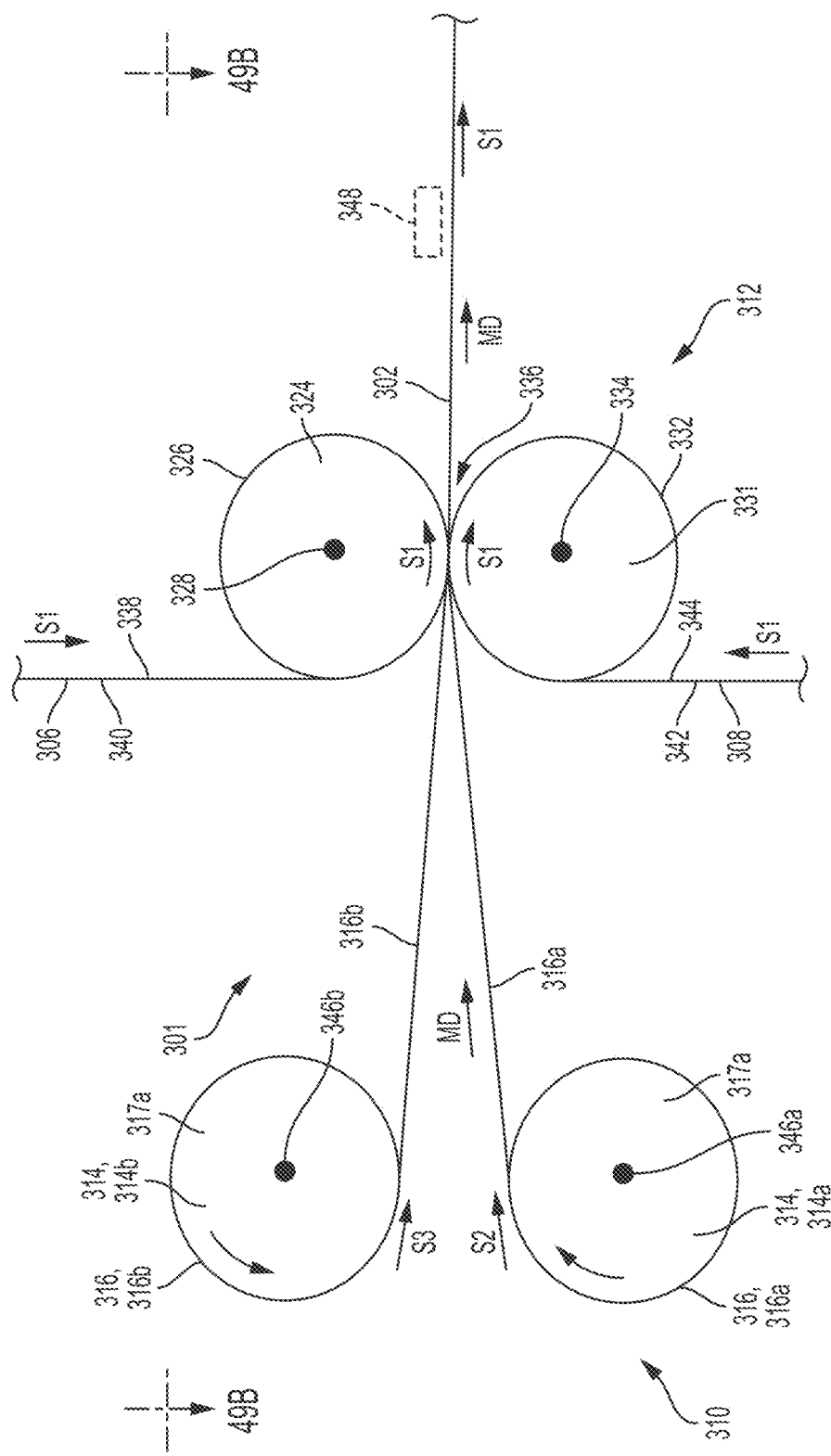

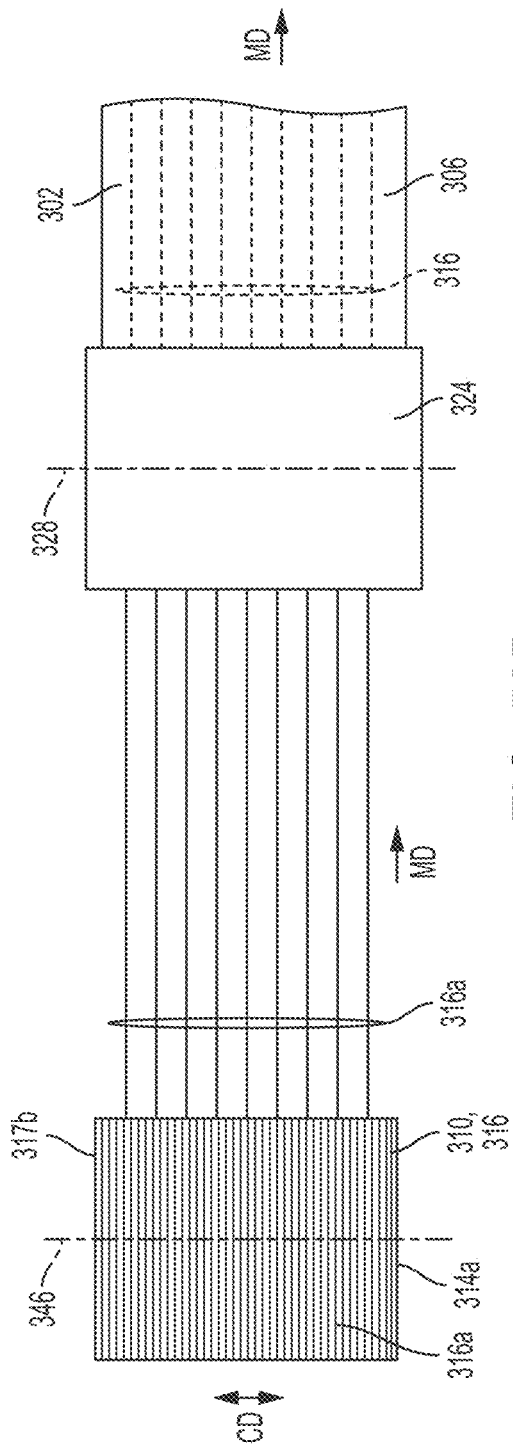
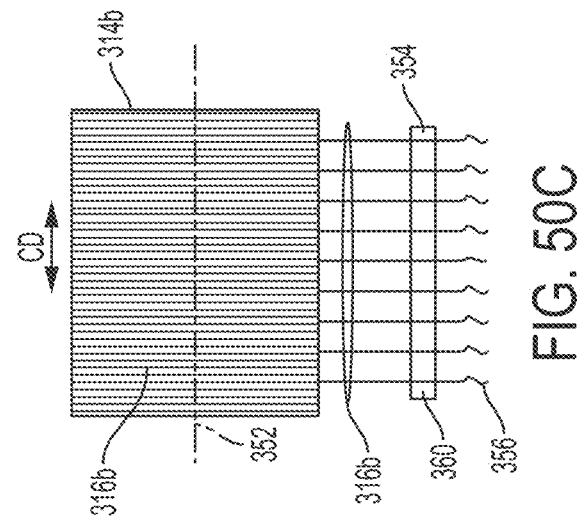
FIG. 50B
FIG. 50C

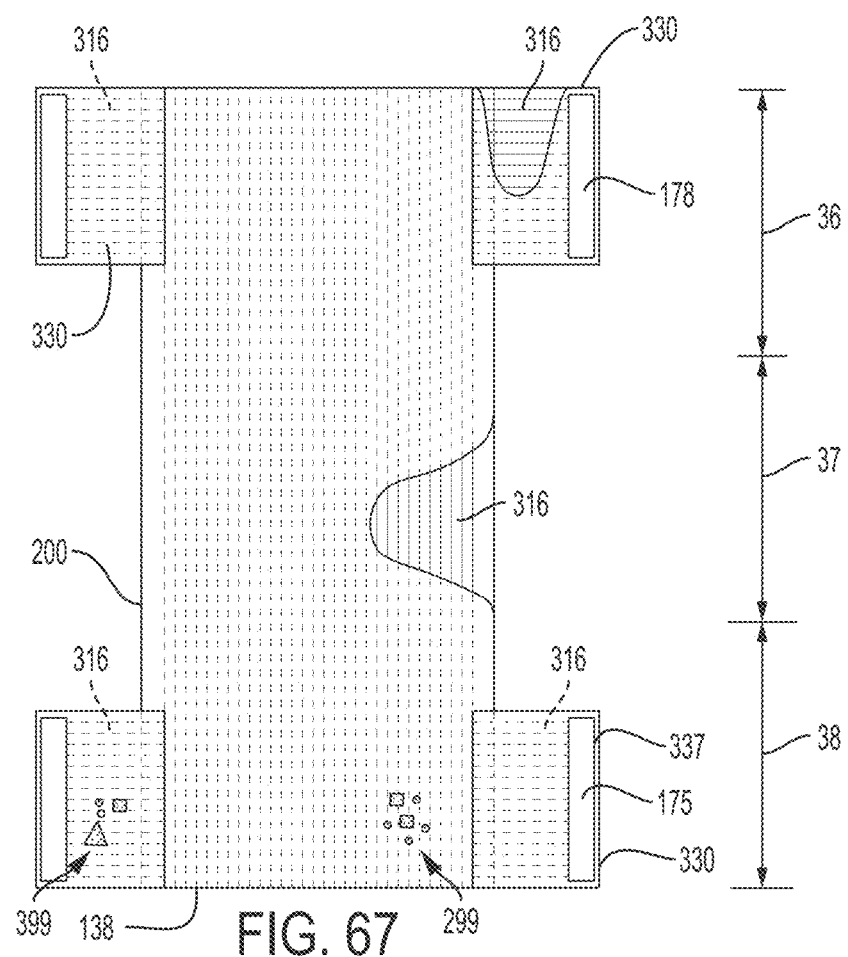

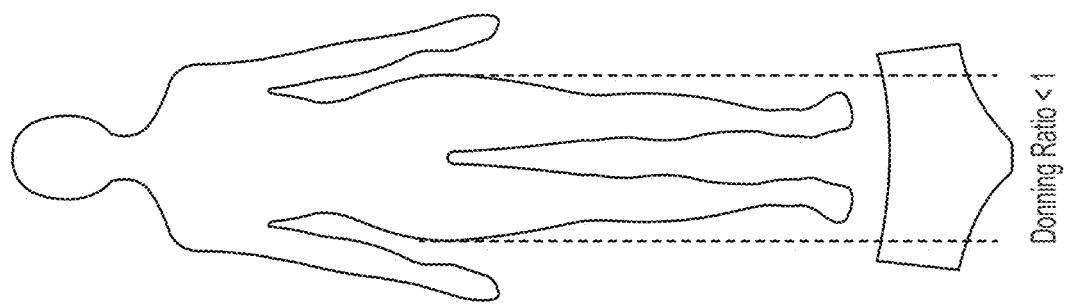
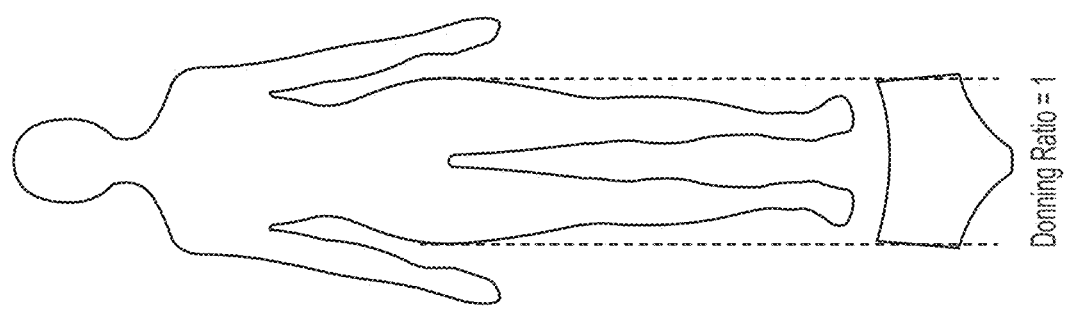
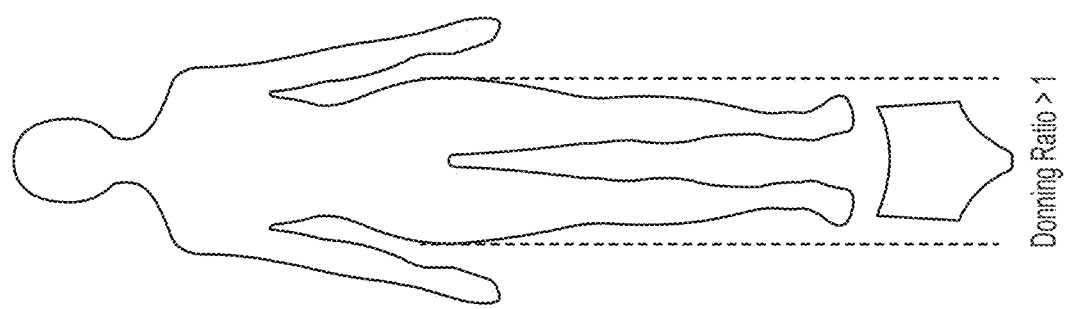
FIG. 85

LAMINATE(S) COMPRISING BEAMED ELASTICS AND ABSORBENT ARTICLE(S) COMPRISING SAID LAMINATE(S)

CROSS-REFERENCE TO RELATED APPLICATIONS

This application is a continuation of U.S. patent application Ser. No. 15/846,341, filed on Dec. 19, 2017, which claims the benefit, under 35 USC 119(e), to U.S. Provisional Patent Application No. 62/436,589, filed on Dec. 20, 2016 (P&G 14618P); U.S. Provisional Patent Application No. 62/483,965, filed on Apr. 11, 2017 (P&G 14778P); U.S. Provisional Patent Application No. 62/553,149, filed on Sep. 1, 2017 (P&G 14917P); U.S. Provisional Patent Application No. 62/553,171, filed on Sep. 1, 2017 (P&G 14918P); U.S. Provisional Patent Application No. 62/553,538, filed on Sep. 1, 2017 (P&G 14921P); and U.S. Provisional Patent Application No. 62/581,278, filed on Nov. 3, 2017 (P&G 15007P); each of which are herein incorporated by reference in their entirety.

FIELD OF THE INVENTION

The present disclosure relates to absorbent articles, more particularly, to disposable absorbent articles comprising elastic laminates configured to perform in various components of the disposable absorbent articles.

BACKGROUND OF THE INVENTION

The present disclosure details elastomeric laminates comprising a greater number of elastic strands having a greater fineness and a closer spacing than has been previously disclosed or practiced in disposable absorbent articles. Further, the present disclosure details combinations of these elastic elements in groupings, including groupings with traditional elastics (e.g., strands, films, extruded strands, scrims, elastomeric nonwovens, etc.) that have not been previously disclosed.

These improved elastomeric laminates can be used as disposable absorbent article (for, example, taped diapers, pants, pads, and liners) components for fit and gasketing at the waist, legs, crotch and sides of the wearer to generally provide the greatest level of extensibility, the most comfortable wearing conditions, improved leakage protection and a better fit.

More particularly, these improved elastomeric laminates offer several advantages, including improved textures and less pressure of the elastic elements on the wearer's skin at a given modulus versus traditional elastomeric laminates known today. These improvements result in enhancing application (e.g., making pant articles easier to open for donning), fit, comfort and reduced marking of the wearer's skin. The inventive elastomeric laminates disclosed in this application perform better than traditional stranded and film versions of laminates known today.

Elastic laminates of the prior art have a number of consumer negatives that vary based on the laminate structure. For example, traditional stranded laminates used in absorbent articles known today typically comprise elastic elements of relatively high decitex (also referred to herein as "dtex") and relatively large elastic spacing, which when combined result in high pressure imparted by each elastic on the skin and large uncontrolled rugosities in the laminate both of which leads to increased skin marking, reduced comfort and a non-garment like appearance. Traditional stranded laminates typically comprise elements spaced at least 4 mm apart primarily due to manufacturing limitations and handling of individual strands of elastics via separate material infeeds. With regard to extruded strands and/or extruded scrim materials, they are similar to many elastomeric films in that they typically comprise thermoplastic materials that undergo significant stress relaxation over time and thus do not maintain the proper forces at the waist and legs to provide proper initial and sustained fit and gasketing over the entire wearing time.

Regarding elastic film laminates, they are significantly more occlusive (i.e., less breathable, very low or no air permeability), resulting in greater hydration of the skin and as a result significantly reduced comfort and increased marking associated with the susceptibility of the hydrated skin to marking. Also, film based elastic laminates in general tend to have a higher modulus versus stranded elastic laminates, therefore being more difficult to apply to a wearer (making it difficult to open for donning), therefore requiring more sizes to cover a given fit range of wearers. It is also very difficult to create a force profile across the elastic film laminate or scrim based elastic laminate as they are typically formed via webs with relatively uniform properties.

There has therefore been a long standing unmet consumer need which is to create a product that delivers very low pressure on the skin, high level of breathability, adequate force for sustained fit, low modulus, high extensibility and a smooth uniform texture. Such an absorbent article would provide improved skin condition, skin marking, skin hydration, ease of application, ease of removal, improved sustained fit, improved gasketing, as well as improved body conformity and wearer comfort.

To deliver against all of the unmet consumer needs requires a complete structural redesign of the elastomeric laminates used in the absorbent article. The balance of elastic decitex, elastic strand spacing, number of elastics and elastic pre-strain required to deliver such a unique blend of properties requires elastic decitex that are very low, well below that of the prior art, disposed at elastic to elastic spacing that are also very low, also well below the prior art, which in turn requires a larger number of elastics well above that known in the prior art, and elastic strains that are also low and well below nearly all of the known prior art. In addition to the very specific combinations of decitex, spacing, number of elastics and pre-strain required to deliver against the range of unmet consumer needs an additional factor of nonwoven choice, basis weight, composition, etc. is also critical to creating the overall desired structure.

Elastomeric laminates of the present disclosure have higher body contact and improved textures versus the prior art as demonstrate by the Surface Topography Method and less pressure of the elastic elements on the wearer's skin at a given modulus and reduced marking of the wearer's skin versus traditional elastic laminates known today as demonstrated by the Pressure-Under-Strand method. These improvements result in enhancing application (e.g., making pant articles easier to open for donning), fit, comfort as evidenced by the Product Measurement Test. These inventive elastomeric laminates also provide a very high level of breathability as evidenced by the WVTR Method and by the Air Permeability method. The inventive elastomeric laminates disclosed in this application perform better than traditional stranded and film versions of laminates known today.

The specific set of criteria required to deliver against all of the aforementioned unmet consumer needs with a single product not only requires unique elastomeric laminate structures but it requires a new process, beamed elastic (a plurality of elastics formed on and delivered from a beam or spool), for delivery of such a large number of low decitex elastics, at low pre-strain and low spacing in order to achieve the right balance of laminate properties. Such an approach to the best of our knowledge has never before been disclosed or attempted in the field of absorbent articles; hygiene articles, taped diapers, diaper pants, adult incontinence articles, menstrual products, etc.

SUMMARY OF THE INVENTION

In one disclosed example, the absorbent article may comprise a chassis and an elastic laminate. The chassis may comprise a topsheet, a backsheet and an absorbent core may be disposed between the topsheet and the backsheet. The elastic laminate may comprise a first plurality of elastics between inner and outer nonwovens. The elastic laminate may form at least a portion of at least one of the group consisting of a belt, a side panel, a topsheet, a backsheet, an ear panel, a waistband, a waistcap, an inner leg cuff, an outer leg cuff, and a transverse barrier. The first plurality of elastics may have an Average-Strand-Spacing from about 0.25 mm to about 4 mm. The Average-Dtex of the first plurality of elastics may be from about 10 to about 500. The Pressure-Under-Strand of the first plurality of elastics may be from about 0.1 to about 1 psi.

The elastic laminate may form at least a portion of at least one of the group consisting of a belt, a side panel, a topsheet, a backsheet, and an ear panel, and the first plurality of elastics may comprise from about 40 to about 1000 elastic strands.

The elastic laminate may form at least a portion of at least one of the group consisting of a waistband, a waistcap, an inner leg cuff, an outer leg cuff, and a transverse barrier, and the first plurality of elastics may comprise from about 10 to about 400 elastic strands.

The first plurality of elastics may have an Average-Strand-Spacing from about 0.5 mm to about 3 mm; where the Average-Dtex of the first plurality of elastics may be from about 30 to about 400; where the Pressure-Under-Strand of the first plurality of elastics may be from about 0.2 to about 0.8 psi.

The elastic laminate may have a Pressure-Under-Strand from about 0.2 to about 0.9 psi, and the elastic laminate may have an open area from about 80% to about 90%.

In another disclosed example, an absorbent article may comprise a chassis, a back belt, a lateral axis and a longitudinal axis. The chassis may comprise a topsheet, a backsheet and an absorbent core may be disposed between the topsheet and the backsheet. The chassis may comprise a front waist region and a back waist region. The back belt may be disposed in the back waist region overlapping and extending outboard of the back waist region of the chassis. The back belt may comprise a first plurality of elastics comprising greater than about 40 elastic strands. The back belt may be divided into 4 equal sections, where Section 4 may comprise a proximal end edge of the back belt. Section 1 may comprise a distal end edge of the back belt. Section 2 may be proximate to Section 1 and Section 3 may be proximate to Section 4, where at least two of the sections each have greater than 10 elastic strands. The first plurality of elastics may have an Average-Strand-Spacing of less than 4 mm.

A front belt may be disposed in the front waist region overlapping and extending outboard of the front waist region of the chassis. The front belt may be divided into 4 equal sections, where Section 4 may comprise a proximal end edge of the front belt. Section 1 may comprise a distal end edge of the front belt. Section 2 may be proximate to Section 1 and Section 3 may be proximate to Section 4, where at least one of the sections may have greater than 10 elastic strands. The front belt may comprise a second plurality of elastics comprising greater than about 40 elastic strands.

At least three of the sections of the back belt each have greater than 10 elastic strands. And at least two of the sections of the front belt each have greater than 10 elastic strands.

At least one of the sections of the first plurality of elastics and at least one of the sections of the second plurality of elastics have a different Section-Modulus. And, an area of the back belt may comprise the first plurality of elastics may have an open area greater than about 75%.

The back belt may have a greater longitudinal distance than the front belt along the longitudinal axis. The front and back belts may be substantially co-terminus at the waist opening, and the back belt may comprise one or more sections having a section modulus of between about 4 gf/mm and 10 gf/mm.

In another disclosed example, an absorbent article may comprise a chassis comprising a topsheet, a backsheet and an absorbent core may be disposed between the topsheet and the backsheet. Side edges of first and second panels may be joined to opposing lateral side edges of the chassis in a back waist region of the absorbent article. A longitudinal axis may extend from the midpoint of the front waist edge to the midpoint of the back waist edge. A lateral axis may extend perpendicular to the longitudinal axis through the midpoint of the longitudinal axis. The first panel may comprise a first plurality of elastics comprising greater than about 20 elastic strands. The second panel may comprise a second plurality of elastics comprising greater than about 20 elastic strands. The first panel may be divided into 4 equal sections, where Section 4 may comprise a proximal end edge of the first panel. Section 1 may comprise a distal end edge of the first panel. Section 2 may be proximate to Section 1 and Section 3 may be proximate to Section 4, where at least two of the sections each have 5 or more elastic strands.

The second panel may be divided into 4 equal sections, where Section 4 may comprise a proximal end edge of the first panel. Section 1 may comprise a distal end edge of the second panel, Section 2 may be proximate to Section 1 and Section 3 may be proximate to Section 4, where at least two of the sections each have 5 or more elastic strands. The first plurality of elastics may have an Average-Strand-Spacing of less than 4 mm. The second plurality of elastics may have an Average-Strand-Spacing of less than 4 mm.

A waistband may be may be disposed between the first and second panels, and the waistband may comprise a third plurality of elastics comprising greater than about 10 elastic strands having an average elastic strand spacing of less than 4 mm, and each of the first and second panels comprise one or more sections having a section modulus of less than about 12 gf/mm.

Third and fourth panels may be joined to opposing lateral side edges of the chassis in a front waist region of the absorbent article, and the third and fourth panels may be joined to the first and second panels to form leg openings and a waist opening, to form a closed-form absorbent article.

In another disclosed example, an absorbent article may comprise a chassis and an elastic laminate. The chassis may comprise a topsheet, a backsheet and an absorbent core may be disposed between the topsheet and the backsheet. The elastic laminate joined to or form a portion of the chassis.

The elastic laminate may comprise a first plurality of elastics between inner and outer nonwovens. The first plurality of elastics may have an Average-Strand-Spacing of less than about 3 mm. The Average-Dtex of the first plurality of elastics may be less than about 600, and the Average-Pre-Strain of the strands of the first plurality of elastics may be less than about 350%.

The first plurality of elastics may comprise from about 125 to about 625 elastic strands, and the Average-Pre-Strain of the first plurality of elastics may be less than about 150%.

The first plurality of elastics may have an Average-Strand-Spacing from about 0.375 mm to about 2.7 mm.

The Average-Dtex of the first plurality of elastics may be from about 20 to about 350, and the Average-Dtex of the first plurality of elastics may be less than about 155.

The Average-Pre-Strain of the first plurality of elastics may be from about 75% to about 300%, and the elastic laminate may have a Pressure-Under-Strand of less than about 1.0 psi.

The elastic laminate may form at least a portion of at least one of the group consisting of a belt, a side panel, a topsheet, a backsheet, and an ear panel having a first plurality of elastics comprising greater than about 40 elastic strands, where the elastic laminate may have an open area greater than about 75%.

The elastic laminate may form at least a portion of at least one of the group consisting of a waistband, a waistcap, an inner leg cuff, an outer leg cuff, and a transverse barrier, and may have a first plurality of elastics comprising greater than about 10 elastic strands.

BRIEF DESCRIPTION OF THE DRAWINGS

FIG. 30B is a simplified view of the apparatus of FIG. 30A with a pant placed on the apparatus.

FIG. 49A is a schematic side view of a second configuration of a converting apparatus joining elastic strands between a first substrate and a second substrate, wherein the elastic strands drawn from different beams are stretched to have different elongations.

FIG. 50B is a view of the converting apparatus of FIG. 50A taken along line 50B-50B.

FIG. 50C is a view of the converting apparatus of FIG. 50A taken along line 50C-50C.

FIG. 67 is a plan view of a pant comprising transversely extending elastics 316 in the front and back side panels 330 in the front and back waist regions and longitudinally extending elastics 316 in the chassis 200.

FIG. 77A is a perspective side view of a comparative outer leg cuff 140 comprising an existing elastic profile of strands showing a grouping of large irregular and uncontrolled gathers indicative of less uniform and higher elastic stress that will result in higher pressure on the wearer's skin (versus the outer leg cuff of FIG. 77B).

Figure 77A:
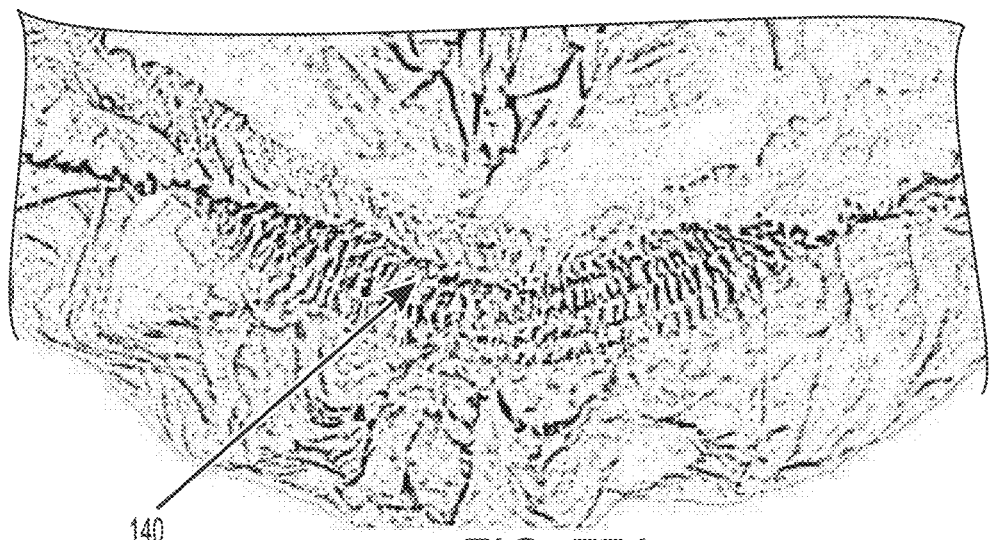
Figure 77B:
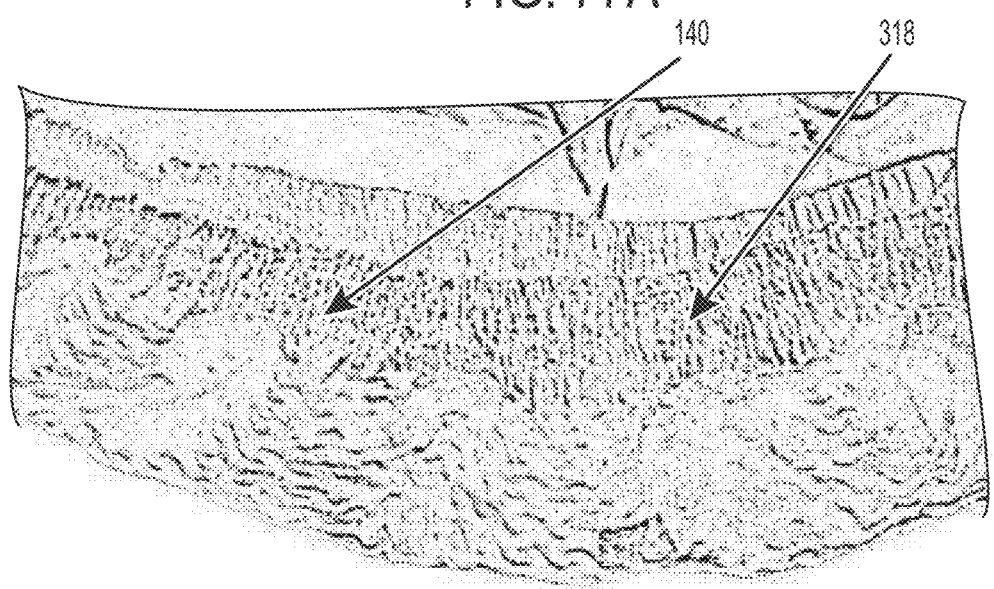

FIG. 77B is a perspective side view of an inventive outer leg cuff 140 comprising an inventive elastomeric laminate 302. The inventive texture zone 318 of the outer leg cuff in FIG. 77B is meant to be directly compared to same areas of the outer leg cuff in FIG. 77A.

Figure 78:
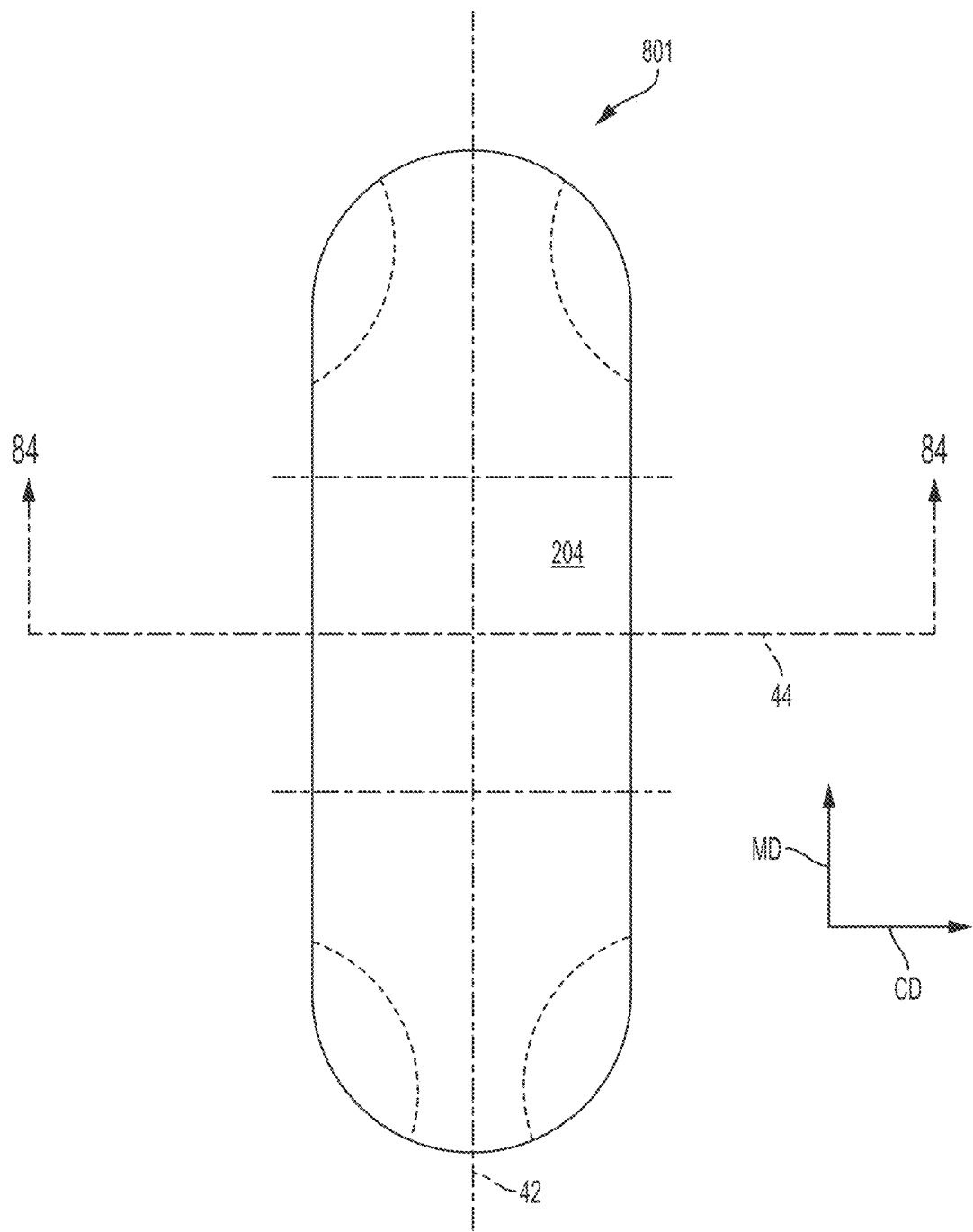

FIG. 78 is an exterior plan view of a feminine hygiene article 801, specifically a liner.

Figure 79:
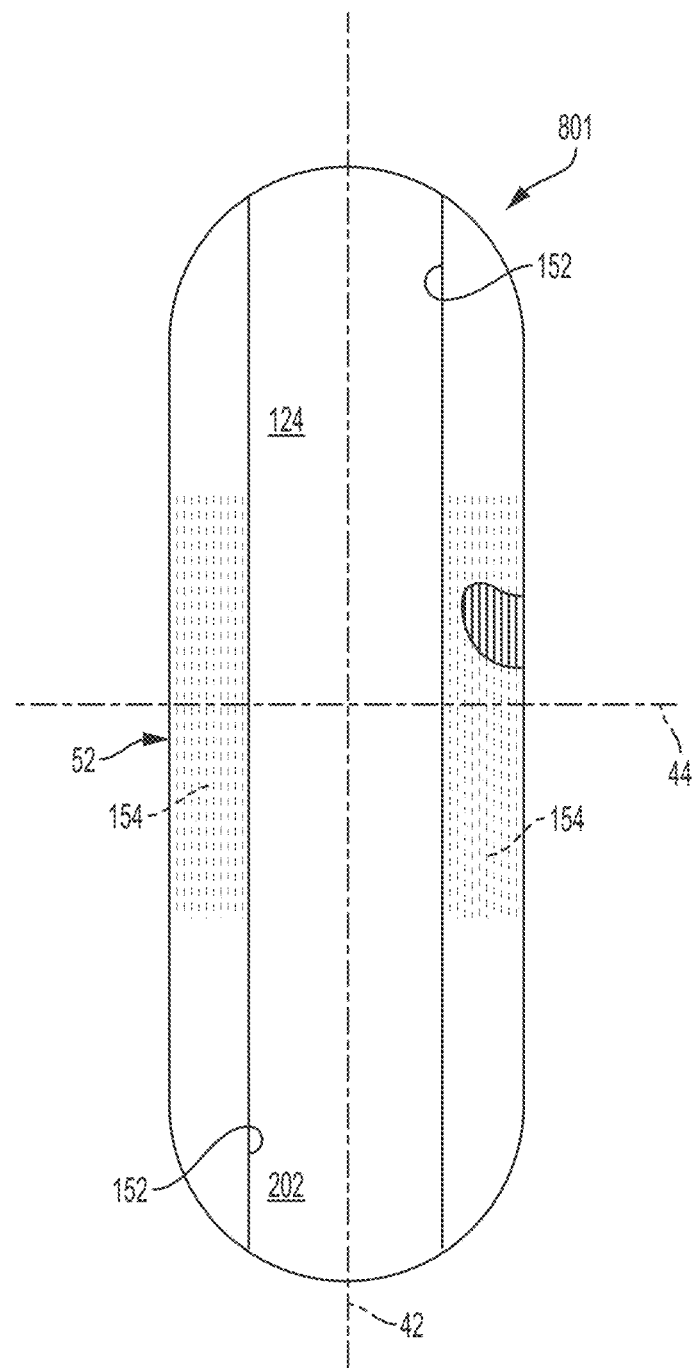

FIG. 79 is an interior plan view of the feminine hygiene article 801 of FIG. 78 illustrating leg cuffs 52.

Figure 80:
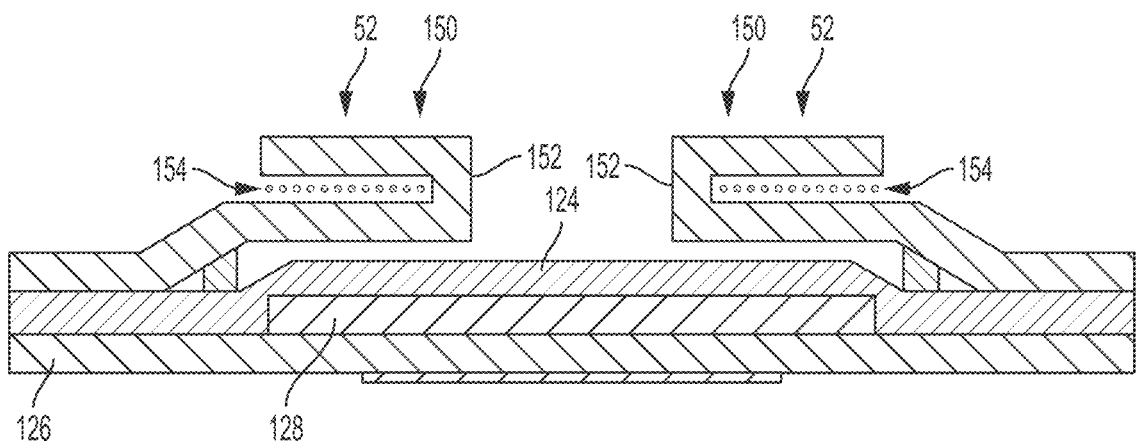

FIG. 80 is a cross section view of the feminine hygiene article 801, along line 80-80 of the feminine hygiene article 801 of FIG. 78.

Figure 81:
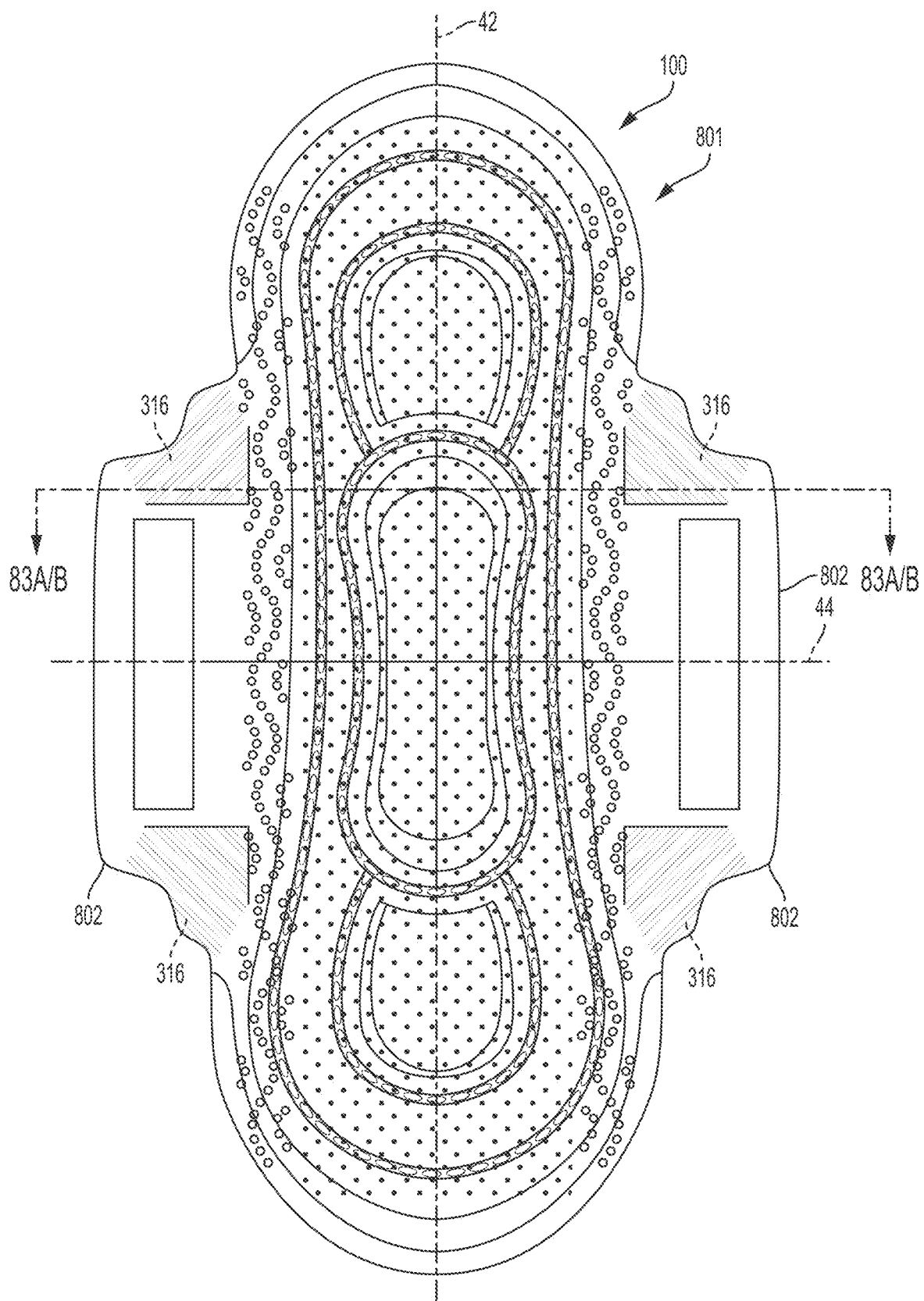

FIG. 81 is an interior plan view of a feminine hygiene article 801, specifically a pad, illustrating elasticized wings 802.

Figure 82:
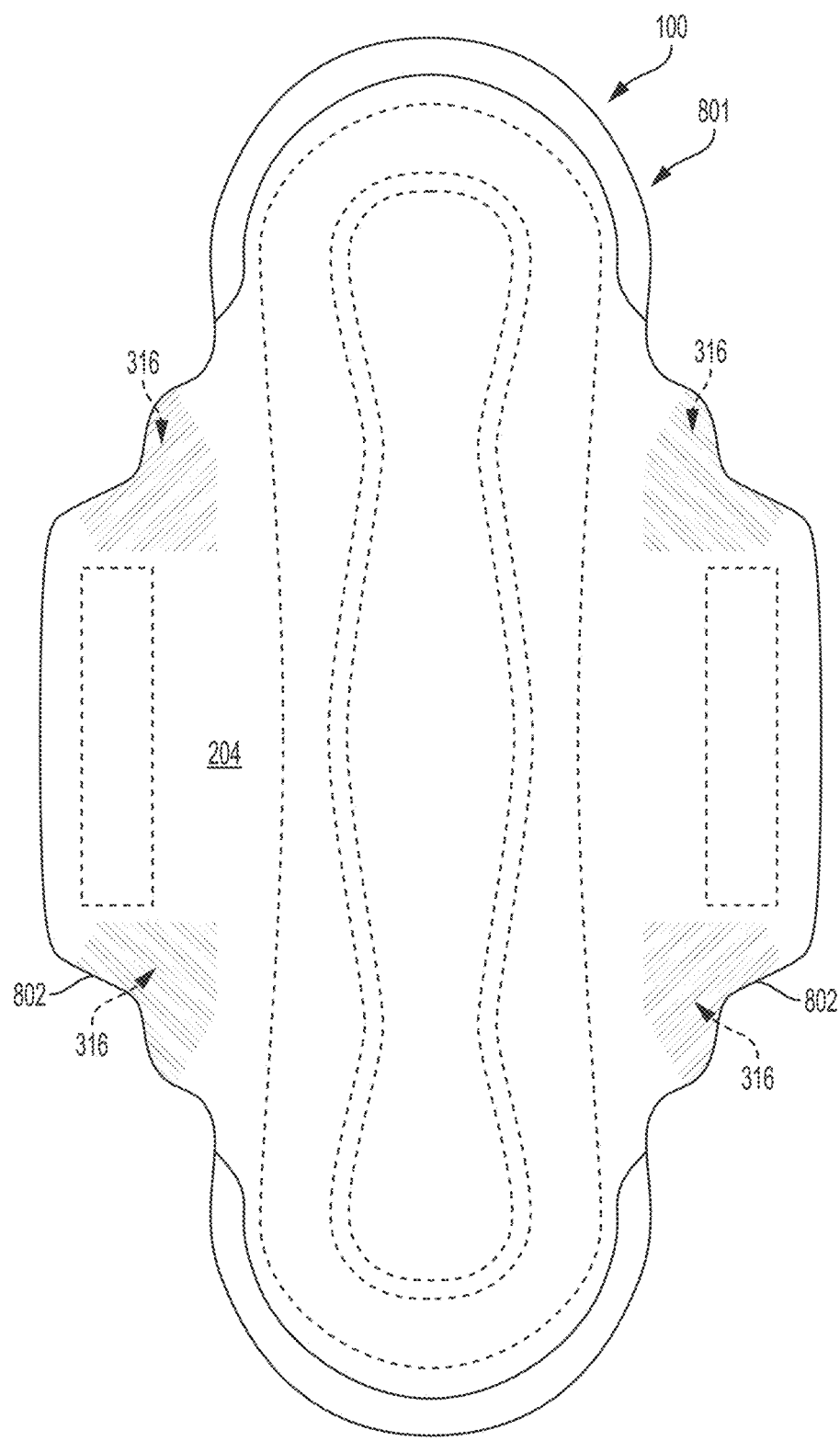

FIG. 82 is an exterior plan view of the feminine hygiene article 801 of FIG. 81 illustrating elasticized wings 802.

Figure 83A:
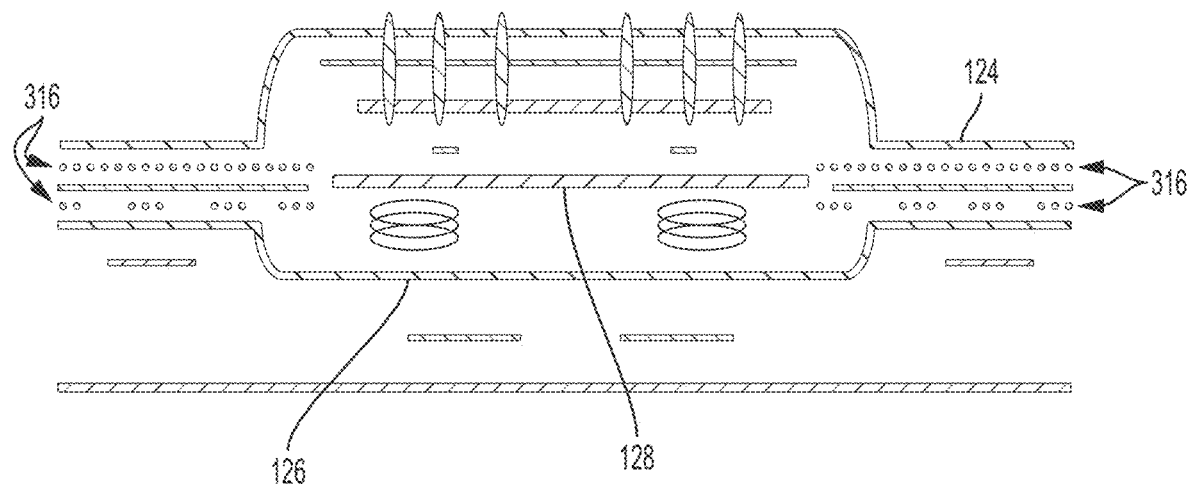

FIG. 83A is a cross section view of the feminine hygiene article 801, along line 83A/B-83A/B of the feminine hygiene article 801 of FIG. 81, illustrating strands between the layers making up the wings.

Figure 83B:
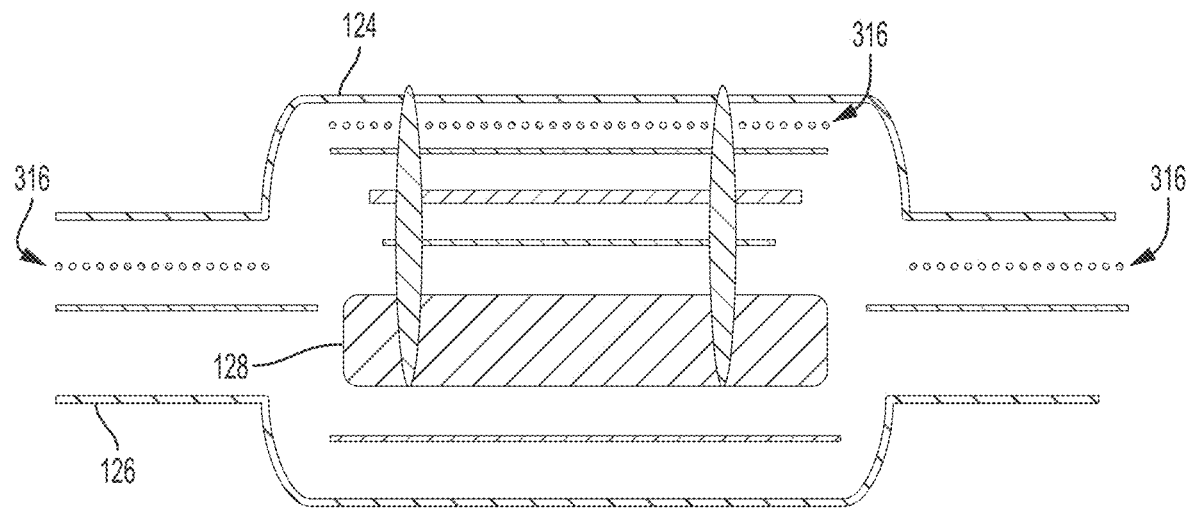

FIG. 83B is a cross section view of an alternative embodiment of the feminine hygiene article 801, along line 83A/B-83A/B of the feminine hygiene article 801 of FIG. 81, illustrating strands between the layers making up the wings, as well as strands underlying or forming a portion of the topsheet 124.

Figure 84:
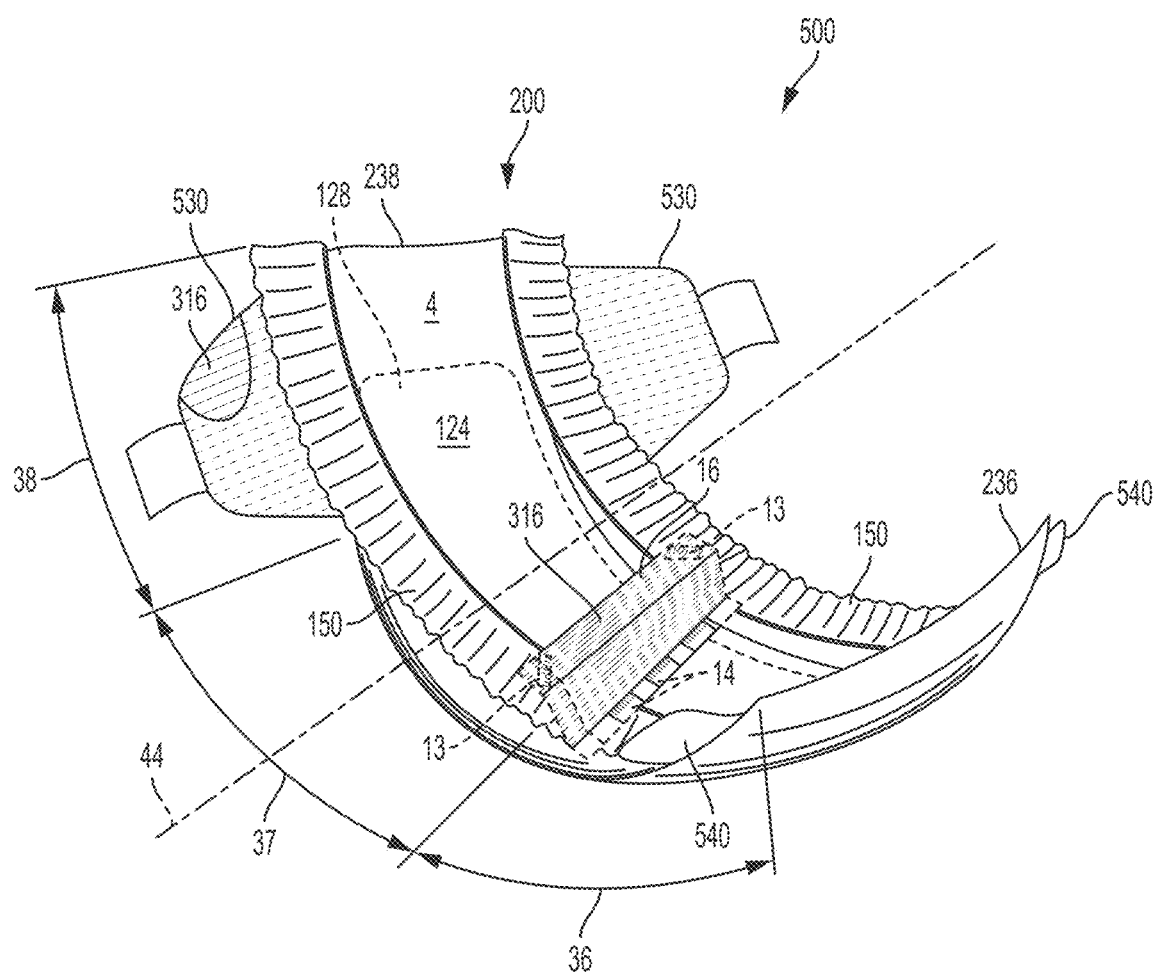

FIG. 84 is a perspective interior top view of a taped article comprising a transverse barrier.

FIG. 85 illustrates the Donning-Ratio.

Figure 86:
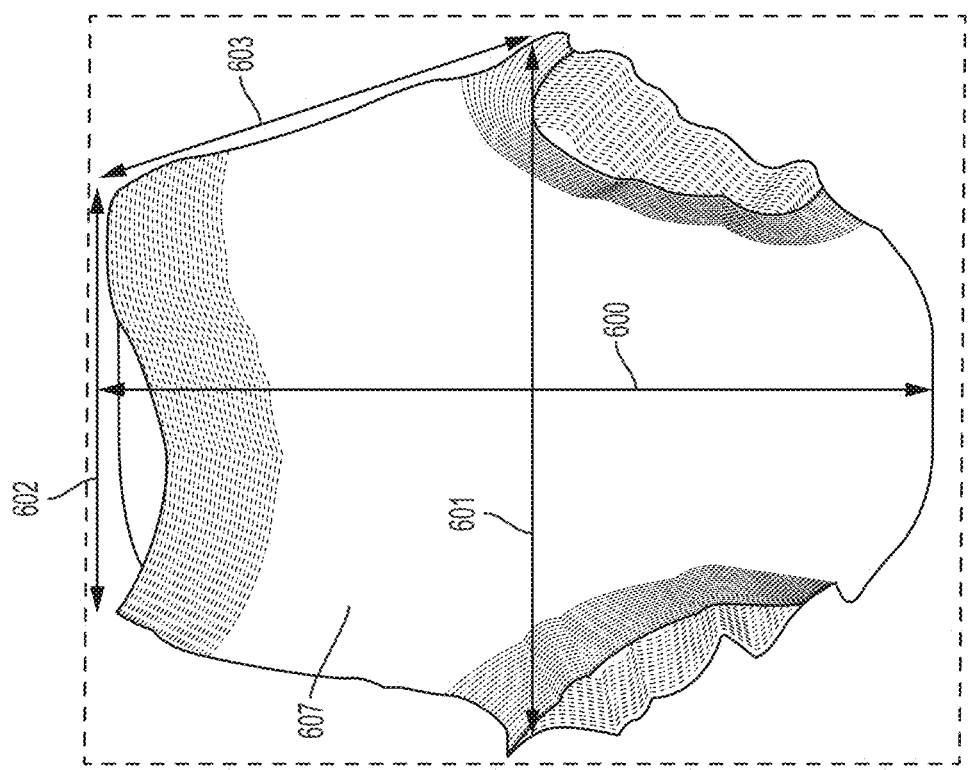

FIG. 86 shows a perspective front view of a closed-form pant product in its laid out, relaxed, and unfolded state.

Figure 87:
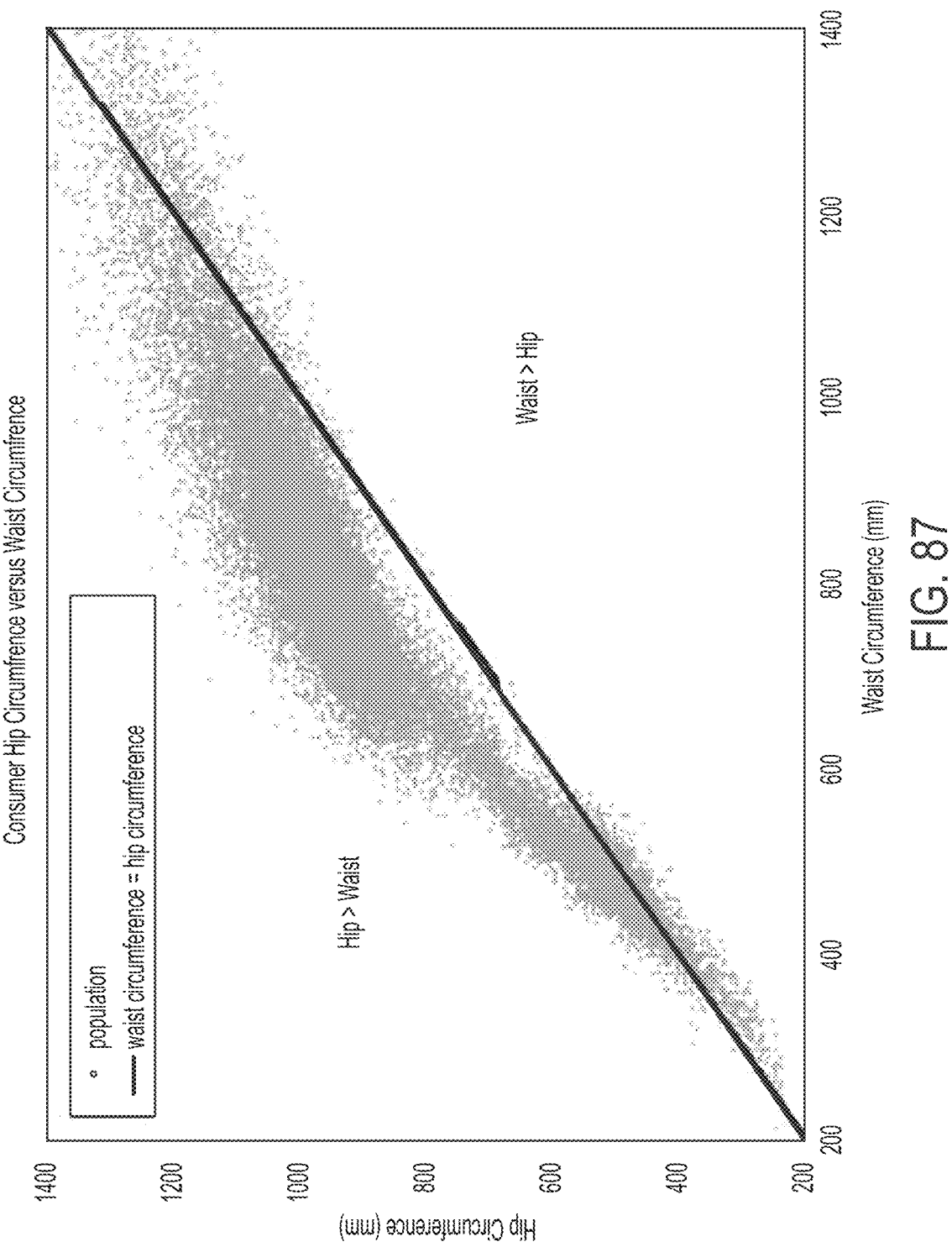

FIG. 87 is a chart showing the relationship between a wearer's waist circumference and hip circumference, and that the hip circumference is the larger of the two for over 90% all wearers.

Figure 88:
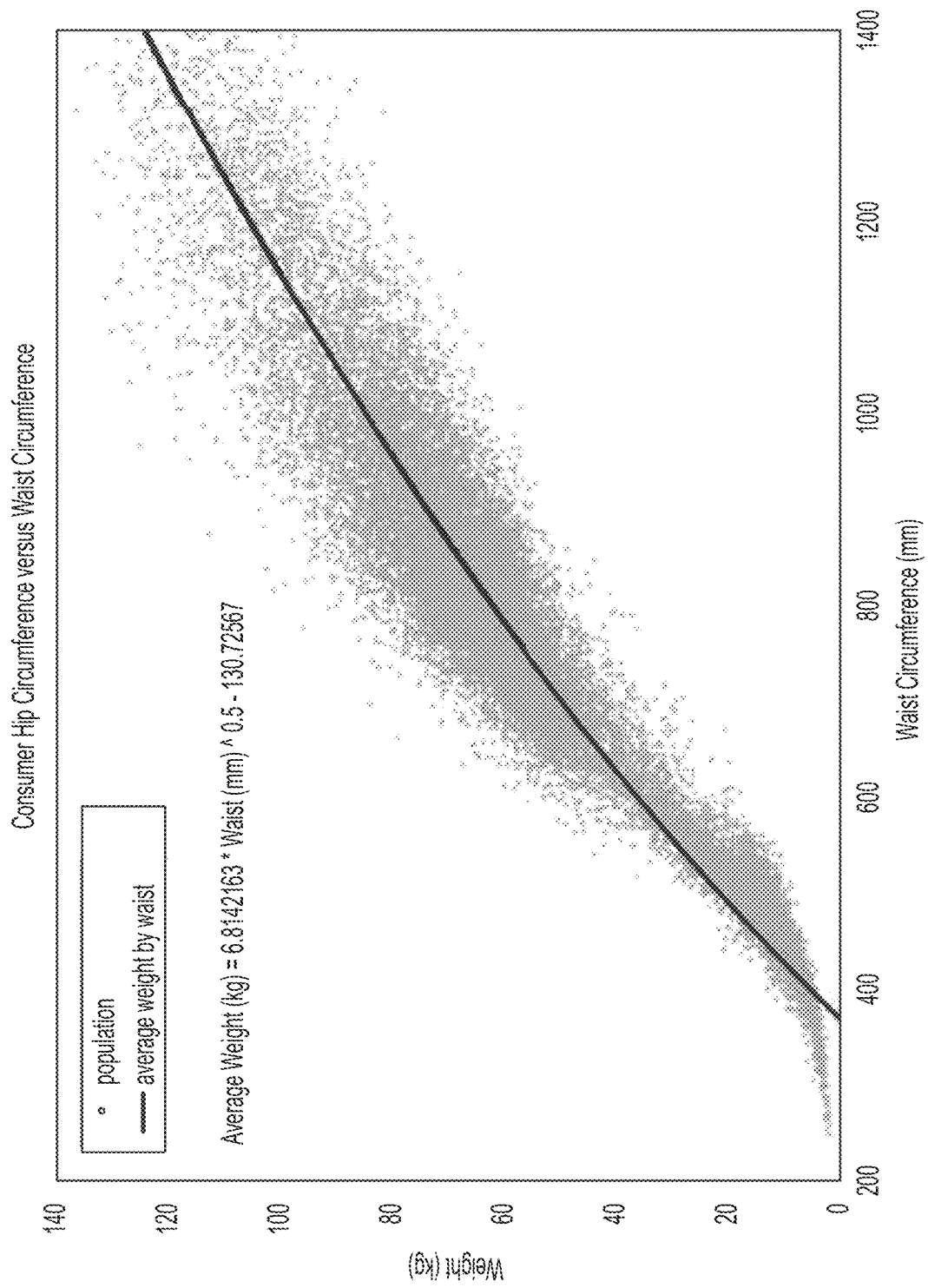

FIG. 88 is a chart showing the relationship between a wearer's body weight and waist circumference, and that the average weight versus waist can be reasonably predicted, especially for larger wearers.

Figure 89:
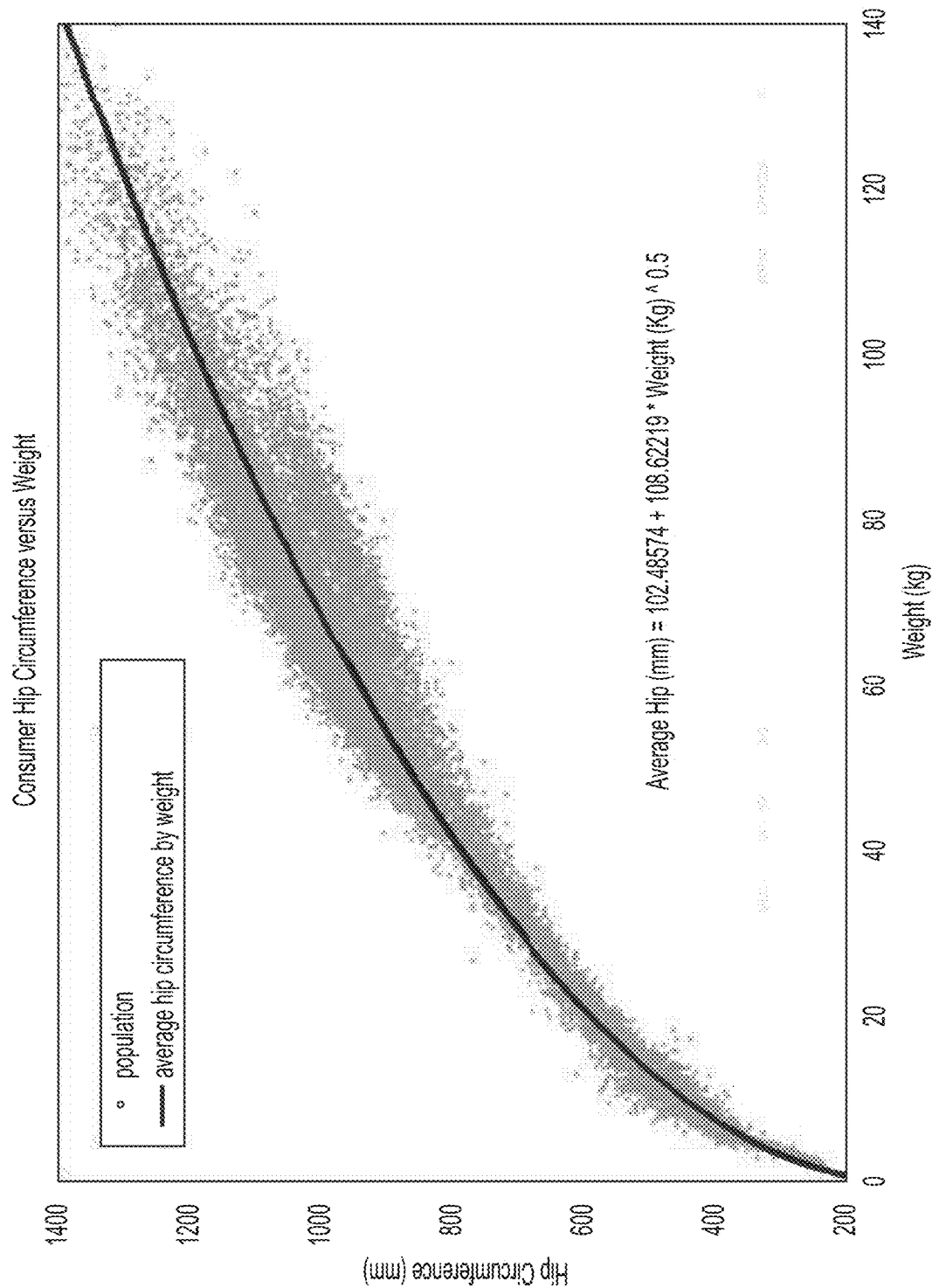

FIG. 89 is a chart showing the relationship between a wearer's hip circumference and body weight, and that the average hip circumference versus weight can be reasonably predicted.

Figure 90:
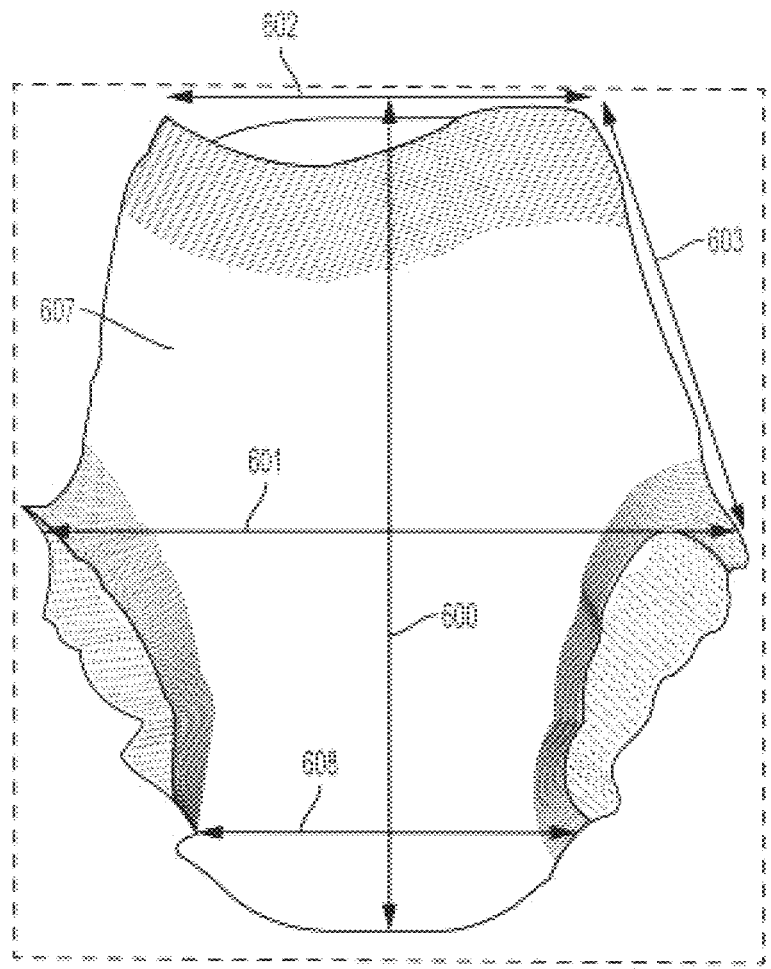

FIG. 90 shows a flat, unfolded closed-form pant.

Figure 91A:
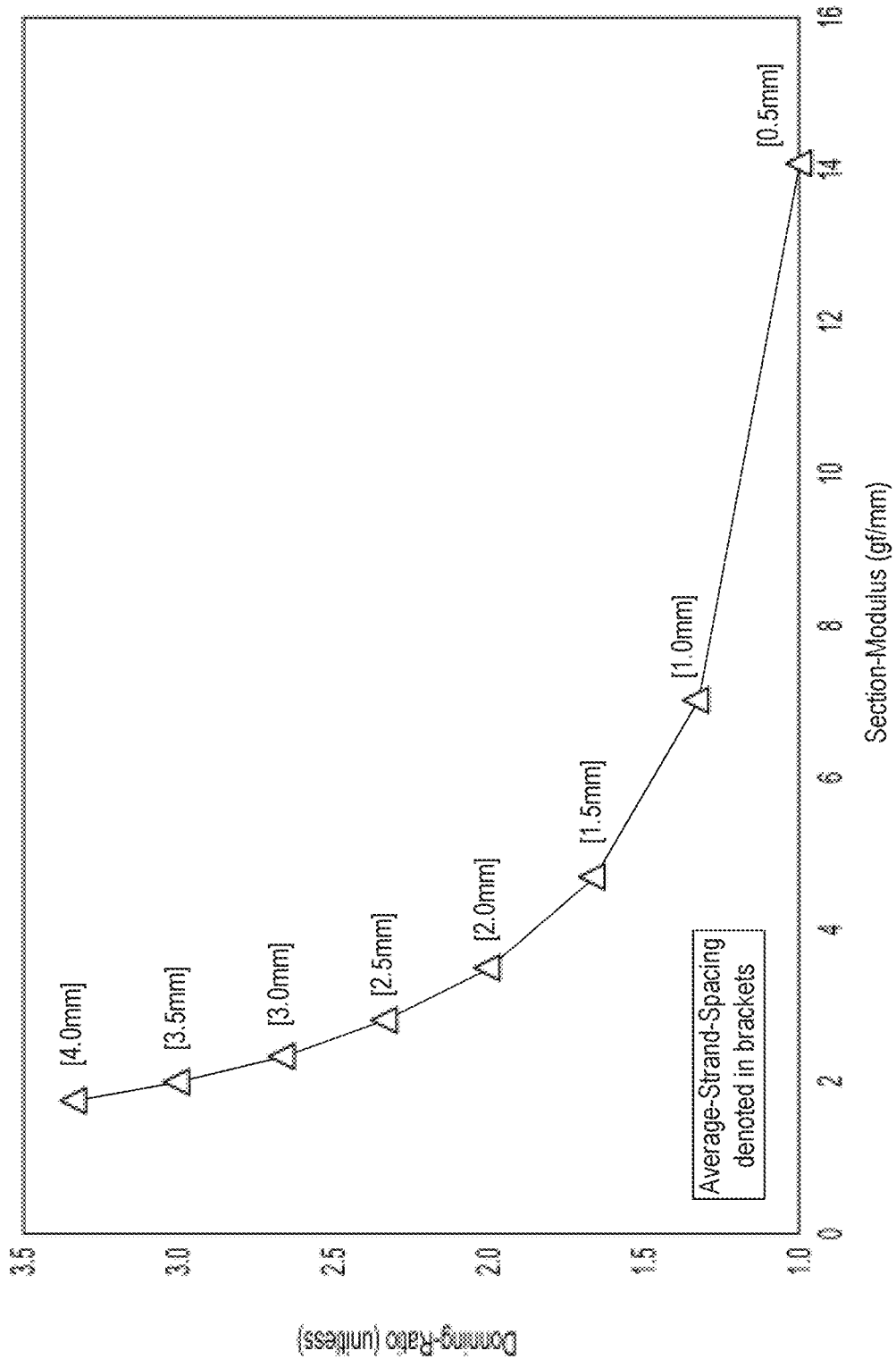

FIG. 91A is a chart showing the relationship between strand spacing, modulus and Donning-Ratio for a stranded belt having a constant hoop force and constant strand decitex.

Figure 91B:
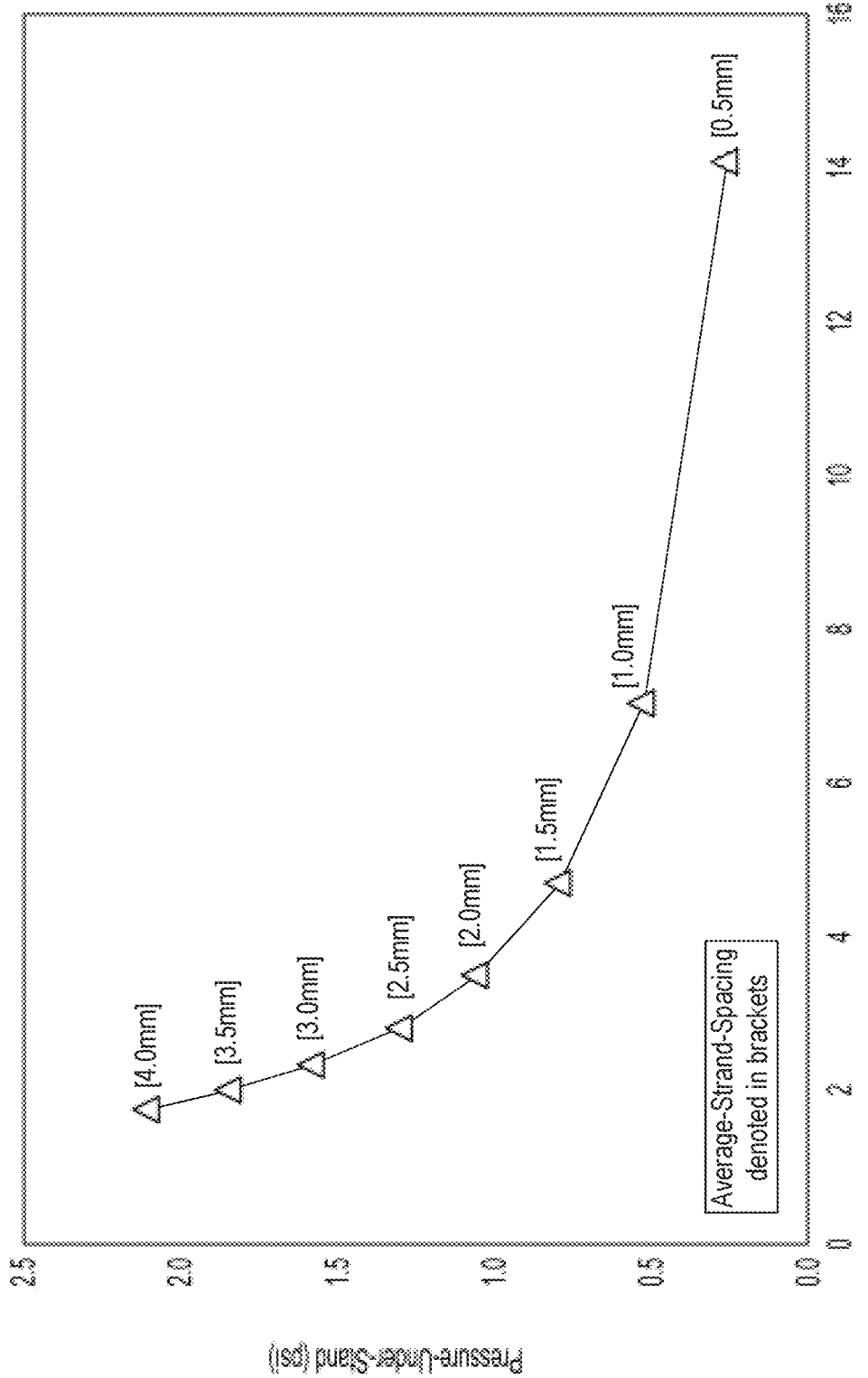

FIG. 91B is a chart showing the relationship between strand spacing, modulus and Pressure-Under-Strand for a stranded belt having a constant hoop force and constant strand decitex.

Figure 92:
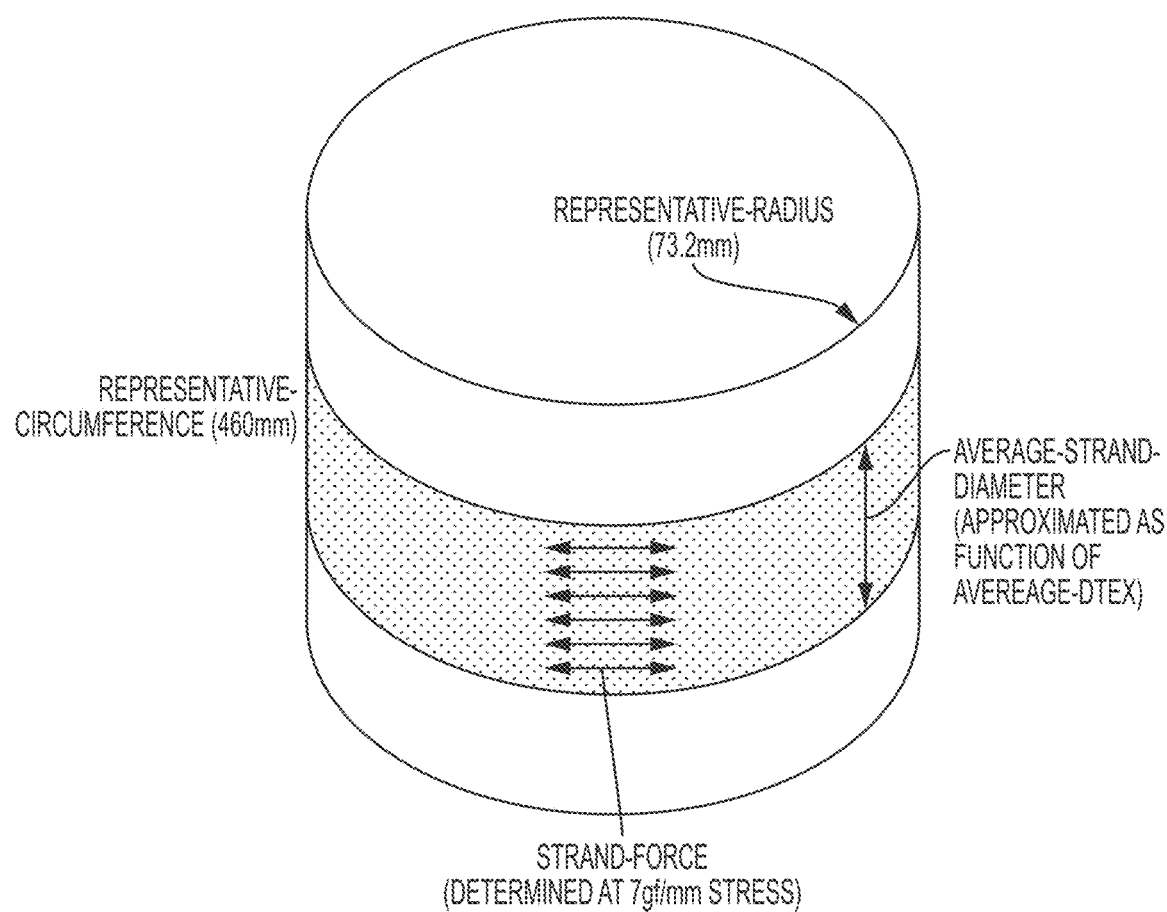

FIG. 92 illustrates Pressure-Under-Strand.

Figure 93:
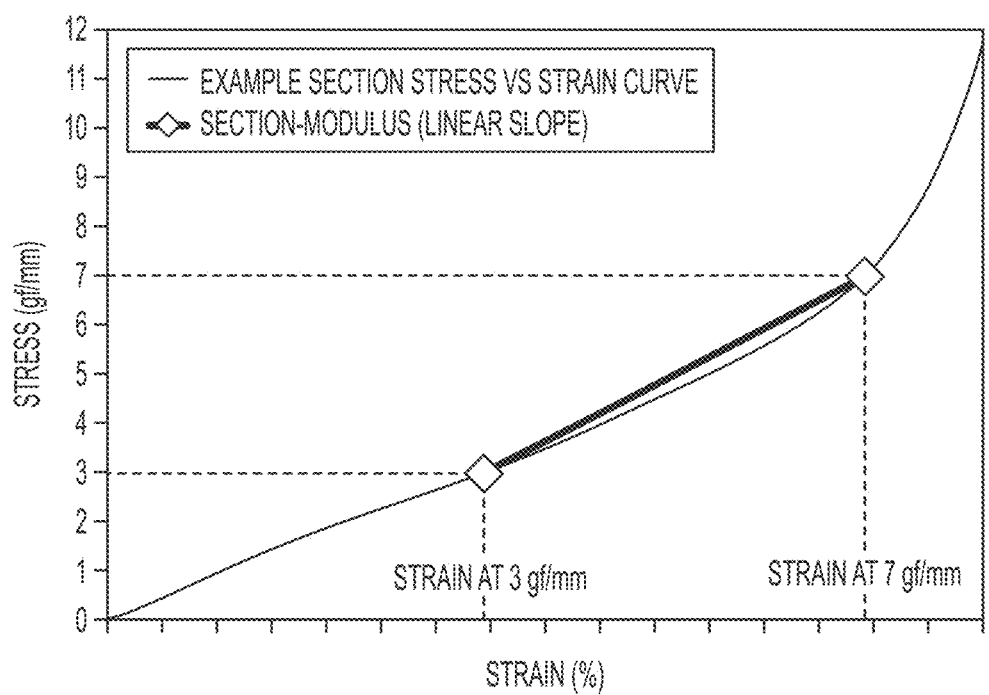

FIG. 93 Illustrates the SECTION-MODULUS.

Figure 94:
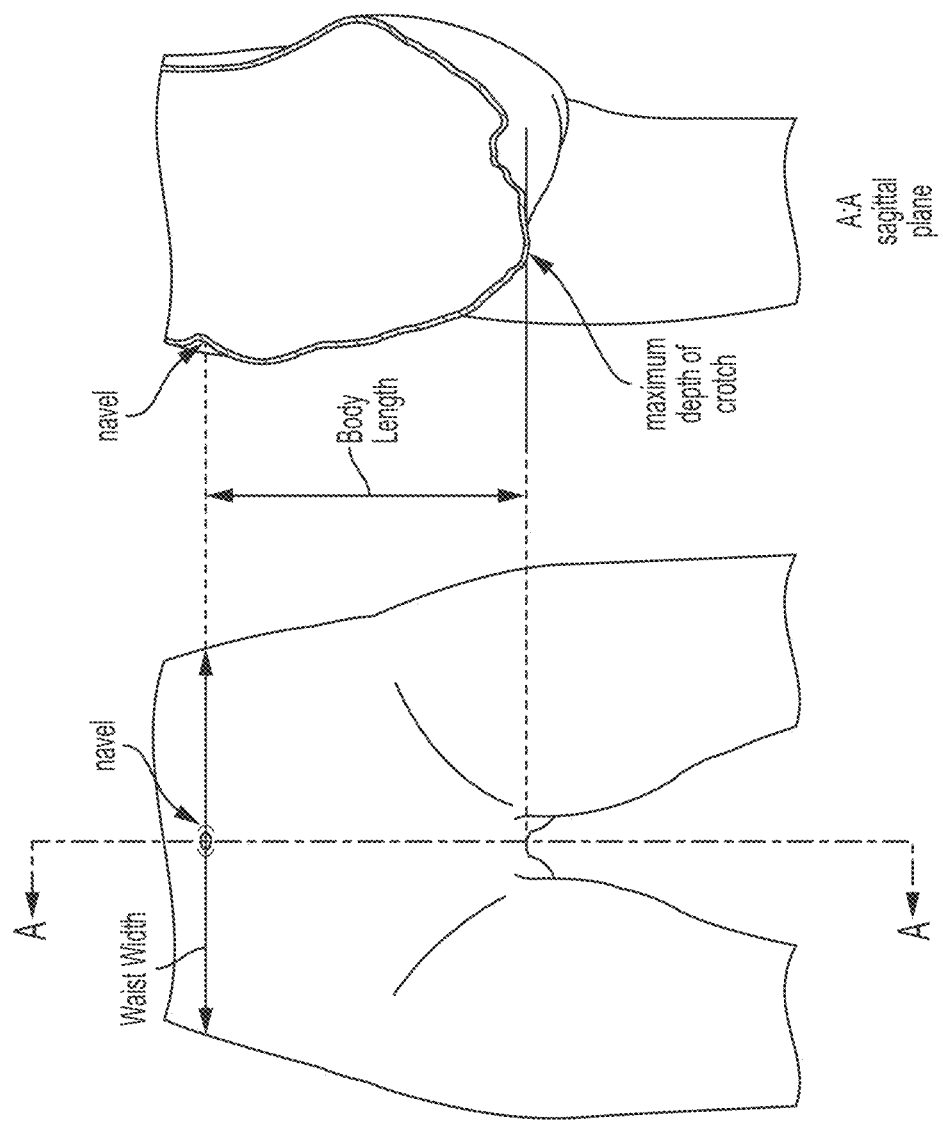

FIG. 94 shows Body Length and Waist Width against a body shape.

Figure 95:
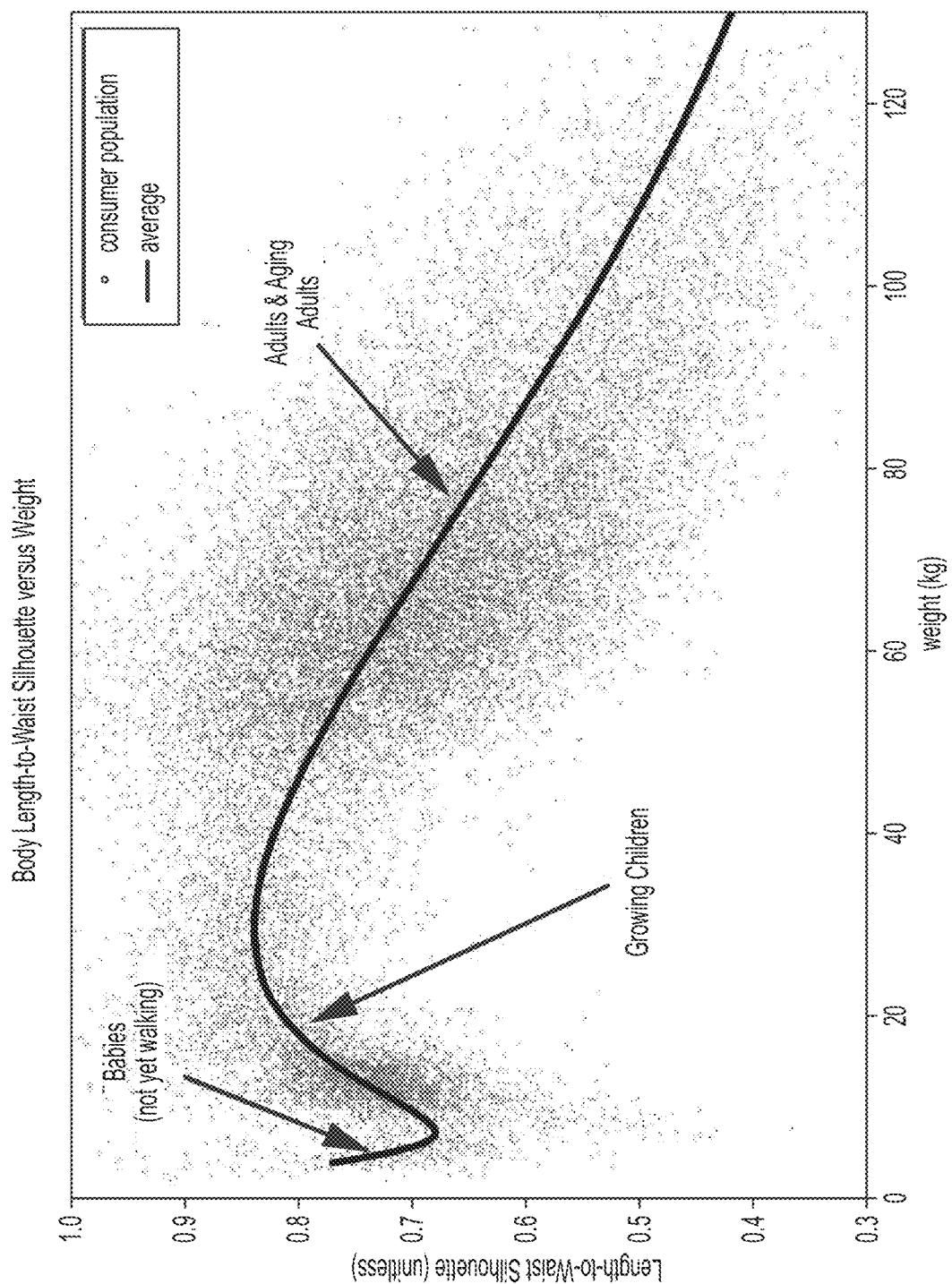

FIG. 95 is a chart which shows how the Body Length-to-Waist Silhouette and Average Body Length-to-Waist Silhouette changes as body weight increases.

Figure 96:
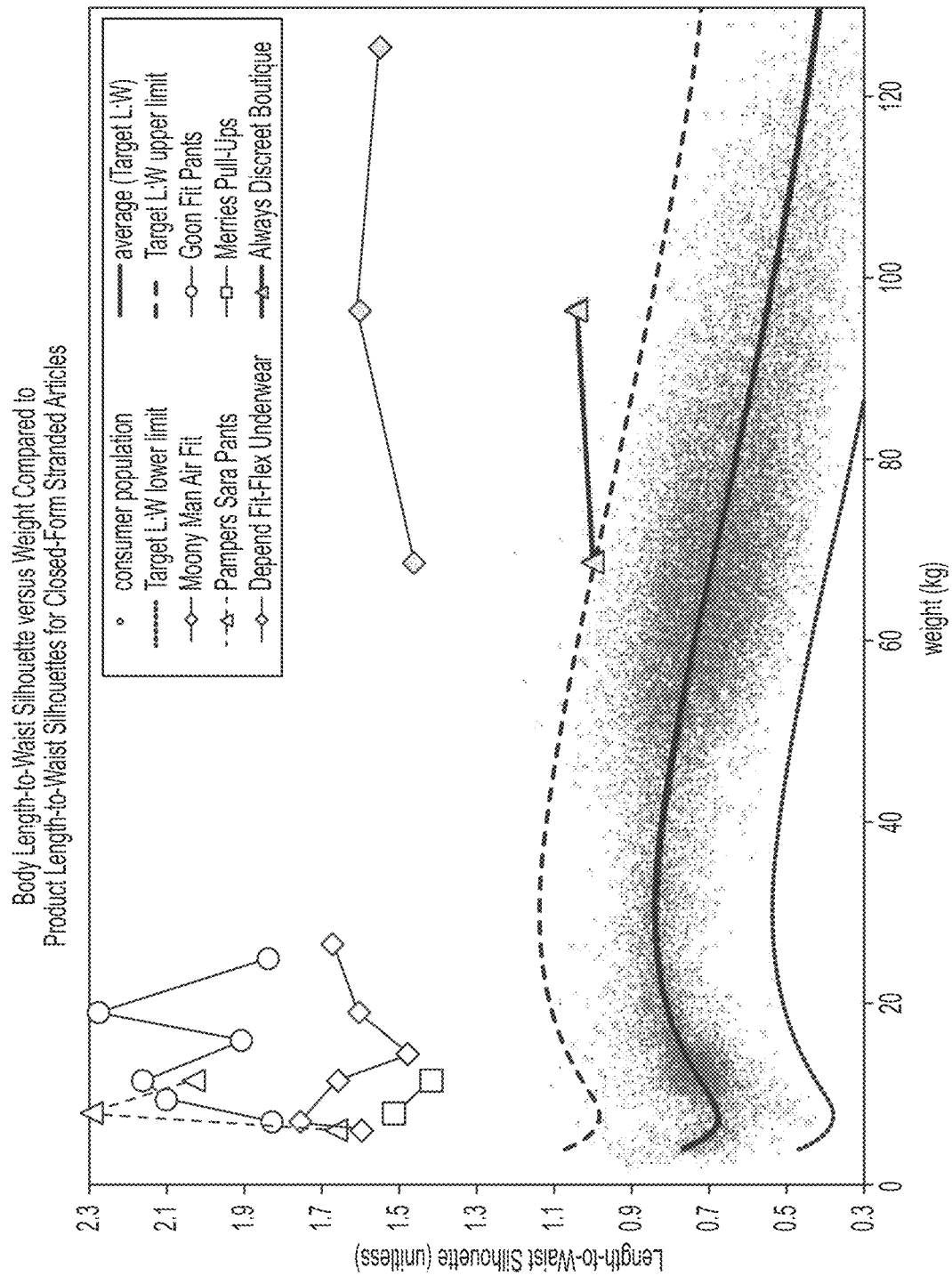

FIG. 96 is a chart which shows examples of existing product arrays, and how their Product Length-to-Waist Silhouettes compare to the Body Length-to-Waist Silhouettes for the weight range each product is targeted to fit.

Figure 97:
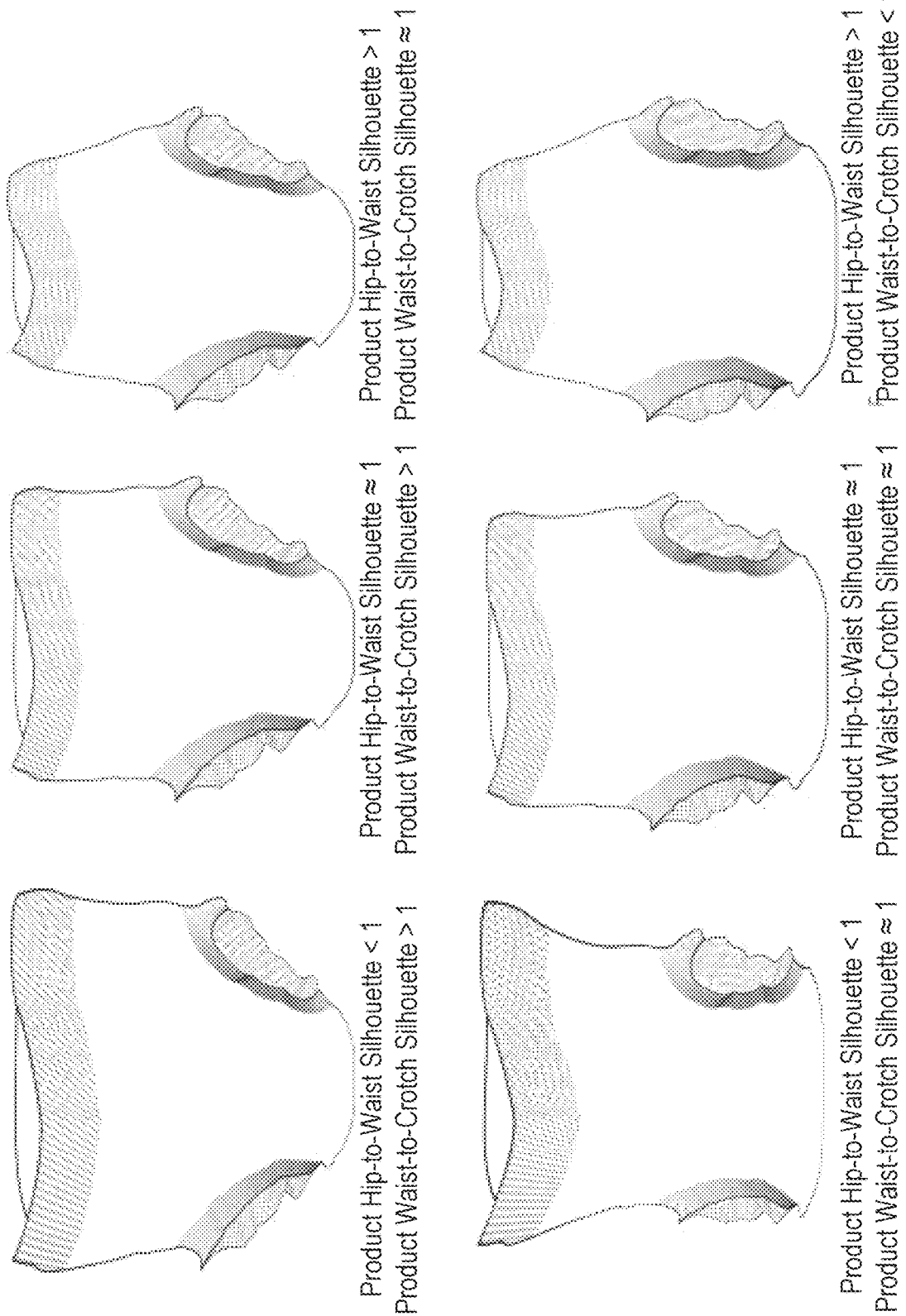
Figure 98:
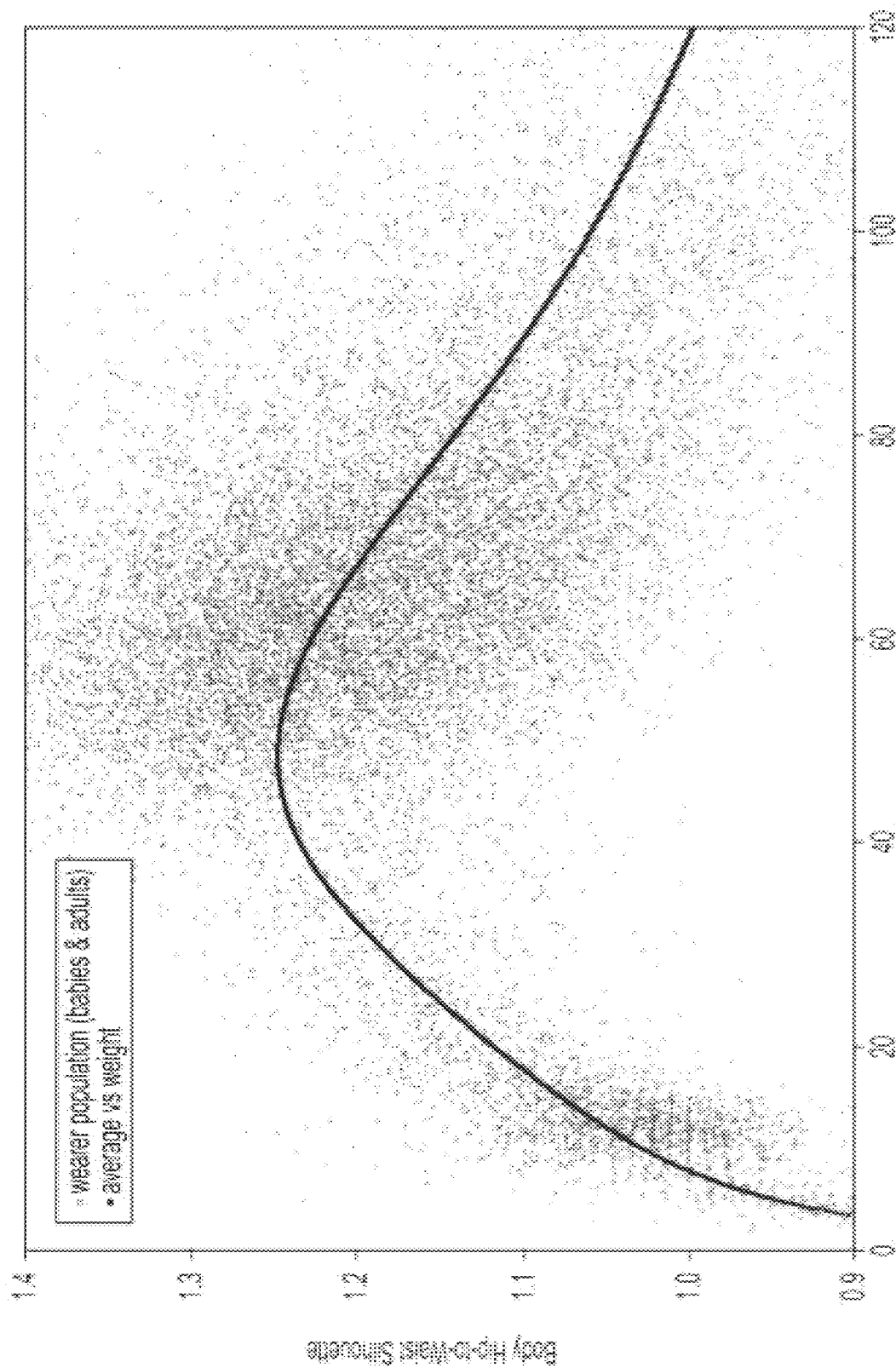

FIG. 97 shows illustrates the Product Hip-to-Waist Silhouette and Product Waist-to-Crotch Silhouette FIG. 98 is a chart which shows how the Body Hip-to-Waist Silhouette and Average Body Hip-to-Waist Silhouette changes as body weight increases.

Figure 99:
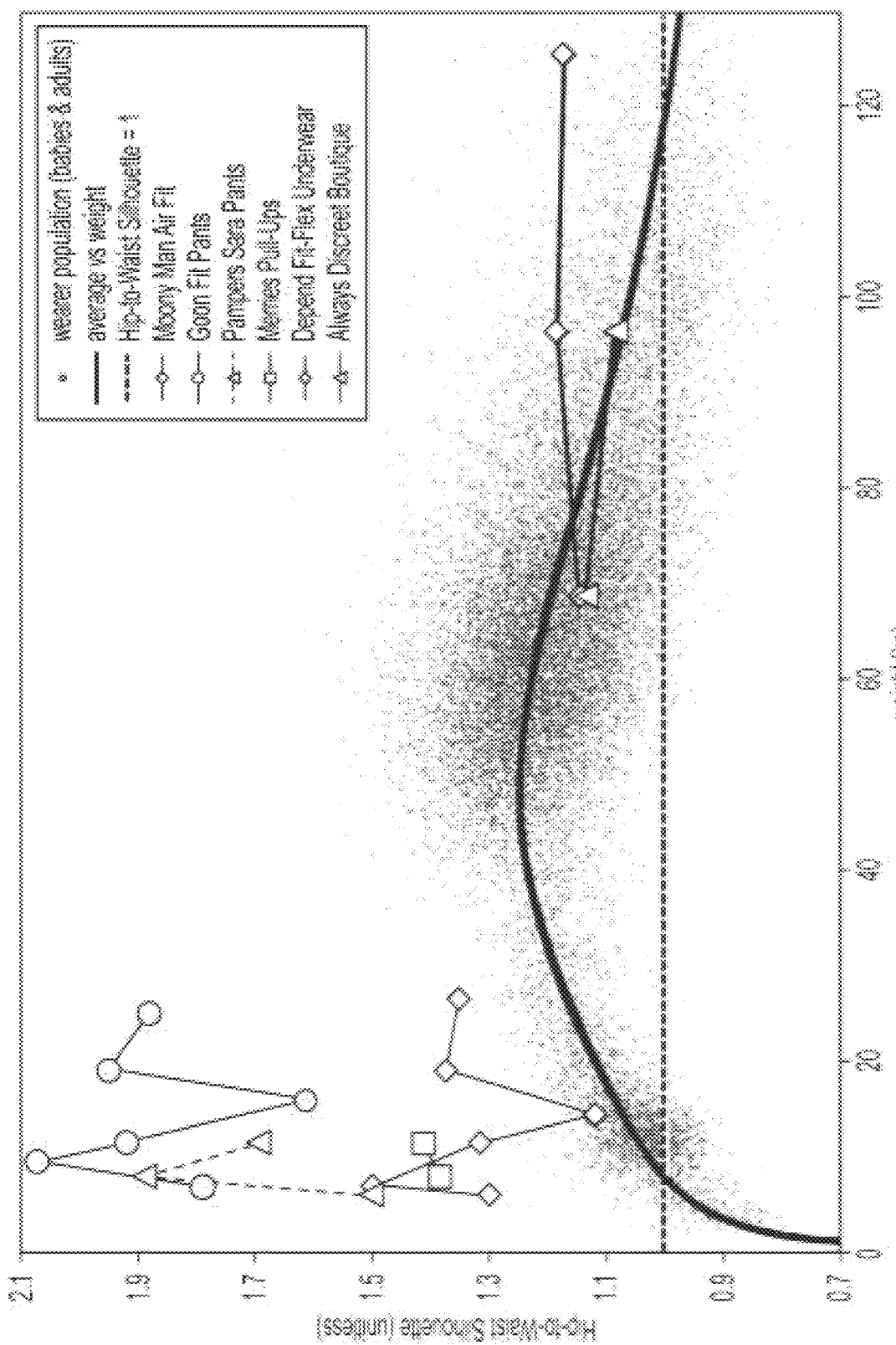

FIG. 99 is a chart which shows examples of existing product arrays and how their Product Hip-to-Waist Silhouettes compare to the Body Hip-to-Waist Silhouettes for the weight range each product is targeted to fit.

Figure 100:
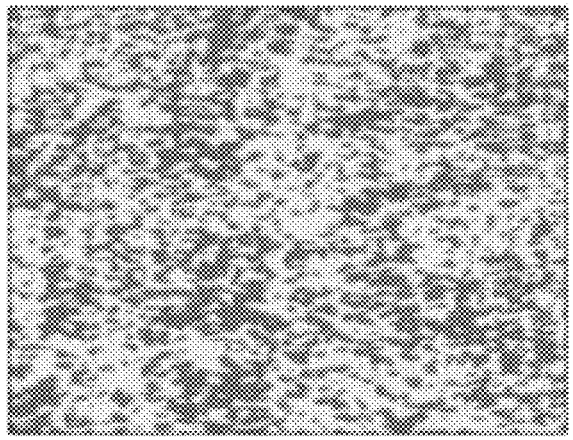

FIG. 100 is an image of inventive elastomeric laminate 150 of the present disclosure showing the contact area taken from the Surface Topography Method.

Figure 100A:
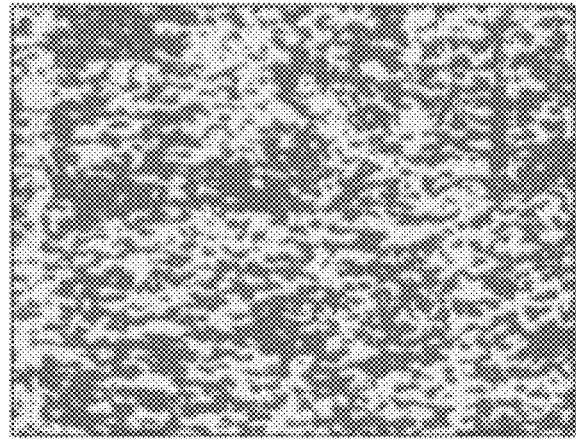

FIG. 100A is an image of inventive elastomeric laminate 120 of the present disclosure showing the contact area taken from the Surface Topography Method.

Figure 101:
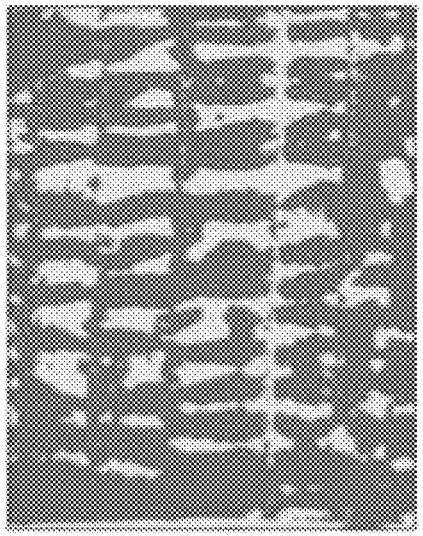

FIG. 101 is an image of current market product 6 of the present disclosure showing the contact area taken from the Surface Topography Method.

Figure 101A:
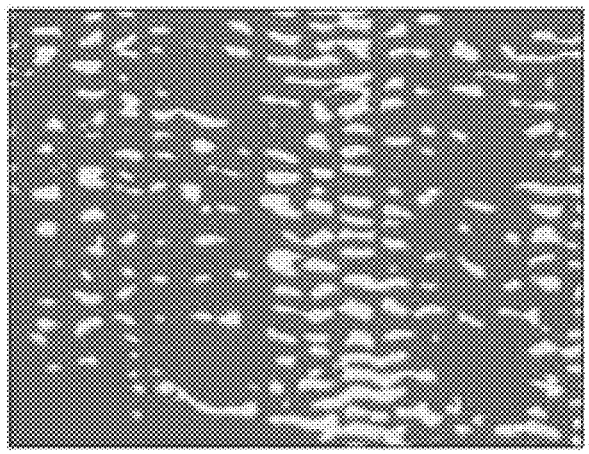

FIG. 101A is an image of current market product 7 of the present disclosure showing the contact area taken from the Surface Topography Method.

Figure 102:
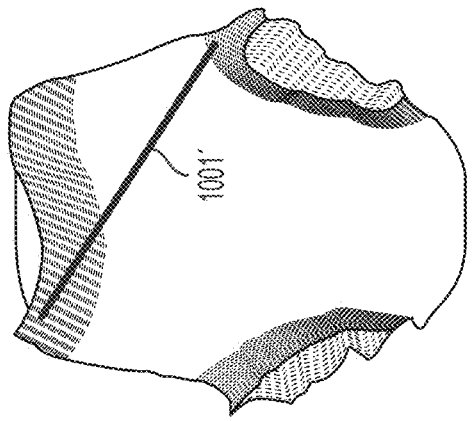

FIG. 102 is an exterior view of an article in an extended state, the article comprising an inventive elastomeric laminate 302 forming a belt 430 with the scribed line (1001 (extended)) for graphic distortion testing.

Figure 102A:
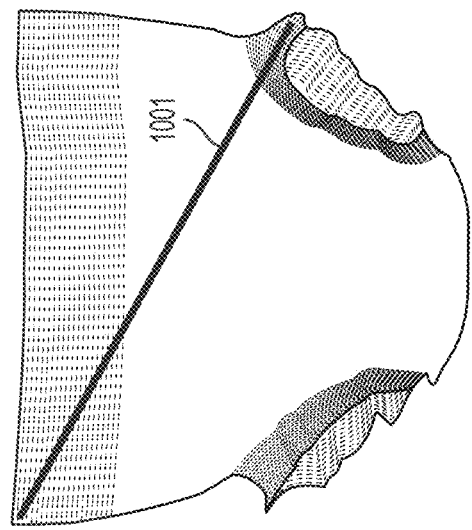

FIG. 102A is an exterior view of the article of FIG. 102 in a contracted state, the article comprising an inventive elastomeric laminate 302 forming a belt 430 with the scribed line (1001' (contracted)) for graphic distortion testing.

Figure 103:
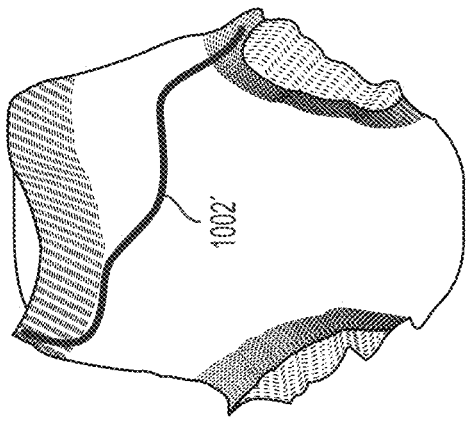

FIG. 103 is an exterior view of an article in an extended state, the article comprising a comparative (non-inventive) elastic belt of the prior art with the scribed line (1002 (extended)) for graphic distortion testing.

Figure 103A:
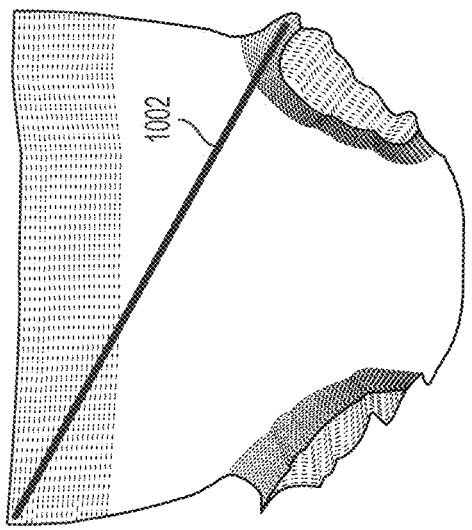

FIG. 103A is an exterior view of the article of FIG. 103 in a contracted state, the article comprising an elastic belt of the prior art with the scribed line (1002' (contracted)) for graphic distortion testing.

Figure 104:
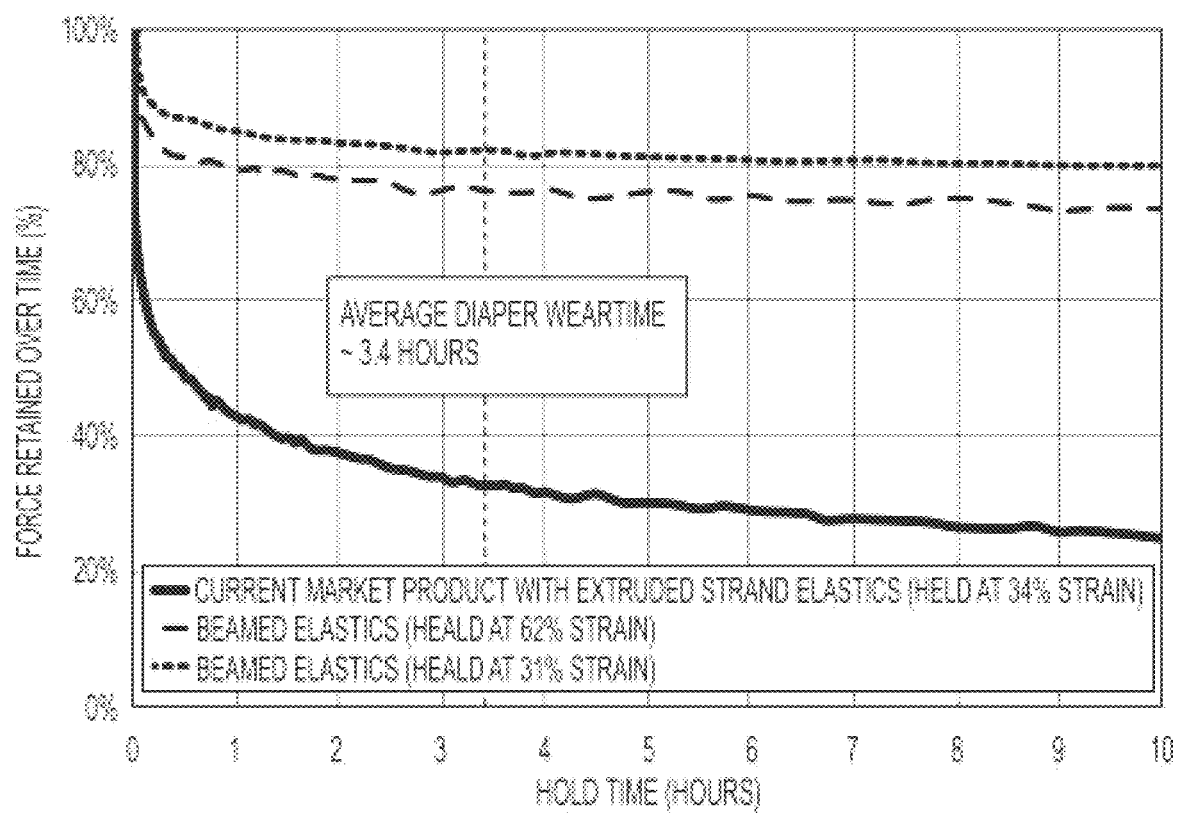

FIG. 104 is a chart showing force relaxation over time for various elastomeric laminates.

Figure 105:
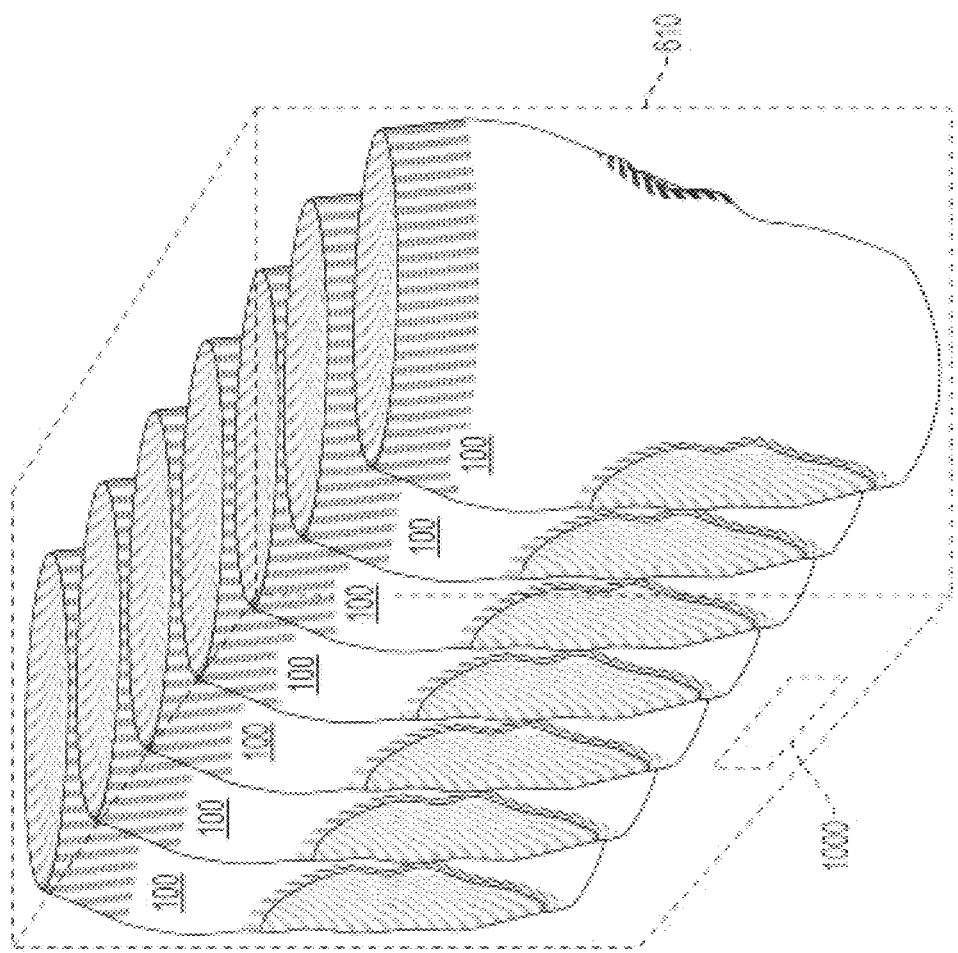

FIG. 105 illustrates packaged articles with a sizing indicia.

DETAILED DESCRIPTION OF THE INVENTION

The following term explanations may be useful in understanding the present disclosure:

"Disposable," in reference to absorbent articles, means that the absorbent articles, are generally not intended to be laundered or otherwise restored or reused as absorbent articles (i.e., they are intended to be discarded after a single use and, preferably, to be recycled, composted or otherwise discarded in an environmentally compatible manner). Disposable absorbent articles often comprise adhesive between the layers and/or elements to hold the article together (e.g., ear panels, side panels, and belts are joined to the chassis via adhesive and the layers of the ear panels, side panels, belts, and chassis are joined together using adhesive). Alternatively, heat and/or pressure bonding are used with the adhesive or in place of the adhesive. In such instances portions of the material layers may become partially melted and pressed together such that once cooled they are physically bonded together. Nonwovens (including, for example, polypropylene, polyethylene, etc.) adhesives (including, for example, styrenic block copolymers (e.g., SIS, SBS)), and absorbent gelling material (AGM 51—see FIG. 57A-C) make up more than 50%, more than 75%, and often more than 90% of the disposable absorbent article weight. And, a core comprising the AGM 51 is often held within the chassis in a manner that would cause ripping and tearing of the other layers of the chassis (e.g. topsheet, backsheet, core wrap, etc.) to remove it under normal conditions. Such disposable absorbent articles typically have an absorbent capacity of greater than about 100 mL of fluid and can have capacities of up to about 500 mL of fluid or more. Stitching (including the use of thread) and/or woven materials are typically not used to make a disposable absorbent article. If stitching or woven materials are used, they make up an extremely small percentage of the disposable absorbent article. Some landing zones of disposable absorbent articles for fasteners can comprise a woven material, but no other part of a disposable absorbent article typically comprises woven materials.

"Absorbent article" refers to devices, which absorb and contain body exudates and, more specifically, refers to devices, which are placed against or in proximity to the body of the wearer to absorb and contain the various exudates discharged from the body. Exemplary absorbent articles include diapers, training pants, pull-on pant-type diapers (i.e., a diaper having a pre-formed waist opening and leg openings such as illustrated in U.S. Pat. No. 6,120,487), refastenable diapers or pant-type diapers, incontinence briefs and undergarments, diaper holders and liners, feminine hygiene garments such as panty liners, absorbent inserts, menstrual pads and the like.

"Proximal" and "Distal" refer respectively to the location of an element relatively near to or far from the longitudinal or lateral centerline of a structure (e.g., the proximal edge of a longitudinally extending element is located nearer to the longitudinal axis than the distal edge of the same element is located relative to the same longitudinal axis).

"Body-facing" and "garment-facing" refer respectively to the relative location of an element or a surface of an element or group of elements. "Body-facing" implies the element or surface is nearer to the wearer during wear than some other element or surface. "Garment-facing" implies the element or surface is more remote from the wearer during wear than some other element or surface (i.e., element or surface is proximate to the wearer's garments that may be worn over the disposable absorbent article).

"Longitudinal" refers to a direction running substantially perpendicular from a waist edge to an opposing waist edge of the article and generally parallel to the maximum linear dimension of the article. Directions within 45 degrees of the longitudinal direction are considered to be "longitudinal."

"Lateral" refers to a direction running from a longitudinally extending side edge to an opposing longitudinally extending side edge of the article and generally at a right angle to the longitudinal direction. Directions within 45 degrees of the lateral direction are considered to be "lateral."

"Disposed" refers to an element being located in a particular place or position.

"Joined" encompasses configurations whereby an element is directly secured to another element by affixing the element directly to the other element, and configurations whereby an element is indirectly secured to another element by affixing the element to intermediate member(s), which, in turn are affixed to the other element.

"Water-permeable" and "water-impermeable" refer to the penetrability of materials in the context of the intended usage of disposable absorbent articles. Specifically, the term "water-permeable" refers to a layer or a layered structure having pores, openings, and/or interconnected void spaces that permit liquid water, urine, or synthetic urine to pass through its thickness in the absence of a forcing pressure. Conversely, the term "water-impermeable" refers to a layer or a layered structure through the thickness of which liquid water, urine, or synthetic urine cannot pass in the absence of a forcing pressure (aside from natural forces such as gravity). A layer or a layered structure that is water-impermeable according to this definition may be permeable to water vapor, i.e., may be "vapor-permeable."

"Elastic," "elastomer," or "elastomeric" refers to materials exhibiting elastic properties, which include any material that upon application of a force to its relaxed, initial length can stretch or elongate to an elongated length more than 10% greater than its initial length and will substantially recover back to about its initial length upon release of the applied force. Elastomeric materials may include elastomeric films, scrims, nonwovens, ribbons, strands and other sheet-like structures.

"Pre-strain" refers to the strain imposed on an elastic or elastomeric material prior to combining it with another element of the elastomeric laminate or the absorbent article. Pre-strain is determined by the following equation Pre-strain=((extended length of the elastic-relaxed length of the elastic)/relaxed length of the elastic)*100.

"Decitex" also known as Dtex is a measurement used in the textile industry used for measuring yarns or filaments. 1 Decitex=1 gram per 10,000 meters. In other words, if 10,000 linear meters of a yarn or filament weights 500 grams that yarn or filament would have a decitex of 500.

"Substrate" is used herein to describe a material which is primarily two-dimensional (i.e. in an XY plane) and whose thickness (in a Z direction) is relatively small (i.e. 1/10 or less) in comparison to its length (in an X direction) and width (in a Y direction). Non-limiting examples of substrates include a web, layer or layers of fibrous materials, nonwovens, films and foils such as polymeric films or metallic foils. These materials may be used alone or may comprise two or more layers laminated together. As such, a web is a substrate.

"Nonwoven" refers herein to a material made from continuous (long) filaments (fibers) and/or discontinuous (short) filaments (fibers) by processes such as spunbonding, meltblowing, carding, and the like. Nonwovens do not have a woven or knitted filament pattern.

"Machine direction" (MD) is used herein to refer to the direction of material flow through a process. In addition, relative placement and movement of material can be described as flowing in the machine direction through a process from upstream in the process to downstream in the process.

"Cross direction" (CD) is used herein to refer to a direction that is generally perpendicular to the machine direction.

"Taped diaper" (also referred to as "open diaper") refers to disposable absorbent articles having an initial front waist region and an initial back waist region that are not fastened, pre-fastened, or connected to each other as packaged, prior to being applied to the wearer. A taped diaper may be folded about the lateral centerline with the interior of one waist region in surface to surface contact with the interior of the opposing waist region without fastening or joining the waist regions together. Example taped diapers are disclosed in various suitable configurations U.S. Pat. Nos. 5,167,897, 5,360,420, 5,599,335, 5,643,588, 5,674,216, 5,702,551, 5,968,025, 6,107,537, 6,118,041, 6,153,209, 6,410,129, 6,426,444, 6,586,652, 6,627,787, 6,617,016, 6,825,393, and 6,861,571; and U.S. Patent Publication Nos. 2013/0072887 A1; 2013/0211356 A1; and 2013/0306226 A1.

"Pant" (also referred to as "training pant", "pre-closed diaper", "diaper pant", "pant diaper", and "pull-on diaper") refers herein to disposable absorbent articles having a continuous perimeter waist opening and continuous perimeter leg openings designed for infant or adult wearers. A pant can be configured with a continuous or closed waist opening and at least one continuous, closed, leg opening prior to the article being applied to the wearer. A pant can be pre-formed or pre-fastened by various techniques including, but not limited to, joining together portions of the article using any refastenable and/or permanent closure member (e.g., seams, heat bonds, pressure welds, adhesives, cohesive bonds, mechanical fasteners, etc.). A pant can be pre-formed anywhere along the circumference of the article in the waist region (e.g., side fastened or seamed, front waist fastened or seamed, rear waist fastened or seamed). Example diaper pants in various configurations are disclosed in U.S. Pat. Nos. 4,940,464; 5,092,861; 5,246,433; 5,569,234; 5,897, 545; 5,957,908; 6,120,487; 6,120,489; 7,569,039 and U.S.

Patent Publication Nos. 2003/0233082 A1; 2005/0107764 A1, 2012/0061016 A1, 2012/0061015 A1; 2013/0255861 A1; 2013/0255862 A1; 2013/0255863 A1; 2013/0255864 A1; and 2013/0255865 A1, all of which are incorporated by reference herein.

"Closed-form" means opposing waist regions are joined, as packaged, either permanently or refastenably to form a continuous waist opening and leg openings.

"Open-form" means opposing waist regions are not initially joined to form a continuous waist opening and leg openings but comprise a closure means such as a fastening system to join the waist regions to form the waist and leg openings before or during application to a wearer of the article.

"Channel," as used herein, is a region or zone in an absorbent material layer that has a substantially lower basis weight (e.g., less than 50%, less than 70%, less than 90%) than the surrounding material in the material layer. The channel may be a region in a material layer that is substantially absorbent material-free (e.g., 90% absorbent material-free, 95% absorbent material-free, or 99% absorbent material-free, or completely absorbent material-free). A channel may extend through one or more absorbent material layers. The channel generally has a lower bending modulus than the surrounding regions of the absorbent material layer, enabling the material layer to bend more easily and/or rapidly distribute more bodily exudates within the channel than in the surrounding areas of the absorbent material layer. Thus, a channel is not merely an indentation in the material layer that does not create a reduced basis weight in the material layer in the area of the channel.

Absorbent Articles

Products comprising elastomeric laminates 302 of the present disclosure may comprise absorbent articles 100 of differing structure and/or form that are generally designed and configured to manage bodily exudates such as urine, menses and/or feces, such as disposable taped diapers and pants, including baby and adult disposable absorbent articles and menstrual pads.

As shown in FIGS. 2, 9, 11, 31, 38-41, 43-47, and 55-56 the absorbent articles 100 of the present disclosure may comprise a chassis 200 comprising a topsheet 124, a backsheet 125, and an absorbent core 128 disposed at least partially between the topsheet 124 and the backsheet 125. The chassis 200 may further comprise an inner leg cuff 150 and an outer leg cuff 140 (the cuffs generally referred to as 52). Various chassis embodiments are shown in the figures, including FIGS. 7, 11, 39, 41, 43, 46, and 47.

Figure 1:
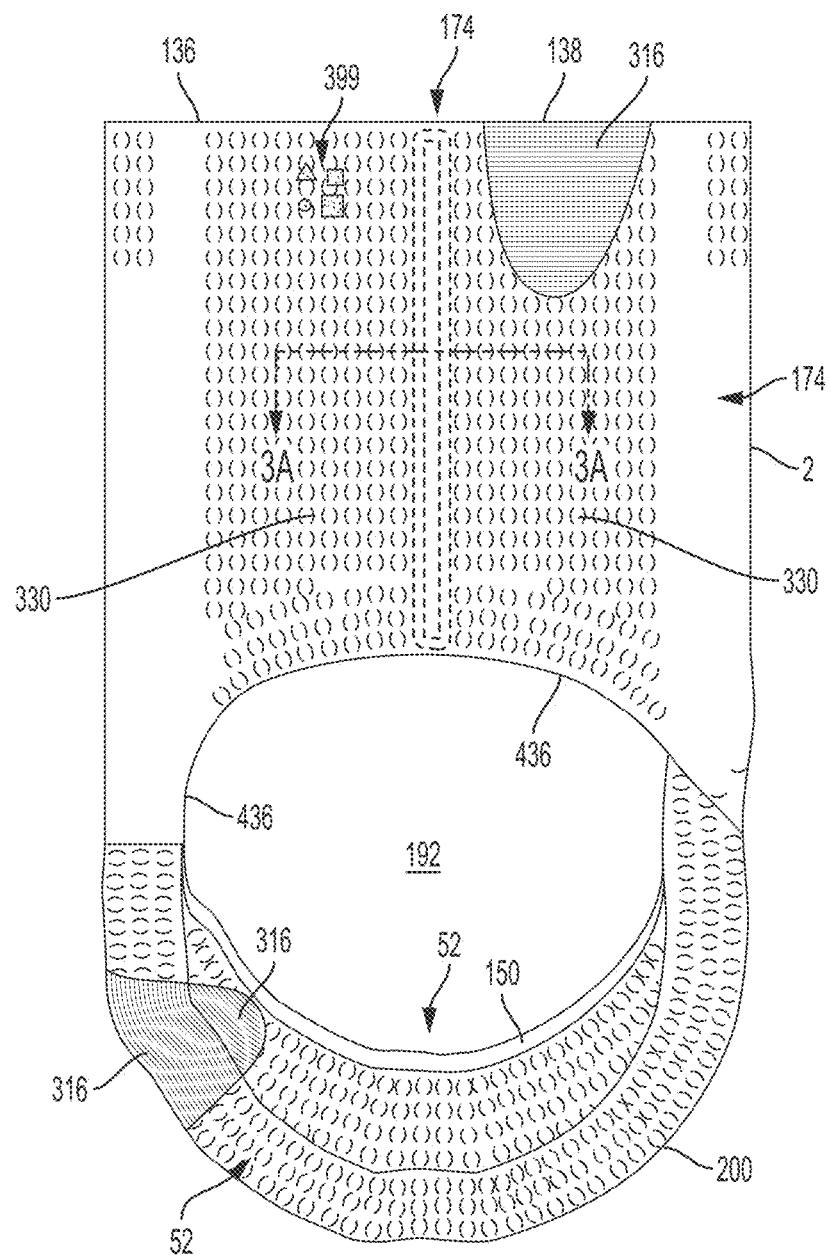
FIG. 1 is a side view of a pant comprising side panels with refastenable side seams.
Figure 2:
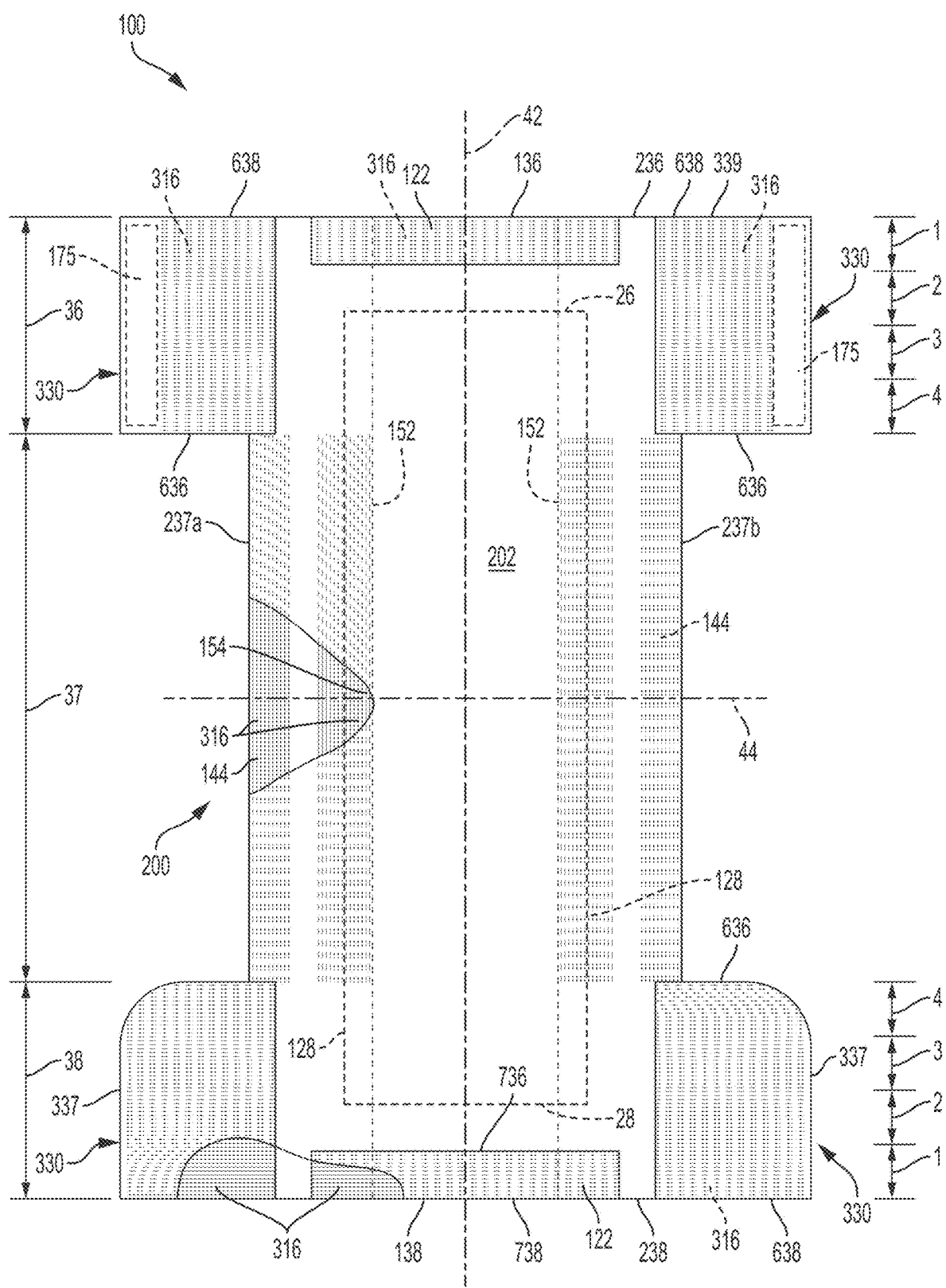
FIG. 2 is a plan view of a pant comprising side panels with refastenable seams.

FIG. 2 is a simplified plan view of the precursor structure of the pant shown in FIG. 1. Referring to FIG. 2, one end portion of an absorbent article 100 may be configured as a front waist region 36 and the longitudinally opposing end portion may be configured as a back waist region 38. An intermediate portion of the absorbent article 100 extending longitudinally between the front waist region 36 and the back waist region 38 may be configured as a crotch region 37. Although not illustrated as such, the length of each of the front waist region 36, the back waist region 38 and the crotch region 37 may be about ⅓ of the length of the absorbent article 100, for example (see, for example, FIGS. 39, 44, and 46). Alternatively, the length of each of the front waist region 36, the back waist region 38, and the crotch region 37 may have other dimensions (e.g., defined by the belt or ear panel or side panel dimensions—see for example FIGS. 2, 7, and 11). The absorbent article 100 may have a laterally extending front waist end edge 136 in the front waist region 36 and a longitudinally opposing and laterally extending back waist end edge 138 in the back waist region 38.

Referring further to FIG. 2, a chassis 200 of the absorbent article 100 may comprise a first longitudinally extending side edge 237*a* and a laterally opposing and second longitudinally extending side edge 237*b*. Both of the side edges 237 may extend longitudinally between the front waist end edge 136 and the back waist end edge 138. The chassis 200 may form a portion of the laterally extending front waist end edge 136 in the front waist region 36 and a portion of the longitudinally opposing and laterally extending back waist end edge 138 in the back waist region 38. Furthermore, the chassis 200 may comprise a chassis interior surface 202, a chassis exterior surface 204 (see FIG. 8A), a longitudinal axis 42, and a lateral axis 44. The longitudinal axis 42 may extend through a midpoint of the front waist end edge 136 and through a midpoint of the back waist end edge 138, while the lateral axis 44 may extend through a midpoint of the first side edge 237*a* and through a midpoint of the second side edge 237*b*.

Figure 11:
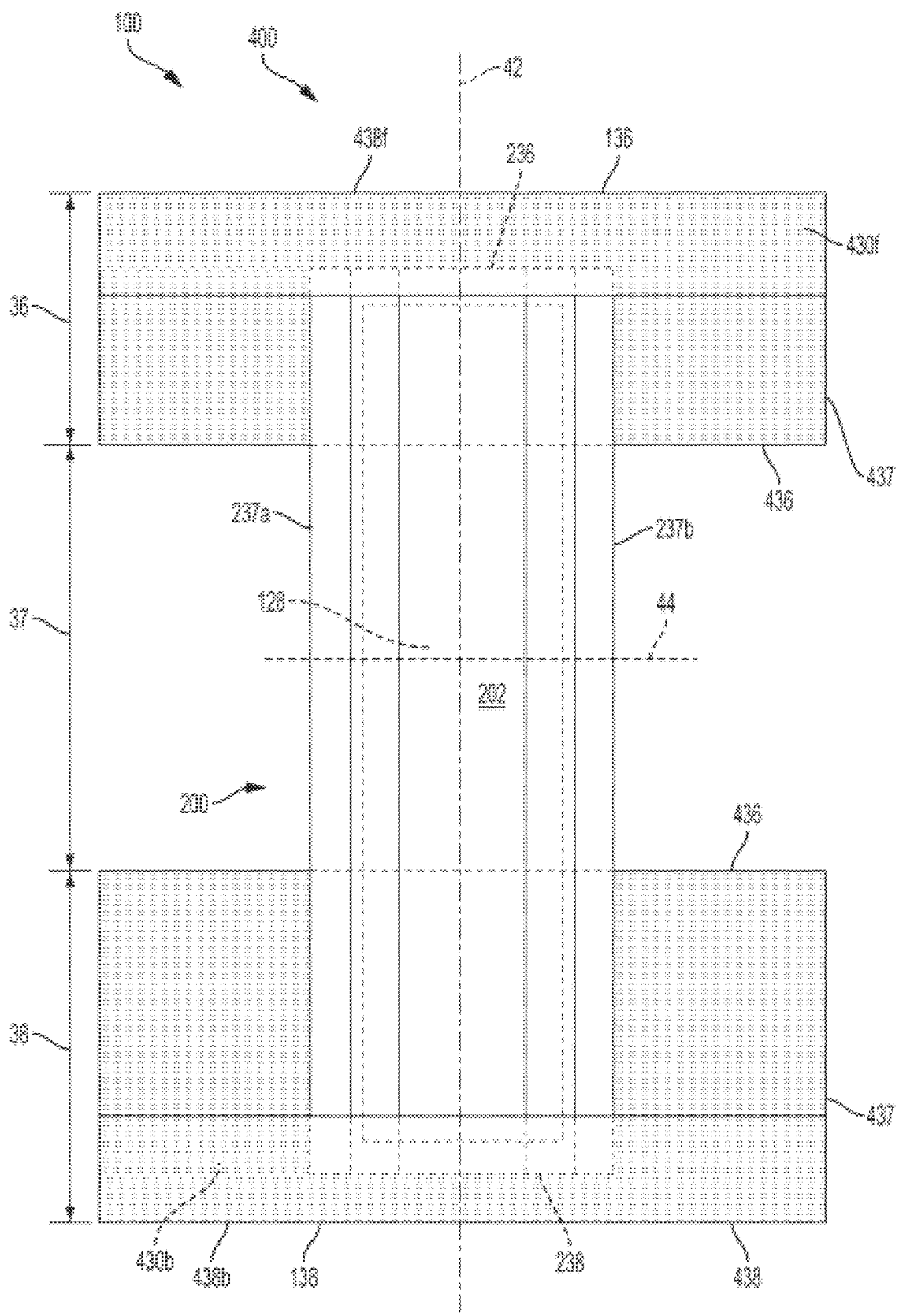
FIG. 11 is a plan view of the belt pant of FIG. 10.

Referring to FIG. 11, the chassis 200 may have a length measured along the longitudinal axis 42 that is less than the length of the absorbent article 100. Both of the side edges 237 of the chassis 200 may not extend longitudinally to one or both of the front waist end edge 136 and the back waist end edge 138. The chassis 200 may not form a portion of one or both of the laterally extending front waist end edge 136 in the front waist region 36 and the longitudinally opposing and laterally extending back waist end edge 138 in the back waist region 38. Furthermore, the chassis 200 may comprise a chassis interior surface 202, a chassis exterior surface 204, a longitudinal axis 42, and a lateral axis 44.

Figure 55:
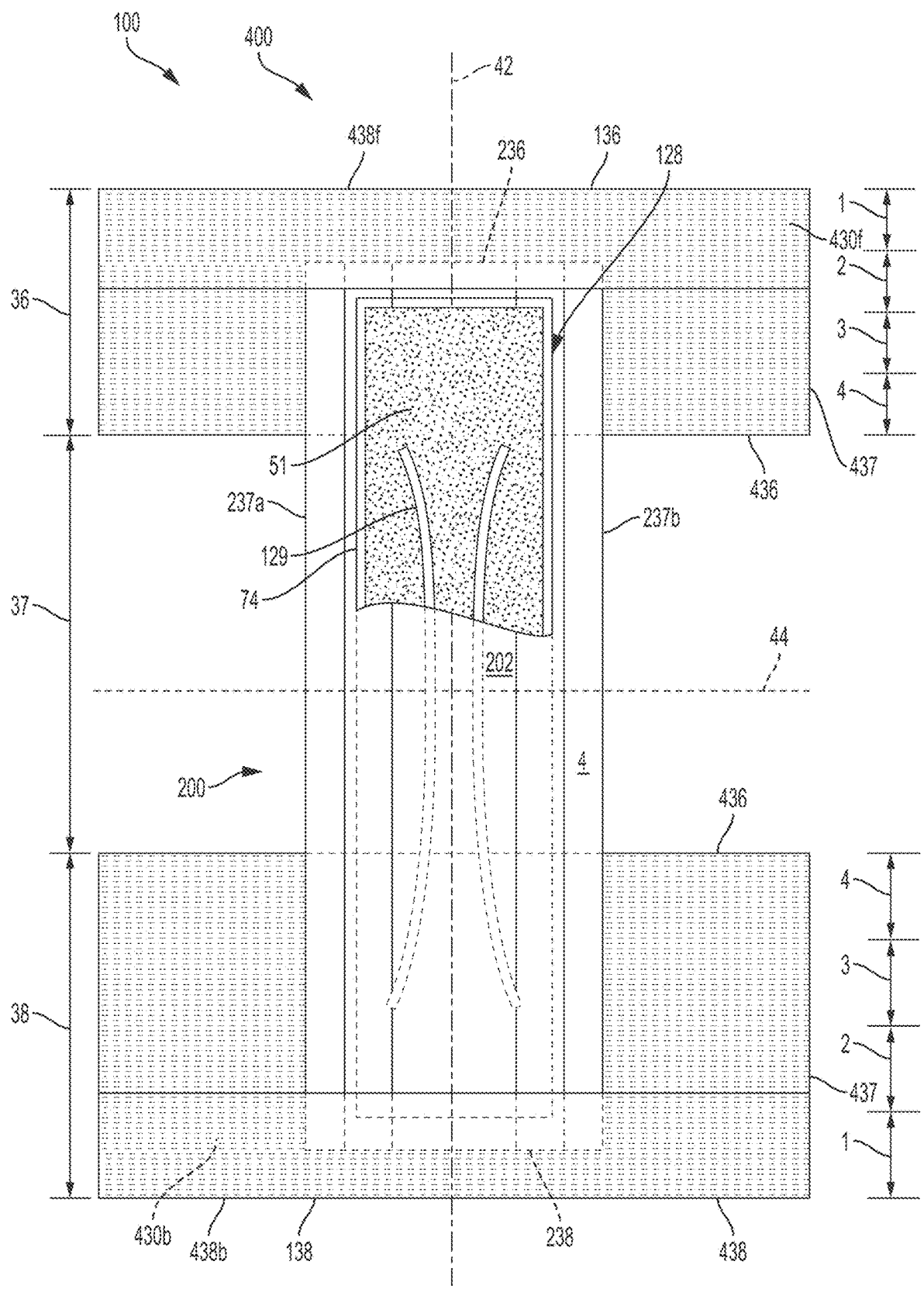
FIG. 55 is a plan view of a belt pant comprising an absorbent core comprising longitudinally extending core channels.

Referring to FIG. 55, often true for belted absorbent articles, the chassis 200 may have a length measured along the longitudinal axis 42 that is less than the length of the absorbent article 100. Both of the side edges 237 of the chassis 200 may not extend longitudinally to one or both of the front waist end edge 136 and the back waist end edge 138. The chassis 200 may not form a portion of one or both of the laterally extending front waist end edge 136 in the front waist region 36 and the longitudinally opposing and laterally extending back waist end edge 138 in the back waist region 38.

Figure 57A:
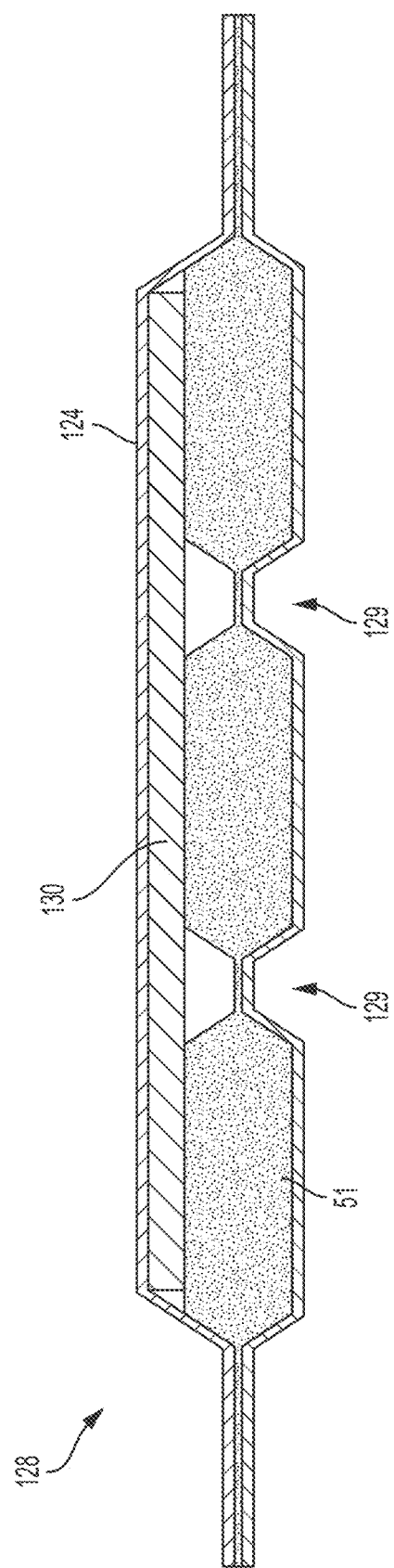
FIG. 57A is a cross section view of the absorbent core comprising an acquisition layer 130 and a storage layer comprising core channels.
Figure 57B:
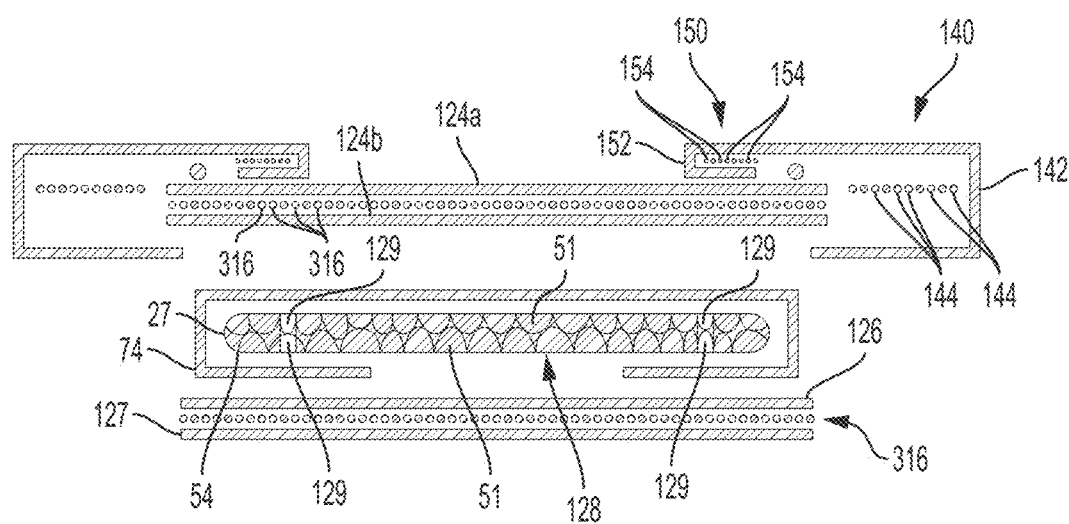
FIG. 57B is a cross section view of the pant of FIG. 56 taken along the transverse axis, illustrating the elasticized topsheet (showing a plurality of elastics 316 oriented parallel with the longitudinal axis 42) and the elasticized backsheet (showing a plurality of elastics 316 oriented parallel with the longitudinal axis 42).
Figure 57C:
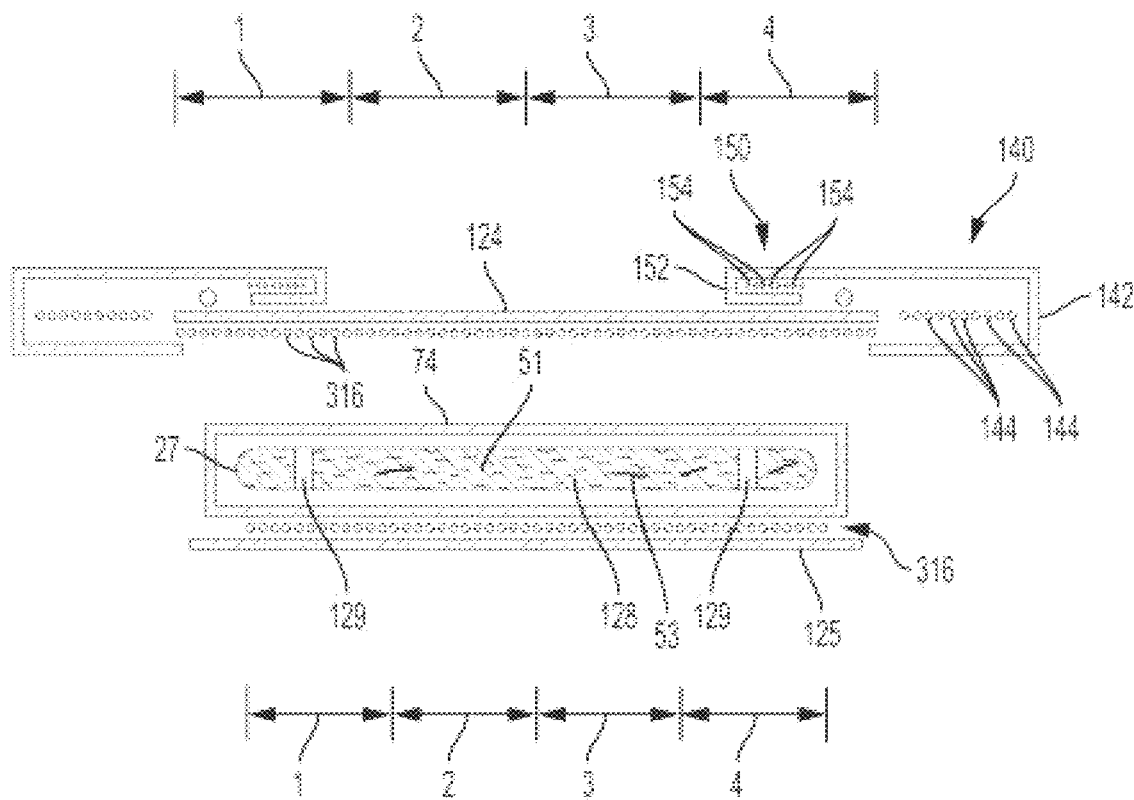
FIG. 57C is a cross section view of an alternate embodiment of the pant of FIG. 56 taken along the transverse axis, wherein the core wrap completely surrounds the core 128, wherein a plurality of elastics 316 are oriented parallel with the longitudinal axis 42 between the core wrap 74 and the backsheet 125 and oriented parallel with the longitudinal axis 42 between the core wrap 74 and the topsheet 124, and wherein the core 128 comprises AGM 51 mixed with pulp 53.
Figure 57D:
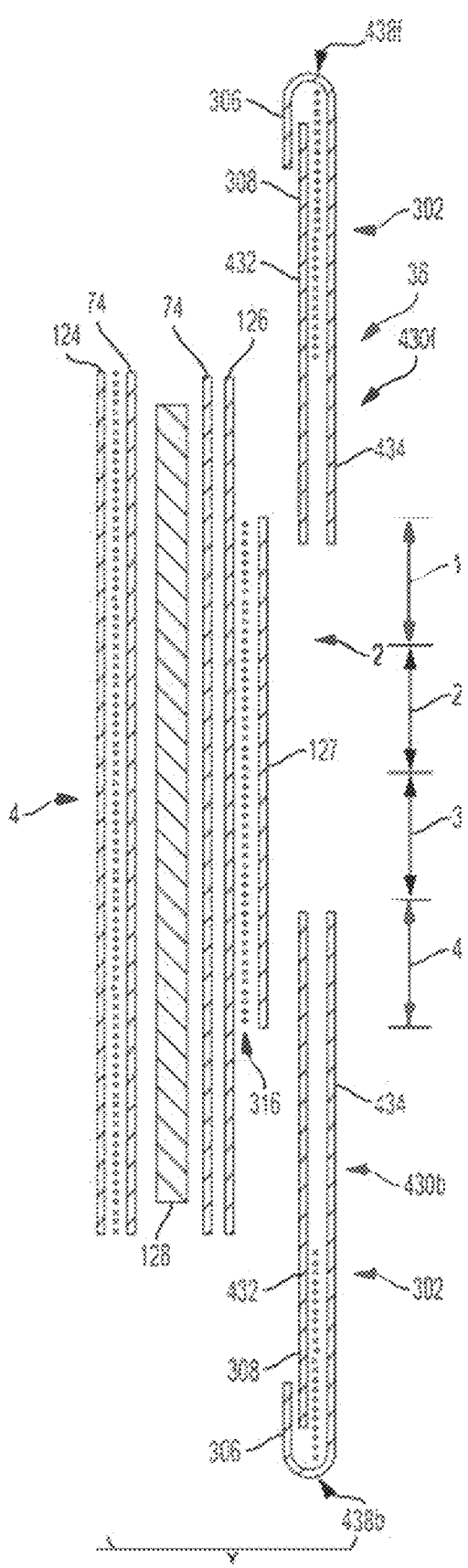
FIG. 57D is a cross section view of an alternate embodiment of the pant of FIG. 55 taken along the longitudinal axis 42, showing longitudinally opposing discrete belts, wherein elastics 316 are oriented parallel to the lateral axis 44 between the core wrap 74 and the topsheet 124 and oriented parallel to the lateral axis 44 between the backsheet film 126 and the backsheet nonwoven 127.

Referring to FIG. 57B, the chassis 200 may comprise elastics 316 oriented parallel to the longitudinal axis 42 between the backsheet nonwoven 127 and backsheet film 126. FIG. 57C shows an alternate embodiment than FIG. 57B, where the chassis 200 has elastics 316 oriented parallel to the longitudinal axis 42 between the core wrap 74 and the backsheet 125. Still further, FIG. 57D shows another alternative embodiment where the chassis 200 comprises elastics 316 oriented parallel with the lateral axis 44 between the backsheet film 126 and the backsheet nonwoven 127. FIG. 57B also shows elastics 316 oriented parallel with the longitudinal axis 42 between a first topsheet layer 124*a* and a second topsheet layer 124*b*, whereas FIG. 57C shows an alternate embodiment where the elastics 316 are between the topsheet 124 and the core wrap 74. Still further, FIG. 57D shows elastics 316 oriented parallel with the lateral axis 44 between the topsheet 124 and the core wrap 74.

Figure 57E:
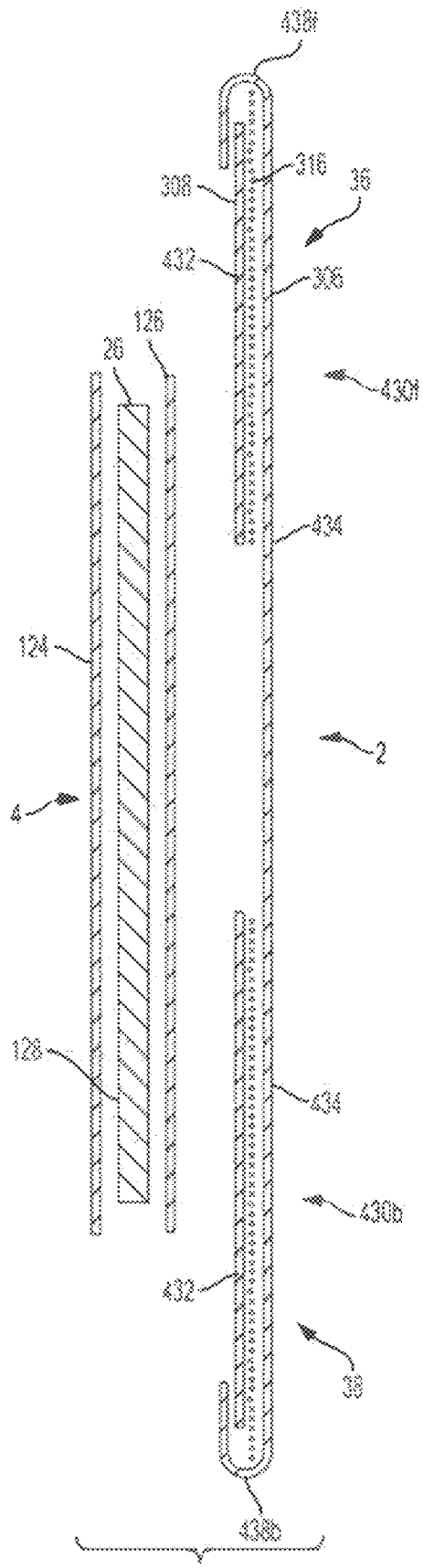
FIG. 57E is a cross section view of an alternate embodiment of the belt pant of FIG. 55 taken along the longitudinal axis 42, showing longitudinally opposing discrete inner belt layers 432 and a common outer belt layer 434, and showing elastic strands 316 extending continuously across the core.
Figure 57F:
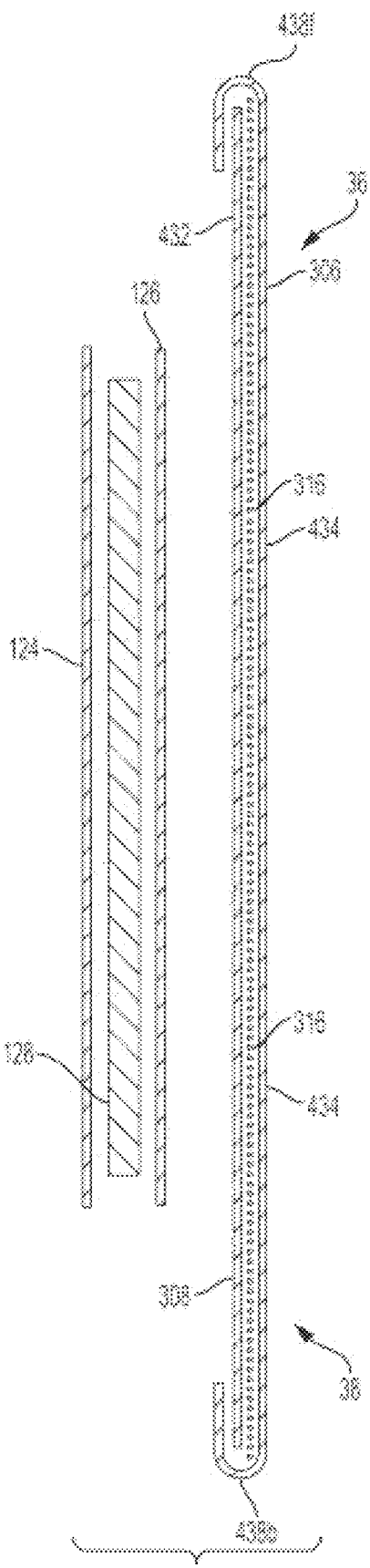
FIG. 57F is a cross section view of an alternate embodiment of the pant of FIG. 55 taken along the longitudinal axis 42, showing a longitudinally continuous elastomeric laminate comprising longitudinally opposing belt portions and an elasticized crotch portion between the belt portions, wherein elastics 316 are oriented parallel to the lateral axis 44 between inner belt layer 432 and outer belt layer 434 and wherein the elastics extend laterally across the core.
Figure 57G:
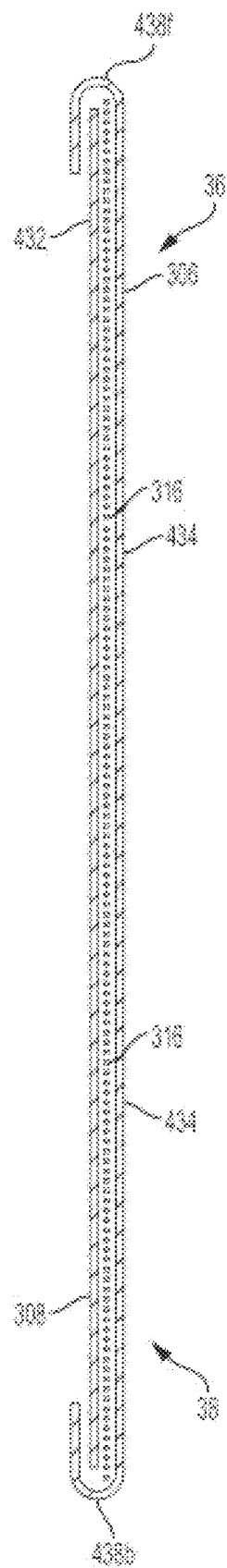
FIG. 57G is a cross section view of an alternate embodiment of the belt pant of FIG. 55 taken along the longitudinal axis 42, forming a wearable article having a longitudinally continuous elastomeric laminate comprising longitudinally opposing belt portions and an elasticized crotch portion between the belt portions, wherein elastics 316 are oriented parallel to the lateral axis 44 between inner belt layer 432 and outer belt layer 434.
Figure 58:
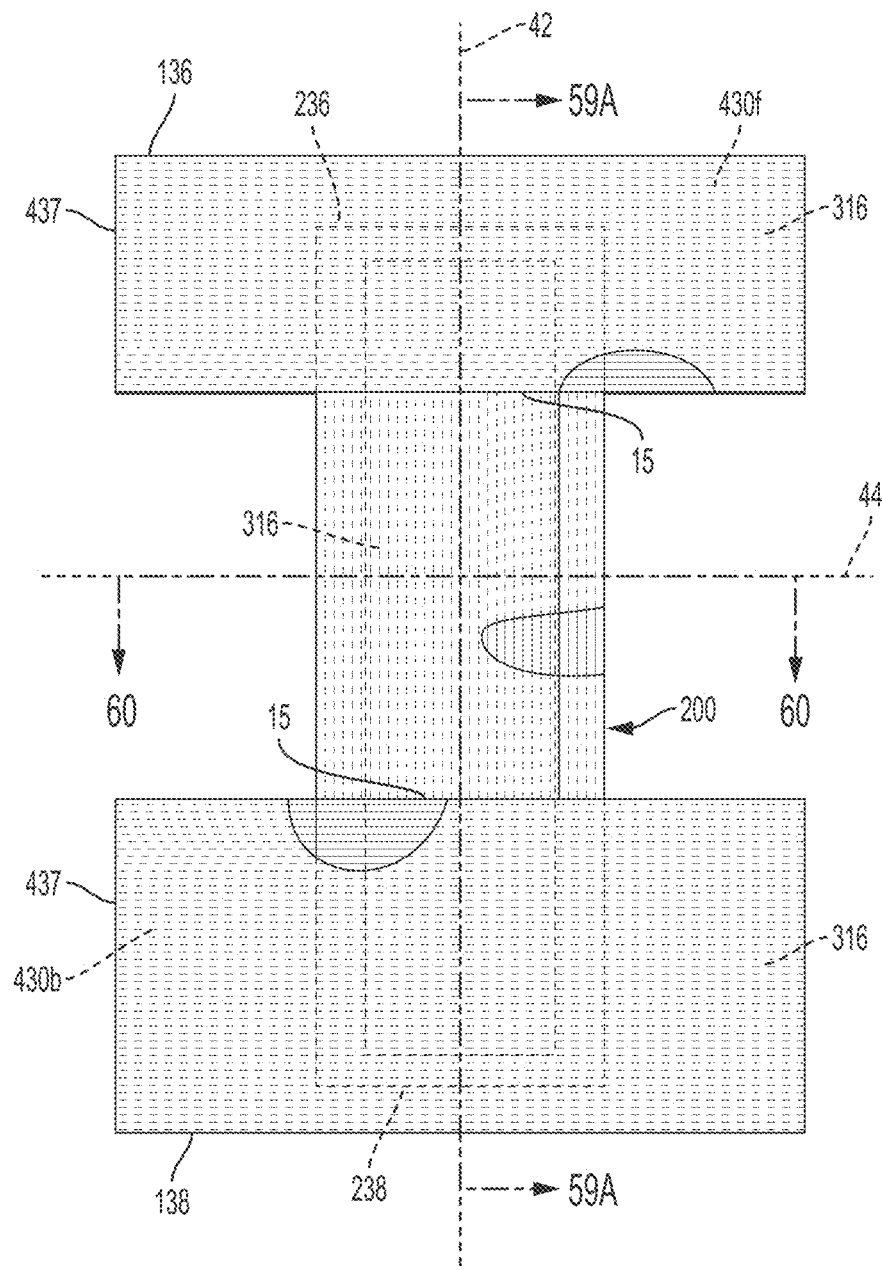
FIG. 58 is a plan view of a pant comprising transversely extending elastics 316 in the front and back belts 430F and B and longitudinally extending elastics 316 in the chassis 200 extending to the belt proximal belt edges.
Figure 59A:
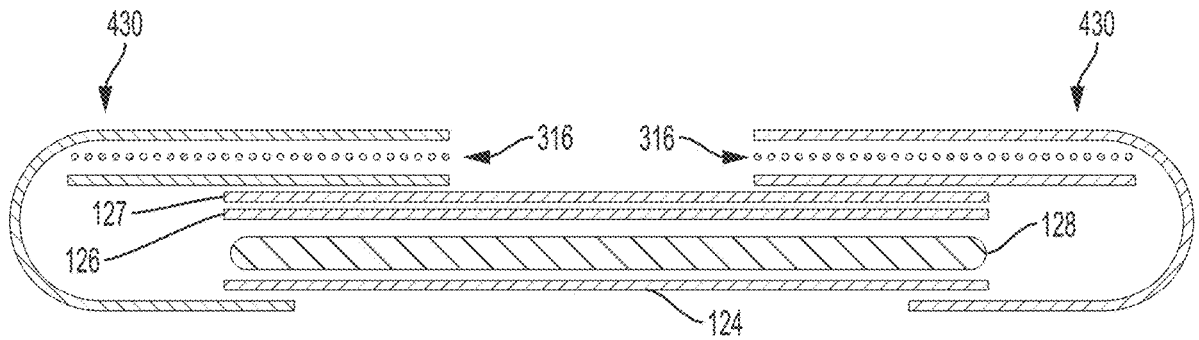
FIG. 59A is cross-sectional view of the pant of FIG. 58 along line 59-59.

Particularly regarding belts 430, as illustrated in FIG. 57E, the inner belt layer 432 and/or the outer belt layer 434 of the first and second elastomeric belts 430 may be formed by a common belt layer as shown in FIG. 57E. When the first and second elastomeric belts 430 have a common belt layer, the common belt layer may extend from a first waist edge in a first waist region to a longitudinally opposing second waist edge in a second waist region, i.e. front waist edge 136 to back waist edge 138. Referring to FIGS. 57F and 57G, the plurality of elastics 316 oriented parallel to the lateral axis 44 may extend continuously from a first waist edge in a first waist region to a longitudinally opposing second waist edge in a second waist region, i.e. front waist edge 136 to back waist edge 138. FIG. 57G shows an auxiliary article or a wearable article that may be used in conjunction with an absorbent insert, pad, or liner—it does not comprise a chassis 200 nor does it comprise an absorbent core 128. It is envisioned that the article shown in FIG. 57G can be washed and/or dried several times before being discarded.

Still regarding an elasticized chassis 200, FIGS. 81, 82, 83A and 83B, show an elasticized chassis 200, where elastics 316 are disposed between layers of the wings 120. FIG. 81 shows elastics 316 oriented at about 45 degrees relative to the longitudinal axis 42 and the lateral axis 44. FIG. 82 is an alternate embodiment of FIG. 81, showing the wing elastics 316 oriented parallel with the longitudinal axis 42. FIG. 83A shows two layers of elastics 316 in the wings 120, both oriented parallel with the longitudinal axis 42, the lower layer of elastics 316 being spaced with gaps between groupings, and separated by a nonwoven wing layer 121. FIG. 83B is an alternate embodiment of FIG. 83A, where there is only one layer of elastics and no nonwoven wing layer 121. FIG. 83B also shows elastics 316 oriented parallel to the longitudinal axis 42 between the topsheet 124 and secondary topsheet 124' (which may alternatively be oriented parallel to the lateral axis 44—not shown), and elastics 316 oriented parallel to the longitudinal axis 42 between the backsheet film 126 and the backsheet nonwoven 127 (which may alternatively be oriented parallel to the lateral axis 44—not shown).

A portion or the entirety of the absorbent article 100 may be made to be laterally elastically extensible. The extensibility of the absorbent article 100 may be desirable in order to allow the absorbent article 100 to conform to a body of a wearer during movement by the wearer. The extensibility may also be desirable, for example, in order to allow the caregiver to extend the front waist region 36, the back waist region 38, the crotch region 37, and/or the chassis 200 to provide additional body coverage for wearers of differing size, i.e., to tailor the fit of the absorbent article 100 to the individual wearer and to aide in ease of application. Such extension may provide the absorbent article 100 with a generally hourglass shape, so long as the crotch region 37 is extended to a relatively lesser degree than the waist regions 36 and/or 38. This extension may also impart a tailored appearance to the absorbent article 100 during use.

Figure 46:
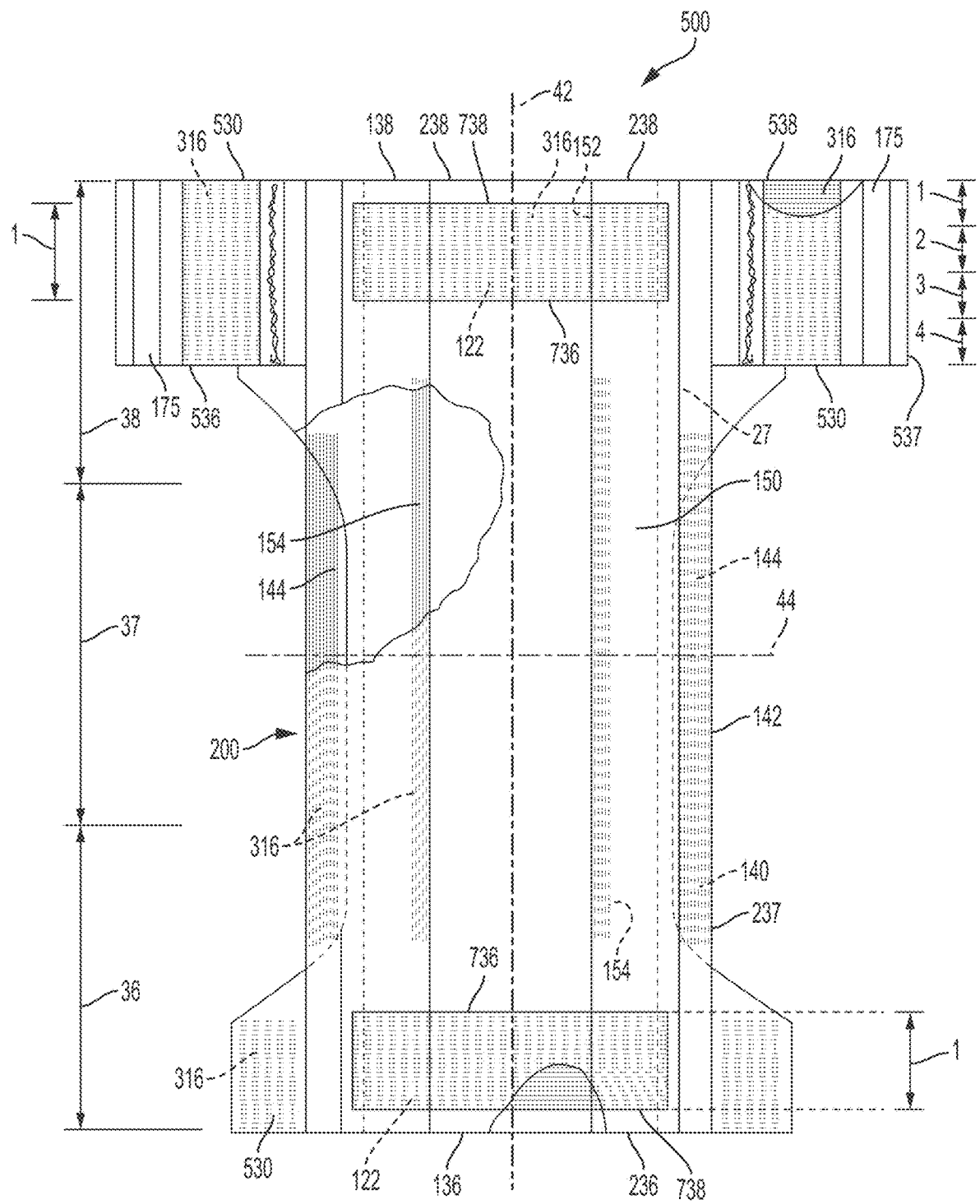
FIG. 46 is a plan view of a taped diaper comprising a pair of discrete elastomeric ear panels and a pair of non-elastomeric ear panels and a shaped chassis.
Figure 47:
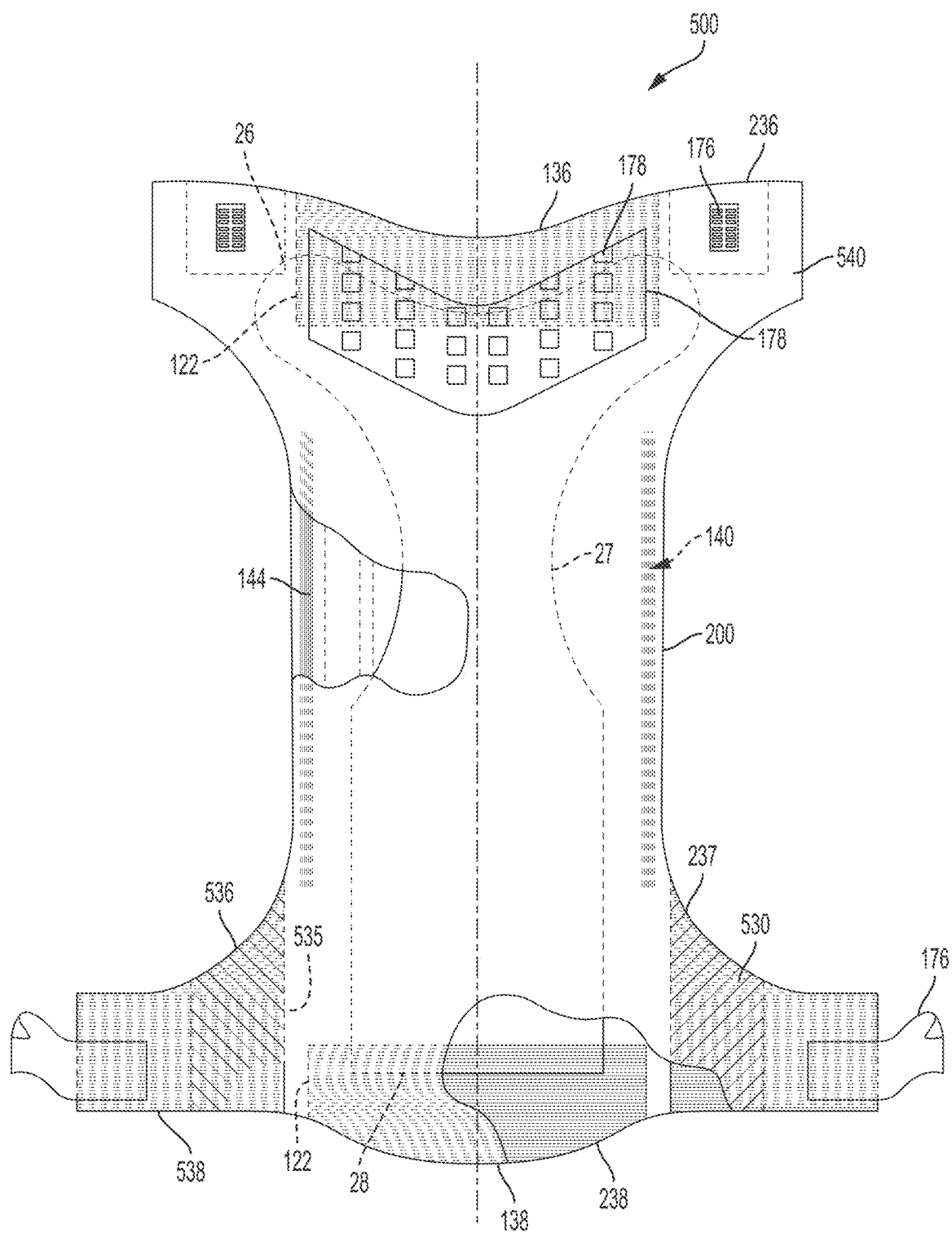
FIG. 47 is a plan view of a taped diaper comprising a pair of integral elastomeric ear panels in the back waist region and a pair of integral non-elastomeric ear panels in the front waist region.
Figure 48:
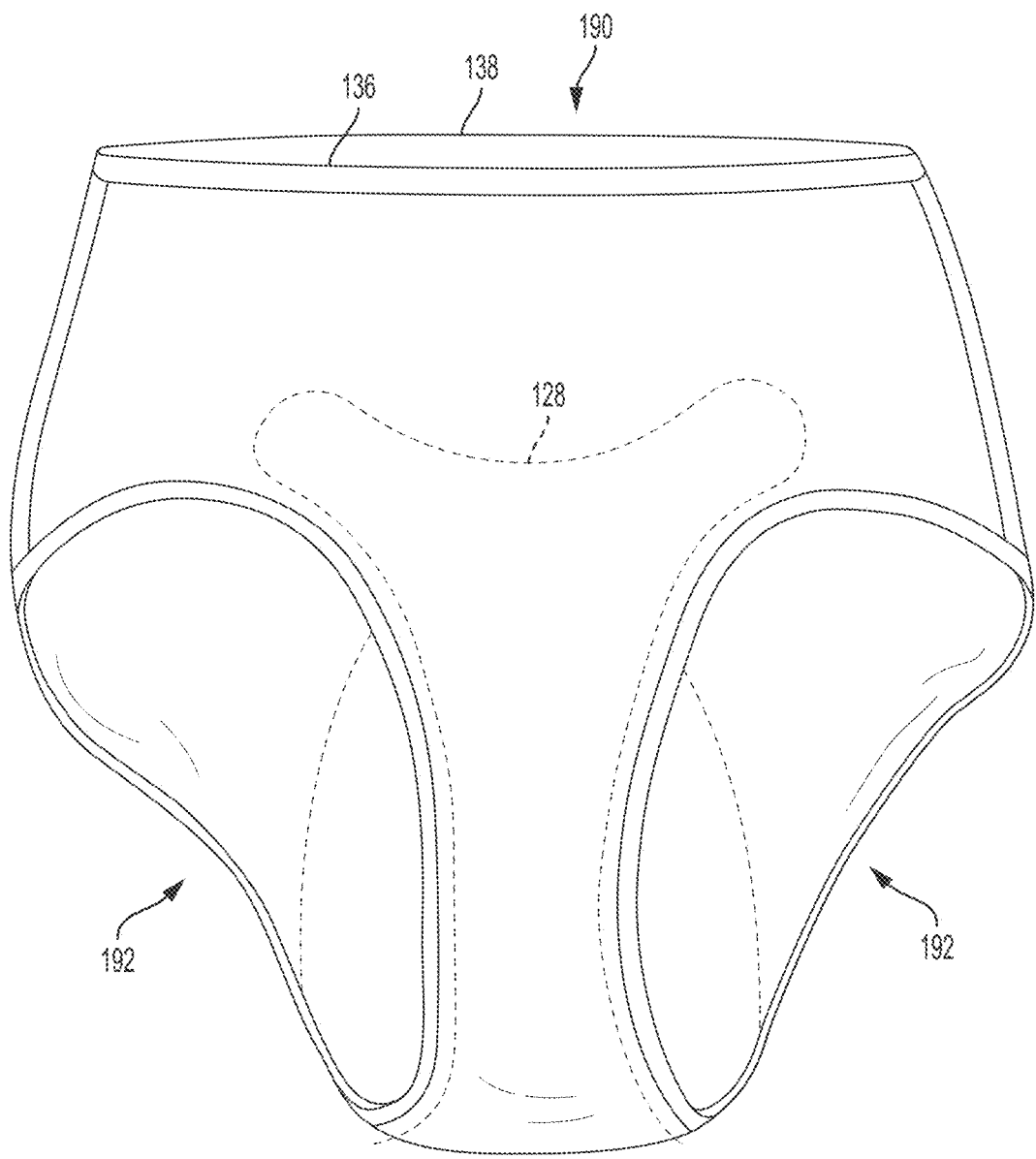
FIG. 48 is a perspective front view of a pant-style absorbent article.

The chassis 200 may be substantially rectangular and may have discrete side panels 330, extensible ear panels 530 and/or non-extensible ear panels 540 joined to the chassis 200 at or adjacent the chassis side edges 237 in one or both of the front waist region 36 and back waist region 38. As shown in FIGS. 1, 2, 10, 19, 32, 33, 38, 42 and 47, the texture of portions of one or both of the surfaces of the side panels 330, extensible ear panels 530, belts 430 and/or non-extensible ear panels 540 may be substantially the same visibly as the texture of one or both of the surfaces of one or more of the center chassis 200, inner leg cuff 150, the outer leg cuff 140, backsheet 125, topsheet 124, and waistband 122. Portions of one or more of the chassis side edges 237, the chassis front end edge 236 and the chassis back end edge 238 may be arcuate or curved either convexly or concavely as shown in FIG. 47. When the chassis 200 is non-rectangular, shaped, the chassis 200 may comprise integral side panels 330, integral extensible ear panels 530, integral belts 430 or integral non-extensible ear panels 540 formed by one or more of the outer cover nonwoven, backsheet film, leg cuff material, topsheet or core wrap disposed in one or both of the front and back waist regions (see, for example, FIG. 7). Alternatively, the chassis 200 may comprise discrete side panels 330, discrete extensible ear panels 530 discrete non-extensible ear panels 540, or discrete belts 430 (see FIGS. 2, 11, 36, 38-40, 44-46, etc.). The chassis may be shaped or non-rectangular, in one waist region and substantially rectangular in the opposing waist region. Alternatively, the chassis may be substantially rectangular in one or both of the waist regions and non-rectangular in the crotch region.

Figure 66A:
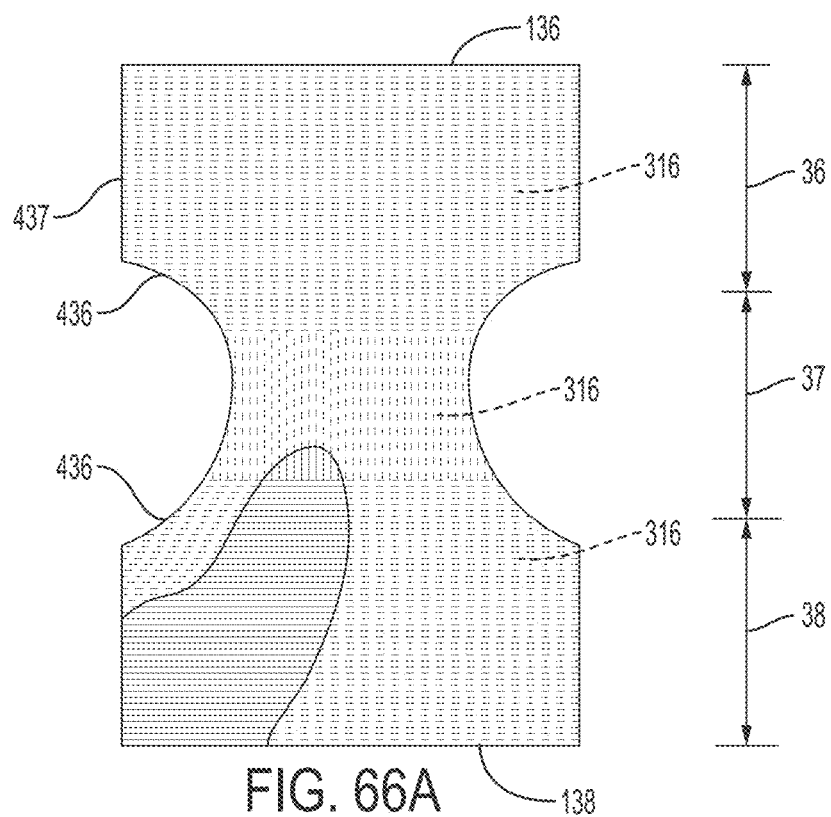
FIG. 66A is a plan view of a pant comprising transversely extending elastics 316 in the front and back waist regions 36 and 38 and longitudinally extending elastics 316 in the crotch region 37, which do not overlap with the transversely extending elastics 316 in the front and back waist regions.
Figure 66B:
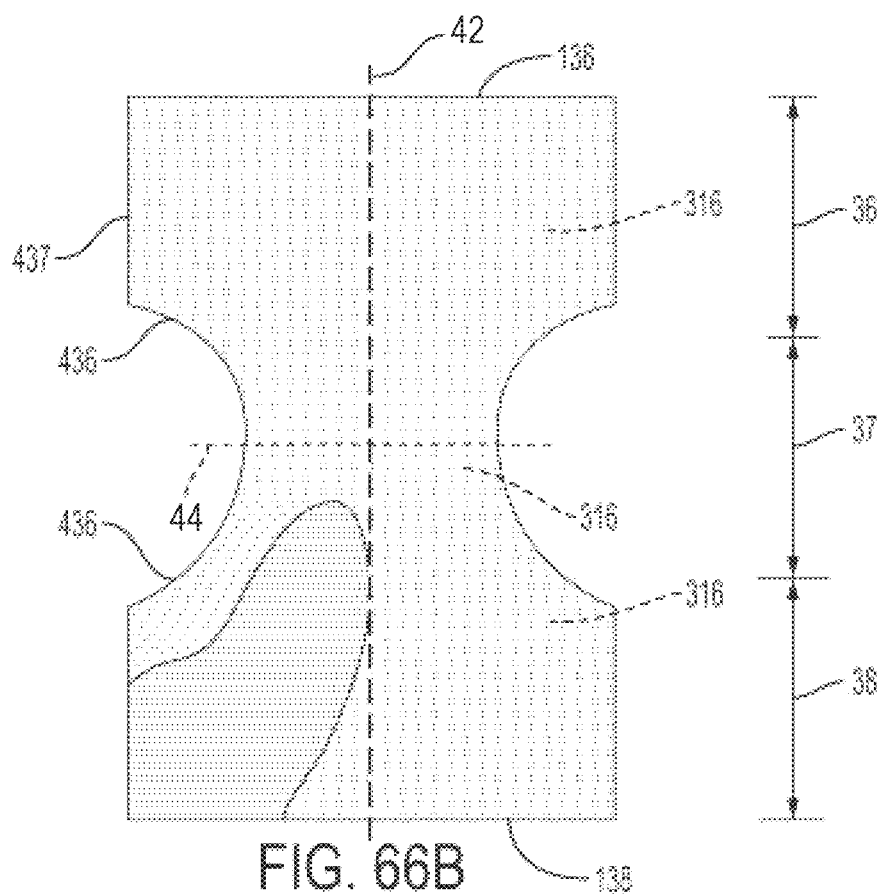
FIG. 66B is a plan view of a pant comprising transversely extending elastics 316 in the front and back waist regions 36 and 38 and the crotch region 37.
Figure 66C:
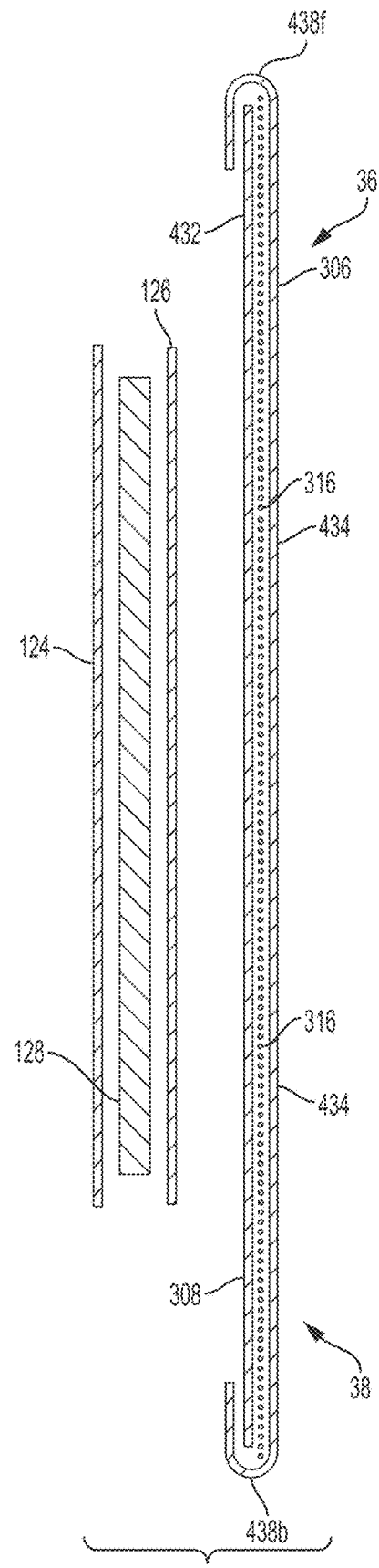
FIG. 66C is a cross sectional view of the pant of FIG. 66B along the longitudinal axis 42 including a chassis 200 comprising a topsheet 124, backsheet film 126 and an absorbent core 128 disposed between the topsheet 124 and backsheet film 126.
Figure 66D:
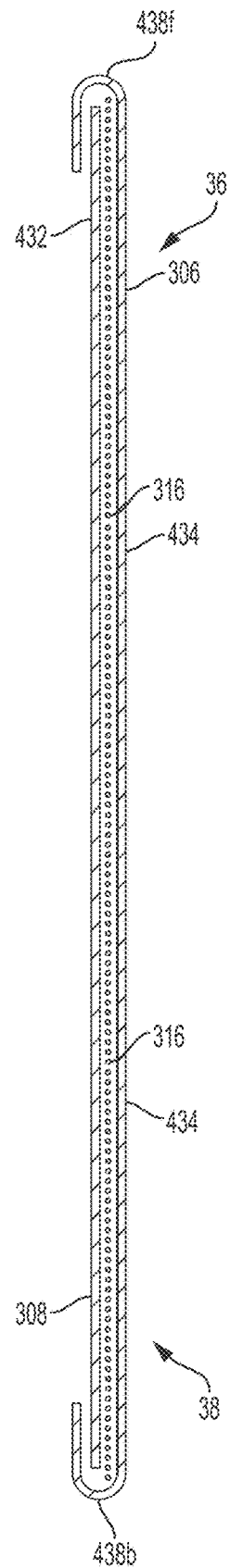
FIG. 66D is a cross sectional view of the pant of FIG. 66B along the longitudinal axis 42 forming a wearable article without a chassis 200 joined thereto.

As shown in FIG. 66B, an absorbent article of the present disclosure may comprise a plurality of laterally extending elastic elements wherein the elastic elements are present in a first waist region, the crotch region and the opposing second waist region and wherein the maximum displacement between any adjacently disposed pair of laterally extending elastics measured parallel to the longitudinal axis may be less than 75 mm, less than 50 mm, less than 25 mm, less than 10 mm, less than 5 mm, alternatively less than 4 mm and may be less than 3 mm.

A wearable article of the present disclosure may comprise one or more elastomeric laminates 302 having a plurality of laterally extending elastic elements wherein the one or more elastomeric laminates 302 may be present in a first waist region, the crotch region 37 and/or in the opposing second waist region and wherein the elastomeric laminate 302 disposed in one or both of the first and second waist regions may comprise a first plurality of elastics 316 having one or more of a higher Average-Dtex, higher Average-Pre-Strain and smaller Average-Strand-Spacing than a second plurality of elastics 316 of the elastomeric laminate 302 disposed in the crotch region 37. Such a wearable article may comprise one or more elastomeric laminates 302 having a first plurality of elastics 316, the first plurality of elastics 316 of the elastomeric laminate 302 comprising from about 100 to about 1500 elastic strands with an Average-Strand-Spacing from about 0.25 mm to about 4 mm, a Average-Dtex from about 10 to about 500, an Average-Pre-Strain from about 50% to about 400% and a first substrate 306 and/or second substrate 308 wherein one or both of the first and second substrate have a basis weight from about 6 grams per square meter to about 30 grams per square meter.

An absorbent article of the present disclosure may have an elastomeric laminate 302 forming at least a portion of one or more of a belt 430, side panel 330, ear panel 530, chassis 200, topsheet 124 and backsheet 125. The elastomeric laminate 302 may comprise a plurality of elastics 316 having a specific Average-Dtex, nonwoven type, nonwoven basis weight, Average-Strand-Spacing and Average-Pre-Strain and the article further comprising an inner leg cuff 150 and/or an outer leg cuff 140 comprising an elastomeric laminate 302 having one or more identical or substantially identical laminate elements, e.g. Average-Dtex, nonwoven type, nonwoven basis weight, Average-Strand-Spacing and Average-Pre-Strain as one or more of a belt 430, side panel 630, elastomeric ear 530, chassis 200, topsheet 124 and backsheet 125.

When the elastomeric laminate 302 forms at least a portion of one or more of the group of article components consisting of a belt 430, a side panel 330, a chassis 200, a topsheet 124, a backsheet 125, and an ear panel 530 and comprises a first plurality of elastics 316, the first plurality of elastics 316 of the elastomeric laminate 302 may comprise from about 40 to about 1000 elastic strands with an Average-Strand-Spacing from about 0.25 mm to about 4 mm, an Average-Dtex from about 10 to about 500, an Average-Pre-Strain from about 50% to about 400% and a first substrate layer 306 and/or second substrate layer 308 wherein one or both of the first and second substrate layers have a basis weight from about 6 grams per square meter to about 30 grams per square meter.

It is also to be appreciated that one or more of the absorbent article components including a belt 430, side panel 330, ear panel 530, waistband 122, chassis 200, topsheet 124 and backsheet 125 may comprise an elastomeric laminate 302 formed from multiple beams of elastic. For example, one beam may form a first portion of one or more absorbent article components including a belt 430, side panel 330, ear panel 530, waistband 122, chassis 200, topsheet 124 and backsheet 125, and a second beam may form a second portion of one or more of an absorbent article component including a belt 430, side panel 330, ear panel 530, chassis 200, topsheet 124 and backsheet 125 wherein the separate beams may comprise a different number of elastics 316, the beams may have elastics having different Average-Dtex, the elastics 316 of the two beams may be disposed at different Average-Strand-Spacing and/or the separate beams may deliver elastics 316 having different Average-Pre-Strain and/or the different beams may deliver elastics having different orientations in the product, e.g. liner, arcuate, angled, etc. The resultant portions of belt 430, side panel 630, elastomeric ear 530, chassis 200, topsheet 124 and/or backsheet 125 created from such a multi-beam approach may have different texture, garment-like appearance, breathability, Section-Modulus and/or different force.

Alternatively, the elastomeric laminate 302 comprising a first plurality of elastics 316 forming one or more of a belt 430, side panel 330, elastomeric ear 530, chassis 200, topsheet 124 and/or backsheet 125 may comprise from about 50 to about 825 elastic strands. In another embodiment, the first plurality of elastics 316 or the elastomeric laminate 302 may comprise from about 100 to about 650 elastic strands. In yet another embodiment, the first plurality of elastics 316 of the elastomeric laminate 302 may comprise from about 150 to about 475 elastic strands.

In certain embodiments, the elastomeric laminate 302 comprising a first plurality of elastics 316 forming one or more of a belt 430, side panel 330, elastomeric ear 530, chassis 200, topsheet 124 and/or backsheet 125 may have an Average-Strand-Spacing from about 0.5 mm to about 3.5 mm. In alternative embodiments, the first plurality of elastics of the elastomeric laminate 302 may have an Average-Strand-Spacing from about 0.75 mm to about 2.5 mm.

In one embodiment, the elastomeric laminate 302 forming one or more of a belt 430, side panel 330, elastomeric ear 530, chassis 200, topsheet 124 and/or backsheet 125 may have an Average-Dtex of the first plurality of elastics 316 from about 30 to about 400. Alternatively, the elastomeric laminate 302 may have an Average-Dtex of the first plurality of elastics 316 from about 50 to about 250.

In some embodiments of the elastomeric laminate 302 forming one or more of a belt 430, side panel 330, elastomeric ear 530, chassis 200, topsheet 124 and/or backsheet 125 may comprise elastics 316 having an Average-Pre-Strain which may be from about 75% to about 300%. Alternatively, the elastomeric laminate 302 may comprise elastics 316 with an Average-Pre-Strain from about 100% to about 250%.

When the elastomeric laminate 302 forms at least a portion of one or more of the group of article components consisting of a waistband 122, waistcap 123, inner leg cuff 150, outer leg cuff 140 and a transverse barrier 165 and comprises a first plurality of elastics 316, the first plurality of elastics 316 may comprise from about 10 to about 400 elastic strands with an Average-Strand-Spacing from about 0.25 mm to about 4 mm, a Average-Dtex from about 10 to about 500, an Average-Pre-Strain from about 50% to about 400% and a first substrate layer 306 and/or second substrate layer 308 each of the first and second substrate layers having a basis weight from about 6 grams per square meter to about 30 grams per square meter.

It is also to be appreciated that one or more of a waistband 122, waistcap 123, inner leg cuff 150, outer leg cuff 140 and/or a transverse barrier 165 may be formed from multiple beams of elastic, for example one beam may form a first portion of one or more of a waistband 122, waistcap 123, inner leg cuff 150, outer leg cuff 140 and/or a transverse barrier 165 and a second beam may form a second portion of one or more of a waistband 122, waistcap 123, inner leg cuff 150, outer leg cuff 140 and/or a transverse barrier 165 wherein the separate beams may comprise a different number of elastics, the beams may have elastics having different decitex, the elastics of the two beams may be disposed at different spacing and/or the separate beams may deliver elastics having different pre-strain and/or the different beams may deliver elastics having different orientations in the product, e.g. liner, arcuate, angled, etc. The resultant portions of the waistband 122, waistcap 123, inner leg cuff 150, outer leg cuff 140 and/or transverse barrier 165 created from such a multi-beam approach may have different texture, garment-like appearance, Section-Modulus and/or different force.

Alternatively, the elastomeric laminate 302 comprising a first plurality of elastics 316 forming one or more of a waistband 122, waistcap 123, inner leg cuff 150, outer leg cuff 140 and/or a transverse barrier 165 may comprise from about 15 to about 300 elastic strands. In another embodiment, the first plurality of elastics 316 of the elastomeric laminate 302 may comprise from about 20 to about 225 elastic strands. In yet another embodiment, the first plurality of elastics 316 or the elastomeric laminate 302 may comprise from about 25 to about 150 elastic strands.

In certain embodiments, the elastomeric laminate 302 comprising a first plurality of elastics 316 forming one or more of a waistband 122, waistcap 123, inner leg cuff 150, outer leg cuff 140 and/or a transverse barrier 165 may have an Average-Strand-Spacing from about 0.5 mm to about 3.0 mm. In alternative embodiments, the first plurality of elastics 316 or the elastomeric laminate 302 may have an Average-Strand-Spacing from about 0.75 mm to about 2.5 mm.

In one embodiment, the elastomeric laminate 302 forming one or more of a waistband 122, waistcap 123, inner leg cuff 150, outer leg cuff 140 and/or a transverse barrier 165 may have an Average-Dtex of the first plurality of elastics 316 from about 30 to about 400. Alternatively, the elastomeric laminate 302 may have an Average-Dtex of the first plurality of elastics 316 from about 50 to about 250.

In some embodiments of the elastomeric laminate 302 forming one or more of a waistband 122, waistcap 123, inner leg cuff 150, outer leg cuff 140 and/or a transverse barrier 165 may comprise elastics having an Average-Pre-Strain from about 75% to about 300%. Alternatively, the elastomeric laminate may comprise elastic elements with an Average-Pre-Strain of between 100% and 250%.

Any one of the belt 430, side panel 330, ear panel 530, chassis 200, topsheet 124, backsheet 125, waistband 122, waistcap 123, inner leg cuff 150, outer leg cuff 140 or transverse barrier may comprise an elastomeric laminate 302 comprising a plurality of elastics 316 having a Pres sure-Under-Strand from about 0.1 psi to about 1 psi, or from about 0.2 psi to about 0.8 psi.

Any one of the belt 430, side panel 330, ear panel 530, chassis 200, topsheet 124, backsheet 125, waistband 122, waistcap 123, inner leg cuff 150, outer leg cuff 140 or transverse barrier may comprise an elastomeric laminate comprising an Air Permeability at 0 gf/mm (no extension) of greater than about 40 cubic meters/square meter/minute and/or a level of Air Permeability at 3 gf/mm (slight extension) of greater than about 60 cubic meters/square meter/minute and/or a level of Air Permeability at 7 gf/mm (moderate extension) of greater than about 80 cubic meters/square meter/minute.

Any one of the belt 430, side panel 330, ear panel 530, chassis 200, topsheet 124, backsheet 125, waistband 122, waistcap 123, inner leg cuff 150, outer leg cuff 140 or transverse barrier may comprise an elastomeric laminate comprising a Water Vapor Transmission Rate of greater than 2000 g/m2/24 hrs, greater than 4000 g/m2/24 hrs or greater than 6000 g/m2/24 hrs.

Any one of the belt 430, side panel 330, ear panel 530, chassis 200, topsheet 124, backsheet 125, waistband 122, waistcap 123, inner leg cuff 150, outer leg cuff 140 or transverse barrier may comprise an elastomeric laminate having a Caliper at 0 gf/mm (no extension) of from about 0.5 mm to about 4 mm and/or a Caliper Retention value at 3 gf/mm (slight extension) of from about 60% to about 95% and/or a Caliper Retention at 7 gf/mm (moderate extension) of from about 40% to about 90%

Any one of the belt 430, side panel 330, ear panel 530, chassis 200, topsheet 124, backsheet 125, waistband 122, waistcap 123, inner leg cuff 150, outer leg cuff 140 or transverse barrier may comprise an elastomeric laminate comprising a Cantilever Bending of less than about 40 mm, alternatively less than about 35 mm.

Any one of the belt 430, side panel 330, ear panel 530, chassis 200, topsheet 124, backsheet 125, waistband 122, waistcap 123, inner leg cuff 150, outer leg cuff 140 or transverse barrier may comprise an elastomeric laminate comprising a Percent Contact Area of greater than about 13% at 100 um and/or greater than about 27% at 200 um and/or greater than about 39% at 300 um and/or a 2%-98% Height Value of <1.6 mm. Alternatively, any one of the belt 430, side panel 330, ear panel 530, chassis 200, topsheet 124, backsheet 125, waistband 122, waistcap 123, inner leg cuff 150, outer leg cuff 140 or transverse barrier may comprise an elastomeric laminate comprising a Percent Contact Area of greater than about 10% at 100 um and/or greater than about 20% at 200 um and/or greater than about 30% at 300 um and/or a 2%-98% Height Value of <2.2 mm.

Any one of the belt 430, side panel 330, ear panel 530, chassis 200, topsheet 124, backsheet 125, waistband 122, waistcap 123, inner leg cuff 150, outer leg cuff 140 or transverse barrier may comprise an elastomeric laminate comprising a Rugosity Frequency of from about 0.2 mm$^{-1}$ to about 1 mm$^{-1}$ and a Rugosity Wavelength of from about 0.5 mm to about 5 mm.

It is also to be appreciated that any one of the belt 430, side panel 330, ear panel 530, chassis 200, topsheet 124, backsheet 125, waistband 122, waistcap 123, inner leg cuff 150, outer leg cuff 140 or transverse barrier may comprise an elastomeric laminate comprising one or more of the parametric values and ranges cited herein above.

The elastomeric laminate 302 may comprise an apertured elastomeric film material, elastic strands, elastomeric scrim materials, elastomeric nonwovens, elastic ribbons, foams and combinations thereof. The elastomeric laminate 302 may comprise a plurality of elastics 316 that may be the same color as one or both of the first substrate layer 306 and second substrate layer 308 so the elastic material may be more hidden, i.e. masked or may be of a different color so the elastic material is visible in the elastomeric laminate 302. Furthermore, the elastic 316 may be transparent or translucent such that it is virtually invisible. Transparency or translucency combined with the very low decitex of the elastic 316 may render the elastic 316 visibly and tactilely unnoticeable by users of absorbent articles comprising elastomeric laminate 302 comprising such elastics 316.

The elastomeric laminate 302 may comprise a plurality of elastics 316 and may be formed from a single beam. The plurality of elastics 316 may have a uniform elastic strand spacing or alternatively may have variable elastic strand spacing throughout the elastomeric laminate 302. The plurality of elastics 316 of the elastomeric laminate may also comprise larger gaps between one or more pairs of elastics wherein the gaps are 2× the Average-Strand-Spacing of the plurality of elastics 316. The gaps may be 4×, 10× or even 20× the Average-Strand-Spacing of the plurality of elastics 316. The elastomeric laminate 302 may comprise a plurality of elastics 316 and may be formed from multiple beams of elastic. A first beam comprising a first plurality of elastics 316a and a second beam comprising a second plurality of elastics 316b may both be disposed between first substrate layer 306 and second substrate layer 308 of the elastomeric laminate 302. One or both of the first plurality of elastics 316a and second plurality of elastics 316b may have a uniform elastic strand spacing or alternatively may have variable elastic strand spacing throughout. One or both of the first plurality of elastics 316a and second plurality of elastics 316b may comprise larger gaps between one or more pairs of elastics wherein the gaps in the first plurality of elastics 316a are 2× the Average-Strand-Spacing of the first plurality of elastics 316a. The gaps may be 4×, 10× or even 20× the Average-Strand-Spacing of the first plurality of elastics 316a. Furthermore, the second plurality of elastics 316b of may comprise larger gaps between one or more pairs of elastics wherein the gaps in the second plurality of elastics 316b are 2× the Average-Strand-Spacing of the second plurality of elastics 316b. The gaps may be 4×, 10× or even 20× the Average-Strand-Spacing of the first plurality of elastics 316b. The elastomeric laminate 302 comprising a plurality of elastics 316 formed from multiple beams of elastic may have a first plurality of elastics 316a of a first beam disposed in a partially overlapping orientation with a second plurality of elastics 316b of a second beam. The elastomeric laminate 302 comprising a plurality of elastics 316 formed from multiple beams of elastic may have a first plurality of elastics 316a of a first beam disposed in an offset orientation from a second plurality of elastics 316b of a second beam wherein the offset creates a gap between the first plurality of elastics 316a and second plurality of elastics 316b. The gap between the first plurality of elastics 316a and second plurality of elastics 316b may be 5×, 10× or even 20× the Average-Strand-Spacing of one of the first plurality of elastics 316a or second plurality of elastics 316b.

Any or all portions of the absorbent article 100 may comprise a bacteriophage composition as described in U.S. Ser. No. 61/931,229, titled Disposable Absorbent Articles Comprising Bacteriophages and Related Methods, and filed on Jan. 24, 2014.

Closed-Form Pant Article

Closed-form, pant-style, absorbent articles are generally disclosed in FIGS. 1, 2, 4A-11, 17, 19, 20, 22, 23, 31-33, 35-37, 48, 55, 56, 58, 61A-67, and are designed to be packaged in closed-form having a waist opening and two leg openings, and designed to be donned onto the wearer like a pair of durable underwear. As shown in FIG. 2, the pant may comprise discrete elastomeric side panels 330 in one or both of the front waist region 36 and back waist region 38. The elastomeric side panels 330 may be formed (joined and/or positioned) in a particular place or position and may be unitary structurally with other elements of the article or as separate discrete elements joined to another element of the article. When the absorbent article comprises front and back elastomeric side panels 330, the front and back side panels 330 on one side of the article may be joined permanently or refastenably to each other and the front and back side panels 330 on the opposing side of the article may be joined permanently or refastenably to each other to create a waist opening 190 and a pair of leg openings 192. The elastomeric side panels 330 provide an elastically extensible feature that provides a more comfortable and contouring fit by initially conformably fitting the article 100 to the wearer 70 and sustaining this fit throughout the time of wear well past when the pant has been loaded with exudates since the elastomeric side panels 330 allow the sides of the pant to expand and contract along with wearer movement. Further, the elastomeric side panels 330 provide ease of application and develop and maintain wearing forces and tensions to maintain the article 100 on the wearer and enhance the fit. The elastomeric side panels 330 enable ease of application allowing the pant to be pulled conformably over the hips of the wearer and positioned at the waist where the side panels 330 conform to the body and provide tension sufficient to maintain the articles position on the wearer. The tension created by the side panels 330 is transmitted from the elastic side panels 330 along the waist opening 190 and along at least a portion of the leg opening 192. Typically, the chassis 200 is disposed between the side panels 330 and extends to form a portion of the waist edge 136 and/or 138 of the pant comprising side panels 300. In other words, a portion of the waist edge 136 and/or 138 in one or both of the front waist region 36 and back waist region 38 may be formed in part by the side panels 330 and in part by the chassis 200. The side panels 330 can be integral with a portion of the chassis 200 or may discrete elements that overlap a portion of the chassis 200 and are joined thereto. The side panels 330 may be formed in part with an elastomeric film layer 317 (which may be apertured) providing a film side panel portion (or film portion of a side panel—see, for example, FIGS. 16D, 16F, 16G, 16I, 16K) having a first Section-Modulus or may be formed in part with elastics 316 providing a stranded side panel portion having a second Section-Modulus wherein the Section-Modulus of the film side panel portion is greater than the Section-Modulus of the stranded side panel portion.

Figure 3:
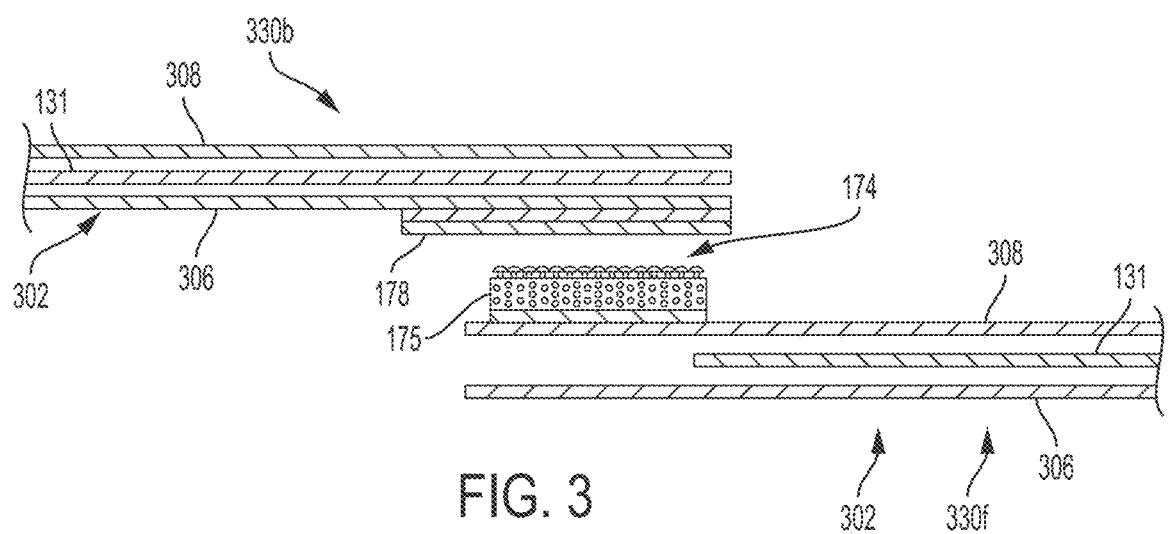
FIG. 3 is a cross section view of a refastenable seam taken along line 3-3 of the pant of FIG. 1.
Figure 4A:
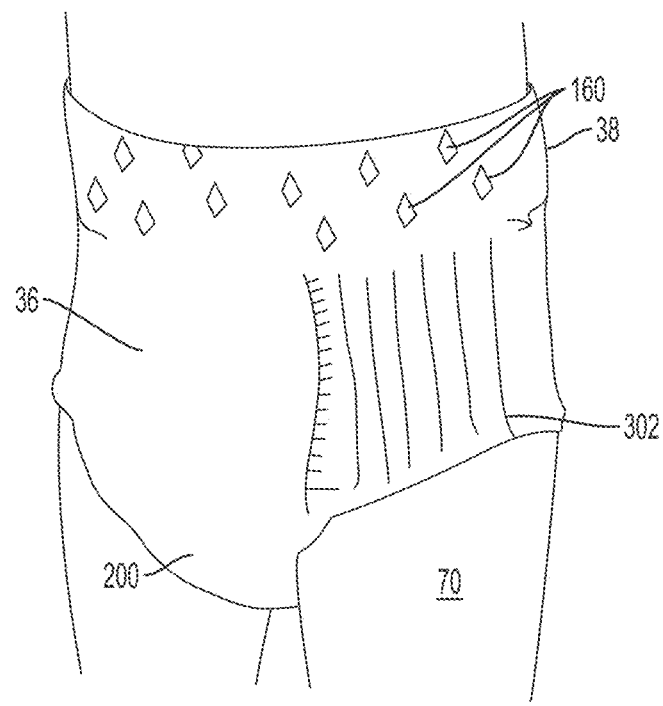
FIG. 4A is a perspective view of a pant comprising apertures fitted on a wearer.
Figure 4B:
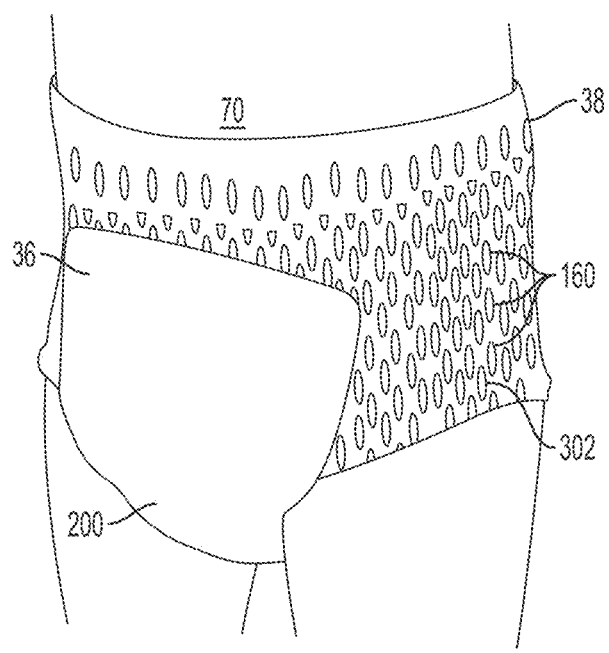
FIG. 4B is a perspective view of a pant comprising apertures fitted on a wearer.

The pant comprising side panels 300 may be formed into a pant in a number of ways. The discrete elastomeric side panels 330 may be disposed in one or both of the waist regions. Observe that side panels 330 (see, for example FIG. 31) may generically refer to a portion of a belt 430 that extends beyond side edges 237 of the chassis 200, whereas discrete side panels attached to a chassis may be referenced as 330 (see, for example, FIG. 2). The pant comprising side panels 300 may also comprise a pair of laterally opposing refastenable seams 174 as illustrated in FIGS. 1-3. The refastenable side seam 174 may be formed by refastenably joining an interior surface of a portion of the article, e.g. a side panel 330, to an exterior surface of another portion of the article 100, e.g. a longitudinally opposing side panel 330 or the chassis 200 to form the refastenable side seam 174. FIG. 3 illustrates a front side panel 330f comprising a fastener 175 comprising hooks facing away from a wearer (the fastener 175 disposed on an exterior surface of the front side panel 330f that refastenably attaches to a mating fastener 178 (loops or a suitable nonwoven in FIG. 3), the mating fastener 178 being disposed on an interior surface of the back side panel 330b. Observe that that FIG. 3 is an alternative embodiment of FIGS. 1 and 2 as the pant of FIGS. 1 and 2 do not comprise a mating fastener 178—rather, the fastener 175 in FIGS. 1 and 2 may refastenably join directly to the back side panels 330. The refastenable seams 174 may comprise a fastening system 179 comprising a primary fastener 175, for example a mechanical fastener, velcro-like fasteners, hooks, etc., or mating fastener 178, for example a nonwoven or loop material intended to mate with a hook fastener, disposed on one or more of the discrete elastomeric side panels 330, for example a first portion of a fastening system 179 may be disposed on a first discrete elastomeric side panel 330 and a second portion of a fastening system 179 may be disposed on a second discrete elastomeric side panel 330. Several options for refastenable seams are illustrated in FIGS. 24-29. Alternatively, the pant comprising side panels 300 may also comprise a first permanent side seam 172 and a laterally opposing second permanent side seam 172 as illustrated, for example, in FIGS. 8A, 8B, and 10. The permanent side seam 172 may be formed by joining an interior surface of a portion of the article 100, e.g. a side panel 330, to an exterior surface of another portion of the article 100, e.g. a longitudinally opposing side panel 330 or the chassis 200 to form the permanent side seam 172. Alternatively, the permanent side seam 172 may be formed by joining an interior surface of a portion of the article 100, e.g. a side panel 330, to an interior surface of another portion of the article 100, e.g. a longitudinally opposing side panel 330 to form the permanent side seam 172. Any of the pant comprising side panels 300 configurations described above may comprise a waistband 122 wherein at least a portion of the waistband 122 (as illustrated in FIG. 2) is disposed at or immediately adjacent the waist edge 136 and/or 138 and overlaps a portion of the center chassis 200. The waistband 122 may extend laterally to overlap portions of the inner leg cuffs 150 and/or portions of the elastomeric side panels 330. The waistband 122 may be disposed on the interior surface 202 of the chassis 200 or alternatively between the topsheet 124 and the backsheet 125.

Figure 10:
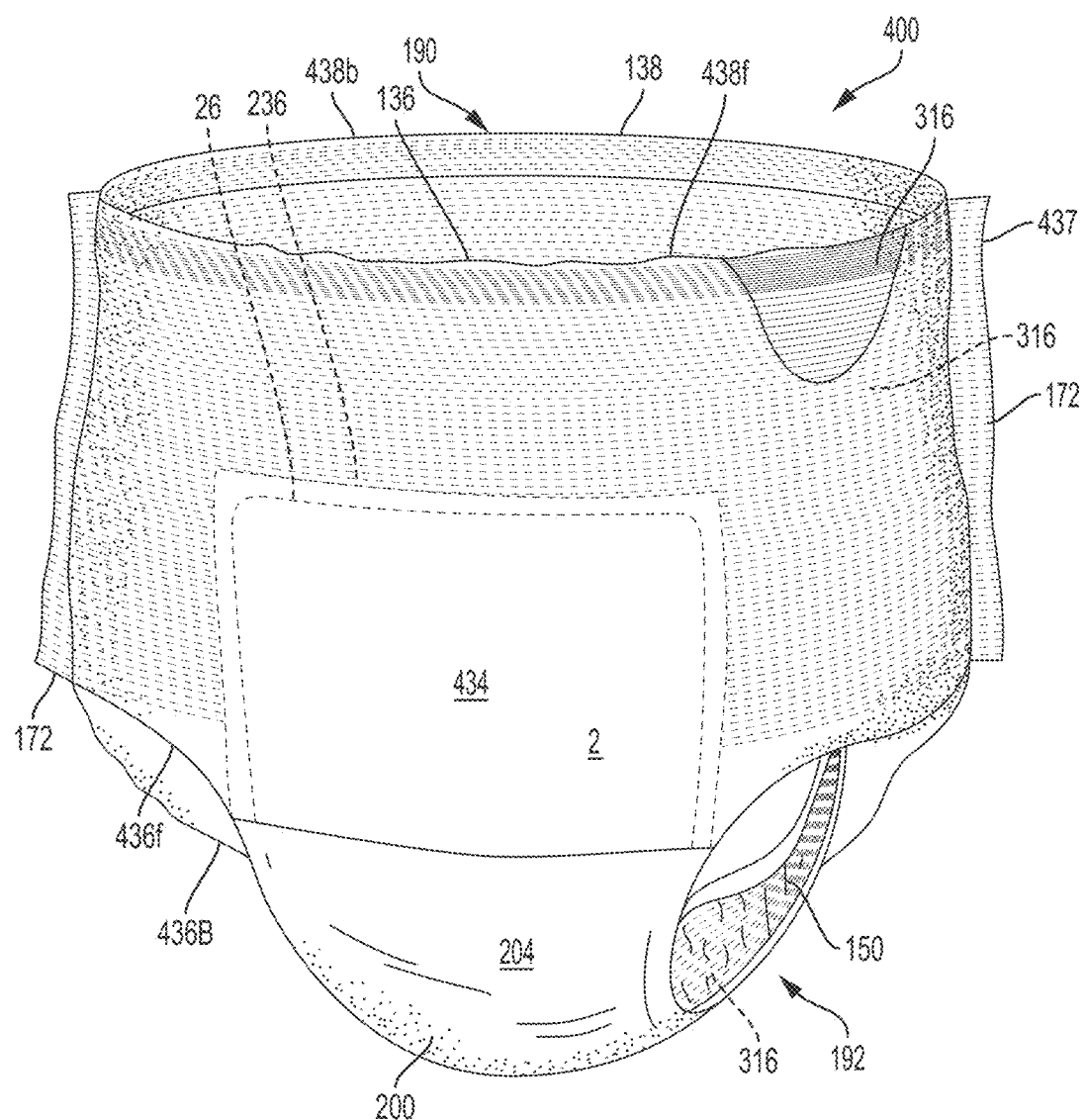
FIG. 10 is a perspective front view of a belt pant comprising discrete belts having both continuous and discontinuous elastics.

As illustrated in FIGS. 10 and 11, the belt pant 400, closed-form article, may comprise elastomeric belts 430 in both of the front waist region 36 and back waist region 38. The elastomeric belts 430 may be formed (joined and/or positioned) in a particular place or position and may be unitary structurally with other elements of the article 100 or as separate discrete elements joined to another element of the article 100. When the absorbent article comprises front and back elastomeric belts 430, the belt 430 in one waist region of the article may be joined permanently or refastenably to the belt 430 in the opposing waist region of the article to create a waist opening 190 and a pair of leg openings 192. The elastomeric belts 430 provide an elastically extensible feature that provides a more comfortable and contouring fit by initially conformably fitting the article 100 to the wearer 70 and sustaining this fit throughout the time of wear well past when the article has been loaded with exudates since the elastic belts 430 allow the waist and sides of the diaper to expand and contract along with the movements of the wearer 70. Further, the elastic belts 430 provide ease of application and develop and maintain wearing forces and tensions to maintain the article 100 on the wearer and enhance the fit. The elastomeric belts 430 enable ease of application allowing the pant to be pulled conformably over the hips of the wearer and positioned at the waist where the belts 430 conform to the body and provide tension sufficient to maintain the articles position on the wearer. The tension created by the belts 430 is transmitted from the elastic belts 430 along the waist opening 190 and along at least a portion of the leg opening 192. The elastomeric belts 430 may be formed in part with elastic strands providing a stranded belt having a belt Section-Modulus wherein belt Section-Modulus of the stranded belt is less than the Section-Modulus of a film side panel 330 described herein. This difference in Section-Modulus enables extension of the elastomeric belt 430 at a lower force than that of an elastomeric film side panel 330 thereby making application of the belt pant 400 (with an elastomeric stranded belt 430) by a wearer easier than a pant comprising side panels 300 (with an elastomeric film side panel 330) enabling the wearer to develop skills valuable for their physiological and psychological development.

Figure 20:
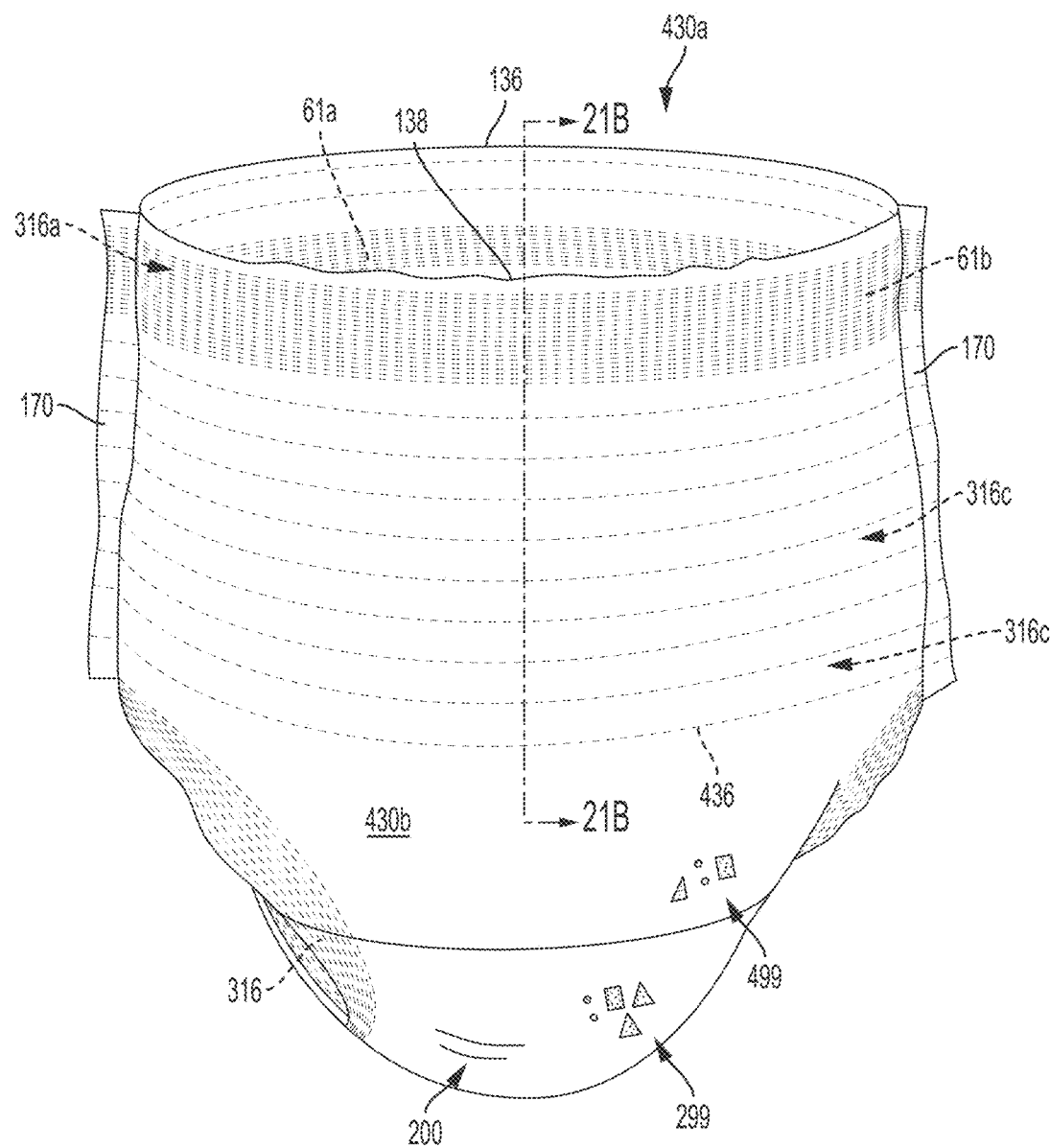
FIG. 20 is a perspective back view of the pant of FIG. 19, showing multiple beam zones disposed in the low motion zones of a potential wearer, showing the elastics responsible for anchoring forces 61a and b.
Figure 21A:
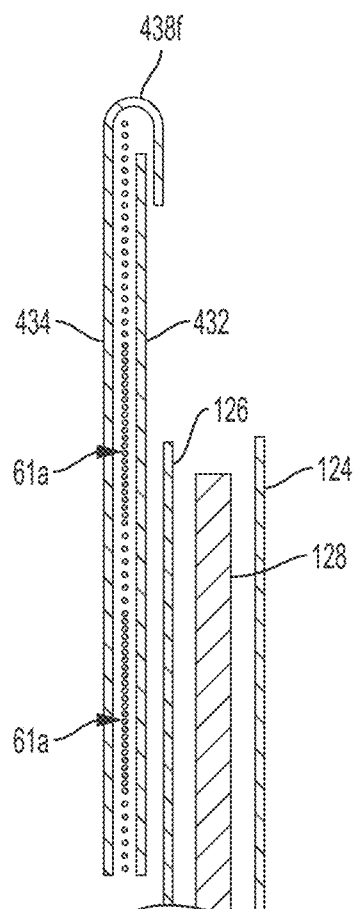
FIG. 21A is a partial cross section view of the front belt 430f of the pant of FIG. 19 taken along line 21A-21A of FIG. 19.
Figure 21B:
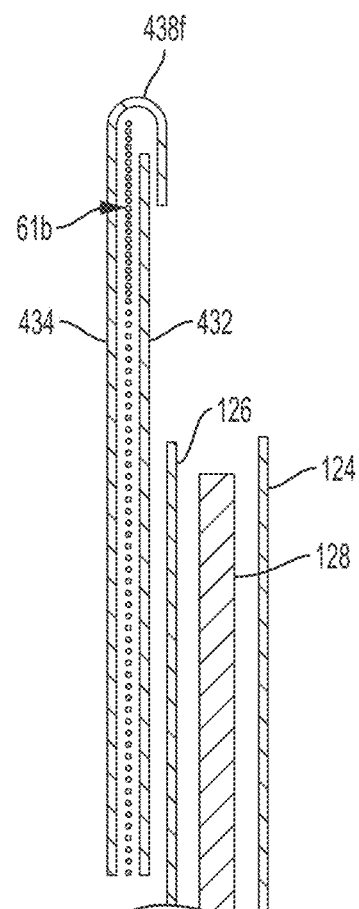
FIG. 21B is a partial cross section view of the back belt 430b of the pant of FIG. 20 taken along line 21B-21B of FIG. 20.
Figure 22:
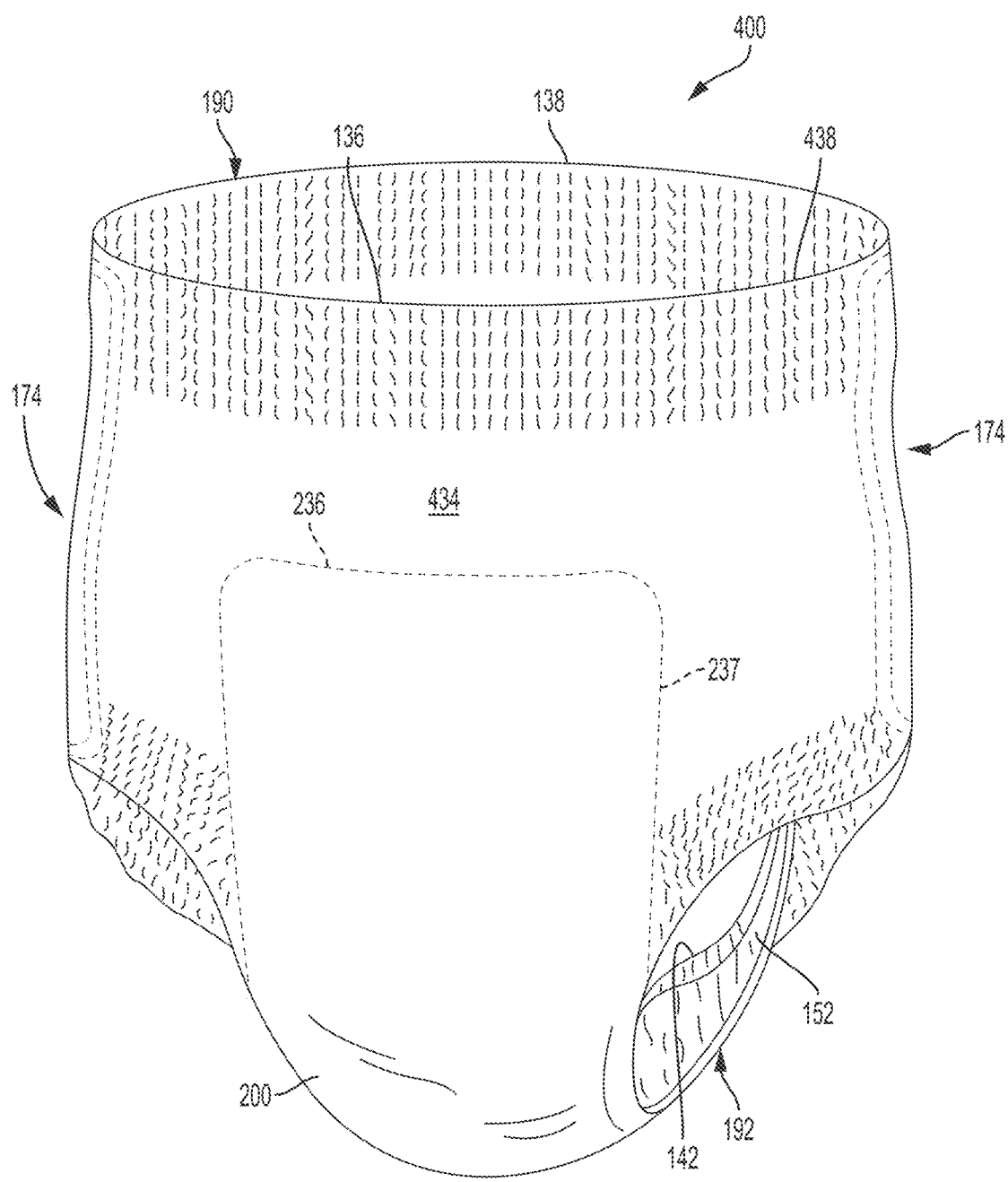
FIG. 22 is a perspective front view of a pant comprising a refastenable side seam 174.
Figure 72B:
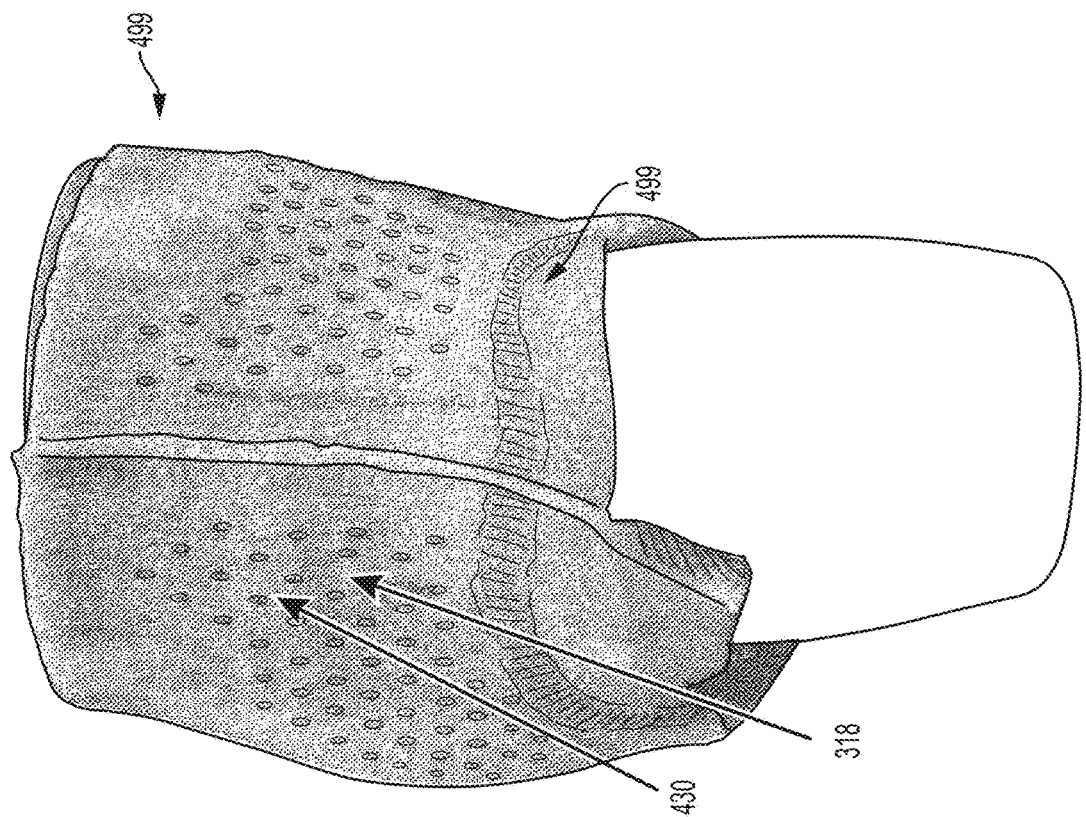
FIG. 72B is a side view of an inventive absorbent article fitted onto a mannequin, the absorbent article comprising an inventive belt 430 comprising an inventive elastomeric laminate 302. The inventive texture zone 318 of the belt 430 in FIG. 72B is meant to be directly compared to same areas of the belt 430 in FIG. 72A.
Figure 72A:
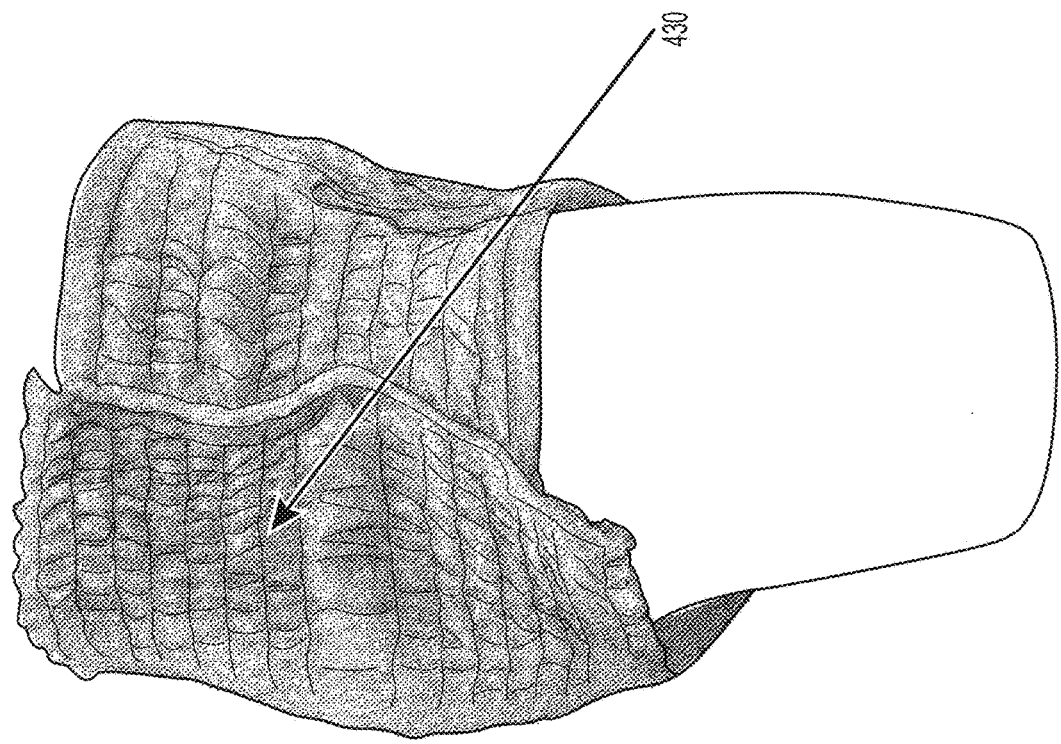
FIG. 72A is a side view of a comparative absorbent article fitted onto a mannequin, the absorbent article comprising a comparative belt 430 comprising an existing elastic profile of strands. The belt 430 of FIG. 72A shows groupings of large uncontrolled gathers indicative of less uniform and higher elastic stress that will result in higher pressure on the wearer's skin (versus the belt 430 of FIG. 72B).

As disclosed in U.S. Ser. No. 11/999,229 the pant may comprise graphics. For instance, one or both of the elastomeric belts 430 may comprise one or more of an arrangement of belt graphics covering greater than about 30% of the surface area of the belt 430 and/or an arrangement of belt graphics when viewed from the outside appear to comprise at least three colors and/or an arrangement of belt graphics being disposed within 30 mm of a waist edge 438 of the belt 430 and/or an arrangement of belt graphics being disposed within about 10 mm of a leg edge 436 (front leg edge 436F or back leg edge 436B) of the belt 430 as illustrated in FIGS. 20 and 72B. One or both of the elastomeric belts 430 may comprise one or more of a belt graphic 499 and/or a colored nonwoven and/or a tinted nonwoven.

Figure 13A:
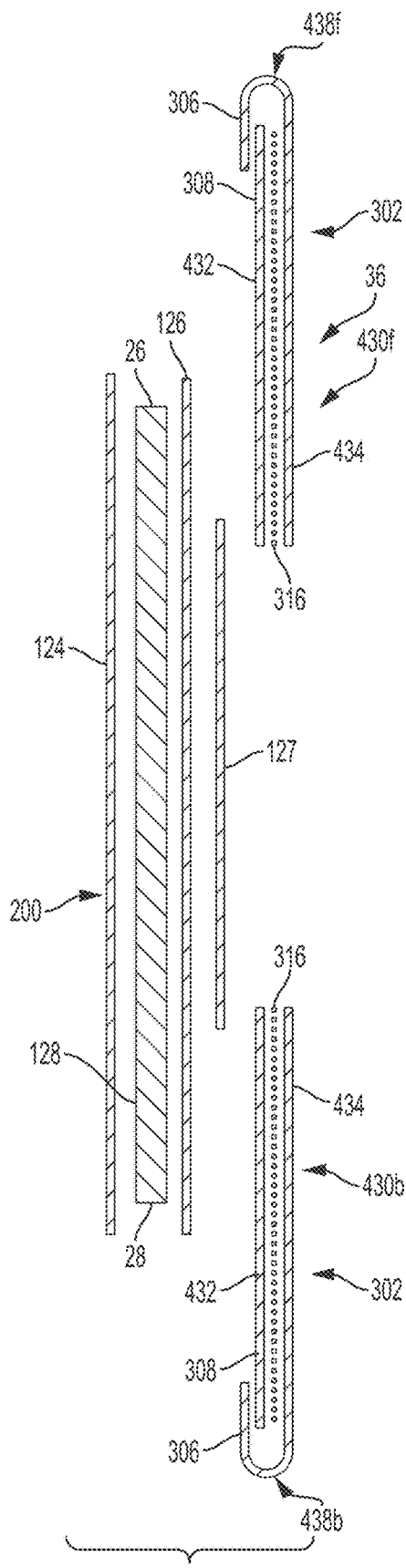
FIG. 13A is a cross section view of an alternate embodiment of the belt pant of FIG. 11 taken along the longitudinal axis 42, showing longitudinally opposing discrete belts.
Figure 13B:
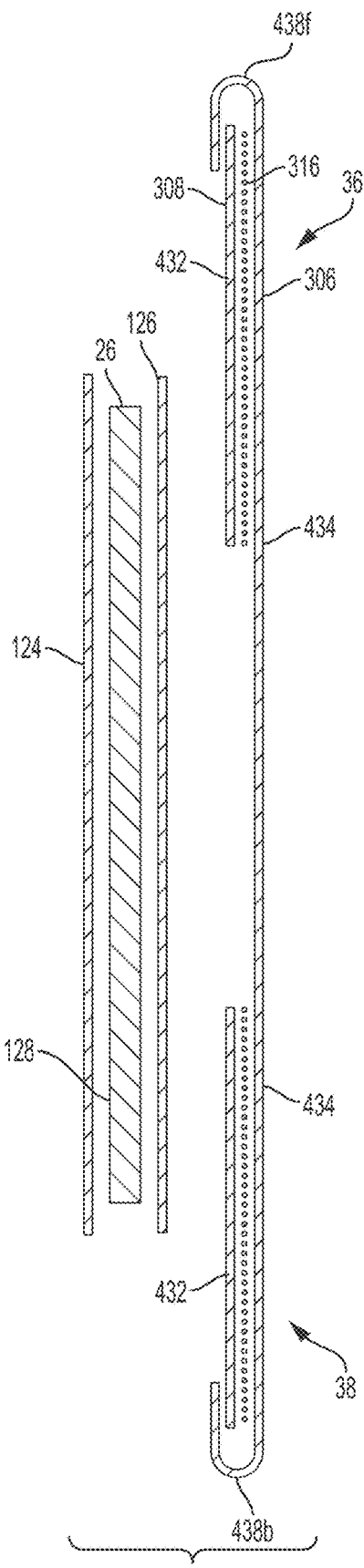
FIG. 13B is a cross section view of an alternate embodiment of the belt pant of FIG. 11 taken along the longitudinal axis 42, showing longitudinally opposing discrete inner belt layers 432 and a common outer belt layer 434.
Figure 14A:
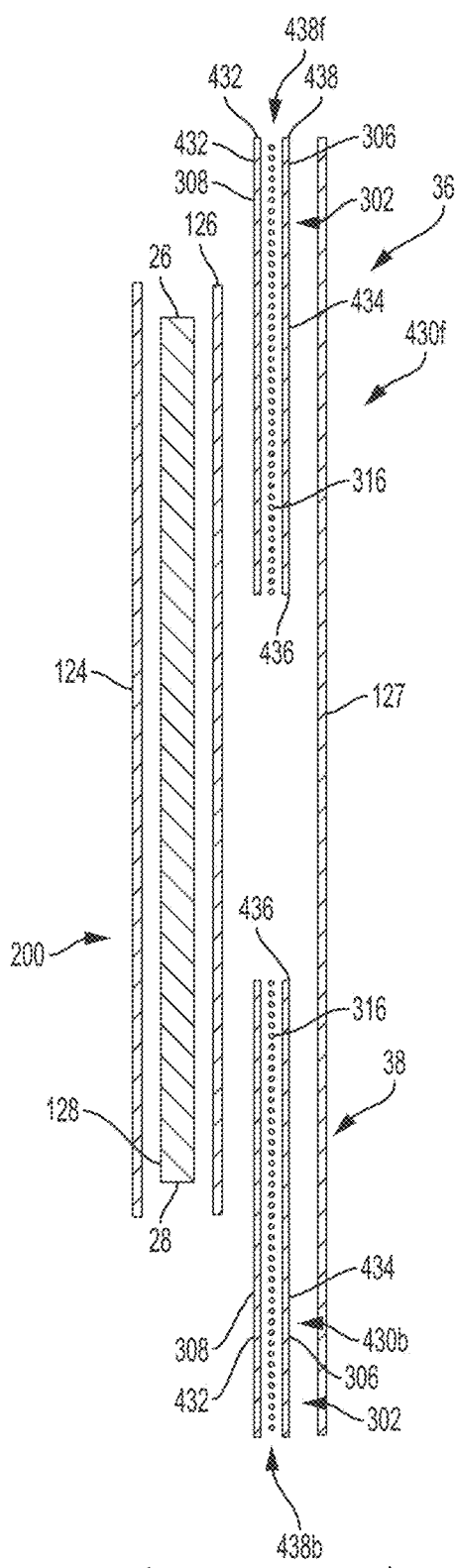
FIG. 14A is a cross section view of an alternate embodiment of the belt pant of FIG. 11 taken along the longitudinal axis 42, showing longitudinally opposing discrete belts.
Figure 14B:
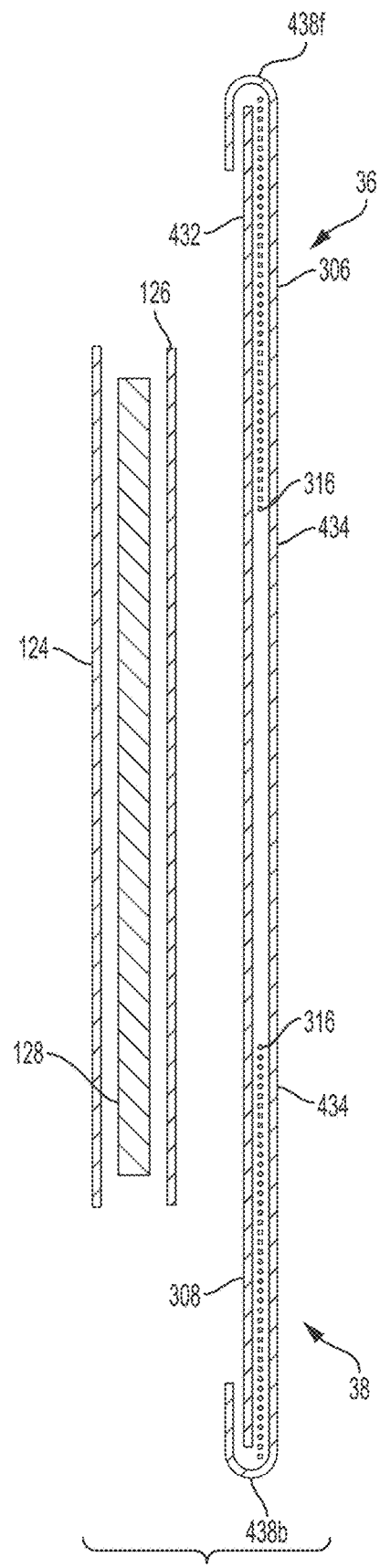
FIG. 14B is a cross section view of an alternate embodiment of the belt pant of FIG. 11 taken along the longitudinal axis 42, showing a common inner belt layer 432 and a common outer belt layer 434.
Figure 15A:
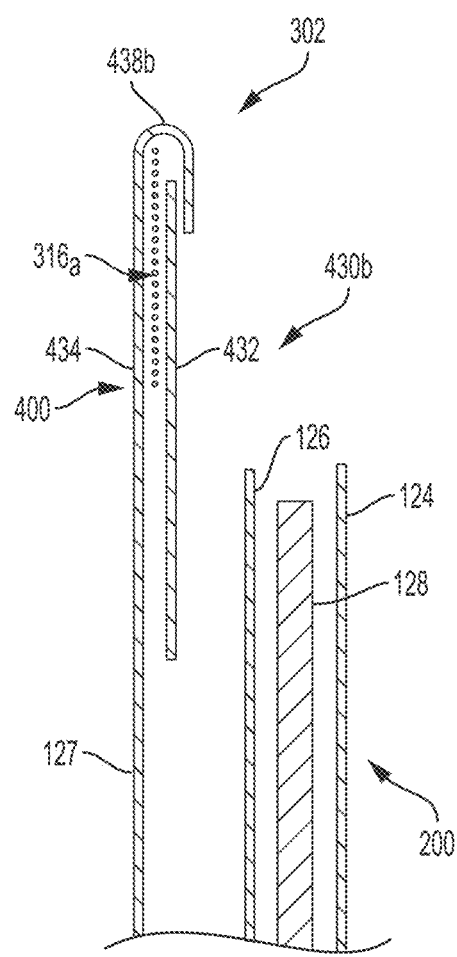
FIG. 15A is a partial cross section view of an alternate embodiment of the belt pant of FIG. 11 taken along the longitudinal axis 42.
Figure 15B:
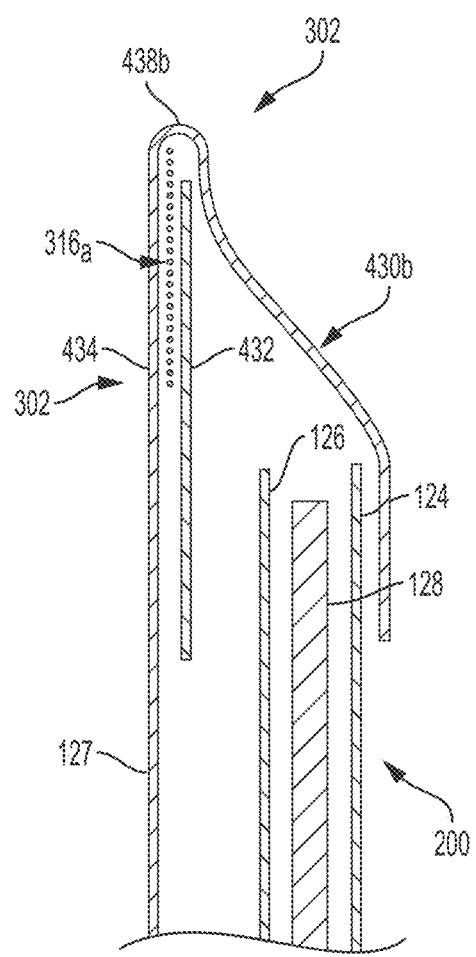
FIG. 15B is a partial cross section view of an alternate embodiment of the belt pant of FIG. 11 taken along the longitudinal axis 42, showing an outer belt layer 434 extending to wrap over a topsheet 124 of the chassis 200.
Figure 15C:
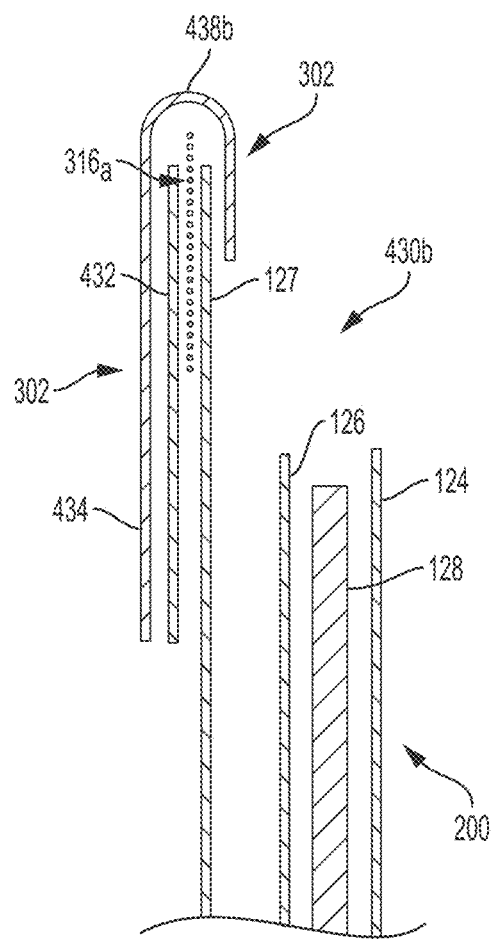
FIG. 15C is a partial cross section view of an alternate embodiment of the belt pant of FIG. 11 taken along the longitudinal axis 42.
Figure 16A:
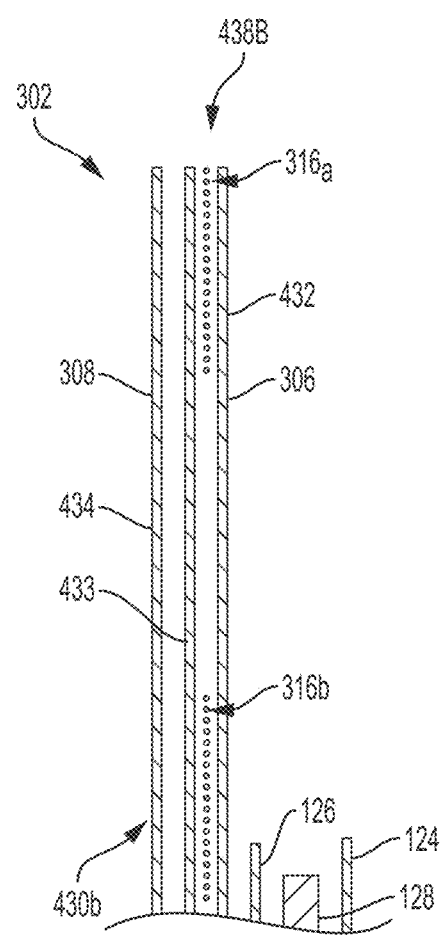
FIG. 16A is a partial cross section view of an alternate embodiment of the belt pant of FIG. 11 taken along the longitudinal axis 42, showing an inner belt layer 432 and an outer belt layer 434 and an intermediate belt layer 433 therebetween.
Figure 16B:
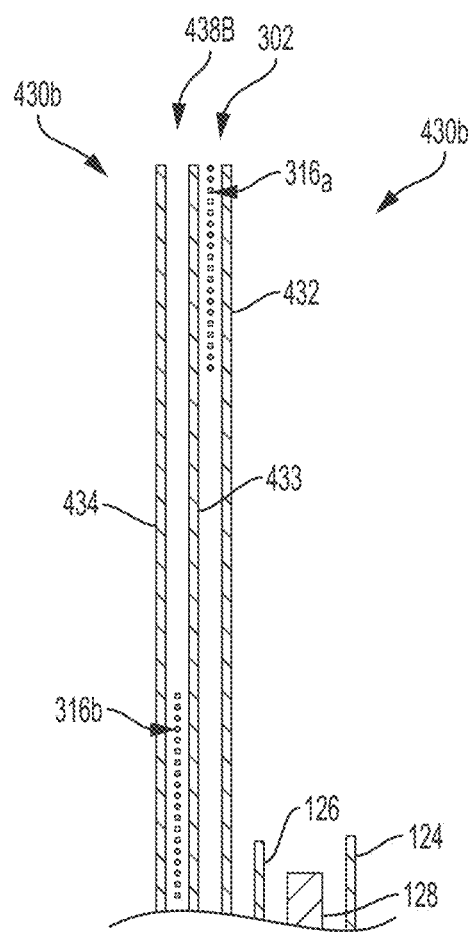
FIG. 16B is a partial cross section view of an alternate embodiment of the belt pant of FIG. 11 taken along the longitudinal axis 42, showing an inner belt layer 432 and an outer belt layer 434 and an intermediate belt layer 433 therebetween.
Figure 16C:
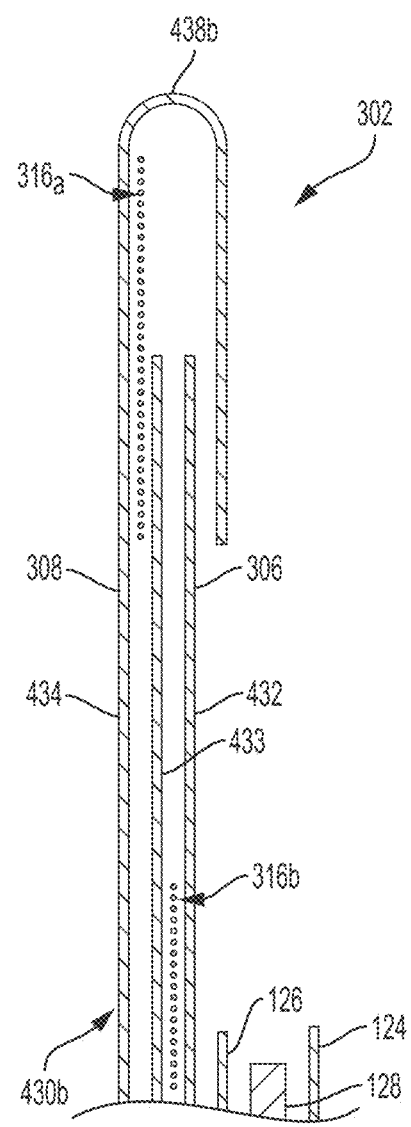
FIG. 16C is a partial cross section view of an alternate embodiment of the belt pant of FIG. 11 taken along the longitudinal axis 42, showing an inner belt layer 432 and an outer belt layer 434 and an intermediate belt layer 433 therebetween, and showing a portion of elastics 316a being immediately sandwiched between the outer belt layer 434.
Figure 16D:
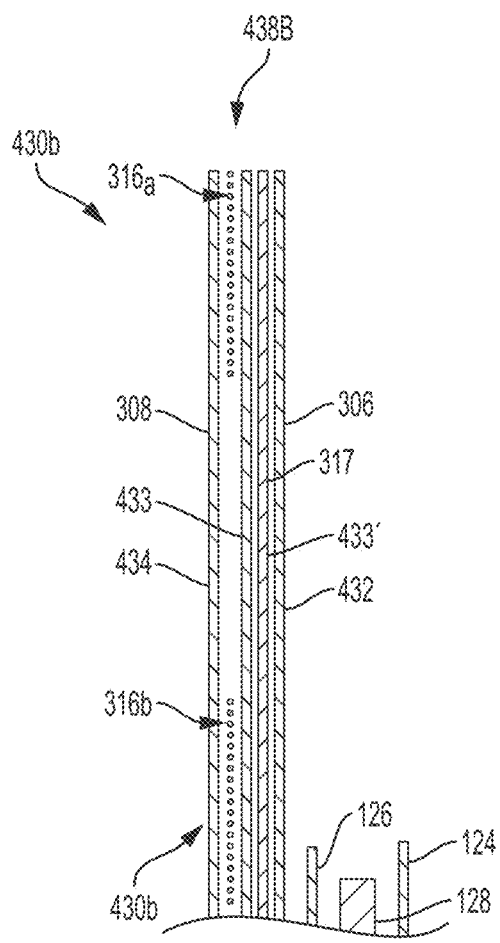
FIG. 16D is a partial cross section view of an alternate embodiment of the belt pant of FIG. 11 taken along the longitudinal axis 42, showing an inner belt layer 432 and an outer belt layer 434 and first and second intermediate layers 433 and 433' therebetween.
Figure 16E:
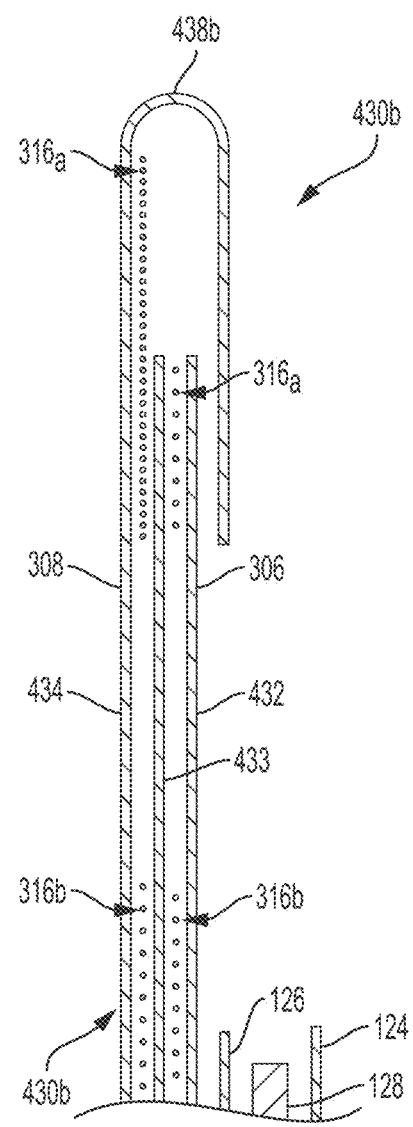
FIG. 16E is a partial cross section view of an alternate embodiment of the belt pant of FIG. 11 taken along the longitudinal axis 42, showing an inner belt layer 432 and an outer belt layer 434 and an intermediate belt layer 433 therebetween, and showing a portion of elastics 316a being immediately sandwiched between the outer belt layer 434, and showing tighter spacing between elastics 316a sandwiched between the outer belt layer 434 and the intermediate belt layer 433 than the spacing of the elastics 316a between the intermediate belt layer 433 and the inner belt layer 432 and also tighter than the elastics 316b.
Figure 16F:
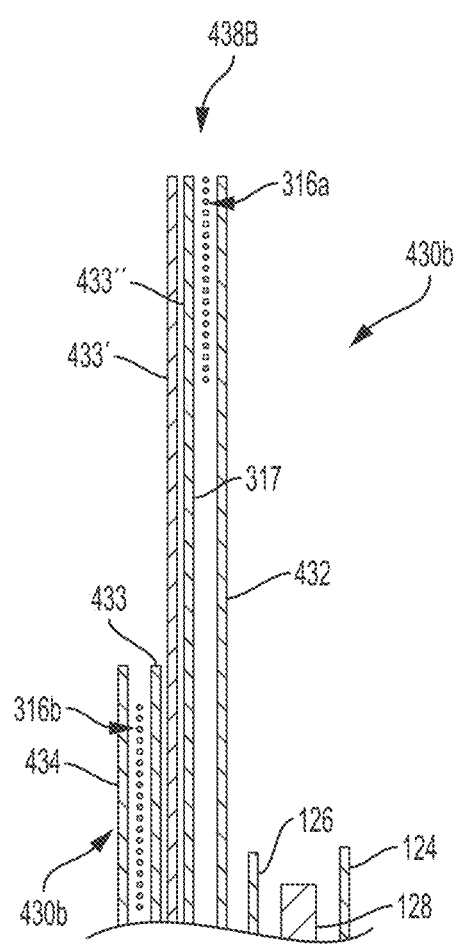
FIG. 16F is a partial cross section view of an alternate embodiment of the belt pant of FIG. 11 taken along the longitudinal axis 42, showing an inner belt layer 432 and an outer belt layer 434 and first, second, and third intermediate layers 433, 433', and 433" therebetween.
Figure 16G:
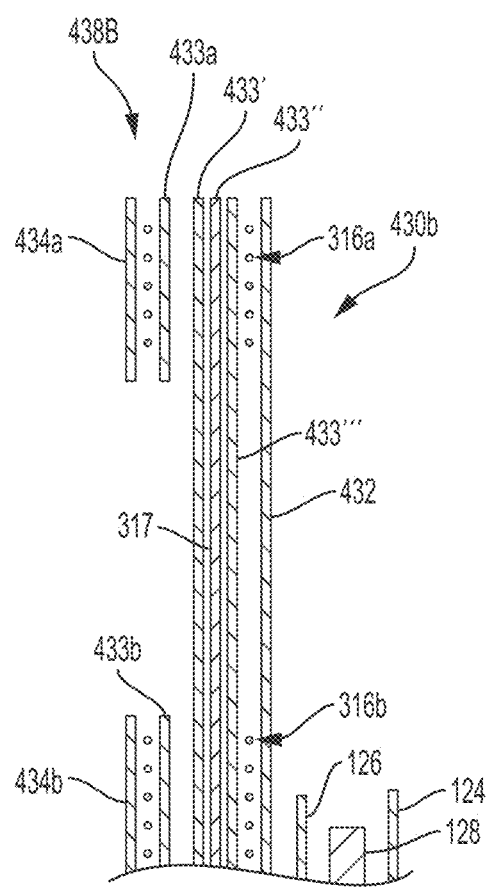
FIG. 16G is a partial cross section view of an alternate embodiment of the belt pant of FIG. 11 taken along the longitudinal axis 42, showing an inner belt layer 432 and an outer belt layer 434 and first, second, third, and fourth intermediate layers 433, 433', 433", and 433'" therebetween, where outer belt layer 433a is longitudinally separated from outer belt layer 433b and the intermediate belt layer 433a is longitudinally separated from intermediate belt layer 433b.
Figure 16H:
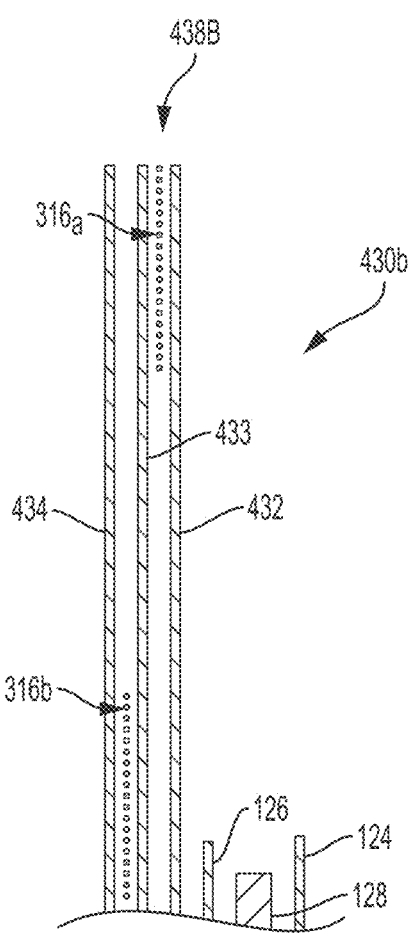
FIG. 16H is a partial cross section view of an alternate embodiment of the belt pant of FIG. 11 taken along the longitudinal axis 42, showing an inner belt layer 432 and an outer belt layer 434 and an intermediate belt layer 433 therebetween.
Figure 16I:
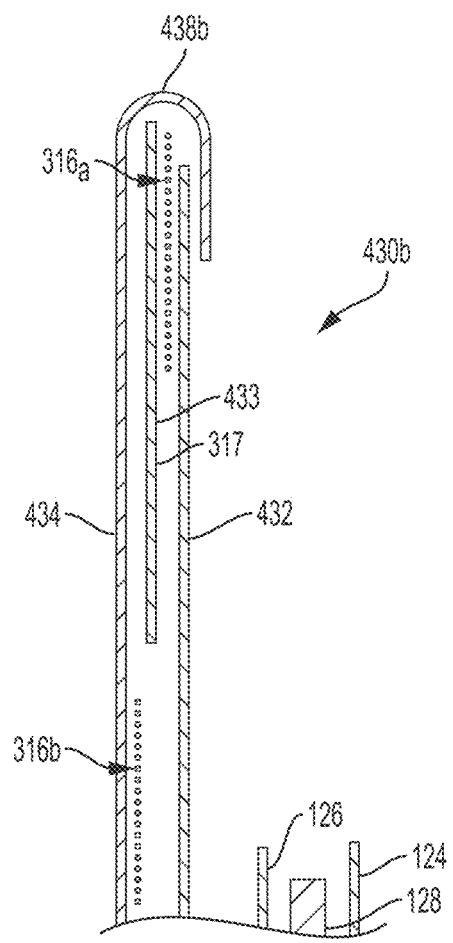
FIG. 16I is a partial cross section view of an alternate embodiment of the belt pant of FIG. 11 taken along the longitudinal axis 42, showing an inner belt layer 432 and an outer belt layer 434 and an intermediate belt layer 433 therebetween, showing elastics 316b between the outer belt layer 434 and inner belt layer 432.
Figure 16J:
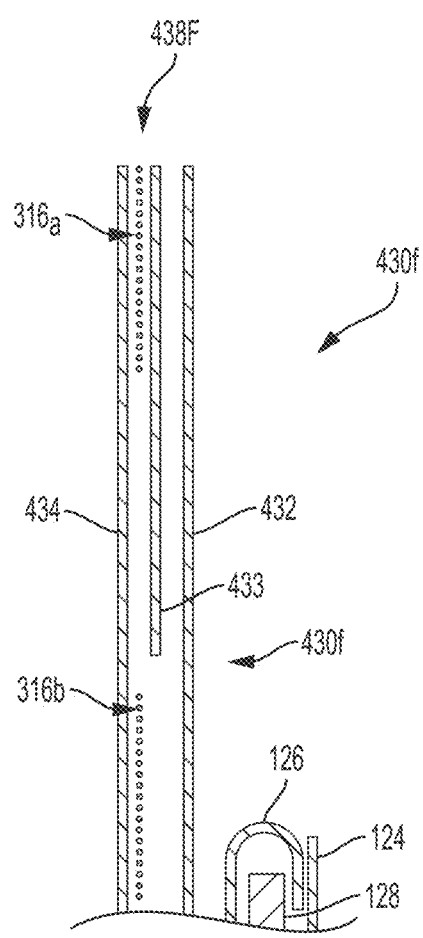
FIG. 16J is a partial cross section view of an alternate embodiment of the belt pant of FIG. 11 taken along the longitudinal axis 42, showing an inner belt layer 432 and an outer belt layer 434 and an intermediate belt layer 433 therebetween, showing elastics 316b between the outer belt layer 434 and inner belt layer 432.
Figure 16K:
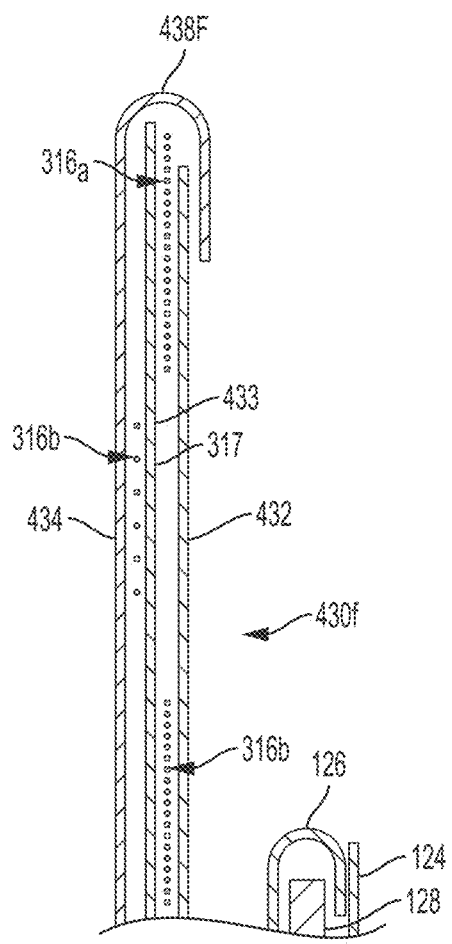
FIG. 16K is a partial cross section view of an alternate embodiment of the belt pant of FIG. 11 taken along the longitudinal axis 42, showing an inner belt layer 432 and an outer belt layer 434 and an intermediate belt layer 433 therebetween, showing tighter spacing between elastics 316a sandwiched between the inner belt layer 432 and the intermediate belt layer 433 than the spacing of the elastics 316b between the intermediate belt layer 433 and the outer belt layer 434.

As shown in FIGS. 10-12, 13A and 14A, the first and second elastomeric belts 430 may be discrete and longitudinally opposed, wherein the first elastomeric belt 430 is disposed in a first waist region and the second elastomeric belt 430 is disposed in a second waist region. The longitudinally opposed belts 430 may be joined along the side edges 437 of the belts 430 by permanent seams 172. The permanent seam 172 may be formed by joining an interior surface of a portion of the article 100, e.g. a belt 430, to an exterior surface of another portion of the article 100, e.g. a longitudinally opposing belt 430 or the chassis 200 to form the permanent seam 172. Alternatively, the permanent seam 172 may be formed by joining an interior surface of a portion of the article 100, e.g. a belt 430, to an interior surface of another portion of the article 100, e.g. a longitudinally opposing belt 430 to form the permanent seam 172. Alternatively, as shown in FIGS. 22-29 the longitudinally opposed belts 430 may be joined at or adjacent the side edges 437 of the belts 430 by refastenable seams 174. FIGS. 24-29 show cross-sections of multiple acceptable alternative embodiments of the refastenable seam 174. The refastenable seam 174 may be formed by refastenably joining an interior surface of a portion of the article 100, e.g. a belt 430, to an exterior surface of another portion of the article 100, e.g. a longitudinally opposing belt 430 or the chassis 200 to form the refastenable seam 174. Alternatively, as disclosed in U.S. Ser. No. 13/929,970 the refastenable seam 174 may comprise an intermediate member which may be permanently or refastenably joined to one of the belts 430 and the intermediate member is refastenably joined to one of the interior surface or exterior surface of a portion of the article 100, e.g. the opposing belt 430 or the chassis 200 to form the refastenable seam 174. Alternatively, one or both of the first and second elastomeric belts 430 may comprise an inner belt layer 432 and an outer belt layer 434. The inner belt layer 432 and/or the outer belt layer 434 of the first and second elastomeric belts 430 may be formed by a common belt layer as shown in FIGS. 13B and 14B. When the first and second elastomeric belts 430 have a common belt layer, the common belt layer may extend from a first waist edge in a first waist region to a longitudinally opposing second waist edge in a second waist region, i.e. front waist edge 136 to back waist edge 138. The belt pant 400 may have a first elastomeric belt 430 disposed in a first waist region having a first longitudinal length and a second elastomeric belt 430 disposed in a second waist region having a second longitudinal length wherein the longitudinal length of the first belt is greater than the longitudinal length of the second belt along the side edge of the belt at or adjacent the side seam as illustrated in FIGS. 11, 31, 32, 37, and 55. This length difference helps provide buttock coverage in the back of the pant providing a more underwear-like appearance.

The belt pant 400 may comprise belts 430 having apertured nonwovens (comprising apertures 160—see FIGS. 4A and 4B) forming one or both of the inner belt layer 432 and outer belt layer 434, as well as through any intermediate nonwoven or elastic layers (e.g., 131). The apertured nonwoven belt layers provide increased breathability and significant air permeability as well as increased softness and a more garment-like feel. The belt layers, outer belt layer 434 and/or inner belt layer 432 (first substrate layer 306 and second substrate layer 308 of elastomeric laminate 302) may be apertured prior to forming the elastomeric belt 430 or elastomeric laminate 302. Alternatively, the belt 430 comprising the outer belt layer 434 and inner belt layer 432 with a plurality of elastics 316 disposed between the outer and inner belt layers may be apertured after the elastomeric belt is formed. Likewise, the elastomeric laminate 302 comprising a first substrate layer 306, second substrate layer 308 and plurality of elastics 316 disposed between the first and second substrate layers may be apertured after the elastomeric laminate 302 is formed. Other article components may also have like apertures in the inner and/or outer layers or elastomeric laminate 302, including the center chassis 200, topsheet 124, waistband 122, waist cap 123, ear panels 530, side panels 330, outer cover nonwoven and outer leg cuffs 140. The apertures may come in a variety of shapes and sizes including but not limited to round holes, elongated holes, slits, slots, arcuate slits or slots, etc.

Figure 23:
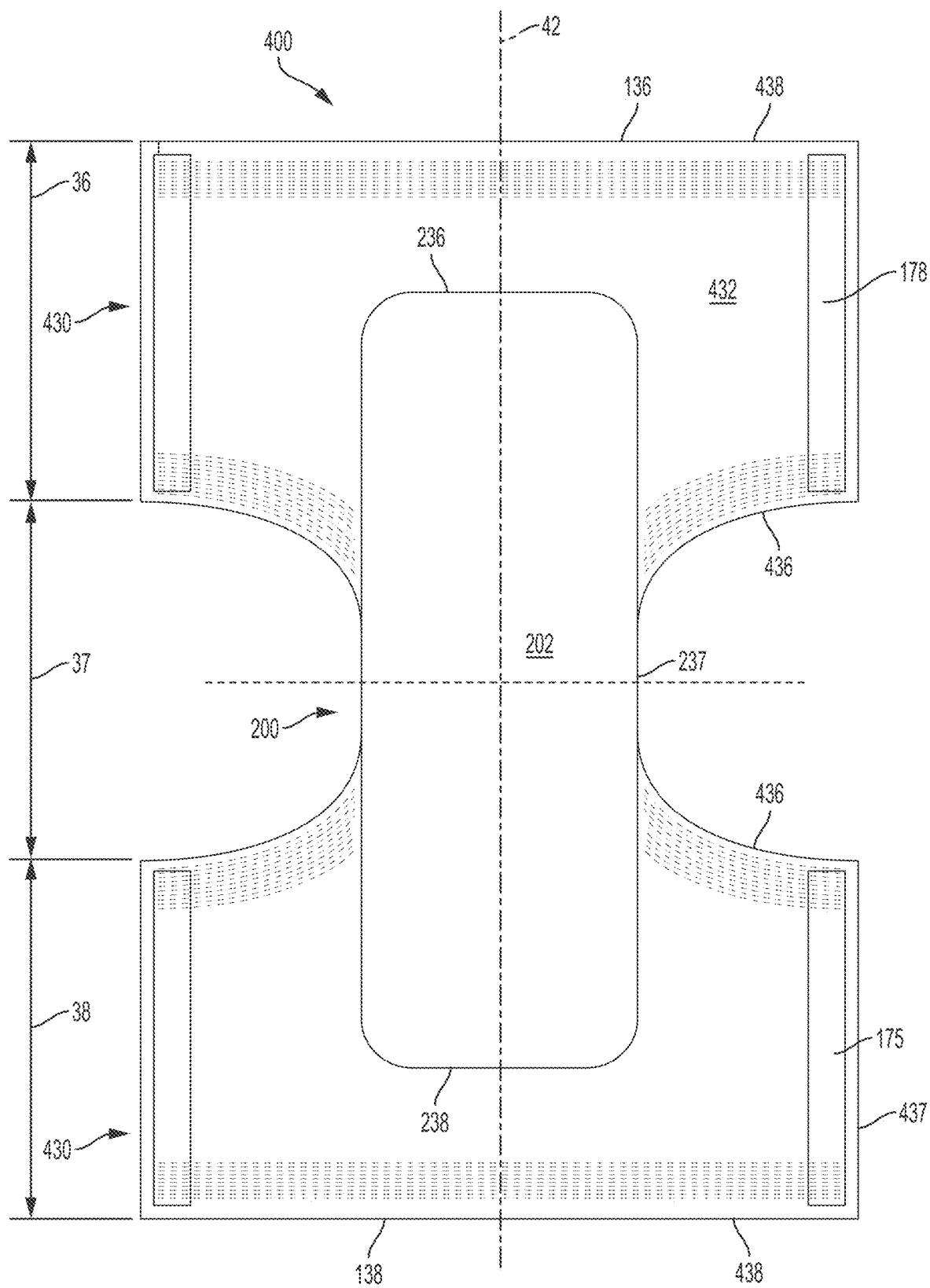
FIG. 23 is a plan view of a pant of FIG. 22.

FIG. 23 is a simplified plan view of the precursor structure (in that it is not formed into a pant having a waist opening and two leg openings) of the pant absorbent article 100 shown in FIG. 1, shown prior to joining of front and rear waist regions 36, 38 along their respective side edges 437. To form pant absorbent article 100, the precursor structure may be folded along lateral axis 44 to bring front and rear waist regions 36, 38 together such that their sides may be joined at or adjacent the side edges 437 along the refastenable seams 174 (as shown in FIG. 1). The embodiment shown in FIG. 23 comprises a fastening system 179 having a fastener 175 and a mating fastener 178 that may be refastenably joined together. Particularly, fastener 175 may be formed with hook elements that join with mating fastener 178 which may be formed with loop elements. Fastener elements 175 may be disposed on an exterior surface of the absorbent article 100, but they may also be placed on an interior surface of the absorbent article 100. Mating Fastener elements 178 may be a discrete member of loop elements or may be an area of loop elements that is part of a nonwoven sheet lining the interior (as shown in FIG. 2) or exterior of the absorbent article 100.

It is understood that when the fastening elements 175 and 178 mate interior surface to interior surface of the absorbent article 100, a flange seam is formed. But, when the fastening elements 175 and 178 mate interior surface to exterior surface of the absorbent article 100, an overlap seam is formed, as illustrated in FIG. 1. The fastening elements 175 and 178 may be fastened during the manufacturing process and/or fastened in the package prior to use by the wearer or caregiver (i.e., the pant may be sold in "closed-form"). Alternatively, the pant may be sold in "open-form," where the fastening elements 175 and 178 are present but are not joined in the package.

Figure 12:
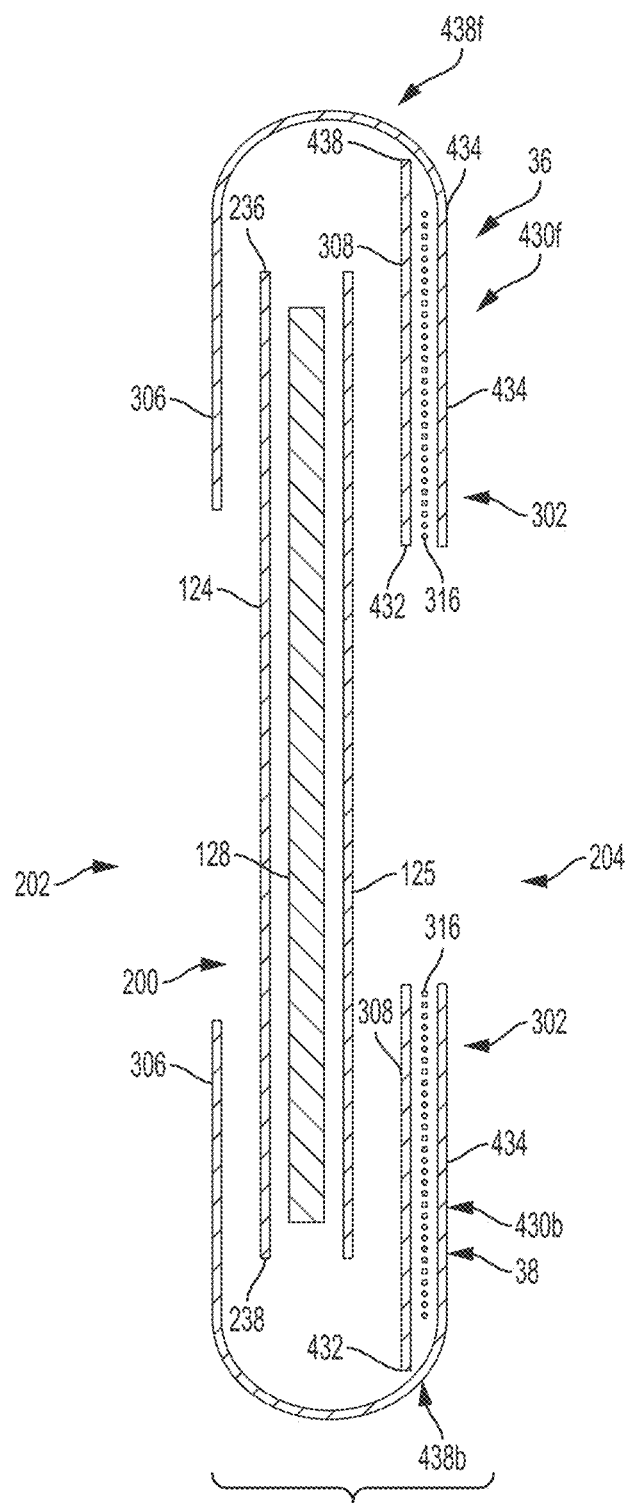
FIG. 12 is a cross section view of the belt pant of FIG. 11 taken along the longitudinal axis 42, showing the longitudinally opposing discrete belts.
Figure 34:
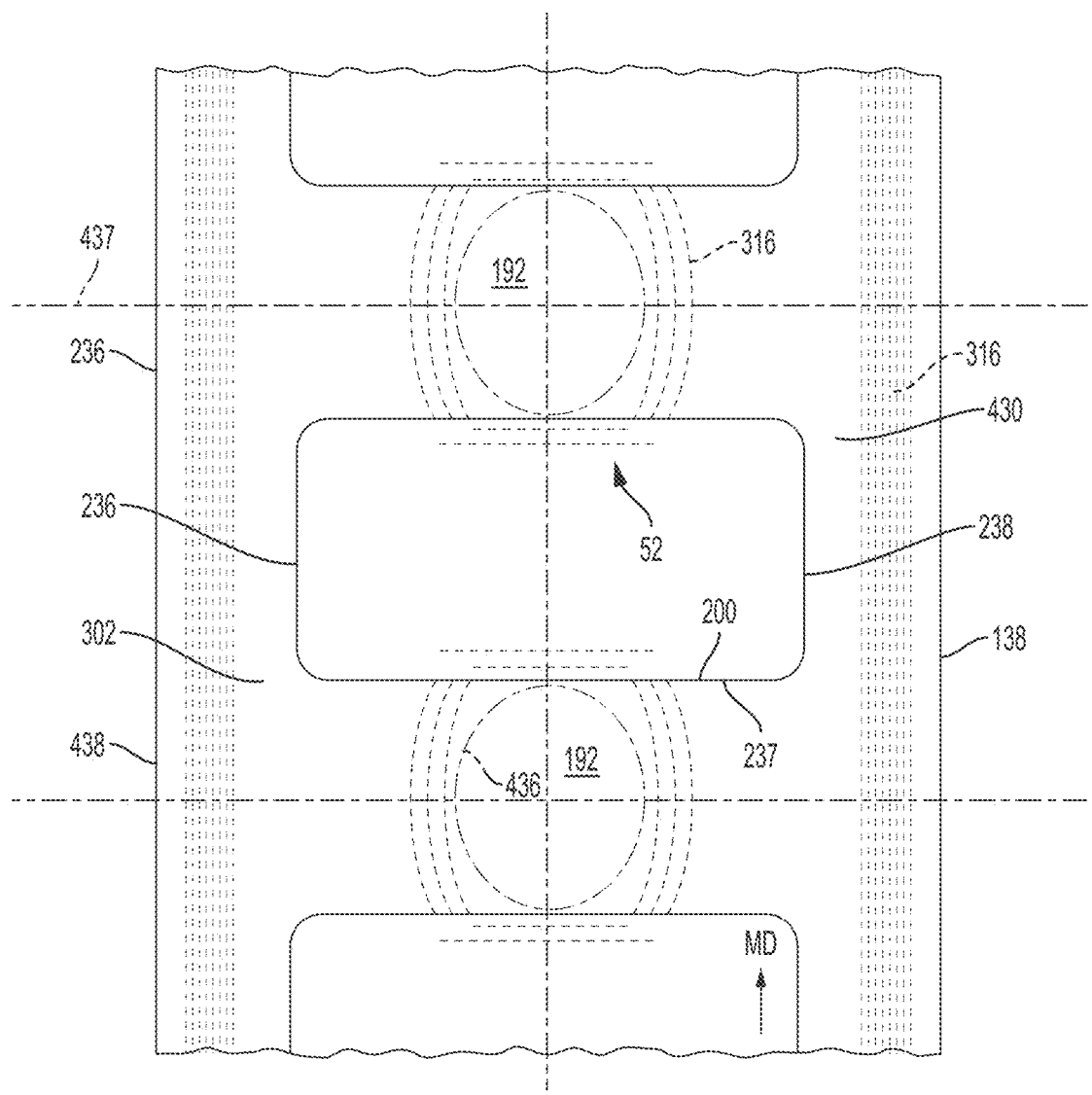
FIG. 34 is a plan view of a continuous web of belt pants comprising shaped front and back belts at the leg openings 192.

Referring to FIGS. 12 and 34, one or both of front and rear waist regions 36, 38 may include an elastomeric laminate 302 of the present disclosure forming at least a portion of one or both of the front and back waist end edges 136, 138 and at least a portion of the leg opening 192. As suggested in FIG. 23, one or a plurality of elastic members forming a portion of the elastomeric laminate 302 at or adjacent the waist may be disposed in a substantially straight lateral orientation, and one or a plurality of leg elastic members forming a portion of the elastomeric laminate 302 at or adjacent the leg opening 192 may be disposed along curvilinear paths to provide hoop wise elastic stretch about the leg openings 192.

Elastic members forming the elastomeric laminate 302, may be in the form of film (e.g., 317) or sections or strips thereof, strips, ribbons, bands, scrims, elastic nonwovens, elastic fibers or strands of circular or any other cross-section, or combinations thereof formed in any configuration of any elastomeric material such as described in, for example, co-pending U.S. application Ser. Nos. 11/478,386 and 13/331,695, and U.S. Pat. No. 6,626,879. A suitable example is LYCRA HYFIT strands, a product of Invista, Wichita, Kans. Some strands for example the aforementioned LYCRA HYFIT may comprise a number of individual fibers wound together to form the strand. With regard to elastic strands formed of a number of individual fibers it has been discovered that the individual fibers can move relative to each other changing the cross sectional shape of the strand as well as becoming unraveled which can lead to poor control of the strands as well as poor bonding/adhering/joining of the elastic strands to one or both of the first substrate layer 306 and second substrate layer 308 of the elastomeric laminate 302. In order to minimize the negatives with regard to strands comprising a plurality of fibers it would be advantageous to minimize the number of fibers in a given strand. It would therefore be desirable to have less than about 40 fibers per strand, less than about 30 fibers per strand, less than about 20 fibers per strand, less than about 10 fibers per strand, less than about 5 fibers per strand and 1 fiber forming the strand. In the case of a single fiber forming the strand which can deliver comparable performance to the multi-fiber strands of the prior art it would be desireable for the fiber to have a fiber decitex from about 22 to about 300 and a fiber diameter from about 50 micrometers to about 185 micrometers.

FIGS. 15A-16K are examples of potential longitudinal partial cross-sections taken along the longitudinal axis 42 through the rear waist region 38 of the elasticized belt and rear region of the pant as shown in FIG. 20, depicting possible configurations. It can be appreciated that in each of these particular examples, the cross-section may substantially mirror a cross-section taken through the front waist region 36 of the elasticized belt 430 and the front region 36 of the pant 100.

Still referring to FIGS. 15A-16K, chassis 200 may have liquid permeable topsheet 124 forming at least a portion of its inner, wearer-facing surface. Topsheet 124 may be formed of a nonwoven web material which is preferably soft and compatible with sensitive skin, and may be formed of and have any of the features of topsheets used in disposable diapers, training pants and inserts including those described in, for example, co-pending U.S. application Ser. No. 12/841,553. Chassis 200 may also have an outward-facing backsheet 125, which may be liquid impermeable. Backsheet 125 may be formed of and have any of the features of backsheets used in disposable diapers and training pants including those described in, for example, the co-pending U.S. patent application referenced immediately above. Chassis 200 may also have an absorbent core 128 disposed between topsheet 124 and backsheet 125. Absorbent core 128 may include one or more absorbent acquisition, distribution and storage material layers and/or components; it may be formed of and have any of the features of absorbent cores used in disposable diapers and training pants.

As suggested in FIGS. 15A-16K, the chassis 200 may be affixed to an elastomeric laminate 302, to the inner, wearer-facing side thereof, or alternatively, to the outer, garment-facing surface thereof. Chassis 200 may be joined to the elastomeric laminate 302 by adhesive, by thermal bonds/welds, mechanical fasteners or a combination thereof. The elastomeric laminate 302, in the form of belts 430 for example, may comprise an elastomeric nonwoven, elastic films, ribbons, scrims, strands or combinations thereof—see FIG. 16G illustrating a belt 430 comprising a film layer 317 in combination with strands 316a and 316b. The elastomeric laminate 302 may be pre-strained prior to joining the elastomeric laminate 302 to the other layers of the article or it may be joined in a relaxed state and subsequently mechanically strained; in such an embodiment, the one or more waist elastic members and the one or more leg elastic members of the elastomeric laminate may be disposed between a first substrate layer 306 and a second substrate layer 308.

Figure 5A:
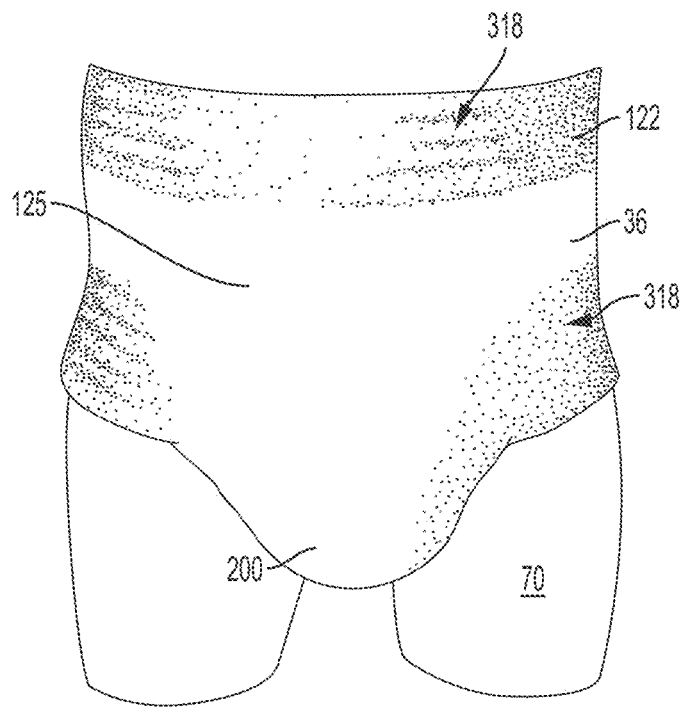
FIG. 5A is a front view of a pant comprising texture fitted on a wearer.
Figure 5B:
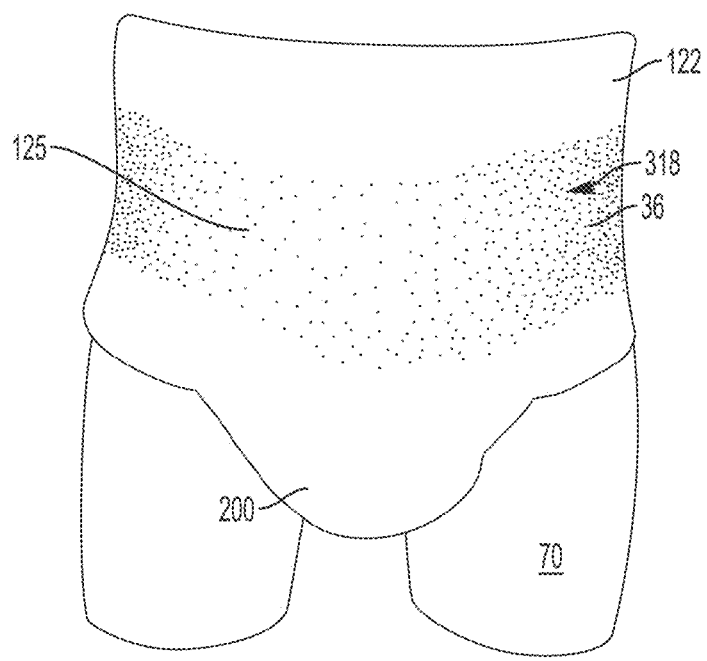
FIG. 5B is a front view of a pant comprising texture fitted on a wearer.
Figure 6A:
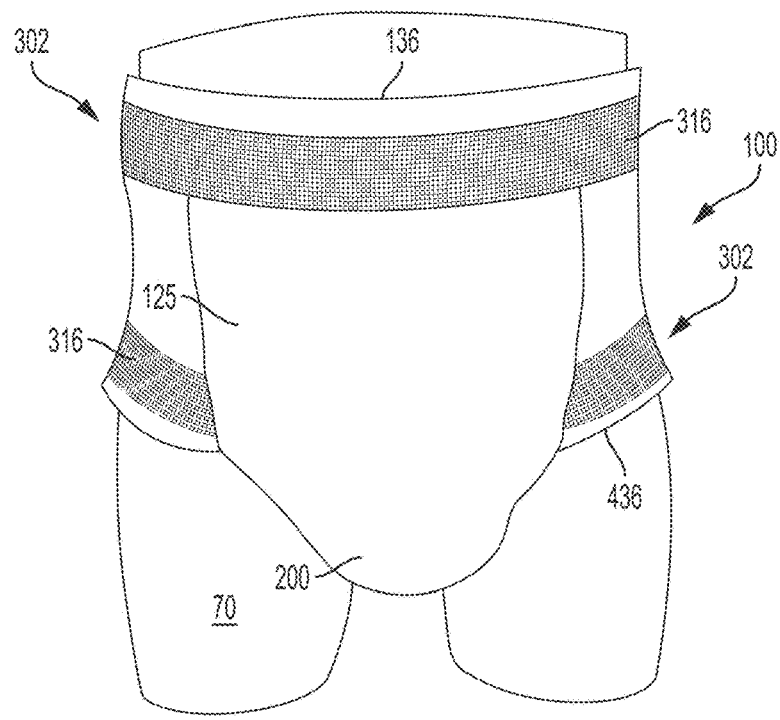
FIG. 6A is a front view of a pant comprising concentrated zones of elastics, the pant fitted on a wearer.
Figure 6B:
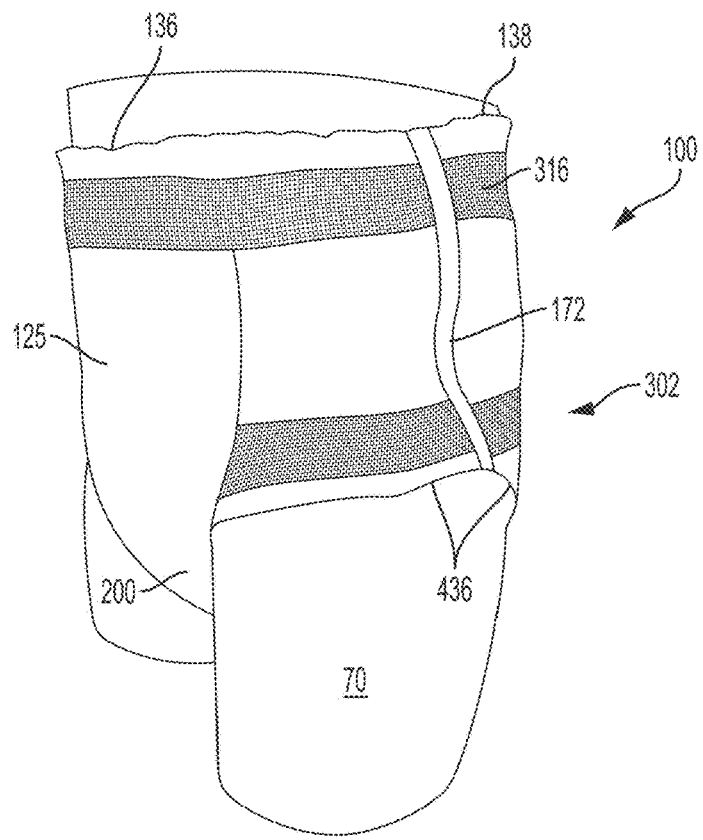
FIG. 6B is a perspective view of a pant comprising concentrated zones of elastics, the pant fitted on a wearer.
Figure 7:
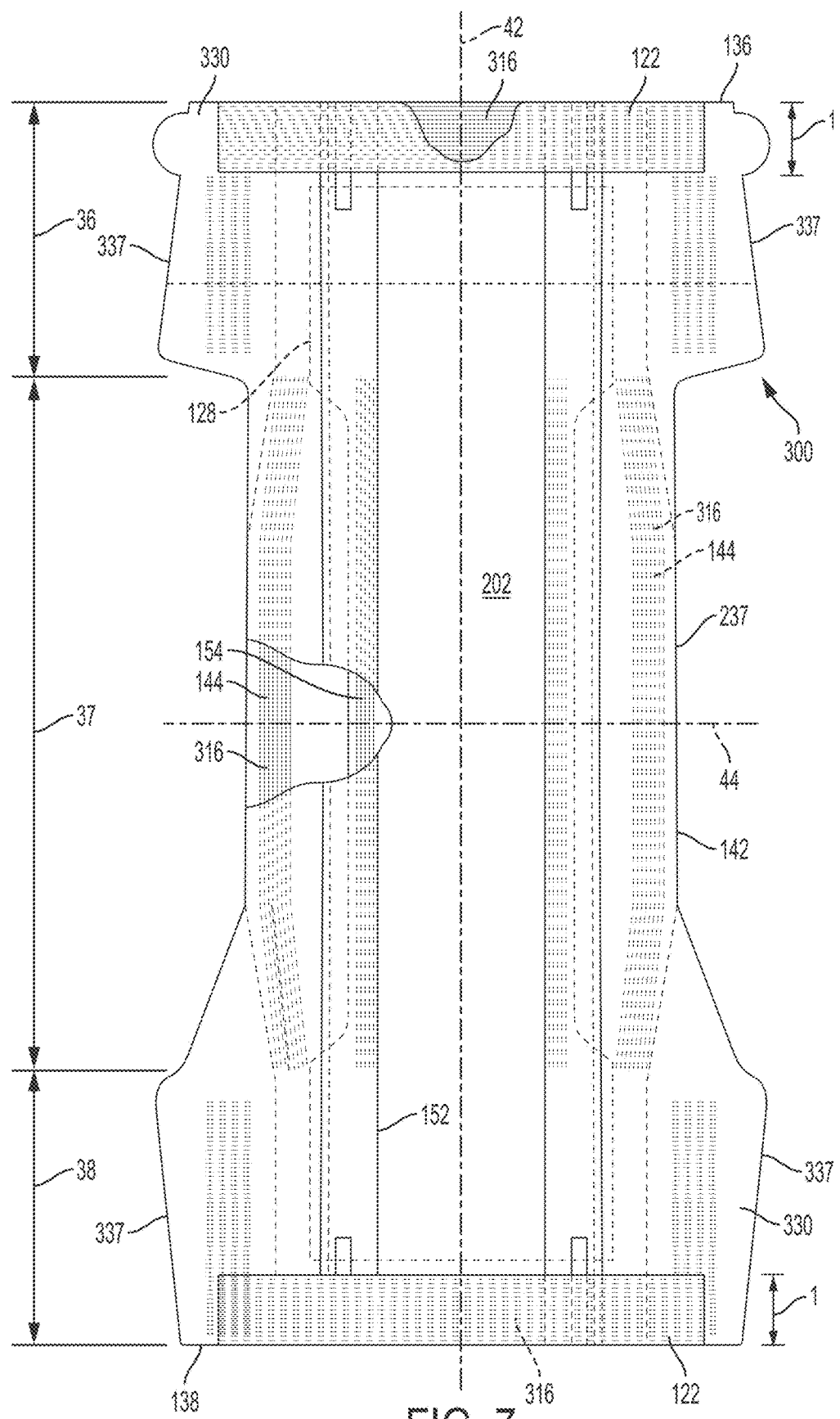
FIG. 7 is a plan view of pant comprising integral side panels.

It should be understood that the elastomeric laminates 302 may be formed in part in accordance with FIGS. 15A-16K as disclosed herein above, as well as in accordance with the disclosure of U.S. 61/646,999, filed on May 15, 2012. Further methods of manufacture and the resulting texture as disclosed by U.S. Ser. Nos. 61/647,061, 61/647,071, 61/647,078, each filed on May 15, 2012, may be used, as well. And, portions of the elastomeric laminates 302 may incorporate the stress, strain, and spacing of the elastics as disclosed in U.S. Ser. No. 61/598,012, filed Feb. 13, 2012. Texture zones 318 may be disposed along the waist edges and leg edges as illustrated in FIG. 5A or along a central area of the article as disclosed in FIG. 5B.

One or more of the absorbent articles described above may comprise texture zones 318 disposed on the chassis 200, as well as on one or each of the side panels 330, elastomeric ear panels 530, belts 430, inner leg cuffs 150, outer leg cuffs 140, waistbands 122, waistcaps 123, chassis 200, topsheet 124 and backsheet 125 such that the texture zones are substantially aligned with each other or they collectively form a large textured zone or unified textural appearance. An overall textural appearance is desired to deliver a holistic garment-like look and feel. It is therefore beneficial if two or more of the aforementioned absorbent article structures (chassis 200, side panels 330, elastomeric ear panels 530, non-elastomeric ear panel 540, belts 430, inner leg cuffs 150, outer leg cuffs 140, waistbands 122, waistcaps 123, topsheet 124 and backsheet 125) comprise materials having one or more identical or substantially identical structural elements selected from the group of Average-Dtex between 10 decitex and 500 decitex (within a +/−50 decitex range), Average-Strand-Spacing from about 0.25 mm to about 5.0 mm (within a +/−1 mm range), Average-Pre-Strain from about 50% to about 400% (within a +/−50% range), a substrate basis weight from about 6 grams per square meter to about 30 grams per square meter (within a +/−5 grams per square meter range) and substrate, e.g. nonwoven layer, texture.

Figure 68:
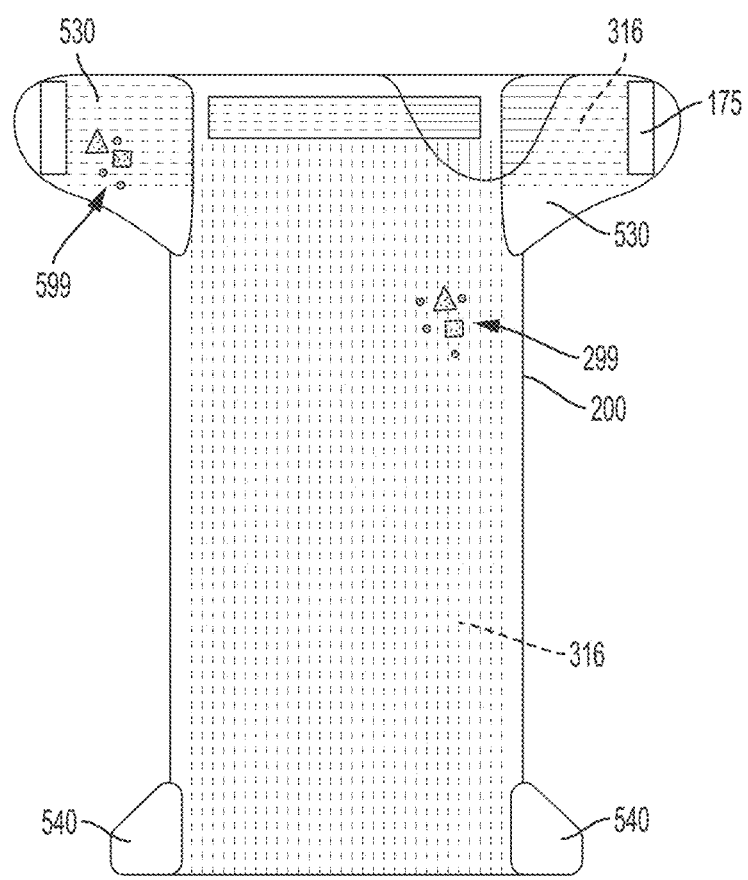
FIG. 68 is a plan view of a pant comprising transversely extending elastics 316 in the elastomeric ear panels 530 and longitudinally extending elastics 316 in the chassis 200.

One or more of the absorbent articles described above may comprise a chassis 200 comprising one or more chassis graphics 299 (see FIG. 20) disposed on or in an overlapping orientation with the chassis 200 and/or a colored backsheet film and/or a tinted backsheet film and/or a colored nonwoven and/or a tinted nonwoven. One or more of the absorbent articles described above may also comprise a chassis 200 comprising one or more chassis graphics 299 disposed on or in an overlapping orientation with the chassis 200 and/or a colored nonwoven and/or a tinted nonwoven and one or more graphics from the group consisting of side panel graphics 399 (see FIG. 67), ear graphics 599 (see FIG. 68), belt graphics 499 (see FIG. 20), waistband graphics 699 (see FIG. 40), and/or outer leg cuff graphics 799 (see FIG. 35), wherein the one or more chassis graphics on the chassis 200 and the one or more graphics disposed on the side panel 330, ear panel 530, belt 430, ear panel 540, waistband 122, and/or outer leg cuff 140 are substantially aligned with each other or they collectively form unified graphic elements or an overall graphical experience.

Donning

The donning benefit of the present disclosure is enabled by elastomeric laminates comprising a greater number of elastic strands having a greater fineness (e.g, a smaller decitex) and a closer spacing than has been previously disclosed or practiced in disposable absorbent articles. These improved laminates can be used as disposable absorbent article (for example, baby and adult taped diapers, baby and adult pants, feminine pads, and feminine liners) components to achieve a variety of benefits in conjunction with and beyond donning, including fit and gasketing at the waist, legs, crotch and sides of the wearer to generally provide the greatest level of extensibility, the most comfortable wearing conditions, improved skin condition (i.e., reduced skin marking), improved leakage protection and a better fit.

Donning-Ratio

Donning ease can be assessed by a Donning-Ratio, as illustrated in FIG. 85. A Donning-Ratio of less than 1 indicates that the consumer's hip width is less than the Relaxed-Product-Waist-Width. Donning-Ratio's less than 1 are not desirable since the products contracted width is greater than the wearer's hip width, and thus, would deliver insufficient pressure against the body to sustain fit. A Donning-Ratio of greater than 1 indicates that the consumer's hip width is greater than the Relaxed-Product-Waist-Width. Donning-Ratio's that approach without falling below 1, while also delivering sufficient pressure for fit, are desirable for ease of donning, wearer comfort, pressure on skin, etc. Donning-Ratio's greater than 2 or even 3 are within the scope of the present disclosure, but require a unique balance of elastic decitex, elastic strand spacing, number of elastics and elastic pre-strain to deliver such a unique blend of properties. The unique set of properties requires elastic decitex that are very low, well below that of the prior art, disposed at elastic to elastic spacing that are also very low, also well below the prior art, which in turn requires a larger number of elastics well above that known in the prior art, and elastic strains that are also low and well below nearly all of the known prior art. The specific set of criteria required to deliver against the aforementioned unmet consumer needs with a single product not only requires unique elastomeric laminate structures but it requires a new process, beamed elastic (a plurality of elastics formed on and delivered from a beam or spool), for delivery of such a large number of low decitex elastics, at low pre-strain and low spacing in order to achieve the right balance of laminate properties. These unique properties enable a higher donning ratio while delivering low force on the skin, Pressure-Under-Strand, ease of application, comfort, fit, etc. Such an approach to the best of our knowledge has never before been disclosed or attempted in the field of absorbent articles; hygiene articles, taped diapers, diaper pants, adult incontinence articles, menstrual products, etc.

The Donning-Ratio is calculated as:

$$\text{Donning-Ratio} = \text{Target-Hip}/[2*\text{Relaxed-Product-Waist-Width}]$$

The Donning-Ratio is unitless. Both the Target-Hip and Relaxed-Product-Waist-Width are in mm.

FIG. 87 shows that for over 90% of consumers, their hip circumference is greater than their waist circumference. Therefore, when donning a closed-form pant, pulling it up over the hip represents the largest body region the pant needs to stretch over.

A product's size range is conveyed to consumers by a weight range and/or a waist range printed on the package. For products recommended by weight range, a Target-Weight is the average of the minimum and maximum recommended weights.

For many adult incontinence products, only a waist recommendation is provided. For these products, a Target-Weight can still be determined by calculating the Average Weight at the minimum and maximum recommended waists. FIG. 88 shows this relationship and calculation.

$$\text{Average Weight (kg)} = 6.8142163*\text{Waist (mm)}^{0.5} - 130.72567$$

Once the Target-Weight for a product is determined, its corresponding Target-Hip is determined as shown on FIG. 89.

$$\text{Target-Hip (mm)} = 102.48574 + 108.62219*\text{Weight (kg)}^{0.5}$$

The tables below show examples of currently marketed stranded closed-form products. The Donning-Ratio's for all are greater than 1.5, with some being as high as 3.0. The tables below illustrate some inventive examples utilizing elastomeric laminates of the present disclosure. The Donning-Ratio's as disclosed herein will make the donning of each easier for consumers and care givers.

| Examples of Donning-Ratio for Existing Stranded Products | | | | | | |
|---|---|---|---|---|---|---|
| | Minimum Weight Target (kg) | Maximum Weight Target (kg) | Average Targeted Weight (kg) | Targeted Hip (mm) | Relaxed Product Waist Width (mm) | Donning-Ratio (unitless) |
| Moony Man Air Fit | | | | | | |
| size S | 4 | 8 | 6.0 | 369 | 122 | 1.51 |
| size M | 5 | 9 | 7.0 | 390 | 111 | 1.76 |
| size LG | 9 | 14 | 11.5 | 471 | 129 | 1.82 |
| size BIG | 12 | 17 | 14.5 | 516 | 146 | 1.76 |
| size BIGGER THAN BIG | 13 | 25 | 19.0 | 576 | 139 | 2.07 |
| size SUPER | 18 | 35 | 26.5 | 662 | 152 | 2.17 |
| Goo.N Yawaraka Fit Pants | | | | | | |
| size S | 5 | 9 | 7.0 | 390 | 93 | 2.10 |
| size M | 7 | 12 | 9.5 | 437 | 84 | 2.59 |
| size LG | 9 | 14 | 11.5 | 471 | 92 | 2.56 |
| size BIG | 12 | 20 | 16.0 | 537 | 105 | 2.55 |
| size BIGGER THAN BIG | 13 | 25 | 19.0 | 576 | 96 | 3.01 |
| size SUPER | 15 | 35 | 25.0 | 646 | 117 | 2.76 |
| Pampers Sara Sara Pants | | | | | | |
| size S | 4 | 8 | 6.0 | 369 | 111 | 1.66 |
| size M | 6 | 10 | 8.0 | 410 | 89 | 2.31 |
| size L | 9 | 14 | 11.5 | 471 | 102 | 2.30 |
| Merries Pull-Ups | | | | | | |
| size M | 6 | 10 | 8.0 | 410 | 125 | 1.64 |
| size L | 9 | 14 | 11.5 | 471 | 131 | 1.79 |
| | Minimum Weight Target (mm) | Maximum Weight Target (mm) | Average Targeted Weight (kg) | Targeted Hip (mm) | Relaxed Product Waist Width (mm) | Donning-Ratio (unitless) |
| Depend Fit-Flex Underwear for Women-Moderate | | | | | | |
| size S/M | 711 | 1016 | 69 | 1003 | 230 | 2.18 |
| size L | 965 | 1270 | 97 | 1170 | 231 | 2.53 |
| size XL | 1219 | 1626 | 126 | 1320 | 249 | 2.65 |
| Always Discreet Boutique | | | | | | |
| size S/M | 711 | 1016 | 69 | 1003 | 286 | 1.75 |
| size L | 965 | 1270 | 97 | 1170 | 304 | 1.92 |

| Examples of Donning-Ratio for Inventive Products | | | | | | |
|---|---|---|---|---|---|---|
| Inventive Beamed Product | Minimum Weight Target (kg) | Maximum Weight Target (kg) | Average Targeted Weight (kg) | Targeted Hip (mm) | Relaxed Product Waist Width (mm) | Donning-Ratio (unitless) |
| size M | 6 | 10 | 8 | 410 | 145 | 1.41 |
| size L | 9 | 14 | 12 | 471 | 170 | 1.38 |
| Inventive Beamed Product | Minimum Weight Target (mm) | Maximum Weight Target (mm) | Average Targeted Weight (kg) | Targeted Hip (mm) | Relaxed Product Waist Width (mm) | Donning-Ratio (unitless) |
| size S/M | 711 | 1016 | 69 | 1003 | 340 | 1.48 |
| size L | 965 | 1270 | 97 | 1170 | 400 | 1.46 |

FIGS. 91A and 91B illustrate the interdependence between: strand decitex; strand spacing; Section-Modulus; Donning-Ratio and Pressure-Under-Strand, and how the unique properties enabled by the elastomeric laminates of the present invention are able to deliver low pressure on the skin, comfortable fit and donning ease while delivering a sufficient hoop force of 7 gf/mm providing sustained fit and gasketing of the article. While this particular example utilizes an Average-Dtex of 150 and a hoop pressure on the body of 7 gf/mm, the relative relationships between the various metrics remain consistent. FIG. 91A shows that as strand spacing decreases, the Donning-Ratio lessens (making donning easier) due to lower required pre-strain needed to deliver the 7 gf/mm thereby enabling improved donning while maintaining the requisite forces for fit and gasketing. FIG. 91B shows that as the strand spacing decreases, the corresponding Pressure-Under-Strand decreases while maintaining a hoop pressure on the body of 7 gf/mm thereby maximizing overall comfort and skin health while maintaining the requisite forces for fit and gasketing of the article.

Open-Form Taped Article

Open-form, taped-style, absorbent articles are generally disclosed in FIGS. 38-47 and 84. The taped diaper 500, open-form taped article, may comprise elastomeric ear panels 530 in one or both of the front waist region 36 and back waist region 38. The elastomeric ear panels 530 may be formed (joined and/or positioned) in a particular place or position and may be unitary structurally with other elements of the article 100 or as a separate element joined to another element of the article 100. The elastomeric ear panels 530 provide an elastically extensible feature that provides a more comfortable and contouring fit by initially conformably fitting the article 100 to the wearer and sustaining this fit throughout the time of wear well past when the taped diaper 500 has been loaded with exudates since the elastomeric ear panels 530 allows the diaper to expand and contract to fit the wearer 70 and compensate for movements of the wearer 70. Further, the elastomeric ear panels 530 develop and maintain wearing forces (tensions) and enhance the tensions developed and maintained by the fastening system 179, primary fasteners 175, to maintain the article 100 on the wearer and enhance the fit. The elastomeric ear panels 530 especially assist in maintaining the primary line of tension formed by the fastening system 179 allowing the diaper to conformably fit over the hips of the wearer where there is dynamic motion, and initially pre-tensioning the waist opening 190 and leg opening 192 since the diaperer typically stretches the elastomeric ear panels 530 when applying the taped diaper 500 on the wearer so that when the elastomeric ear panels 530 contract, tension is transmitted from the elastomeric ear panels 530 along the waist opening 190 and along at least a portion of the leg opening 192. The elastomeric ear panels 530 further provide more effective application of the diaper since even if the diaperer pulls one elastomeric ear panel further than the other during application (asymmetrically), the diaper will "self-adjust" during wear. While the open-form article of the present disclosure may have the elastomeric ear panels 530 disposed in the back waist region 38, alternatively, the taped diaper 500 may be provided with elastomeric ear panels 530 disposed in the front waist region 36 or in both the front waist region 36 and the back waist region 38. The open-form article may also have elastomeric ear panels 530 disposed in a first waist region and elastomeric ear panels 530 or non-elastomeric ear panels 540 disposed in a second waist region.

As shown in FIGS. 38-40 and 45-47 the taped diaper 500, open-form, may comprise first and second elastomeric ear panels 530 disposed in a first waist region. The taped diaper may also comprise an elastomeric waistband 122 disposed in one or both waist regions. The taped diaper may also comprise a substantially rectangular chassis 200.

Figure 38:
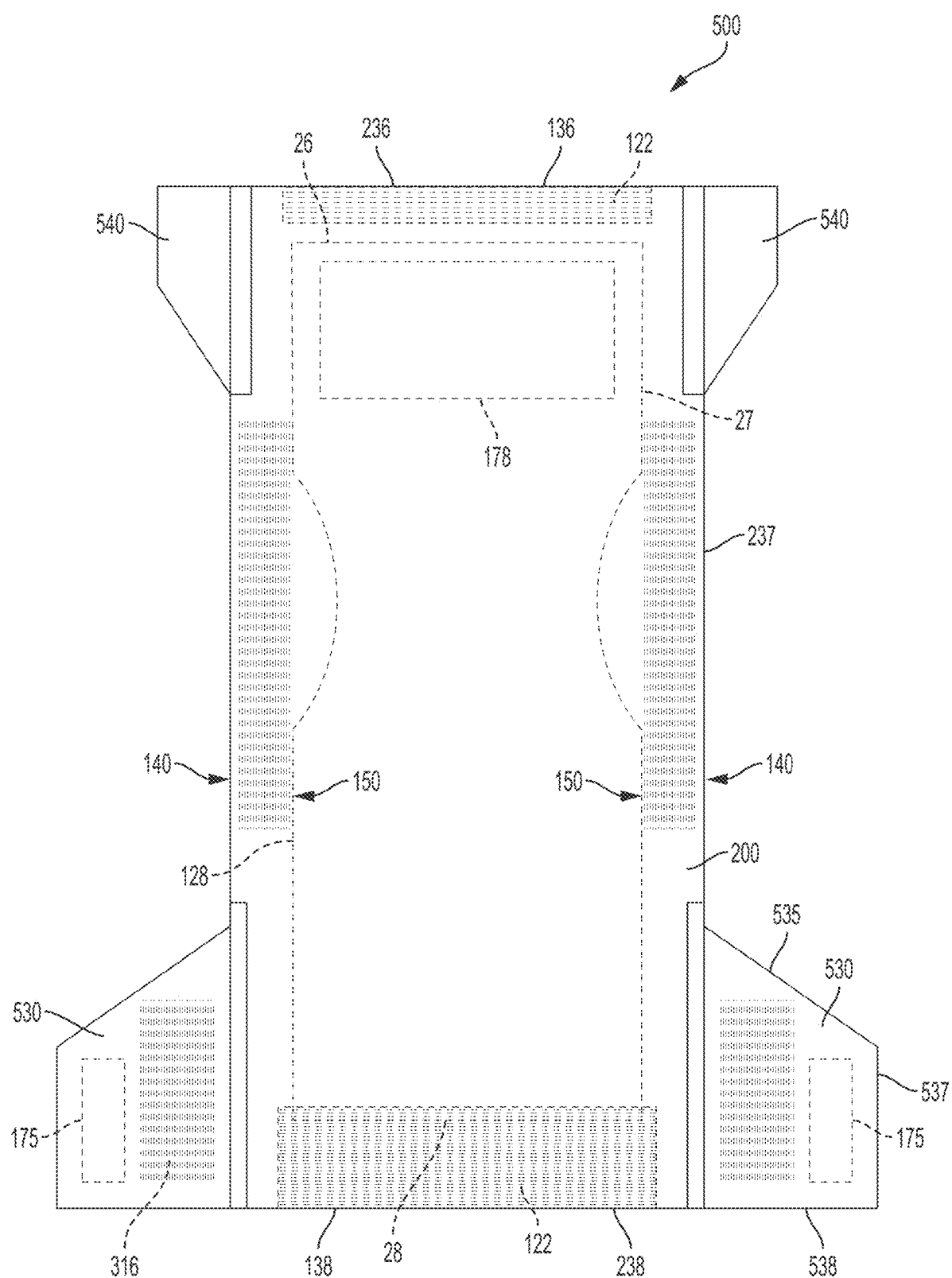
FIG. 38 is a plan view of a taped diaper comprising a rectangular chassis, a pair of shaped discrete elastomeric ear panels 530 and a pair of shaped discrete non-elastomeric ear panels 540.

In addition to a pair of laterally opposing elastomeric ear panels 530 in a first waist region the tape diaper 500 may comprise a pair of laterally opposing discrete non-elastomeric ear panels 540 disposed in a second waist region, wherein one or both of the ear panels 530 and the ear panels 540 are non-rectangular as shown in FIG. 38. Alternatively, as illustrated in FIG. 39, the tape diaper may comprise a pair of laterally opposing elastomeric ear panels 530 disposed in a first waist region and a pair of laterally opposing integral non-elastomeric ear panels 540 formed in part by a portion of one or more of the backsheet 125, topsheet 124, outer leg cuff 140, or landing zone and being disposed in a second waist region.

Figure 39:
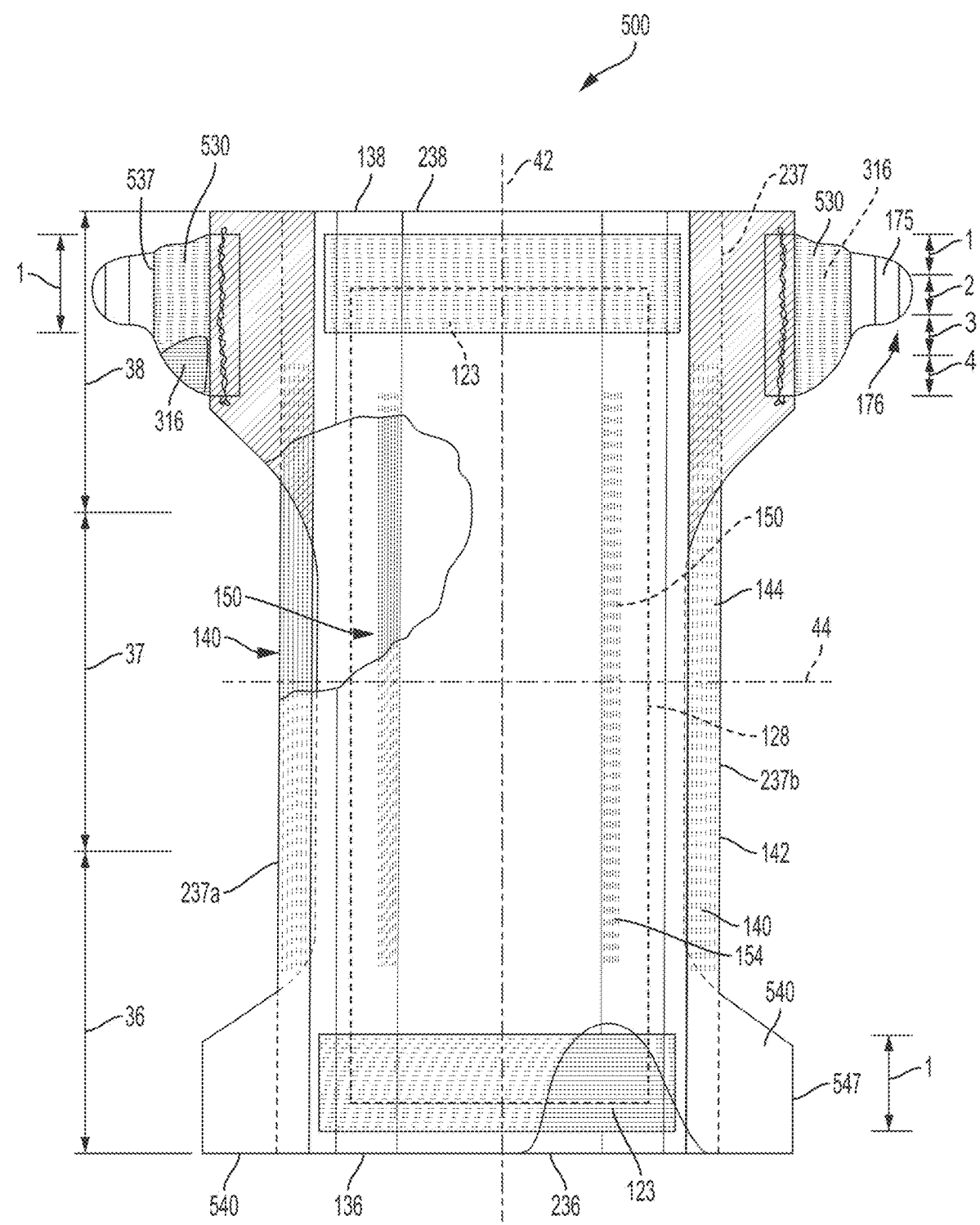
FIG. 39 is a plan view of a taped diaper comprising a rectangular chassis, a pair of shaped discrete elastomeric ear panels 530 and a pair of shaped discrete non-elastomeric ear panels 540.
Figure 40:
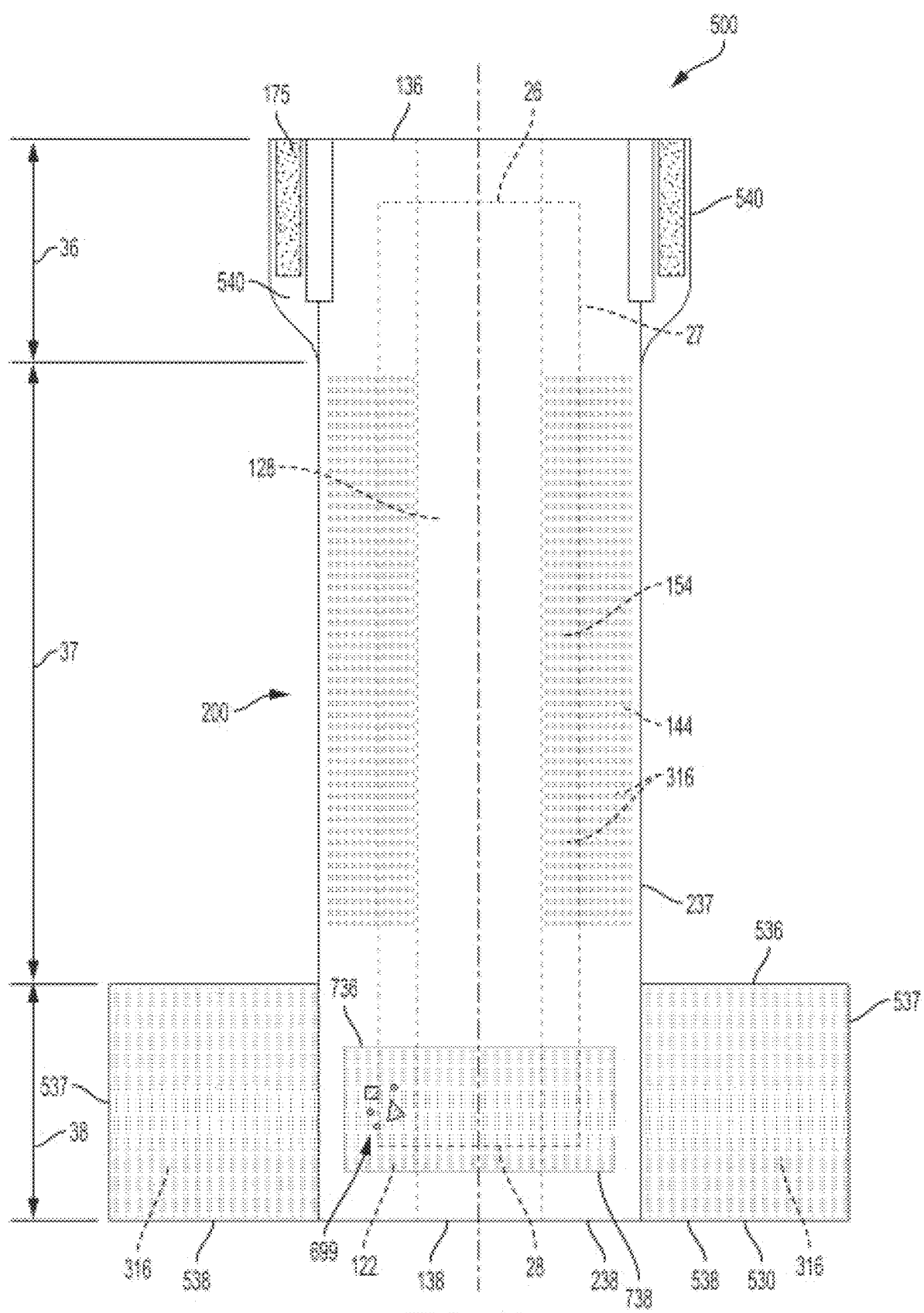
FIG. 40 is a plan view of a taped diaper comprising a rectangular chassis, a pair of shaped discrete elastomeric ear panels 530 and a pair of shaped discrete non-elastomeric ear panels 540.

The taped diaper 500 may comprise first and second non-elastomeric ear panels 540 disposed in a first waist region and an elastomeric waistband 122 disposed in a first waist region as illustrated in FIG. 39.

Figure 41:
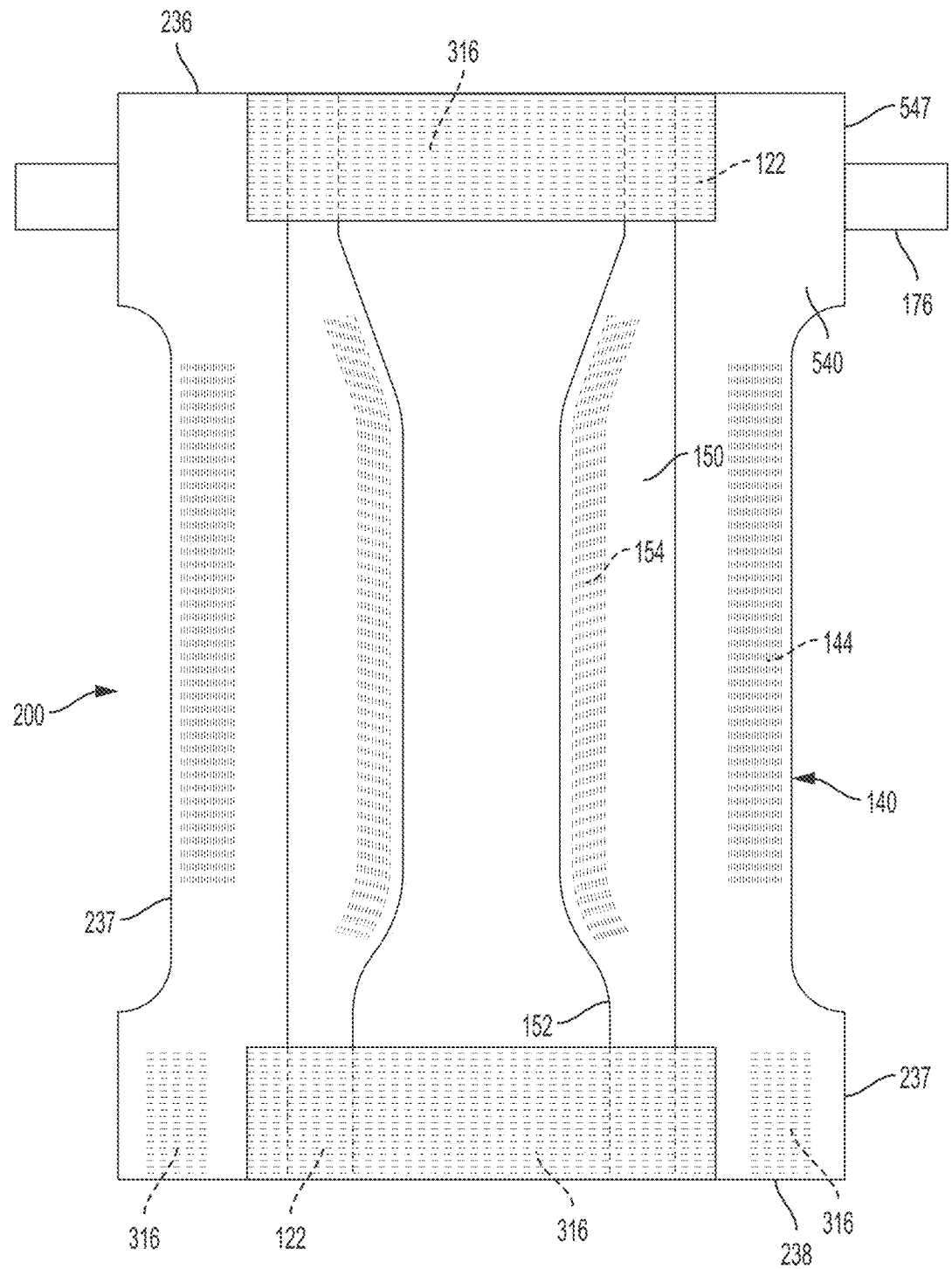
FIG. 41 is a plan view of a taped diaper.

The elastomeric waistband 122 may have a lateral width that is >60% of a lateral width of the center chassis 200 and the center chassis may comprise a pair of laterally opposing fasteners 175 disposed in the same waist region as the waistband 122. The taped diaper 500 may have a waistband 122 that may overlap portions of two or more of an absorbent core 128 and/or a topsheet 124 and/or the inner leg cuffs 150 as illustrated in FIG. 41.

Figure 45:
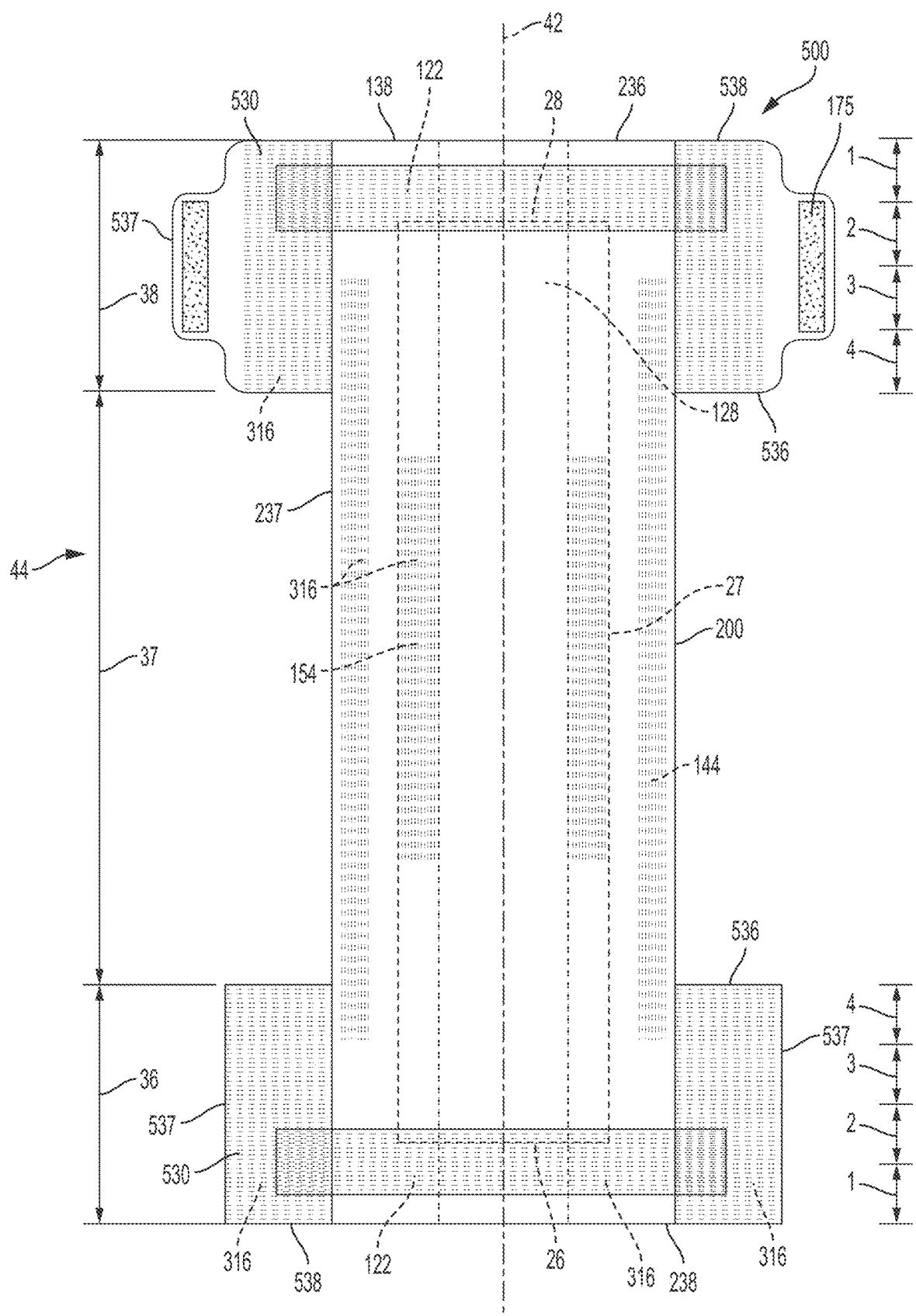
FIG. 45 is a plan view of a taped diaper comprising a pair of discrete elastomeric ear panels in the front and back waist regions, showing waist bands overlapping the elastics of the elastomeric ear panels.

The taped diaper 500 may comprise a pair of laterally opposing front ear panels 540 joined to the chassis 200 in the front waist region 36 and a pair of laterally opposing elastomeric ear panels 530 joined to the chassis 200 in the back waist region 38. The chassis 200 of the taped diaper 500 may be substantially rectangular as shown in FIGS. 38 and 45. Alternatively the chassis 200 may be non-rectangular, e.g. a portion of the laterally opposing side edges 237 or a portion of the longitudinally opposing end edges 136 and 138 of the chassis may be notched or curved either convexly or concavely as shown in FIG. 39 and FIG. 47.

Figure 42:
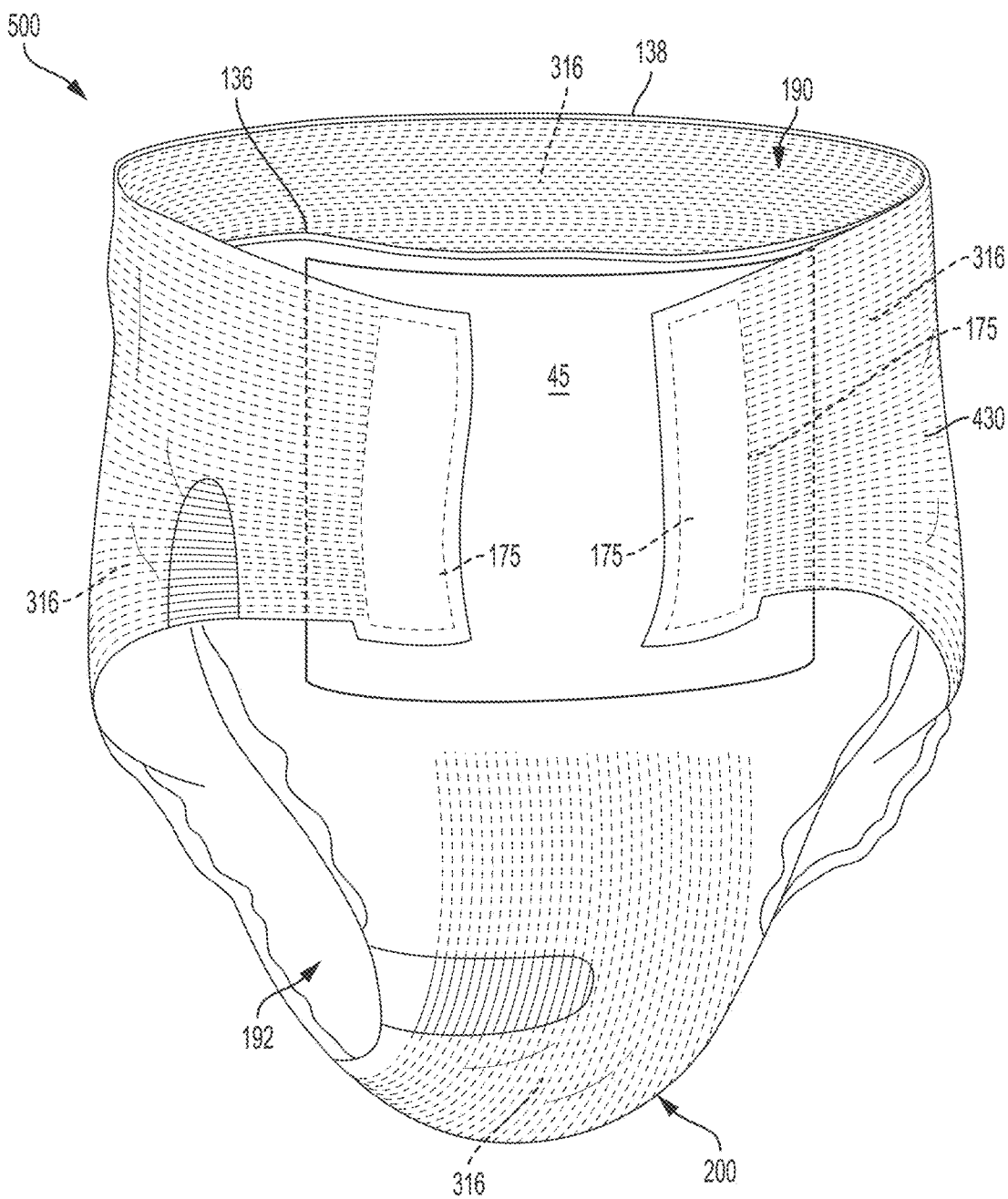
FIG. 42 is a perspective front view of a taped diaper comprising a belt disposed in the back waist region 38 and fastened to the front waist region 36, and showing an elasticized chassis.
Figure 43:
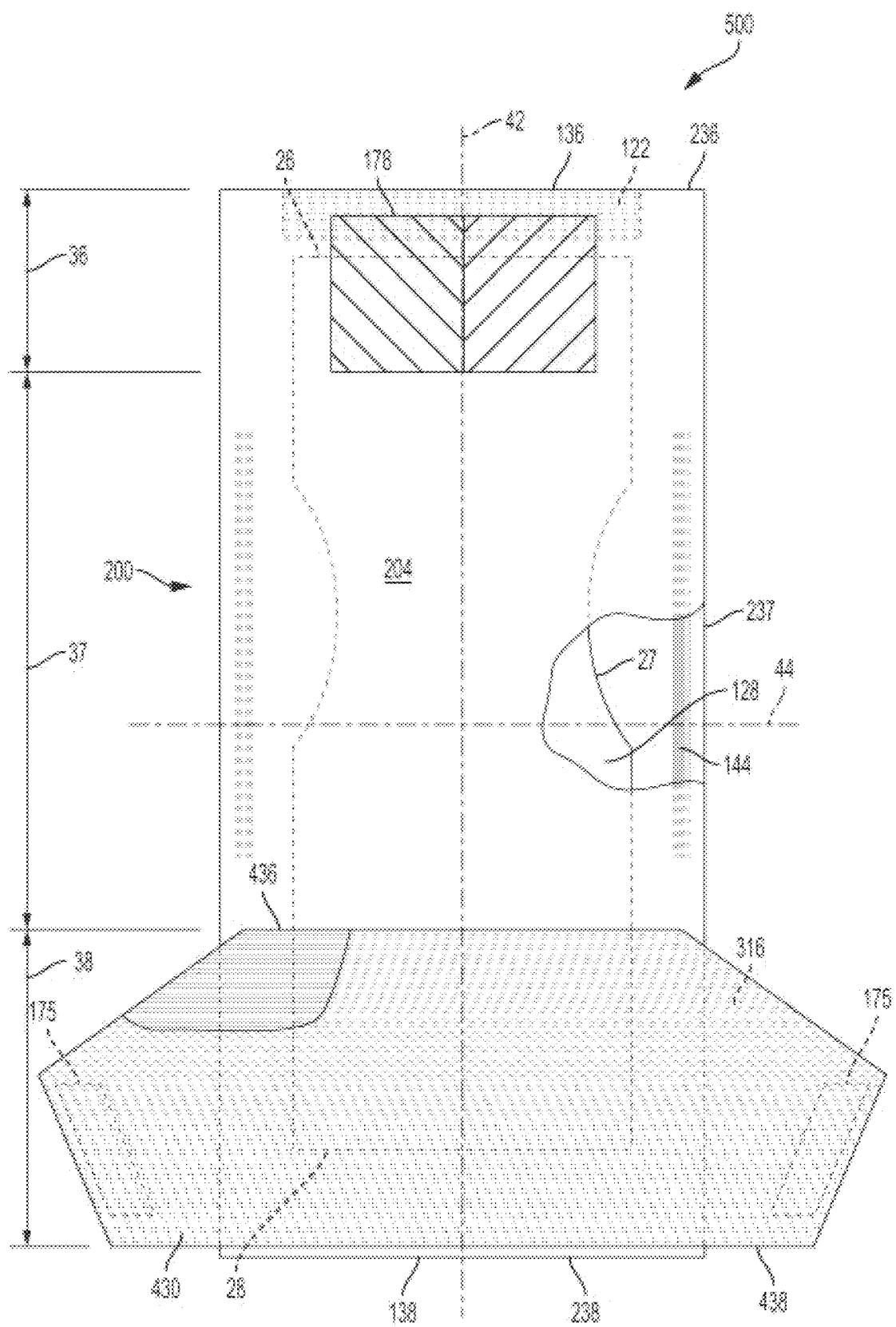
FIG. 43 is a plan view of a taped diaper comprising a shaped, non-rectangular, belt in the back waist region 38.
Figure 44:
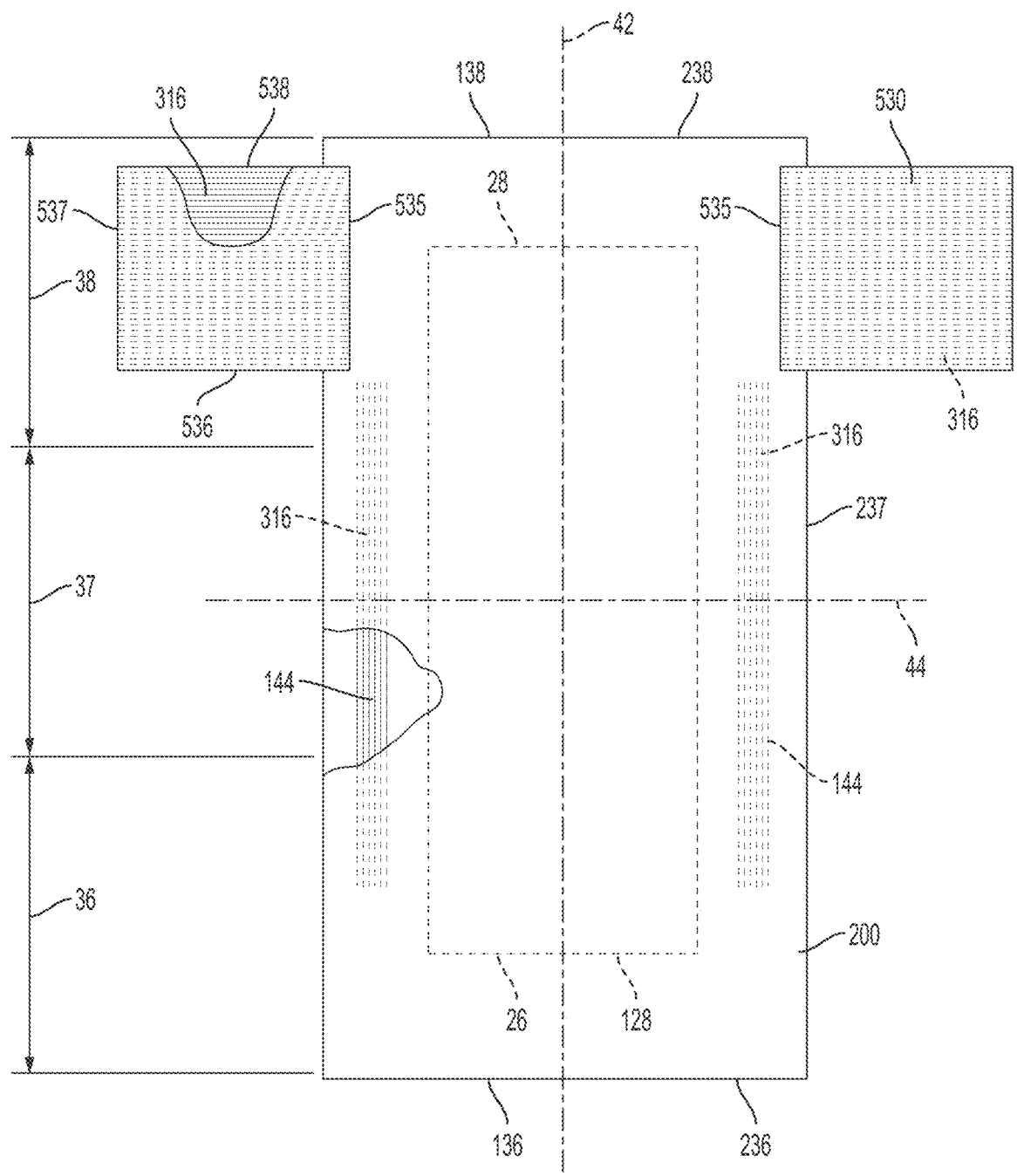
FIG. 44 is a plan view of a taped diaper comprising a pair of discrete elastomeric ear panels 530 and a rectangular chassis 200.

In an alternative embodiment illustrated in FIGS. 42 and 43 the open-form, taped-style, absorbent articles may comprise an elastomeric belt 430 disposed in one of the waist regions. The elastomeric belt 430 may be formed (joined and/or positioned) in a particular place or position and may be unitary structurally with other elements of the article 100 or as a separate element joined to another element of the article 100. The elastomeric belt 430 provides an elastically extensible feature that provides a more comfortable and contouring fit by initially conformably fitting the article 100 to the wearer and sustaining this fit throughout the time of wear well past when the taped diaper 500 has been loaded with exudates. In a preferred embodiment of a belted taped diaper the elastomeric belt 430 is disposed in the back waist region 38. The elastomeric belt 430 may have fasteners disposed at or adjacent the laterally opposing ends of the belt. The fasteners 175, disposed on the interior surface of the belt 430 are designed to engage with a mating fastening component 178 or with the exterior surface 204 of the article to fasten the article on the wearer.

Topsheets

The absorbent articles 100 of the present disclosure may comprise a topsheet 124. The topsheet 124 is the part of the absorbent article 100 that is in contact with the wearer's skin. The topsheet 124 may be joined to portions of the backsheet 125, the absorbent core 128, the leg cuffs 52, and/or any other layers as is known to those of ordinary skill in the art. The topsheet 124 may be compliant, soft-feeling, and non-irritating to the wearer's skin. Further, at least a portion of, or all of, the topsheet may be liquid permeable, permitting liquid bodily exudates to readily penetrate through its thickness. A suitable topsheet may be manufactured from a wide range of materials, such as porous foams, reticulated foams, apertured plastic films, woven materials, nonwoven materials, woven or nonwoven materials of natural fibers (e.g., wood or cotton fibers), synthetic fibers or filaments (e.g., polyester or polypropylene or bicomponent PE/PP fibers or mixtures thereof), or a combination of natural and synthetic fibers. The topsheet may have one or more layers. The topsheet may be apertured, may have any suitable three-dimensional features, and/or may have a plurality of embossments (e.g., a bond pattern). The topsheet may be apertured by overbonding a material and then rupturing the overbonds through ring rolling, such as disclosed in U.S. Pat. No. 5,628,097, to Benson et al., issued on May 13, 1997 and disclosed in U.S. Pat. Appl. Publication No. US 2016/0136014 to Arora et al. Any portion of the topsheet may be coated with a skin care composition, an antibacterial agent, a surfactant, and/or other beneficial agents. The topsheet may be hydrophilic or hydrophobic or may have hydrophilic and/or hydrophobic portions or layers. If the topsheet is hydrophobic, typically apertures will be present so that bodily exudates may pass through the topsheet.

Typical absorbent article topsheets have a basis weight of from about 5 gsm to about 50 gsm, from about 10 to about 35 gsm or from about 12 to about 30 gsm, but other basis weights are within the scope of the present disclosure.

Absorbent articles of the present disclosure may comprise three-dimensional, liquid permeable substrates forming a portion of or all of the topsheet 124 as described in U.S. Ser. Nos. 14/656,820; 14/680,394; and Ser. No. 14/680,426. These substrates may also comprise apertures. The texture of the three dimensional substrates forming the topsheet may be identical or substantially identical to substrates forming one or both surfaces of one or more of the chassis 200, side panels 330, elastomeric ear panels 530, non-elastomeric ear panel 540, belts 430, inner leg cuffs 150, outer leg cuffs 140, waistbands 122, waistcaps 123 and backsheet 125.

The topsheet 124 may also comprise topsheet graphics disposed on one or both surfaces of the topsheet 124. The topsheet graphics may be coordinated with graphics on other components of the article 100, e.g. chassis 200, side panel 330, ear panel 530, belt 430, waistband 122 and backsheet 125. In addition, graphics may be disposed on the exterior of the article 100 that coordinate with the topsheet graphics to make the absorbent article 100 have the appearance of underwear wherein the interior of the article has a similar pattern, color, etc. to the exterior of the article 100. The graphics may also highlight various structural elements within the article, e.g. the channels in the absorbent core.

A portion or the entirety of the topsheet may comprise a first substrate layer 306 and a second substrate layer 308 and may also comprise an elastic material, for example elastic strands 316, disposed between the first and second substrate layers 306 and 308. The first substrate layer 306 and the second substrate layer 308 may be separate and discrete layers or alternatively the first substrate layer 306 and second substrate layer 308 may be formed from a single web of material that is folded to form the first substrate layer 306 and second substrate layer 308 as described previously. In some configurations of the topsheet, the elastic material forming the topsheet may be an elastomeric laminate 302 and may comprise a plurality of elastic strands 316. The topsheet may further comprise one or more large apertures intended to allow bodily exudates to pass easily there through.

Backsheets

The absorbent article 100 of the present disclosure may comprise a backsheet 125. The backsheet 125 is generally that portion of the absorbent article 100 positioned proximate to the garment-facing surface of the absorbent core 128. The backsheet 125 may be joined to portions of the topsheet 124, the absorbent core 128, and/or any other layers of the absorbent article by any attachment methods known to those of skill in the art. The backsheet film 126 prevents, or at least inhibits, the bodily exudates absorbed and contained in the absorbent core 128 from soiling articles such as bedsheets, undergarments, and/or clothing. The backsheet is typically liquid impermeable, or at least substantially liquid impermeable. The backsheet may, for example, be or comprise a thin plastic film, such as a thermoplastic film having a thickness of about 0.012 mm to about 0.051 mm. Other suitable backsheet materials may include breathable materials which permit vapors to escape from the absorbent article, while still preventing, or at least inhibiting, bodily exudates from passing through the backsheet.

A portion or the entirety of the backsheet 125 may be formed by an elastomeric laminate 302 comprising a first substrate layer 306 and a second substrate layer 308 and an elastic material, for example elastic strands 316, disposed between the first and second substrate layers 306 and 308. The first substrate layer 306 and the second substrate layer 308 may be separate and discrete layers or alternatively the first substrate layer 306 and second substrate layer 308 may be formed from a single web of material that is folded to form the first substrate layer 306 and second substrate layer 308 as described previously. In some configurations the backsheet film 126 of the backsheet 125, may form the first substrate layer 306 and the backsheet nonwoven 127 may form the second substrate layer 308 of the elastomeric laminate 302. In an alternative embodiment, one of the belt layers, inner belt layer 432 or outer belt layer 434 may form one of the first or second substrate layers 306 and 308 of the elastomeric laminate 302 overlaying and forming a portion of the backsheet 125 in the crotch region 37 of the absorbent article 100.

Leg Cuffs

The absorbent articles 100 of the present disclosure may comprise leg cuffs 52, which include inner leg cuffs 150 and outer leg cuffs 140. The inner leg cuffs 150 may be positioned laterally proximal of outer leg cuffs 140. Each barrier leg cuff 32 may be formed by a piece of material which is bonded to the absorbent article 100 so it can extend upwards from a wearer-facing surface of the absorbent article 100 and provide improved containment of body exudates approximately at the junction of the torso and legs of the wearer. The inner leg cuffs 150 are delimited by a proximal edge joined directly or indirectly to the topsheet and/or the backsheet and a free terminal edge, which is intended to contact and form a seal with the wearer's skin. The inner leg cuffs 150 may extend at least partially between the front end edge 136 and the back end edge 138 of the absorbent article 100 on opposite sides of the longitudinal axis 42 and may be at least present in the crotch region 37. The inner leg cuffs 150 may each comprise one or more elastics 316 (e.g., elastic strands or strips) near or at the free terminal edge. These elastics 3316 cause the inner leg cuffs 150 to help form a seal around the legs and torso of a wearer. The outer leg cuffs 140 extend at least partially between the front end edge 136 and the back end edge 138. The outer leg cuffs 140 essentially cause portions of the absorbent article 100 proximate to the chassis side edges 237a and 237b to help form a seal around the legs of the wearer. The outer leg cuffs 140 may extend at least within the crotch region 37.

Figure 52:
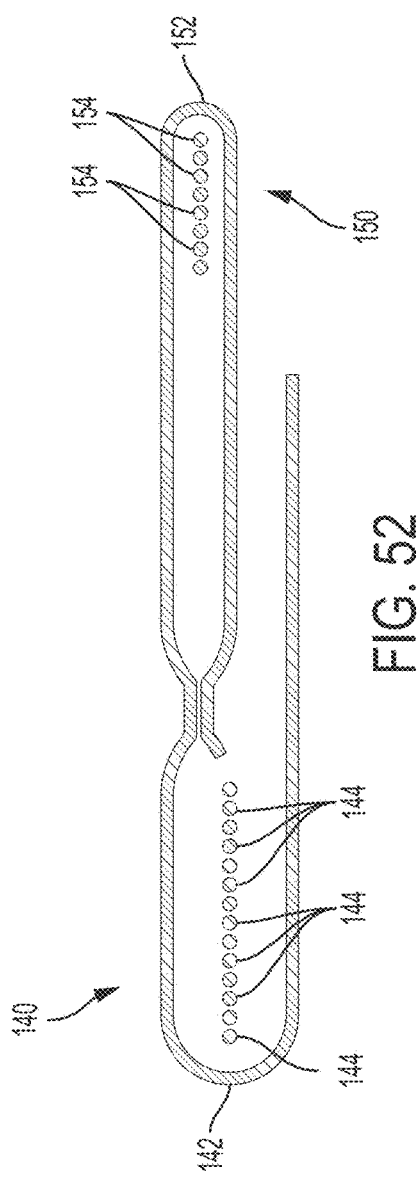
FIG. 52 is a cross section view of an inner leg cuff 150 and outer leg cuff 140 structure formed by a folded nonwoven web.
Figure 53:
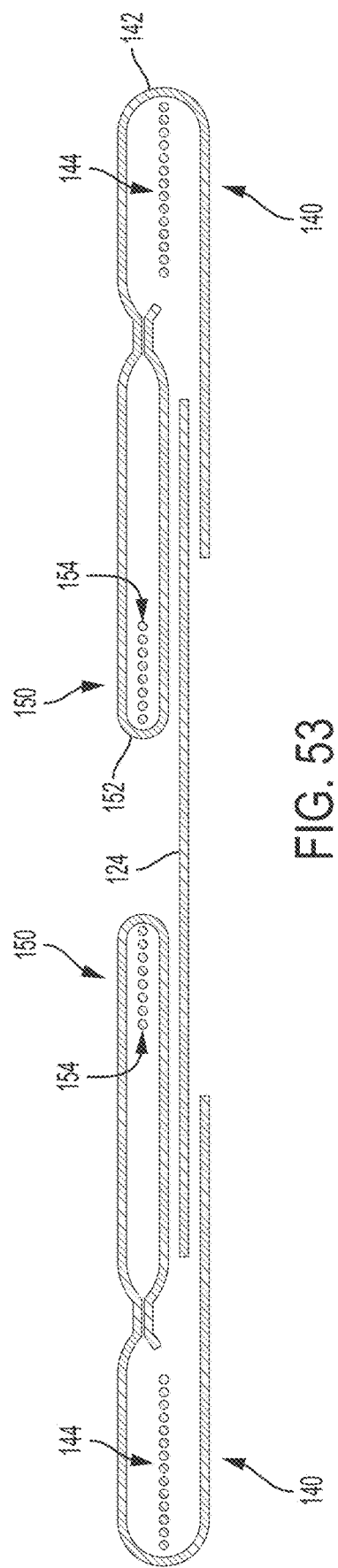
FIG. 53 is a cross section view of an absorbent article comprising a pair of opposing inner leg cuff and outer leg cuff structures bonded to a topsheet layer 124.
Figure 54:
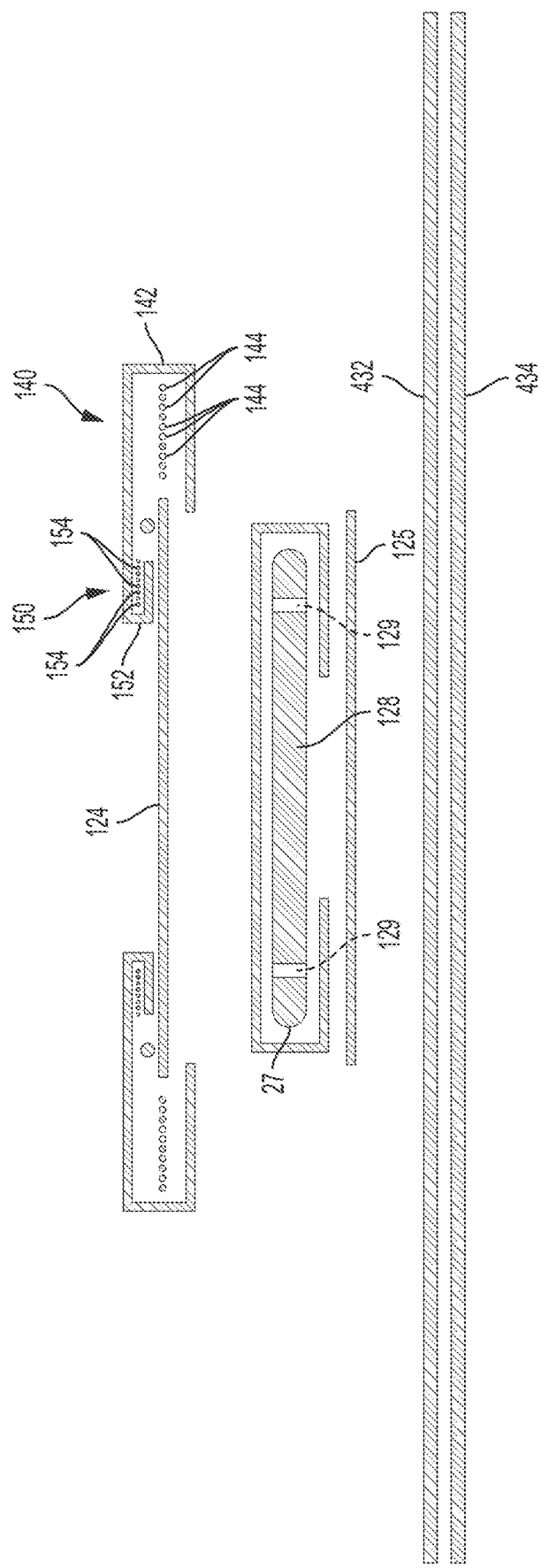
FIG. 54 is a cross section view of the pant of FIG. 55 comprising a pair of opposing inner leg cuff and outer leg cuff structures, and showing channels 129 through the absorbent core 129.

The absorbent article 100 may comprise an outer leg cuff 140 formed by a film, e.g. the backsheet film 126, a nonwoven, and an elastic material disposed between the backsheet film 126 and the nonwoven at or adjacent the side edge 237 of the chassis 200. Alternatively, as illustrated in FIGS. 52-54, the absorbent article 100 may comprise an inner leg cuff 150 and/or an outer leg cuff 140 wherein one or both of the inner leg cuff 150 the outer leg cuff 140 may be formed from a folded nonwoven web and comprise inner cuff elastics 154 and outer cuff elastics 144 disposed between layers of the folded nonwoven web. Wherein a first fold in the folded nonwoven web forms the proximal edge 152 of the inner leg cuff 150 and a second fold in the folded nonwoven web forms the distal edge 142 of the outer leg cuff 140. The distal edge 142 of the outer leg cuff 140 may extend beyond the side edges of the backsheet and form a portion of the side edge 237 of the chassis 200 as illustrated in FIGS. 39 and 46. A portion of the outer leg cuff 140 may be formed by a folded nonwoven web with elastic elements 316 disposed between layers of the folded nonwoven and may extend outwardly from the side edges of the backsheet 125 forming a portion of the side edge 237 of the chassis 200 providing a finished more cloth-like outer cuff thereby providing a more underwear-like appearance.

The web of material forming at least a portion of the inner and outer leg cuffs 150 and 140 may be folded laterally inward to form the outer cuff folded edge, i.e. distal cuff edge 142, first substrate layer 306 and/or second substrate layer 308 of the elastomeric laminate 302 forming the outer cuff and the web material may be folded laterally outward to form the inner cuff folded edge, i.e. proximal cuff edge 152, first substrate layer 306 and/or second substrate layer 308 of the elastomeric laminate 302 forming the inner cuff and the web of material may extend from the front waist end edge 136 to the back waist end edge 138 of the chassis 200 and may be joined to the topsheet 124 and/or backsheet 125 between the inner cuff folded edge, proximal cuff edge 152, and the outer cuff folded edge, distal cuff edge 142, in the crotch region 37. Elastic members, for example elastic strands 316, are disposed between the first and second substrate layers, 306 and 308, of the outer leg cuff 140 to form an elasticized outer leg cuff 140 and elastic members, for example elastic strands 316, are disposed between the first and second substrate layers 306 and 308 of the inner leg cuff 150 to form an elasticized inner leg cuff 150.

The elastic members forming the inner leg cuff 150 and the outer leg cuff 140 may be spaced apart from each other differently, i.e. one has greater spacing between the elastic elements than the other, such that the outer leg cuff 140 and the inner leg cuff 150 have differing tactile and aesthetic characteristics that create varying garment-like appearance, level of contraction and/or variation in amplitude and frequency of the texture formed in the first and second substrate layers 306 and 308. The elastic members forming the inner leg cuff 150 and/or the outer leg cuff 140 may be spaced evenly or irregularly to create contracted regions of uniform or changing amplitude and frequency in the outer leg cuff 140 and/or the inner leg cuff 150 such that a variety of garment-like appearances may be achieved.

As illustrated in FIGS. 7, 31, 39, 41, 45, and 46, the glued length (length wherein the elastic is glued to the cuff web) of the elastic 154 forming the inner leg cuff may be longer than the glued length of the elastic 144 forming the outer leg cuff. Alternatively, the glued length (length wherein the elastic is glued to the cuff web) of the elastic 154 forming the inner leg cuff may be shorter than the glued length of the elastic 144 forming the outer leg cuff. Still in other embodiments, the glued length (length wherein the elastic is glued to the cuff web) of the elastic 154 forming the inner leg cuff may be identical or substantially identical to the glued length of the elastic 144 forming the outer leg cuff. In some embodiments, the elastic 154 forming the inner leg cuff and/or the elastic 144 forming the outer leg cuff may comprise curvilinear segments.

One or more of the Average-Dtex, Average-Strand-Spacing, Average-Pre-Strain, nonwoven basis weight and/or nonwoven texture of one or both of the inner leg cuff 150 and outer leg cuffs 140 may be identical or substantially identical to one or more of the chassis 200, side panels 330, elastomeric ear panels 530, non-elastomeric ear panels 540, belts 430, waistbands 122, topsheet 124 and backsheet 125.

One or both of the inner leg cuff 150 and the outer leg cuff 140 may be formed by an elastomeric laminate 302 comprising a first substrate layer 306 and a second substrate layer 308 and an elastic material, for example elastic strands 316, disposed between the first and second substrate layers 306 and 308. The first substrate layer 306 and the second substrate layer 308 may be separate and discrete layers or alternatively the first substrate layer 306 and second substrate layer 308 may be formed from a single web of material that is folded to form the first substrate layer 306 and second substrate layer 308 as described previously. In some configurations of the outer leg cuffs 140, the one or both of the first and second substrate layers 306 and 308 may be formed in part or whole by one or more of the backsheet nonwoven 127 and backsheet film 126.

The inner and/or outer leg cuffs 150 and 140 may be formed from multiple beams of elastic, for example one beam may form the inner leg cuff 150 and a second beam may form the outer leg cuff 140, wherein the separate beams may comprise a different number of elastics, the beams may have elastics having different decitex, the elastics of the two beams may be disposed at different spacing and/or the separate beams may deliver elastics having different pre-strain. The resultant inner and/or outer leg cuffs 150 and 140 created from such a multi-beam approach may have different texture, garment-like appearance, Section-Modulus and/or different force.

Waistbands/Waistcaps

The absorbent articles 100 of the present disclosure may comprise one or more elastic waistbands 122. The elastic waistbands 122 may be positioned on the garment-facing surface or the wearer-facing surface or may be formed therebetween. As an example, a first elastic waistband 122 may be present in the front waist region 36 near the front waist edge 136 and a second elastic waistband 122 may be present in the back waist region 38 near the back waist edge 138. The elastic waistbands 122 may aid in sealing the absorbent article 100 around a waist of a wearer and at least inhibiting bodily exudates from escaping the absorbent article 100 through the waist opening circumference. In some instances, an elastic waistband may fully surround the waist opening 190 of the absorbent article 100. A waist cap 123 may be formed by an extension of the waistband 122 and may remain unattached to the underlying structure in the central portion of the waist cap 123 to allow bodily exudates that flow along the topsheet 124 to be trapped between the topsheet 124 and the underside of the waist cap 123. In other words, the waist cap 123 may be joined to the underlying structure, e.g., center chassis 200 of the absorbent article 100 along the longitudinally distal edge of the waist cap 123 and/or along the laterally opposing side edges of the waist cap 123.

The elastomeric waistband 122 especially assists in maintaining the primary line of tension formed by the primary fastening system 179 and/or ear panels/flaps/panels allowing the article to conformably fit around the waist of the wearer where there is dynamic motion, and initially pre-tensioning the waist since the article typically is stretched at the waist when applying the article 100 on the wearer so that when the waistband 122 contracts and tension is transmitted from the waistband 122 along the waist opening 190. While some of the articles of the present disclosure may have the elastomeric waistband 122 disposed in the back waist region 38, alternatively, the articles 100 may be provided with elastomeric waistbands 122 disposed in the front waist region 36 or in both the front waist region 36 and the back waist region 38. In order for the waistband 122 to receive and maintain tension created by the fastening components, when present, it may be desirable that a portion of the waistband 122 is longitudinally aligned with at least a portion of the fastening system 179. In other words, a laterally extending line drawn through the fastener 175 and parallel to the lateral centerline will extend through at least a portion of the elastomeric waistband 122.

When the elastomeric waistband 122 is present in only one waist region, e.g. back waist region 38, it may be desirable that the waistband 122 be disposed laterally inward from the waist end edge, e.g. back waist end edge 138, of the article 100; alternatively, as shown in FIG. 2, the distal end edge 738 of the waistband 122 may be substantially co-terminus with the back waist end edge 138. Further, a proximal end edge 736 may be disposed longitudinally more distal than a distal end edge 536 (see FIG. 40) of an ear panel or distal end edge 636 as illustrated at least in FIGS. 2, 40, 45, and 46. If the waistband 122 is disposed in both waist regions, front waist region 36 and back waist region 38, it may be desirable that the waistband 122 be disposed at or immediately adjacent the front and back waist end edges 136 and 138 of the article 100. The waistband 122 may have a longitudinal length as measured parallel to the longitudinal axis 42. The waistband 122 may be spaced laterally inward from the waist end edge, e.g. back waist end edge 138, a distance that is less than the longitudinal length of the waistband 122. Alternatively, the waistband 122 may be disposed at or adjacent the waist end edge 236 or 238 of the chassis 200. The waistband 122 may be disposed between the ear panels/panels or may overlap a portion of the ear panels/panels to ensure transmission of the tensioning forces generated by the fastener and/or the ear panels/panels.

The waistband 122 may be disposed between the topsheet 124 and backsheet 125 of the chassis 200 or may be disposed on the interior surface 202 of the chassis 200. The waistband 122 may be disposed in the same waist region as two elastomeric ear panels/panels or alternatively may be disposed in the same waist region as two non-elastomeric ear panels 540. When the absorbent article comprises an elastomeric waistband 122 and non-elastomeric ear panels 540, the waistband 122 may provide the primary tension along the waist region of the article. The waistband 122 may be disposed wholly between the non-elastomeric ear panels 540 of the article as illustrated in FIG. 41 or a portion of the waistband 122 may be disposed in an overlapping relationship with the non-elastomeric ear panels 540. The elasticized waistband 122 may be constructed in a number of different configurations including those described in U.S. Pat. Nos. 4,515,595 and 5,151,092.

A taped diaper may comprise a discrete waistband 122 disposed in at least one of the front and back waist regions 36 and 38, wherein the waistband 122 is spaced longitudinally inward from the respective front and back waist end edges 136 and 138 of the article 100 at least about 10 mm or at least about 20 mm. The distance the waistband 122 is spaced from the front and/or back waist edge 136 and 138 of the article 100 may be less than the longitudinal length of the waistband 122.

In either of the article forms above, a portion of the elastomeric waistband 122 may be disposed on an interior surface of one or more of the center chassis 200, the topsheet 124, the absorbent core 128 and the inner leg cuffs 150 in one or both of the waist regions of the absorbent article 100. Furthermore, a portion of the elastomeric waistband 122 may be disposed in an overlapping configuration with at least a portion of one or both of the laterally opposing panels/flaps/ears, e.g. elastomeric side panels 330, elastomeric ear panels 530 and non-elastomeric ear panels 540. Alternatively, a portion of the waistband 122 may be disposed between the topsheet 124 and the backsheet 125 in one or both of the waist regions.

The waistband 122 may be substantially rectangular. Alternatively, the waistband 122 may have one or more edges that are arcuate as shown in FIG. 47. The waistband 122 may take on a number of different sizes, shapes, configurations, and materials. For example, the waistband may comprise a plurality of elastic members, for example elastic strands 316, disposed between a first substrate layer 306 forming at least a portion of the inner surface of the waistband 122 and a second substrate layer 308 forming at least a portion of the outer surface of the waistband 122 and may have varying widths, lengths, thickness, shapes, textures, Average-Strand-Spacing, Average-Dtex, Average-Pre-Strain, etc.

The waistband 122 may be the same width as the center chassis 200 or may be wider or narrower than the center chassis 200. When the absorbent article comprises multiple waistbands, the waistband 122 in a first waist region, for example the front waist region 36, may have a different, shape, width, length, thickness, texture or elastic configuration than the waistband 122 in a second waist region, for example the back waist region 38.

The waistband 122 may extend longitudinally over one or both of the longitudinally opposing end edges 26 and 28 of the absorbent core 128 to form an elasticized waist cap 123. Such an elasticized waist cap 123 may be formed by an extension of the waistband 122 and may remain unattached to the underlying structure in the central portion of the waist cap 123 to allow bodily exudates that flow along the topsheet 124 to be trapped between the topsheet 124 and the underside of the waist cap 123. In other words, the waist cap 123 may be joined to the underlying structure, e.g. center chassis 200 of the absorbent article 100 along the longitudinally distal edge of the waist cap 123 and/or along the laterally opposing side edges of the waist cap 123.

The elasticized waistband 122 or waist cap 123 may be formed by an elastomeric laminate comprising a first substrate layer 306 and a second substrate layer 308 and may also comprise an elastic material, for example elastic strands 316, disposed between the first and second substrate layers 306 and 308. The first substrate layer 306 and the second substrate layer 308 may be separate and discrete layers or alternatively the first substrate layer 306 and second substrate layer 308 may be formed from a single web that is folded to form the first substrate layer 306 and the second substrate layer 308. In some configurations of the waist band 122 or waist cap 123 the elastic material disposed in the waistband 122 or waist cap 123 may comprise a plurality of elastic strands 316.

The absorbent article may comprise a waistband 122 disposed in both the front waist region 36 and the back waist region 38. In such embodiments, the waistband 122 in the front waist region 36 and the waistband 122 in the back waist region 38 may be formed from multiple beams of elastic, for example one beam may form the waistband 122 in the front waist region 36 and a second beam may form the waistband 122 in the back waist region 38, wherein the separate beams may comprise a different number of elastics, the beams may have elastics having different decitex, the elastics of the two beams may be disposed at different spacing and/or the separate beams may deliver elastics having different pre-strain. The resultant waistbands 122 in the front and back waist regions 36 and 38 created from such a multi-beam approach may have different texture, garment-like appearance, Section-Modulus and/or different force. It should also be appreciated that the two waistbands may be discrete from each other or may be made from a common web of material but have distinctly different physical properties.

One or more of the Average-Dtex, Average-Strand-Spacing, Average-Pre-Strain, nonwoven basis weight and/or nonwoven texture of one or both of the front and back waistbands may be identical or substantially identical to one or more of the chassis 200, side panels 330, elastomeric ear panels 530, non-elastomeric ear panel 540, belts 430, inner leg cuff 150, outer leg cuff 140, topsheet 124 and backsheet 125.

Side Panels

The side panels 330 may be discrete from or integral with the chassis 200. A discrete side panel is formed as separate element, which is joined to the chassis 200. In some embodiments, this includes a plurality of side panels, e.g. 2 or 4 being joined to the side edges 237 of the chassis 200 in the front and/or rear waist regions 36 and 38. Discrete side panels may be formed of one or more layers. A waistband 122 may be placed across a portion of the chassis 200 and may overlap a portion of the side panels 330 to create a multi-piece continuous belt-like structure.

Alternatively, the absorbent article 100 may comprise a pair of discrete elastomeric side panels 330 disposed in a first waist region and a pair of discrete non-elastomeric ear panels 540 disposed in a second waist region.

Alternatively, the article may comprise a pair of discrete elastomeric side panels 330 disposed in a first waist region and a pair of integral non-elastomeric ear panels 540 in a second waist region wherein the integral non-elastomeric ear panels 540 may be formed in part by one or more of the backsheet nonwoven 127, backsheet film 126, cuff material, landing zone material and topsheet 124.

The discrete elastomeric side panels 330 may overlap the side edges 237 of the chassis 200 and may be disposed on the innermost surface 202 of the chassis 200 or alternatively to the outermost surface 204 of the chassis 200. Alternatively, the elastomeric side panels 330 may overlap a portion of the chassis 200 and may be disposed between layers of the chassis 200 for example between the backsheet 125 and the outer leg cuff 140, or between the backsheet 125 and the topsheet 124. The side panels 330 may be bonded to the chassis 200 adhesively, mechanically, thermally or by combinations thereof.

The elastomeric side panels 330 may comprise an apertured elastomeric film material, elastic strands, elastomeric scrim materials, elastomeric nonwovens, elastic ribbons, foams and combinations thereof. The elastomeric material of the side panel 330 may be the same color as the nonwoven of the side panel 330 or may be of a different color so the elastomeric material is visible in the elastomeric side panel 330.

The side panels 330 may be substantially rectangular or may have a shape, i.e. the side panels 330 are substantially non-rectangular. In addition to shape the side panels 330 may also comprise two or more visually distinct textural regions disposed on the side panel 330. Finally, one or more of the side panels 330 of the pant comprising side panels 300 may comprise a side panel graphic 399 and the chassis 200 may comprise a chassis graphic 299 wherein portions of the side panel graphic and portions of the chassis graphics are substantially aligned and/or when combined form a composite graphic element.

The side panels 330 may be discrete elements attached to the chassis 200 at or adjacent the side edges 237 of the chassis 200. Alternatively, the side panels 330 may be integral with the chassis 200, i.e. formed in part by one or more of the backsheet nonwoven 127, backsheet film 126, outer cuff material, topsheet 124 and core wrap.

The absorbent article may comprise side panels 330 disposed in both the front waist region 36 and the back waist region 38. In such embodiments, the side panels 330 in the front waist region 36 and the side panels 330 in the back waist region 38 may be formed from multiple beams of elastic, for example one beam may form at least a portion of the side panels 330 in the front waist region 36 and a second beam may form at least a portion of the side panels 330 in the back waist region 38, wherein the separate beams may comprise a different elastic composition, different number of elastics, the beams may have elastics having different decitex, the elastics of the two beams may be disposed at different spacing and/or the separate beams may deliver elastics having different pre-strain. The resultant side panels 330 in the front and back waist regions 36 and 38 created from such a multi-beam approach may have different texture, garment-like appearance, Section-Modulus and/or different force.

The side panel 330 may also be provided with differential extensibility along the longitudinal axis when stretched in the lateral direction. As used herein, the term "differential extensibility" refers to a non-uniform degree of elastic extension properties, as measured in the direction of stretching at various points along an axis oriented substantially perpendicular to the direction of stretching. The differential extensibility can be achieved in a number of different ways. The elasticized side panel 330 can comprise a variety of elastomeric materials, multiple configurations of the elastomeric materials (elastic spacing), or the extension properties (pre-strain) of the elastomeric material or other materials making up the elasticized belt, such as the first substrate layer 306 and/or second substrate layer 308 may be non-uniform. For example, differential extensibility can be achieved in selected adjacent portions of the elasticized side panel 330 by using elastomeric materials having varying extension or contractive forces, Section-Modulus, or other inherent properties such that more or less (varying) lateral extensibility is achieved in one portion of the elasticized side panel 330 than the adjacent portion. The elastomeric materials may also have varying lengths, sizes, and shapes that provide differential extensibility. Other ways of varying the properties of materials that form the elasticized side panel 330 as are known in the art may also be used. The differential extensibility may be achieved by leveraging multiple beams of elastic to deliver elastics having different material type, decitex, strain, spacing, etc.

The elasticized side panel 330 may be formed by an elastomeric laminate comprising a first substrate layer 306 and a second substrate layer 308 and may also comprise an elastic material, for example elastic strands 316, disposed between the first and second substrate layers 306 and 308. The first substrate layer 306 and the second substrate layer 308 may be separate and discrete layers or alternatively the first substrate layer 306 and second substrate layer 308 may be formed from a single web that is folded to form the first substrate layer 306 and the second substrate layer 308. In some configurations of the side panel 330 the elastic material disposed in the side panel 330 may comprise a plurality of elastic strands 316.

The absorbent article may comprise side panels 330 disposed in one or both of the front waist region 36 and the back waist region 38. In such embodiments, the side panels 330 in the front waist region 36 and the side panels 330 in the back waist region 38 may be formed from multiple beams of elastic, for example one beam may form the side panels 330 in the front waist region 36 and a second beam may form the side panels 330 in the back waist region 38, wherein the separate beams may comprise a different number of elastics, the beams may have elastics having different decitex, the elastics of the two beams may be disposed at different spacing and/or the separate beams may deliver elastics having different pre-strain. The resultant side panels 330 in the front and back waist regions 36 and 38 created from such a multi-beam approach may have different texture, garment-like appearance, Section-Modulus and/or different force.

One or more of the elastic Average-Dtex, Average-Strand-Spacing, Average-Pre-Strain, nonwoven basis weight and/or nonwoven texture of the side panels 330 may be identical or substantially identical to one or more of the chassis 200, waistbands 122, non-elastomeric ear panel 540, inner leg cuff, outer leg cuff, topsheet 124 and backsheet 125.

Belts

The belts 430 (front belt 430F and back belt 430B) disposed on a belt pant 400 may comprise an inner belt layer 432 and an outer belt layer 434 layer and an elastomeric material disposed there between. The inner and outer nonwoven layers 432 and 434 may be joined using adhesives, thermal bonds, pressure bonds or thermoplastic bonds. Various suitable belt configurations can be found in U.S. Pub. No. 2013-0211363.

A belt pant 400 may comprise a first elastomeric belt 430 extending outwardly from a first end edge, e.g., back end edge 238, of the chassis 200 and a longitudinally opposing second elastomeric belt 430 extending outwardly from a longitudinally opposing second end edge, e.g. front end edge 236 of the chassis 200. The longitudinally distal edge of the first elastomeric belt and the longitudinally distal edge of the second elastomeric belt may form a portion of a waist opening 190 (e.g., 438 illustrated in FIGS. 12-14).

The absorbent article 100 may comprise a first belt 430 disposed in a first waist region, e.g. the front waist region 36, and a second belt 430 disposed in a longitudinally opposing second waist region, e.g. the back waist region 38, wherein one of the belts has a greater longitudinal length than the longitudinally opposing belt as measured along the side edge 437 of the belt 430 at or adjacent the side seam 170.

An absorbent belt pant 400 may comprise a first elastomeric belt 430 and a second elastomeric belt 430 that are discrete from one another. Each of the belts may comprise an inner belt layer 432 and an outer belt layer 434 wherein the inner belt layer 432 on the first belt 430 is separated by a gap from the inner belt layer 432 on the second belt 430 and the outer belt layer 434 on the first belt 430 is separated by a gap from the outer belt layer 434 on the second belt 430 (see FIGS. 11, 12 and 13A).

Alternatively, an absorbent belt pant 400 may comprise a first elastomeric belt 430 in a first waist region and a second elastomeric belt 430 in a second waist region, where each of the belts 430 may comprise an inner belt layer 432 and an outer belt layer 434 wherein one or both of the inner belt layer 432 and the outer belt layer 434 form a common belt layer extending from a first waist region to a second waist region forming a portion of the first belt 430 and a portion of the second belt 430 (see FIGS. 13B and 14B). The common layer may extend from a first waist edge, e.g. the front waist edge 136 to a longitudinally opposing second waist edge, e.g. back waist edge 138 of the article 100.

Figure 35:
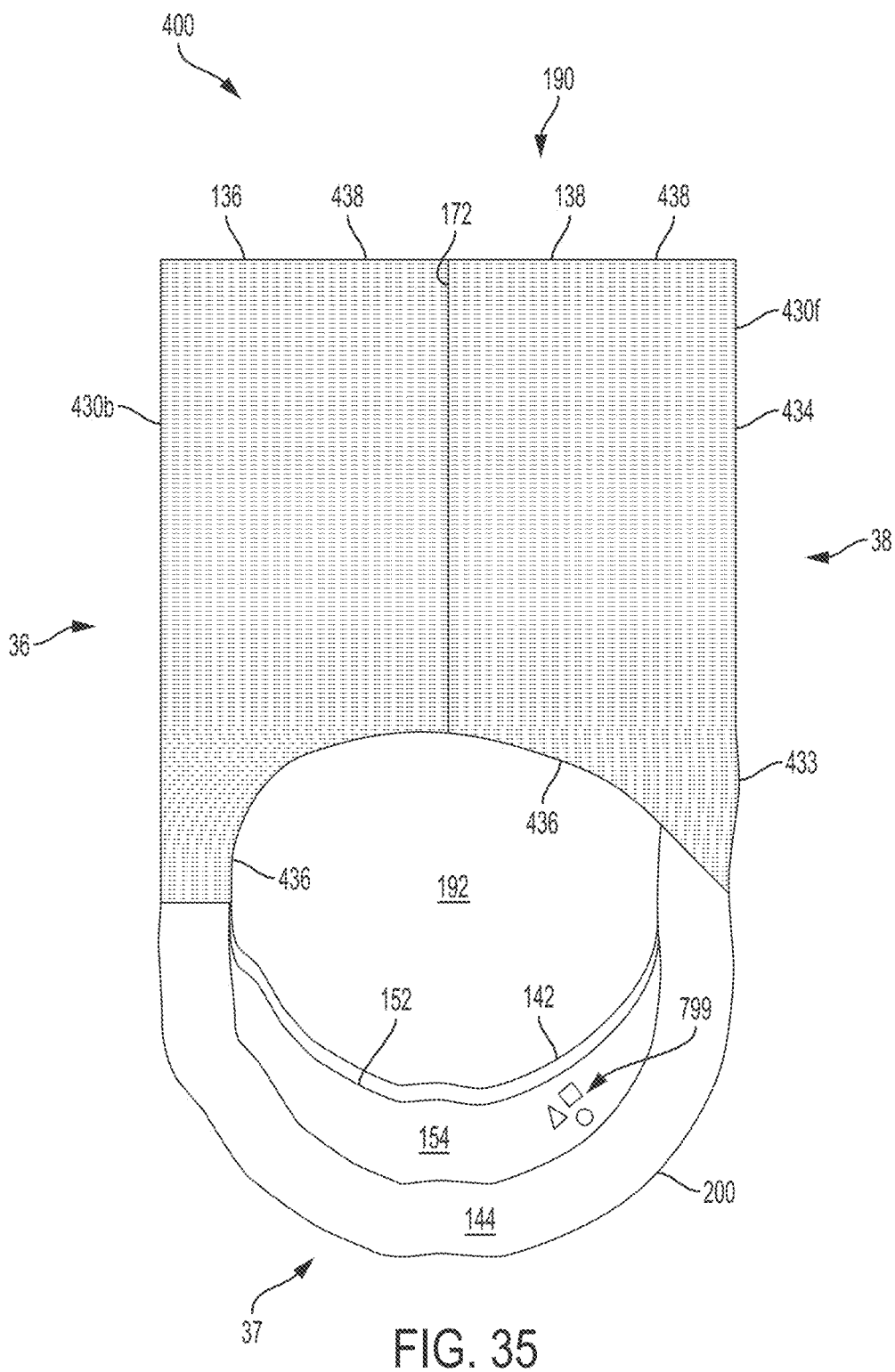
FIG. 35 is a perspective side view of a belt pant showing an outer belt layer 434 and an intermediate belt layer 433.
Figure 36:
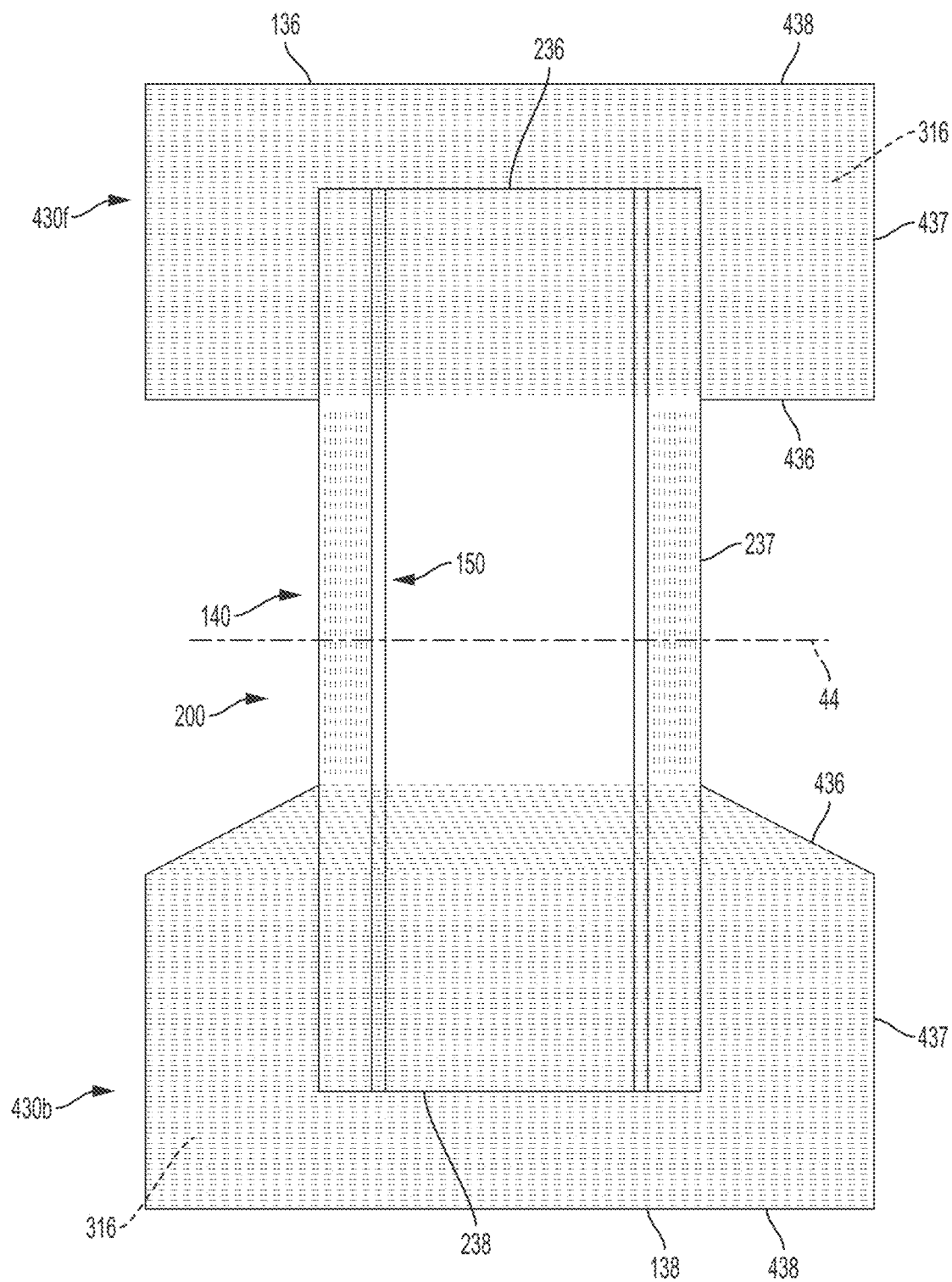
FIG. 36 is a plan view of a belt pant comprising a shaped, non-rectangular back belt.
Figure 37:
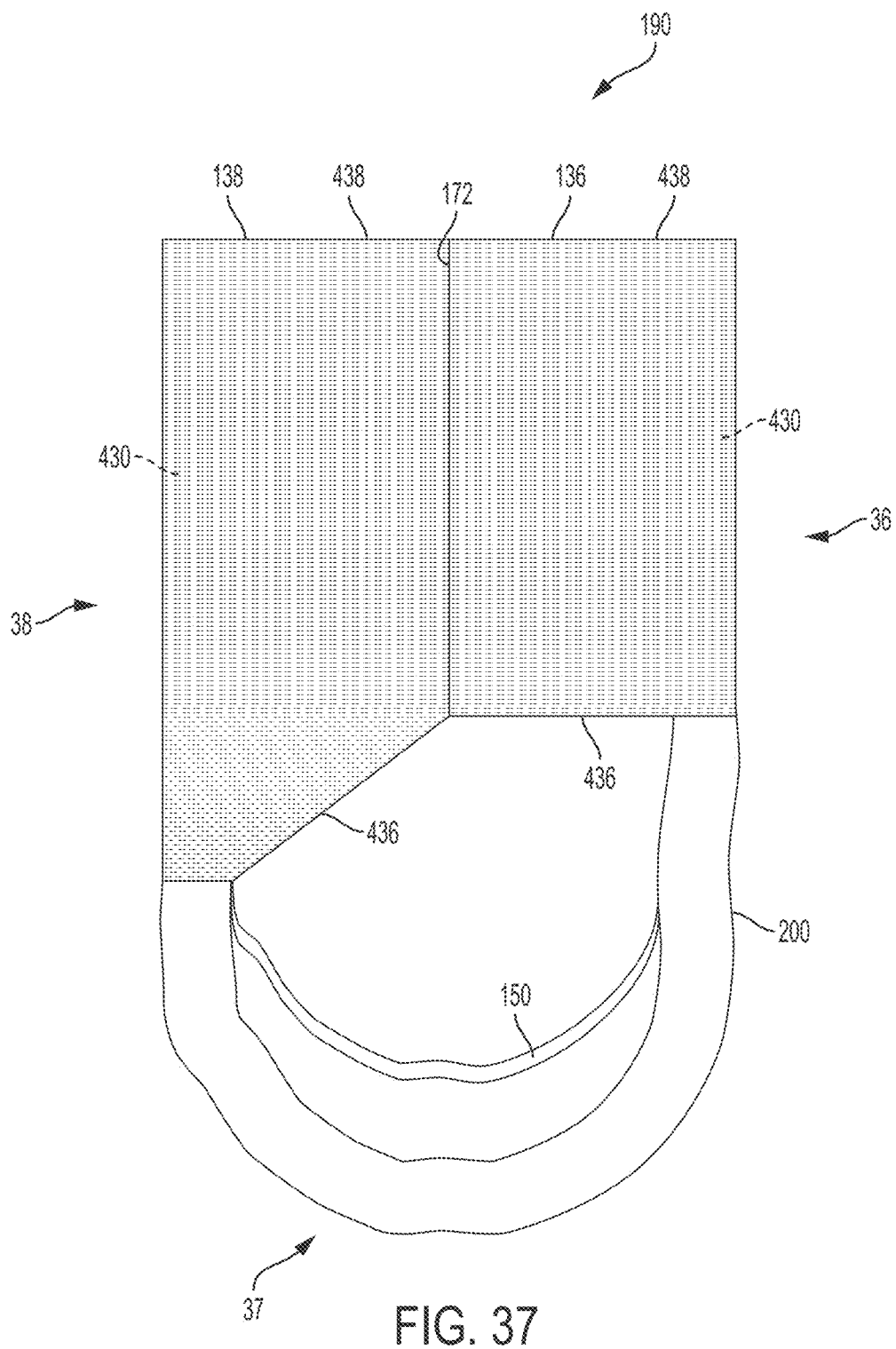
FIG. 37 is a perspective side view of the belt pant of FIG. 36.

The belt 430 may include slits, holes, slots or perforations providing increased breathability and air permeability, softness and garment like texture (see FIGS. 4A and 4B)—these slits, holes, slots or perforations may also extend through one or more layers of the belt 430. Underwear-like appearance can be enhanced by substantially aligning the waist edge, i.e. longitudinally distal edge 438 (which may be a folded edge) and/or leg edge, i.e. longitudinally proximal edge 436 (which may be a folded or cut edge) of the first and second belts 430 of the belt pant 400 providing a smooth waist opening 190 and smooth leg openings 192 as illustrated in FIG. 35.

One or both of the belts 430 on the belt pant 400 may comprise belt graphics 499. The belt graphics 499 may extend substantially around the entire circumference of the belt pant 400. The belt graphic 499 may extend around the circumference at least about 180 degrees or at least about 225 degrees or at least about 270 degrees. The belt graphics 499 (or color scheme) on the belt 430 may be substantially aligned with chassis graphics 299 disposed on the chassis 200 and/or may form a composite graphic element or graphical experience.

In some configurations, the absorbent article 100 may have a first elastic belt 430 and/or a second elastic belt 430 that may comprise curved contours. For example, the inner laterally extending edges, leg edge 436, of the first and/or second elastic belts 430 may include non-linear or curved portions (see FIG. 9). Such curved contours may help define desired shapes to the leg opening 192, such as for example, relatively rounded leg openings. In addition to having curved contours, the elastic belts 430 may include elastic strands 316 that extend along non-linear or curved paths that may correspond with the curved contours of the leg edge 436.

The elasticized belts 430 may comprise a first substrate layer 306 and a second substrate layer 308 and may also comprise an elastic material, for example elastic strands 316, disposed between the first and second substrate layers 306 and 308. The first substrate layer 306 and the second substrate layer 308 may be separate and discrete layers or alternatively the first substrate layer 306 and second substrate layer 308 may be formed from a single web that is folded to form the first substrate layer 306 and second substrate layer 308. In some configurations of the belts 430, the elastic material disposed in the belts 430 may comprise a plurality of elastic strands 316.

The absorbent article may comprise belts 430 disposed in both the front waist region 36 and the back waist region 38. In such embodiments, the belt 430 in the front waist region 36 and the belt 430 in the back waist region 38 may be formed from multiple beams of elastic, for example one beam may form at least a portion of the belt 430 in the front waist region 36 and a second beam may form at least a portion of the belt 430 in the back waist region 38, wherein the separate beams may comprise a different elastic composition, different number of elastics, the beams may have elastics having different decitex, the elastics of the two beams may be disposed at different spacing and/or the separate beams may deliver elastics having different pre-strain. The resultant belts 430 in the front and back waist regions 36 and 38 created from such a multi-beam approach may have different texture, garment-like appearance, Section-Modulus and/or different force.

The belts 430 may also be provided with differential extensibility along the longitudinal axis when stretched in the lateral direction. As used herein, the term "differential extensibility" refers to a non-uniform degree of elastic extension properties, as measured in the direction of stretching at various points along an axis oriented substantially perpendicular to the direction of stretching. This may, for example, include varying the elastic type, elastic spacing, elastic modulus or pre-strain of the elastomeric material(s). The differential extensibility is preferably designed into the elasticized belts 430 so that the lateral extensibility varies longitudinally through at least a portion of the elasticized belt 430. It is believed that differential extensibility along the longitudinal axis when stretched in the lateral direction allows the elasticized belt 430 to differentially stretch and conform to the wearer's waist during use while providing a secure anchor (illustrated by areas or zones of front anchoring force 61A and back anchoring force 61B in FIGS. 17-19, and 21A and B) about the hip of the wearer so as to promote sustained fit and reduce leakage at the waist and legs. Such a configuration may allow more "expansion" in the hip area to accommodate changes in the wearer's body size as the wearer moves and changes positions (standing, sitting, lying). Alternatively, a degree of reduced lateral extensibility in the portion of the elasticized belt 430 adjacent to the end edge of the diaper requires more of the total extension to be assumed by the elasticized belt 430 thereby resulting in more localized stretching of the elasticized belt 430 and a more compliant abdominal fit. Belts having elastics as described in this section above allow for higher Section-Modulus anchoring zones 61A and 61B than was previously possible due to significantly lower pressure on skin enabled by the low decitex elastic materials, low pre-strain and tight elastic spacing of the inventive elastomeric laminate 302. Concentrated zones of elastics (relative adjacent areas) are also illustrated in FIGS. 6A, 6B, 8, and 9. It should also be noted that a portion or the entirety of the elastics disposed within the belt 430 may extend continuously from a first belt side edge 437 to the laterally opposing belt side edge 437 while other elastics disposed within the belt 430 may be disposed in a discontinuous manner having elastic portions disposed laterally outward of the chassis 200 between the chassis edge 237 and the belt side edge 437, but not substantially overlapping the chassis 200.

The differential extensibility can be achieved in a number of different ways. The elasticized belt 430 can comprise a variety of elastomeric materials, multiple configurations of the elastomeric materials (elastic spacing), or the extension properties (pre-strain) of the elastomeric material or other materials making up the elasticized belt, such as the first substrate layer 306 and/or second substrate layer 308 may be non-uniform. For example, differential extensibility can be achieved in selected adjacent portions of the elasticized belt 430 by using elastomeric materials having varying extension or contractive forces, Section-Modulus, or other inherent properties such that more or less (varying) lateral extensibility is achieved in one portion of the elasticized belt 430 than the adjacent portion. The elastomeric materials may also have varying lengths, sizes, and shapes that provide differential extensibility. Other ways of varying the properties of materials that form the elasticized belt 430 as are known in the art may also be used. The differential extensibility may be achieved by leveraging multiple beams of elastic to deliver elastics having different material type, decitex, strain, spacing, etc.

One or more of the Average-Dtex, Average-Strand-Spacing, Average-Pre-Strain, nonwoven basis weight and/or nonwoven texture of the belts 430 may be identical or substantially identical to one or more of the chassis 200, waistbands 122, inner leg cuff 150, outer leg cuff 140, topsheet 124 and backsheet 125.

Figure 9:
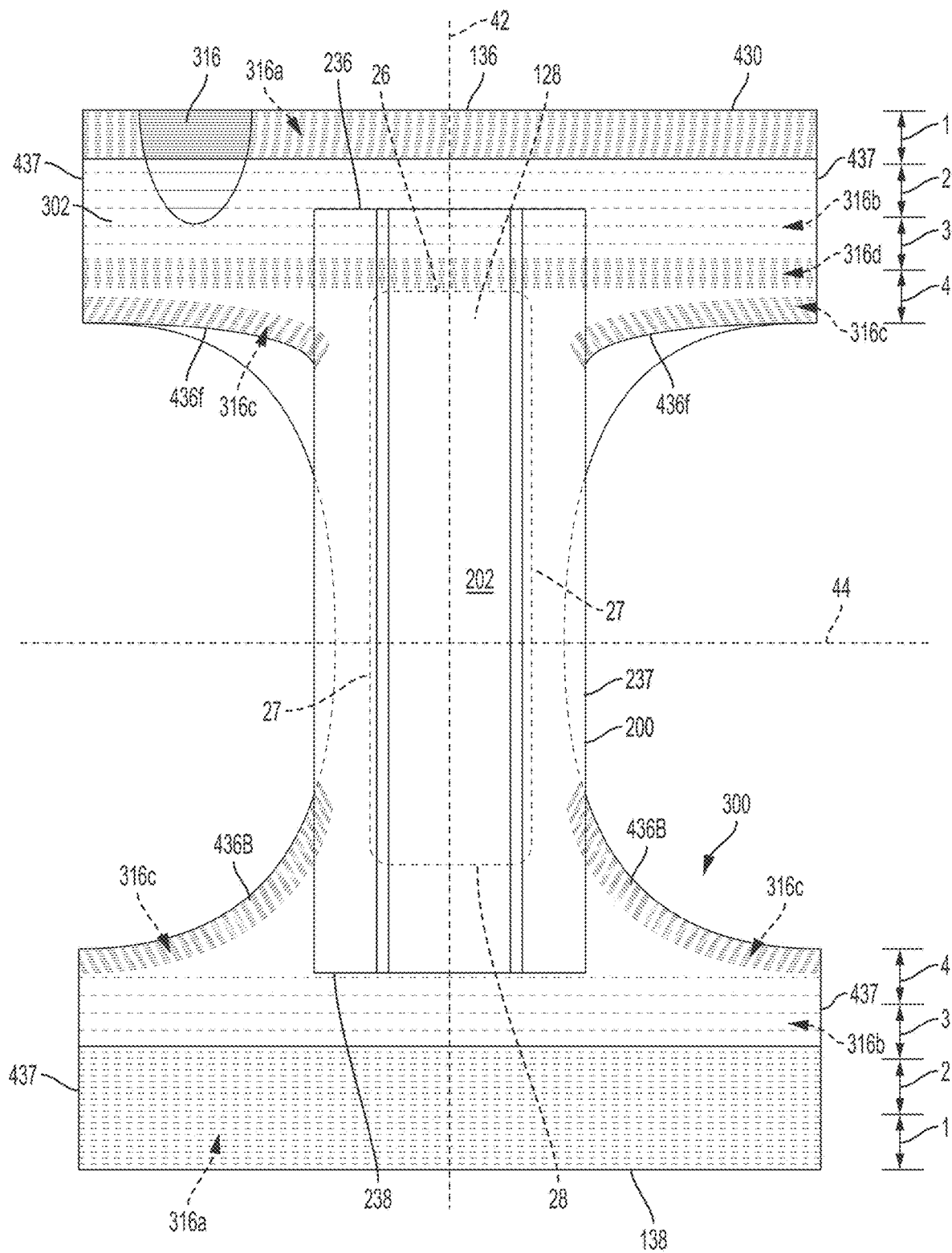
FIG. 9 is a plan view of a pant with multiple beam zones disposed in the low motion zones of the wearer.

As shown in FIG. 9, the absorbent article 100 may comprise belts 430F and B comprising a first plurality of elastics 316a adjacent the waist end edges 136 and 138, a third plurality of elastics 316c adjacent to the leg edges 436F and B, and a second plurality of elastics between the first and third elastics 316a and c. It may be desirable to curve the pluralities of elastics 316 a, b, and/or c. FIG. 9 illustrates the third plurality of elastics of each of the front and back belts 430F and B. The belts 430 may also comprise a fourth plurality of elastic elements (e.g., 316d disposed in the front belt 430F).

Ear Panels

Taped diaper absorbent articles 500 may comprise a first elastomeric ear panel 530 extending outwardly from a first side edge 237 of the chassis 200 and a laterally opposing second elastomeric ear panel 530 extending outwardly from a laterally opposing second side edge 237 of the chassis 200. The taped diaper 500 may comprise a chassis 200 having a longitudinally distal edge, e.g. back end edge 238, disposed in a first waist region, e.g. back waist region 38. The longitudinally distal edge of the chassis 200 and the longitudinally distal end edges 538 of the laterally opposing first elastomeric ear panel 530 and the second elastomeric ear panel 530 form a portion of a waist edge, e.g. back waist edge 138, of the taped diaper 500. The longitudinally proximal end edges 536 of the laterally opposing elastomeric ear panels 530 will form portions of the leg openings when the article is fastened around a wearer.

The taped diaper 500 may also comprise non-elastomeric ear panels 540 that may be combined with an elastomeric waistband 122 to create an elasticized waist opening 190. The non-elastomeric ear panels 540 may be rectangular or may be shaped, substantially non-rectangular. The ear panels may be in one or both of the waist regions and may be discrete and attached to the chassis 200 along the side edges 237 or alternatively they may be integral and formed in part by a portion of one or more of the backsheet 125, topsheet 124, leg cuff 140, or landing zone. In certain executions, the elastomeric ear panels 530 or non-elastomeric ear panels 540 of the taped diaper 500 may comprise one or more visually distinct textured zones.

One or more of the elastomeric ear panels 530 of the taped diaper 500 may comprise an ear graphic 599 disposed thereon. One or more of the elastomeric ear panels 530 comprise an ear graphic 599 and the chassis 200 comprises a chassis graphic 299. In certain executions, the ear graphic 599 disposed on the elastomeric ear panel 530 and the chassis graphic 299 disposed on the chassis 200 may be substantially aligned and/or may form a composite graphic element.

The elastomeric ear panels 530 may overlap a portion of the chassis 200 and may be disposed between layers of the chassis 200 for example between the backsheet 125 and the outer leg cuff 140, or between the backsheet 125 and the topsheet 124 or may be disposed on either the interior surface 202 or exterior surface 204 of the chassis 200. The elastomeric ear panels 530 may be bonded to the chassis 200 adhesively, mechanically, thermally or by combinations thereof.

The elastomeric ear panels 530 may be discrete elements attached to the chassis 200 at or adjacent the side edges 237 of the chassis 200. Alternatively, the elastomeric ear panels 530 may be integral with the chassis 200, i.e. formed in part by one or more of the backsheet nonwoven, backsheet film, outer cuff material, topsheet and core wrap. The ear panels may be elastomeric or may be non-elastomeric.

The elasticized ear panels 530 may comprise a first substrate layer 306 and a second substrate layer 308 and may also comprise an elastic material, for example elastic strands 316 disposed between the first and second substrate layers 306 and 308. The first substrate layer 306 and the second substrate layer 308 may be separate and discrete layers or alternatively the first substrate layer 306 and second substrate layer 308 may be formed from a single web of material that is folded to form the first substrate layer 306 and second substrate layer 308. In some configurations of the elastomeric ear panels 530 the elastic material disposed in the ear panels 530 may comprise a plurality of elastic strands 316.

The elasticized ear panels 530 may also be provided with differential extensibility along the longitudinal axis 42 when stretched in the lateral direction. As used herein, the term "differential extensibility" refers to a non-uniform degree of elastic extension properties, as measured in the direction of stretching at various points along an axis oriented substantially perpendicular to the direction of stretching. This may, for example, include varying the elastic type, elastic spacing, elastic modulus or pre-strain of the elastomeric material(s). The differential extensibility is preferably designed into the elasticized ear panel 530 so that the lateral extensibility varies longitudinally through at least a portion of the elasticized ear.

The differential extensibility can be achieved in a number of different ways. The elasticized ear panel 530 can comprise a variety of elastomeric materials, multiple configurations of the elastomeric materials (elastic spacing), or the extension properties (pre-strain) of the elastomeric material or other materials making up the elasticized ear panel 530, such as the first substrate layer 306 and/or second substrate layer 308 may be non-uniform. For example, differential extensibility can be achieved in selected adjacent portions of the elasticized ear panel 530 by using elastomeric materials having varying extension or contractive forces, Section-Modulus, or other inherent properties such that more or less (varying) lateral extensibility is achieved in one portion of the elasticized ear panel 530 than the adjacent portion. The elastomeric materials may also have varying lengths, sizes, and shapes that provide differential extensibility. Other ways of varying the properties of materials that form the elasticized ear panels 530 as are known in the art may also be used. The differential extensibility may be achieved by leveraging multiple beams of elastic to deliver elastics having different material type, decitex, strain, spacing, etc.

One or more of the elastic Average-Dtex, Average-Strand-Spacing, Average-Pre-Strain, nonwoven basis weight and/or nonwoven texture of the elasticized ear panels 530 may be identical or substantially identical to one or more of the chassis 200, waistbands 122, non-elastomeric ear panels 540, inner leg cuff 150, outer leg cuff 140, topsheet 124 and backsheet 125.

Figure 8A:
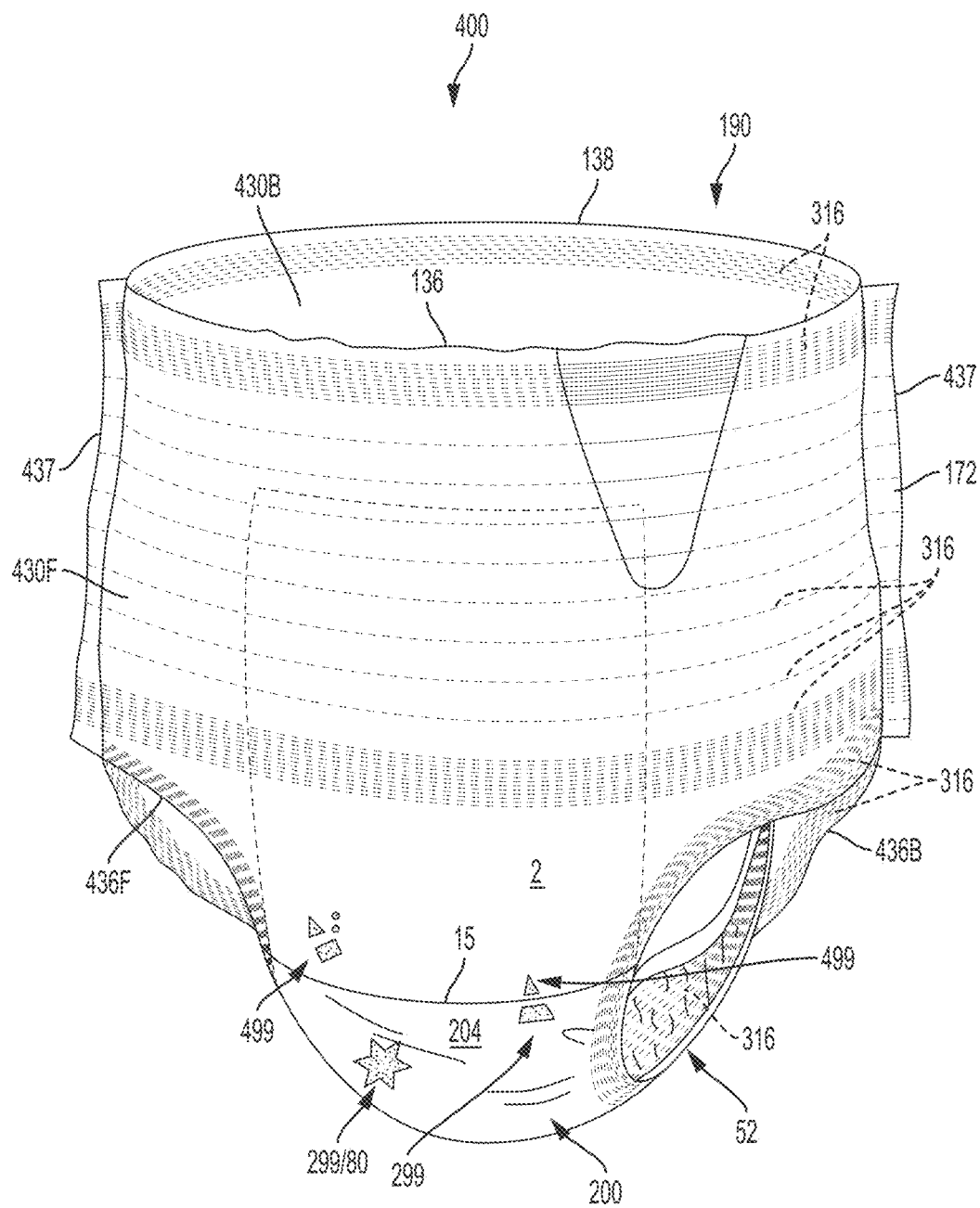
FIG. 8A is a perspective front view of pant with multiple beam zones.
Figure 8B:
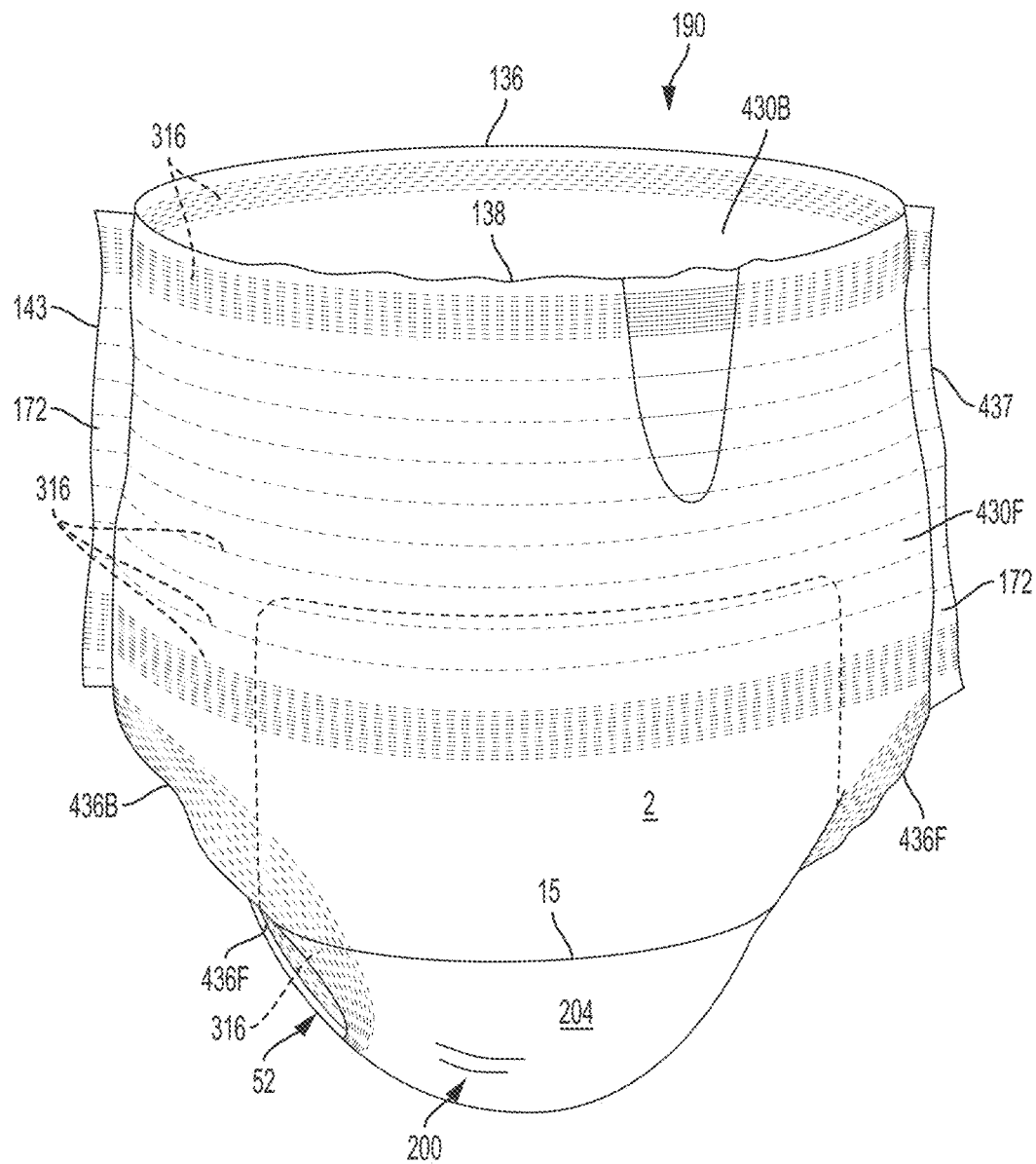
FIG. 8B is a perspective back view of pant with multiple beam zones.

As illustrated in FIGS. 8A and B, 9, and 19, one or more of the belt 430, side panel 330, elastomeric ear panel 530, topsheet 124, backsheet 125 and chassis 200 may comprise a plurality of elastic regions wherein a first elastic region may comprise a first plurality of elastics 316a disposed relative to each other at a first Average-Strand-Spacing and a second elastic region comprising a second plurality of elastics 316b disposed relative to each other at a second Average-Strand-Spacing wherein the second Average-Strand-Spacing is at least 2 times greater than the first Average-Strand-Spacing, at least 6 times greater and in certain embodiments at least 12 times greater. In some embodiments, the first elastic region and the second elastic region may be disposed in an adjacent side by side relationship. Alternatively, the first elastic region and the second elastic region may be disposed in an overlapping relationship wherein at least a portion of one region overlaps with the other region. In other embodiments, the first region and the second region may be separated by an non-elasticized region wherein the non-elasticized region has a width as measured from the last elastic of the first region to the first elastic of the second region of at least about 5 times the first Average-Strand-Spacing, at least 10 times the first Average-Strand-Spacing and in some embodiments at least about 20 times the first Average-Strand-Spacing.

Chassis

The chassis 200 is generally referred to above. It should be further understood that the chassis 200 may be elasticized such that the chassis 200 comprises a first substrate layer 306 and a second substrate layer 308 and may also comprise an elastic material, for example elastic strands 316, disposed between the first and second substrate layers 306 and 308. For example, a plurality of elastics 316 may be disposed on the chassis 200 outwardly of the backsheet film 126, longitudinally and/or laterally as illustrated in FIGS. 58-69, for example between backsheet film 126 and backsheet nonwoven 127. The first substrate layer 306 and the second substrate layer 308 may be separate and discrete layers or alternatively the first substrate layer 306 and second substrate layer 308 may be formed from a single web that is folded to form the first substrate layer 306 and second substrate layer 308. In some configurations of the chassis 200, the elastic material disposed in the chassis may comprise a plurality of elastics 316.

More specifically, the chassis 200 may comprise elastics 316 that do not overlap elastics 316 of the ear panels 530, side panels 330, or belts 430 (see FIGS. 61A, 63, 65, 67, and 68). Alternatively, the chassis elastics 316 may overlap the belt elastics 316, as illustrated in FIG. 64. Elastics 316 of the chassis 200 may be formed from multiple beams of elastic, for example one beam may form at least a portion of the chassis elastics 316 and a second beam may form at least another portion of the chassis elastics 316, wherein the separate beams may comprise a different elastic composition, different number of elastics, the beams may have elastics having different decitex, the elastics of the two beams may be disposed at different spacing and/or the separate beams may deliver elastics having different pre-strain. The resultant portion of the chassis elastics created from such a multi-beam approach may have different texture, garment-like appearance, Section-Modulus and/or different force. For example, the chassis elastics may be oriented longitudinally (316') on each end of the laterally oriented elastics (316") illustrated by FIG. 64 may be formed by different beams.

Figure 60:
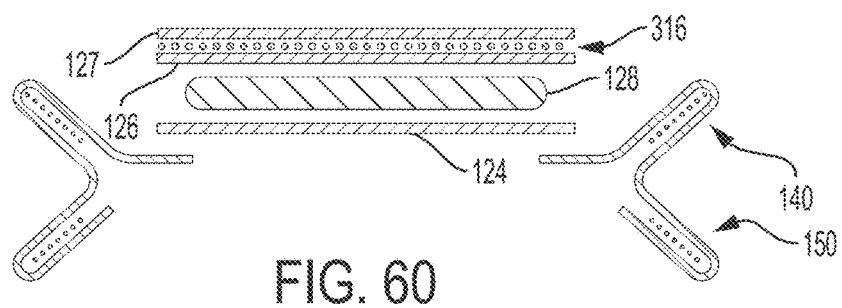
FIG. 60 is cross-sectional view of the pant of FIG. 58 along line 60-60, showing an additional nonwoven 800, sandwiching chassis elastics against the backsheet nonwoven 127.
Figure 61A:
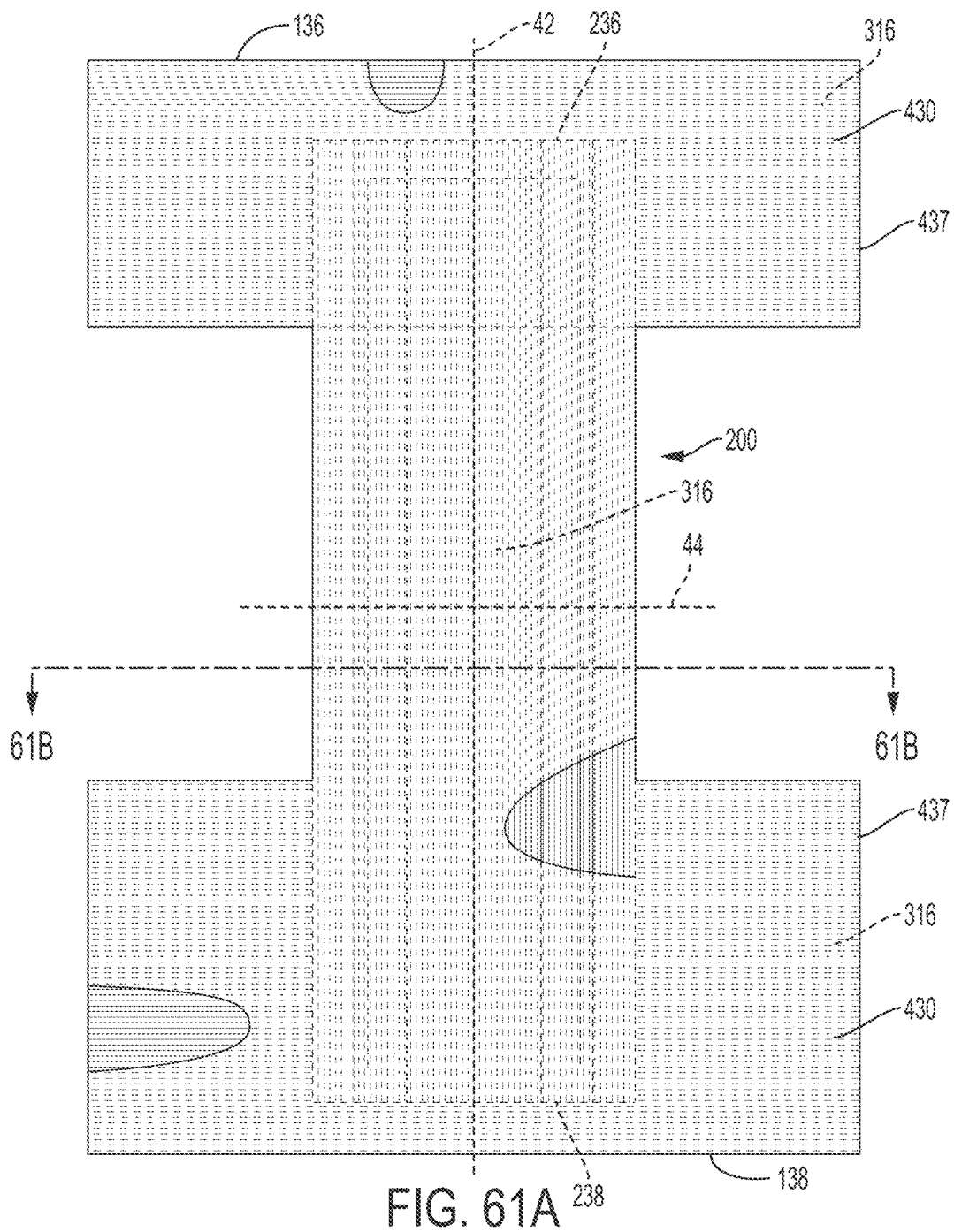
FIG. 61A is a plan view of a pant comprising transversely extending elastics 316 in the front and back belts 430F and B and longitudinally extending elastics 316 in the chassis 200 extending to the end edges of the chassis, but not overlapping the elastics of the belts.
Figure 61B:
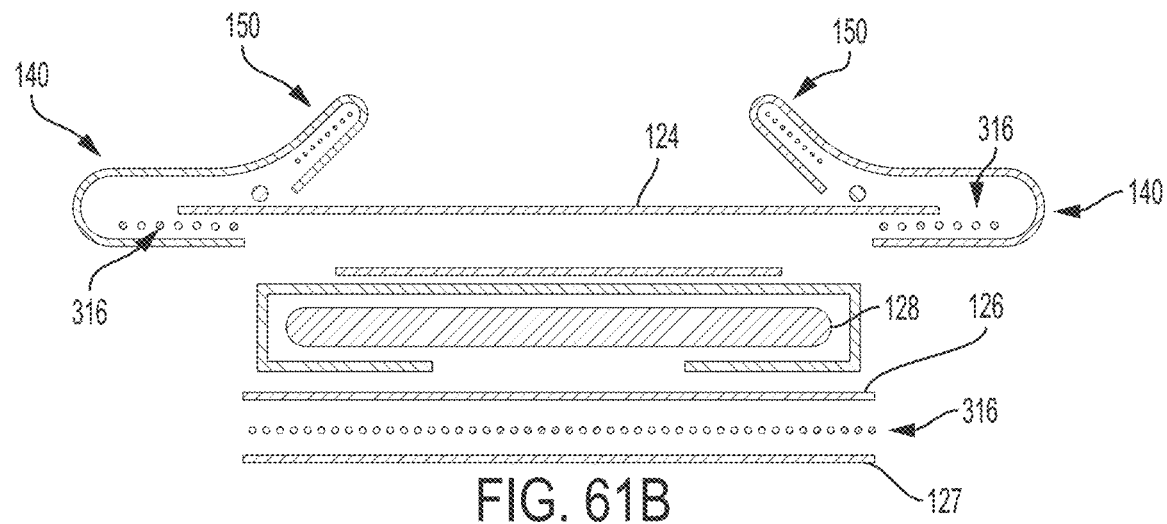
FIG. 61B is cross-sectional view of the pant of FIG. 61A along line 61B-61B, showing the chassis elastics sandwiched between the backsheet film 126 and backsheet nonwoven 127.
Figure 62A:
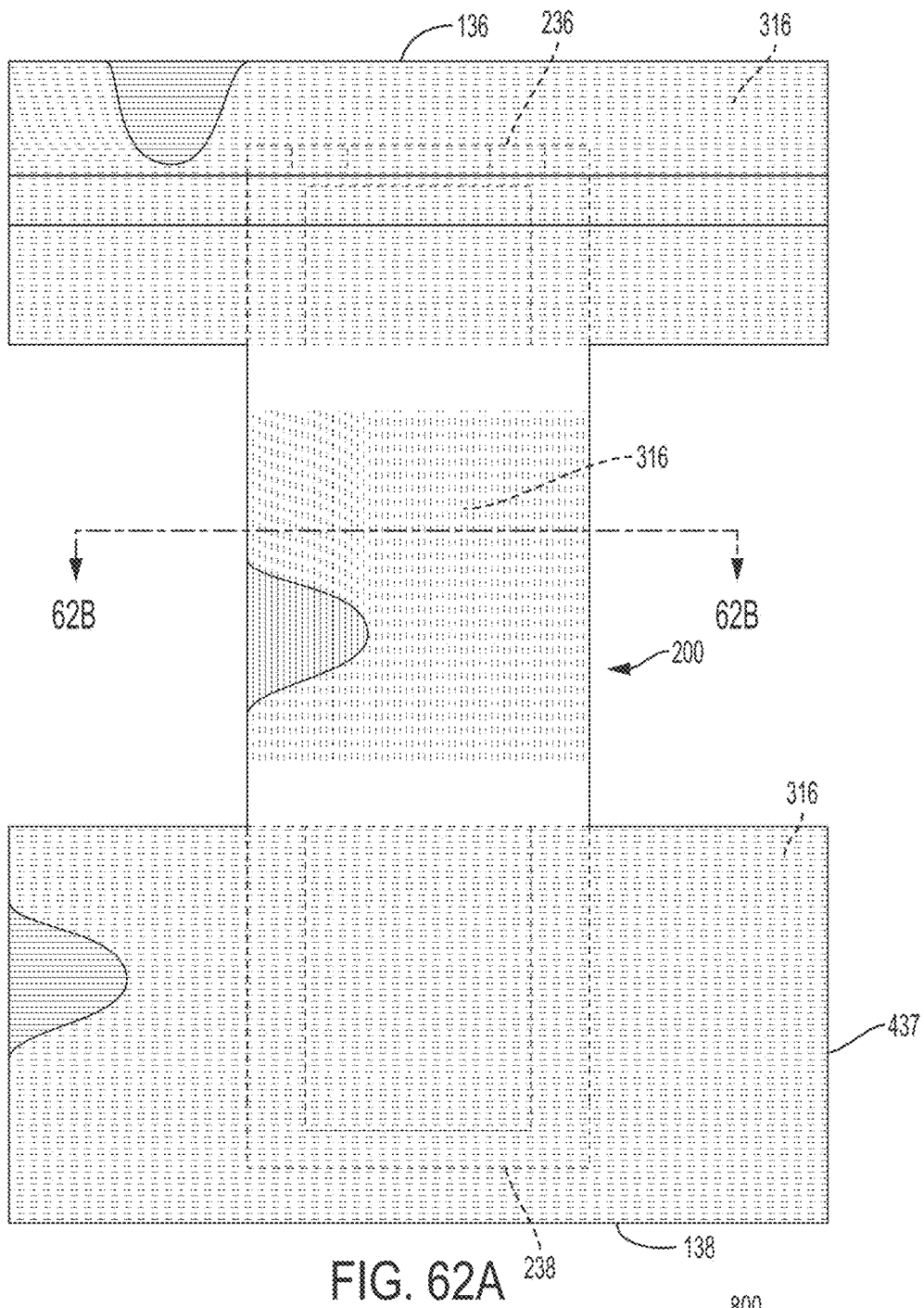
FIG. 62A is a plan view of a pant comprising transversely extending elastics 316 in the front and back belts 430F and B and longitudinally extending elastics 316 in the chassis 200 terminating prior to the proximal edges of the belts.
Figure 62B:
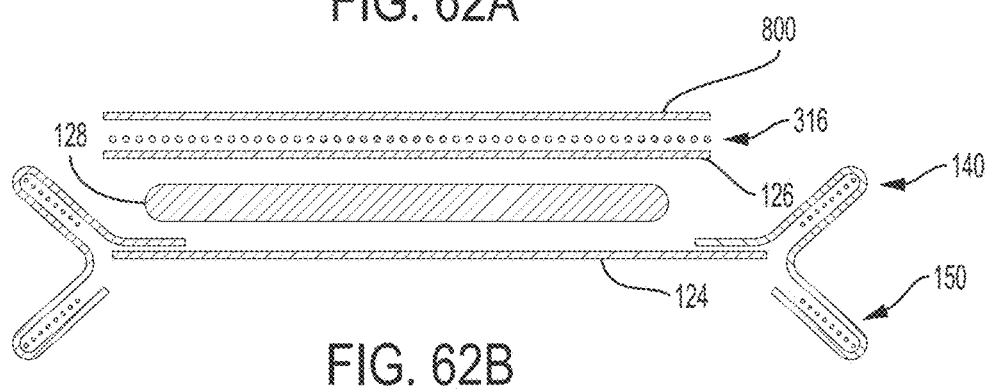
FIG. 62B is cross-sectional view of the pant of FIG. 62A along line 62B-62B, showing the chassis elastics sandwiched between the backsheet film 126 and an additional nonwoven 800.
Figure 63A:
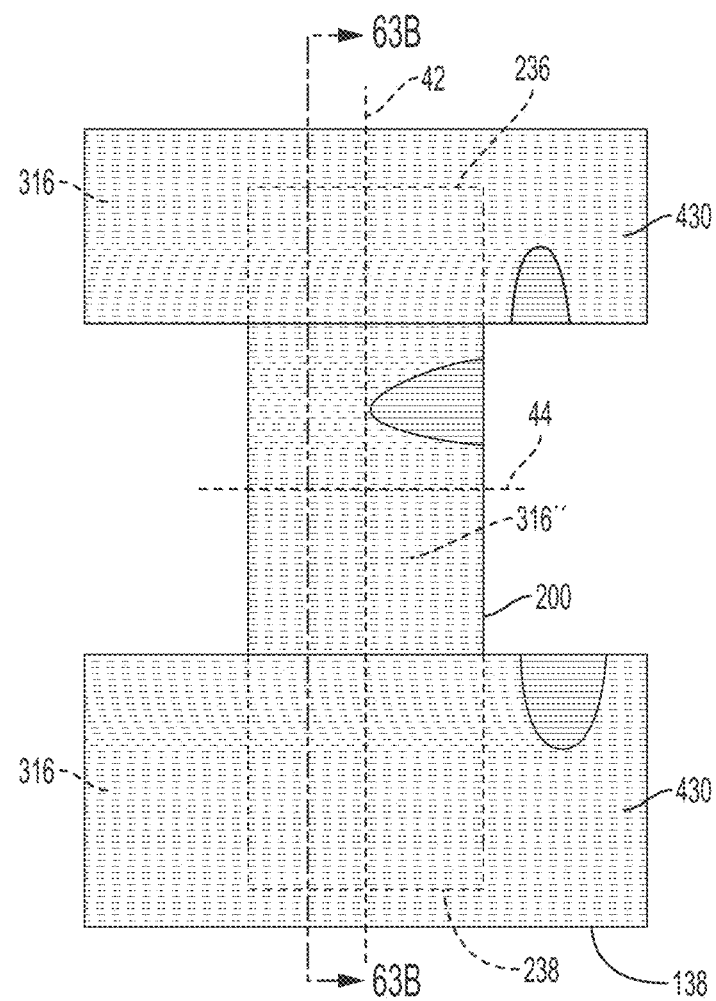
FIG. 63A is a plan view of a pant comprising transversely extending elastics 316 in the front and back belts 430F and B and transversely extending elastics 316 in the chassis 200.
Figure 63B:
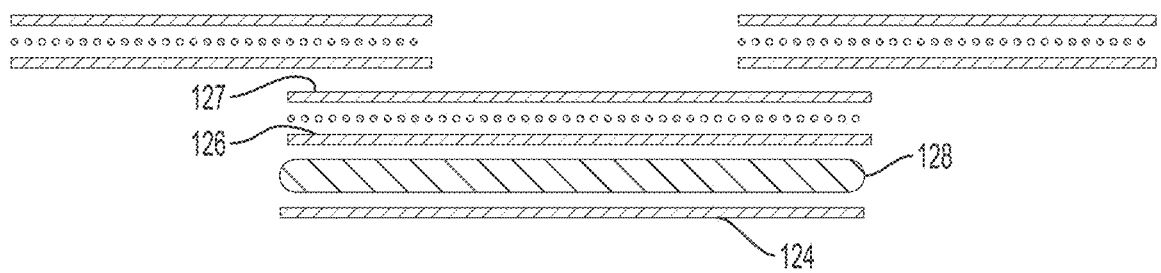
FIG. 63B is cross-sectional view of the pant of FIG. 63A along line 63B-63B, showing the chassis elastics sandwiched between the backsheet film 126 and backsheet nonwoven 127.
Figure 64:
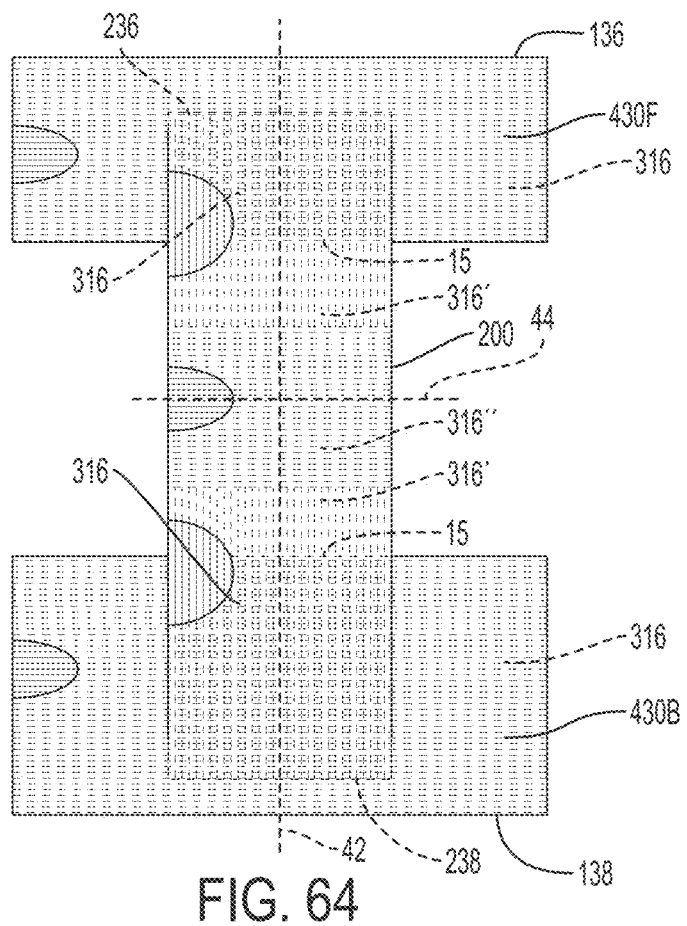
FIG. 64 is a plan view of a pant comprising transversely extending elastics 316 in the front and back belts 430F and B and transversely extending elastics 316" in the chassis 200, as well as longitudinally extending elastics 316' in the chassis which overlap with the transversely extending elastics 316 in the front and back belts.
Figure 65A:
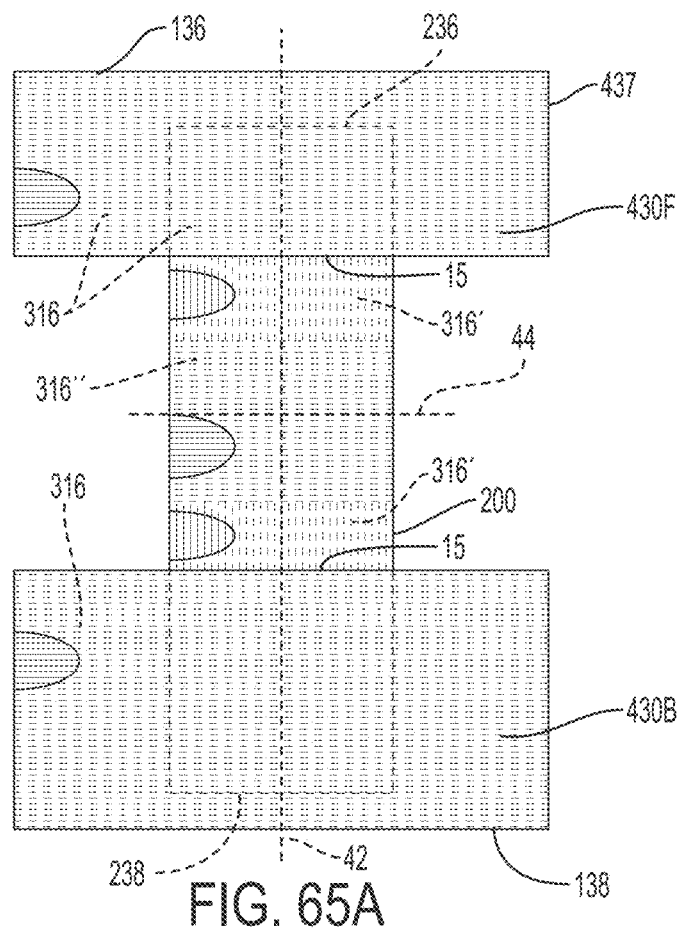
FIG. 65A is a plan view of a pant comprising transversely extending elastics 316 in the front and back belts 430F and B and transversely extending elastics 316" in the chassis 200, as well as longitudinally extending elastics 316' in the chassis which extend to the proximal edges of the front and back belts and do not overlap with the transversely extending elastics 316 in the front and back belts.
Figure 65B:
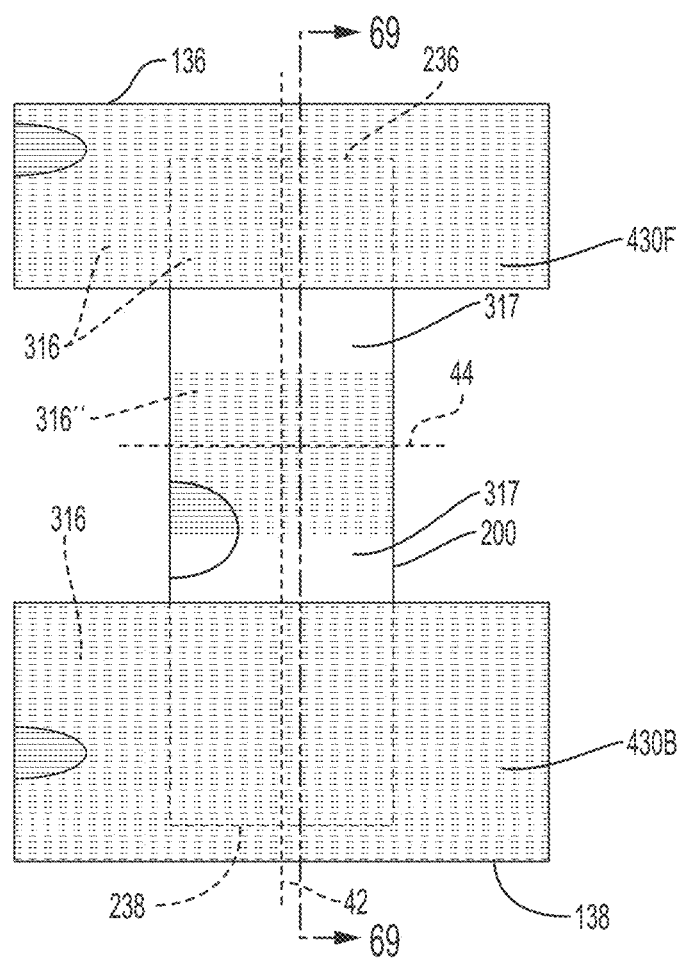
FIG. 65B is a plan view of a pant comprising transversely extending elastics 316 in the front and back belts 430F and B and transversely extending elastics 316" in the chassis 200, as well as elastic-free zones proximate to the proximal edges of the front and back belts.
Figure 69:
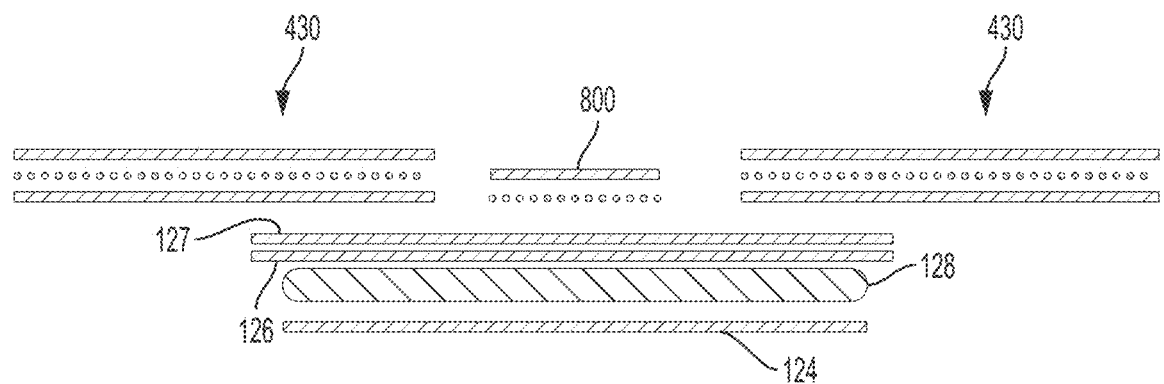
FIG. 69 is cross-sectional view of the pant of FIG. 65B along line 69-69, showing the chassis elastics sandwiched between the backsheet film 126 and additional nonwoven 800.

The laterally oriented chassis elastics (316") illustrated in FIGS. 63, 64, and 65 may be formed between an additional nonwoven 800 adhered to the garment-facing side of the backsheet nonwoven 127 (see FIGS. 60, 62B, and 69). It may be desirable to minimize the overlap of the additional nonwoven 800 with the belt nonwovens, such that the overlap is no greater than 10 mm, 15 mm, or 20 mm at each end edge of the additional nonwoven 800. Alternatively, the longitudinally oriented chassis elastics 316 illustrated in FIGS. 58, 60, and 61 may be disposed between the backsheet film 126 and backsheet nonwoven 127.

The chassis may be shaped or non-rectangular, in one waist region and substantially rectangular in the opposing waist region. Alternatively, the chassis may be substantially rectangular in one or both of the waist regions and non-rectangular in the crotch region.

As shown in FIG. 66B, an absorbent article of the present disclosure may comprise a plurality of laterally extending elastic elements wherein the elastic elements are present in a first waist region, the crotch region and the opposing second waist region and wherein the maximum displacement between any adjacently disposed pair of laterally extending elastics measured parallel to the longitudinal axis may be less than 75 mm, less than 50 mm, less than 25 mm less than 10 mm, less than 5 mm, less than 4 mm and less than 3 mm.

A wearable article of the present disclosure may comprise one or more elastomeric laminates 302 having a plurality of laterally extending elastic elements wherein the one or more elastomeric laminates 302 may be present in a first waist region, the crotch region 37 and/or in the opposing second waist region and wherein the elastomeric laminate 302 disposed in one or both of the first and second waist regions may comprise a first plurality of elastics 316 having one or more of a higher Average-Dtex, higher Average-Pre-Strain and smaller Average-Strand-Spacing than a second plurality of elastics 316 of the elastomeric laminate 302 disposed in the crotch region 37. Such a wearable article may comprise one or more elastomeric laminates 302 having a first plurality of elastics 316, the first plurality of elastics 316 of the elastomeric laminate 302 comprising from about 100 to about 1500 elastic strands with an Average-Strand-Spacing from about 0.25 mm to about 4 mm, an Average-Dtex from about 10 to about 500, an Average-Pre-Strain from about 50% to about 400% and a first substrate 306 and/or second substrate 308 wherein one or both of the first and second substrate have a basis weight from about 6 grams per square meter to about 30 grams per square meter.

In an alternative embodiment, an absorbent article 100 comprising a chassis 200 having a topsheet 124, a backsheet 125 and an absorbent core 128 disposed between the topsheet 124 and the backsheet 125 wherein the backsheet 125 comprises a backsheet film 126 and a backsheet nonwoven 127. The backsheet being formed at least in part by an elastomeric laminate 302 comprising a first plurality of elastics 316 disposed between a first substrate layer 306 and a second substrate layer 308. The first plurality of elastics 316 comprises greater than about 10 elastic strands having an Average-Strand-Spacing of from about 0.5 about 5 mm, an Average-Dtex of from about 10 about 500 and an Average-Pre-Strain of from 75% to about 350% and being disposed substantially parallel with the longitudinal axis 42. The backsheet film 126 and backsheet nonwoven 127 may form one or both of the first substrate layer 306 and second substrate layer 308. In other words, the first plurality of elastics 316 may be disposed between the backsheet film 126 and the backsheet nonwoven 127. The absorbent article 100 also comprises at least one from the group consisting of a belt 430, an ear panel 530, a side panel 330, a waistband 122, an inner leg cuff 150 and an outer leg cuff 140 joined to the chassis 200. The belt 430, ear panel 530, side panel 330 and waistband 122 when present may comprise an elastomeric laminate 302 comprising a second plurality of elastics 316 disposed between a first substrate layer 306 and a second substrate layer 308 and being disposed substantially parallel with the lateral axis 44. The second plurality of elastics 316 may comprise greater than 40 elastics with an Average-Strand-Spacing of less than 4 mm and Average-Pre-Strain of from 75% to about 300%. In embodiments, wherein the chassis comprises laterally opposed inner leg cuffs 150 and/or outer leg cuffs 140, each of the cuffs may comprise at least 6 elastic strands disposed substantially parallel with the first plurality of elastics 316 and having an Average-Strand-Spacing of less than about 3 mm and Average-Pre-Strain of between about 75% and 300%. In certain embodiments, a portion of the first plurality of elastics 316a may overlap with a portion of the second plurality of elastics 316b. The first plurality of elastics 316a may have one or more of: a) an Average-Strand-Spacing that is greater than the second plurality of elastics, b) an Average-Dtex that is lower than the second plurality of elastics 316b, c) an Average-Pre-Strain that is lower the second plurality of elastics 316b, and d) a number of elastics that is lower than the second plurality of elastics. A portion of the first plurality of elastics 316a may be disposed in an arcuate shape or may be disposed at an angle relative to one or both of the longitudinal axis 42 and lateral axis 44. A portion of the second plurality of elastics 316b may be disposed in an arcuate shape or may be disposed at an angle relative to one or both of the longitudinal axis 42 and lateral axis 44.

In yet another embodiment, an extensible article may comprise an elastomeric laminate 302 formed by a first substrate layer 306 and a second substrate layer 308 and a first plurality of elastics 316a, a second plurality of elastics 316b and a third plurality of elastics 316c disposed between the first substrate layer 306 and the second substrate layer 308. The first plurality of elastics 316a may be disposed in a first waist region, the second plurality of elastics 316b may be disposed in a second waist region and a third plurality of elastics 316c may be disposed in a crotch region. The first plurality of elastics 316a may comprise greater than about 40 elastic strands, the second plurality of elastics 316b may comprise greater than about 40 elastic strands and the third plurality of elastics 316c may comprise greater than about 10 elastic strands. One or more of the first plurality of elastics 316a, second plurality of elastics 316b and third plurality of elastics 316c may have an Average-Strand-Spacing from about 0.25 mm to about 5 mm. The Average-Dtex of one or more of the first plurality of elastics 316a, second plurality of elastics 316b and third plurality of elastics 316c is from about 10 to about 500. The Average-Pre-Strain of one or more of the first plurality of elastics 316a, second plurality of elastics 316b and third plurality of elastics 316c is from about 75% to about 300%. The elastic strands of each of the first plurality of elastics 316a, second plurality of elastics 316b and third plurality of elastics 316c are disposed substantially parallel to a lateral axis 44. The Pressure-Under-Strand of one or more of the first plurality of elastics 316a, the second plurality of elastics 316b and the third plurality of elastics 316c is from about 0.1 to about 1.0 psi. One or both of the first substrate layer 306 and second substrate layer 308 may have a basis weight of between about 6 grams per square meter to about 30 grams per square meter. The third plurality of elastics 316c may have one or more of: a) an Average-Strand-Spacing that is greater than one or both of the first plurality of elastics 316a and the second plurality of elastics 316b, b) an Average-Dtex that is lower than one or both of the first plurality of elastics 316a and the second plurality of elastics 316b, c) an Average-Pre-Strain that is lower than one or both of the first plurality of elastics 316a and the second plurality of elastics 316b, and d) a number of elastics that is lower than one or both of the first plurality of elastics 316a and the second plurality of elastics 316b.

In an alternative embodiment, an extensible article may comprise an elastomeric laminate 302 formed by a first substrate layer 306 and a second substrate layer 308 and a first plurality of elastics 316a, a second plurality of elastics 316b and a third plurality of elastics 316c disposed between the first substrate layer 306 and the second substrate layer 308. The first plurality of elastics 316a may be disposed in a first waist region, the second plurality of elastics 316b may be disposed in a second waist region and a third plurality of elastics 316c may be disposed in a crotch region. The first plurality of elastics 316a may comprise from about 100 to about 600 elastic strands, the second plurality of elastics 316b may comprise from about 100 to about 600 elastic strands and the third plurality of elastics 316c may comprise from about 20 to about 200 elastic strands. One or more of the first plurality of elastics 316a, second plurality of elastics 316b and third plurality of elastics 316c may have an Average-Strand-Spacing from about 0.5 mm to about 2.5 mm. The Average-Dtex of one or more of the first plurality of elastics 316a, second plurality of elastics 316b and third plurality of elastics 316c is from about 30 to about 250. The Average-Pre-Strain of one or more of the first plurality of elastics 316a, second plurality of elastics 316b and third plurality of elastics 316c is from about 75% to about 300%. The elastic strands of each of the first plurality of elastics 316a, second plurality of elastics 316b and third plurality of elastics 316c are disposed substantially parallel to a lateral axis 44. In an alternative embodiment, the third plurality of elastics 316c may be disposed substantially parallel to the longitudinal axis 42. The Pressure-Under-Strand of one or more of the first plurality of elastics 316a, the second plurality of elastics 316b and the third plurality of elastics 316c is from about 0.2 to about 0.8 psi. One or both of the first substrate layer 306 and second substrate layer 308 may have a basis weight of between about 6 grams per square meter to about 25 grams per square meter. The third plurality of elastics 316c may have one or more of: a) an Average-Strand-Spacing that is greater than one or both of the first plurality of elastics 316a and the second plurality of elastics 316b, b) an Average-Dtex that is lower than one or both of the first plurality of elastics 316a and the second plurality of elastics 316b, c) an Average-Pre-Strain that is lower than one or both of the first plurality of elastics 316a and the second plurality of elastics 316b, and d) a number of elastics that is lower than one or both of the first plurality of elastics 316a and the second plurality of elastics 316b.

In yet another embodiment, an extensible article may comprise one or more elastomeric laminate 302 formed by a first substrate layer 306 and a second substrate layer 308, and a first plurality of elastics 316a, a second plurality of elastics 316b, and a third plurality of elastics 316c disposed between the first substrate layer 306 and the second substrate layer 308. The first plurality of elastics 316a may be disposed in a first waist region, the second plurality of elastics 316b may be disposed in a second waist region and a third plurality of elastics 316c may be disposed in a crotch region. The first plurality of elastics forms a back belt 430B, the second plurality of elastics forms a front belt 430F and the third plurality of elastics forms an extensible crotch. The first plurality of elastics 316a may comprise greater than about 40 elastic strands, the second plurality of elastics 316b may comprise greater than about 40 elastic strands and the third plurality of elastics 316c may comprise greater than about 10 elastic strands. One or more of the first plurality of elastics 316a, second plurality of elastics 316b and third plurality of elastics 316c may have an Average-Strand-Spacing from about 0.25 mm to about 5 mm. The Average-Dtex of one or more of the first plurality of elastics 316a, second plurality of elastics 316b and third plurality of elastics 316c is from about 10 to about 500. The Average-Pre-Strain of one or more of the first plurality of elastics 316a, second plurality of elastics 316b and third plurality of elastics 316c is from about 75% to about 300%. The elastic strands of one or more of the first plurality of elastics 316a, second plurality of elastics 316b and third plurality of elastics 316c are disposed substantially parallel to a lateral axis 44. The Pressure-Under-Strand of one or more of the first plurality of elastics 316a, the second plurality of elastics 316b and the third plurality of elastics 316c is from about 0.1 to about 1.0 psi. One or both of the first substrate layer 306 and second substrate layer 308 may have a basis weight of between about 6 grams per square meter to about 30 grams per square meter. The third plurality of elastics 316c may have one or more of: a) an Average-Strand-Spacing that is greater than one or both of the first plurality of elastics 316a and the second plurality of elastics 316b, b) an Average-Dtex that is lower than one or both of the first plurality of elastics 316a and the second plurality of elastics 316b, c) an Average-Pre-Strain that is lower than one or both of the first plurality of elastics 316a and the second plurality of elastics 316b, and d) a number of elastics that is lower than one or both of the first plurality of elastics 316a and the second plurality of elastics 316b.

Length-to-Waist Silhouette

A key benefit of having the Product Length-to-Waist Silhouette closer to that of the Body Length-to-Waist Silhouette and designed to change accordingly with body weight is that the product itself more closely matches the shape of the body. This results in the product being deformed to a significantly lesser degree during application than one that is generically designed to fit a bigger range as illustrated by the current marketed products. It also results in a product fit, which is more tailored to the body shape, providing more effective gasketing and less extraneous material in the crotch. Product designs which mimic the general shape of the body convey to consumers a better, more tailored fit as the Product Length-to-Waist Silhouettes are more similar to consumers' Body Length-to-Waist Silhouettes. The designs enabled by the present disclosure are more targeted by design and therefore provide a greater level of fit, gasketing, comfort and discretion.

Desirably, an absorbent article should be designed and sized to maintain contact with and conform as closely as possible to a wearer's body. Such a body-conforming design may increase the effectiveness of the absorbent article by reducing the possibility that urine, or the like, will spread or travel along the wearer's body and leak out of rather than be absorbed into the absorbent article. However, current stranded absorbent articles on the market do not adequately address body shape or product shape and therefore do not fit a broad range of users adequately or provide the desired level of close fit.

It may be desirable to link the Product Length-to-Waist Silhouette to that of the targeted consumers Body Length-to-Waist Silhouette in order to achieve a better fitting, better conforming, better gasketing product. This may increase the wearing comfort for each consumer while reducing leakage.

In order to deliver sufficient pressure on the body, which is necessary for good fit, closed-form pant products currently in the market which comprise of elastic strands for the waist belt tend to have a narrower Relaxed Product Waist Width. This is due to their strand spacing's and strand decitex, which result is a relatively low modulus and therefore require more stretch to deliver the necessary pressure. They achieve this greater in-use stretch via greater pre-strain, which results in their relaxed waists being significantly smaller than the body of the user.

A key benefit of present disclosure is that the improved elastic laminates deliver sufficient wearing pressure, necessary for good fit, without the amount of pre-strain required in today's currently marketed stranded closed-form pant articles. This results in closed-form pant articles that have a Relaxed Product Waist Width closer to that of the Body Waist Width.

FIG. 96 shows how the Product Length-to-Waist Silhouettes of these products compare to the consumers' Body Length-to-Waist Silhouettes. It can be seen that for these comparative products, their Product Length-to-Waist Silhouettes fail to match those of their target consumers. The result of this mismatch is that the products provide an inferior level of fit, comfort, coverage and gasketing across much of the consumer population than products that are designed in line with the anthropometric measures across the same population.

The table below illustrates inventive stranded products, whose Product Length-to-Waist Silhouettes match the trends of the consumers that they are targeted to fit and thereby provide better fit & comfort while reducing the chance of leakage. These inventive products are provided simply as non-limiting examples.

"Waist Width" is defined as the width of the body measured horizontally in the front of the body at the omphalion (center of navel). See FIG. 94.

"Body Length" means the vertical distance from the navel to the maximum depth of the crotch, determined by the maximum depth of the crotch within the sagittal plane. See FIG. 94.

"Body Length-to-Waist Silhouette" means the Body Length (mm) divided by the Waist Width (mm). See FIG. 94.

"Relaxed Product Length" means the longitudinal distance between the longitudinally distal most point in the crotch region and the longitudinally distal most point along the front waist edge. The longitudinal distance is measured parallel to the longitudinal axis of the product. Refer to FIG. 86.

"Relaxed Product Waist Width" means the lateral distance from the distal most point at the right side of the front waist edge to the distal most point at the left side of the front waist edge. The lateral distance is measured perpendicular to the longitudinal axis of the product. Refer to FIG. 86.

"Product Length-to-Waist Silhouette" means Relaxed Product Length (600) (mm) divided by the Relaxed Product Hip Width (601) (mm). See FIG. 86.

A product's size range is conveyed to consumers by a weight range and/or a waist range printed on the package. For products recommended by weight range, a Target-Weight is the average of the minimum and maximum recommended weights.

For many adult incontinence products, only a waist recommendation is provided. For these products, a Target-Weight can still be determined by calculating the Average Weight at the minimum and maximum recommended waists. FIG. 88 shows this relationship and calculation.

FIG. 95 shows how the Body Length-to-Waist Silhouette changes by weight. For newborn babies, up to when they start walking, they tend to have larger waists. This results in a higher Body Length-to-Waist Silhouette. As babies start walking, and growing through childhood and into adulthood, their waists on average do not grow as fast as their body lengths, resulting in increasing Body Length-to-Waist Silhouettes. At adulthood and as consumers grow older, their waist's again increase without a corresponding body length increase, hence decreasing Body Length-to-Waist Silhouettes. At each development stage, the Product Length-to-Waist Silhouette would need to be different do address the differing body shapes.

A Target Body Length-to-Waist Silhouette can be approximated, as shown on FIG. 95, by curve fitting the population Body Length-to-Waist Silhouette as a function of body weight. This approximation is:

$$\text{Target Body Length-to-Waist Silhouette} = a + b^*w + c/w + d^*w^2 + e/w^2 + f^*w^3 + g/w^3$$

Where:
w=weight in kg
a=1.401979E+00
b=−9.012608E−03
c=−1.086641E+01
d=7.314561E−06
e=5.678403E+01
f=6.589002E−08
g=−9.152613E+01

The closer the Product Length-to-Waist Silhouette is to the Target Body Length-to-Waist Silhouette, the better fitting, better gasketing that product will be.

| Examples of Product Length-to-Waist Silhouette Existing Stranded Products | | | | | | | |
|---|---|---|---|---|---|---|---|
| | Minimum Weight Target (kg) | Maximum Weight Target (kg) | Average Targeted Weight (kg) | Target Body Length-to-Waist Silhouette | Relaxed Product Waist Width (mm) | Relaxed Product Length (mm) | Product Length-to-Waist Silhouette | Delta versus Target |
| Moony Man Air Fit | | | | | | | | |
| size S | 4 | 8 | 6.0 | 0.69 | 122 | 195 | 1.59 | 0.90 |
| size M | 5 | 9 | 7.0 | 0.68 | 111 | 195 | 1.75 | 1.07 |
| size LG | 9 | 14 | 11.5 | 0.72 | 129 | 214 | 1.66 | 0.93 |
| size BIG | 12 | 17 | 14.5 | 0.76 | 146 | 216 | 1.48 | 0.71 |
| size BIGGER THAN BIG | 13 | 25 | 19.0 | 0.81 | 139 | 222 | 1.60 | 0.80 |
| size SUPER | 18 | 35 | 26.5 | 0.84 | 152 | 254 | 1.67 | 0.83 |
| Goo.N Yawaraka Fit Pants | | | | | | | | |
| size S | 5 | 9 | 7.0 | 0.68 | 93 | 170 | 1.82 | 1.15 |
| size M | 7 | 12 | 9.5 | 0.70 | 84 | 177 | 2.10 | 1.40 |
| size LG | 9 | 14 | 11.5 | 0.72 | 92 | 199 | 2.16 | 1.43 |
| size BIG | 12 | 20 | 16.0 | 0.78 | 105 | 201 | 1.90 | 1.12 |
| size BIGGER THAN BIG | 13 | 25 | 19.0 | 0.81 | 96 | 218 | 2.28 | 1.47 |
| size SUPER | 15 | 35 | 25.0 | 0.83 | 117 | 214 | 1.84 | 1.00 |
| Pampers Sara Sara Pants | | | | | | | | |
| size S | 4 | 8 | 6.0 | 0.69 | 111 | 184 | 1.66 | 0.97 |
| size M | 6 | 10 | 8.0 | 0.68 | 89 | 204 | 2.29 | 1.61 |
| size L | 9 | 14 | 11.5 | 0.72 | 102 | 208 | 2.03 | 1.31 |

-continued

Examples of Product Length-to-Waist Silhouette Existing Stranded Products

Merries Pull-Ups

| | | | | | | | | |
|---|---|---|---|---|---|---|---|---|
| size M | 6 | 10 | 8.0 | 0.68 | 125 | 189 | 1.51 | 0.83 |
| size L | 9 | 14 | 11.5 | 0.72 | 131 | 186 | 1.41 | 0.69 |

| | Minimum Weight Target (mm) | Maximum Weight Target (mm) | Average Targeted Weight (kg) | Target Body Length-to-Waist Silhouette | Relaxed Product Waist Width (mm) | Relaxed Product Length (mm) | Product Length-to-Waist Silhouette | Delta versus Target |
|---|---|---|---|---|---|---|---|---|
| Depend Fit-Flex Underwear for Women-Moderate | | | | | | | | |
| size S/M | 711 | 1016 | 69 | 0.69 | 230 | 335 | 1.46 | 0.77 |
| size L | 965 | 1270 | 97 | 0.55 | 231 | 371 | 1.60 | 1.05 |
| size XL | 1219 | 1626 | 126 | 0.43 | 249 | 385 | 1.55 | 1.11 |
| Always Discreet Boutique | | | | | | | | |
| size S/M | 711 | 1016 | 69 | 0.69 | 286 | 286 | 1.00 | 0.31 |
| size L | 965 | 1270 | 97 | 0.55 | 304 | 317 | 1.04 | 0.49 |

Examples of Product Length-to-Waist Silhouette for Inventive Products

| Inventive Beamed Product | Minimum Weight Target (kg) | Maximum Weight Target (kg) | Average Targeted Weight (kg) | Target Body Length-to-Waist Silhouette | Relaxed Product Waist Width (mm) | Relaxed Product Length (mm) | Product Length-to-Waist Silhouette | Delta versus Target |
|---|---|---|---|---|---|---|---|---|
| size M | 6 | 10 | 8 | 0.68 | 145 | 142 | 0.98 | 0.30 |
| size L | 9 | 14 | 12 | 0.72 | 170 | 174 | 1.02 | 0.30 |

| Inventive Beamed Product | Minimum Weight Target (mm) | Maximum Weight Target (mm) | Average Targeted Weight (kg) | Target Body Length-to-Waist Silhouette | Relaxed Product Waist Width (mm) | Relaxed Product Length (mm) | Product Length-to-Waist Silhouette | Delta versus Target |
|---|---|---|---|---|---|---|---|---|
| size S/M | 711 | 1016 | 69 | 0.69 | 340 | 337 | 0.99 | 0.30 |
| size L | 965 | 1270 | 97 | 0.55 | 400 | 341 | 0.85 | 0.30 |

Hip-to-Waist Silhouette

A key benefit of having the Relaxed Product Waist Width, the Relaxed Product Hip Width, and the Relaxed Product Crotch Width (each defined below) relatively equal to each other is that they combine to create a more rectangular, more uniform, and, hence, a more stable package. Absorbent articles are generally distributed to consumers in packages of multiple stacked articles, as illustrated in FIG. 105. The more dimensionally rectangular the articles (see FIG. 97), in particular at lateral and longitudinal distal edges, the greater the uniformity and stability of the package. The stability of the package is further enhanced if the lateral distal edges are roughly parallel to each other and longitudinal distal edges are roughly parallel to each other. This creates a generally rectangular shape, enabling improved package stability, which allows greater ease of shipping and storing (e.g., in trucks and on store shelves). For Adult incontinence diapers, due to their larger overall dimensions, the Product Waist-to-Crotch Silhouette can be from about 0.8 up to about 2.8. This still facilitates rectangular, stable packages without the necessity for a Relaxed Product Crotch Width that is too large relative to the size of the wearer.

In one embodiment, an absorbent article 100, comprises a chassis 200 having a topsheet 124, a backsheet 125 and an absorbent core 128 disposed between the topsheet 124 and the backsheet 125. The absorbent article 100 also comprises a back belt 430B joined to the back waist region 38 of the chassis 200 and extending outboard of the back waist region 38 of the chassis 200. The article also comprising a front belt 430F joined to the front waist region 36 of the chassis 200 and extending outboard of the front waist region 36 of the chassis 200. The front belt 430F may be joined to the back belt 430B at or adjacent the laterally opposing belt side edges 437 to form leg openings 192 and a waist 190 opening to form a closed-form pant 400. The back belt 430B having a first plurality of elastics 316a comprising greater than about 40 elastic strands and the front belt 430F having a second plurality of elastics 316b comprising greater than about 40 elastics strands. The first plurality of elastics 316a having an Average-Strand-Spacing of less than about 4 mm. The second plurality of elastics 316b having an Average-Strand-Spacing of less than about 4 mm. One or both of the first plurality of elastics 316a and second plurality of elastics 316b having a portion that overlaps with the absorbent core 128. The absorbent article 100 having a Product Hip-to-Waist Silhouette from about 0.8 to about 1.1, alternatively from about 0.9 to about 1.0. The absorbent article 100 may have a Product Waist-to-Crotch Silhouette is from about 0.8 to about 2.0, alternatively from about 0.9 to about 1.5, in another embodiment the Product Waist-to-Crotch Silhouette may be from about 1.2 to about 1.35. The absorbent article may also have a Relaxed Product Waist Width from about 80 mm to about 270 mm, alternatively from about 170 mm to about 270 mm and in other embodiments from about 80 mm to about 180 mm. The absorbent article may also have a Relaxed Product Hip Width from about 80 mm to about 300 mm, alternatively from about 80 mm to about 200 mm. The absorbent article may also have a Relaxed Product length from about 200 mm to about 300 mm.

The back belt 430B may be divided into 4 equal sections, the first section, Section 1, including the distal most elastic, the fourth section, Section 4, including the proximal most elastic, the second section, Section 2, is disposed adjacent the first section and the third section, Section 3, is disposed between the second section and the fourth section, Section 4. The front belt 430F may also be divided into 4 equal sections, the first section, Section 1, including the distal most elastic, the fourth section, Section 4, including the proximal most elastic, the second section, Section 2, is disposed adjacent the first section and the third section, Section 3, is disposed between the second section and the fourth section, Section 4. One or more of the sections forming the front belt 430F may have a different Section-Modulus from the remaining sections of the front belt 430F. One or more of the sections forming the back belt 430B may have a different Section-Modulus from the remaining sections of the front belt 430B. Alternatively, one or more of the sections forming the front belt 430F may have a different Section-Modulus from one or more of the sections forming the back belt 430B The back belt 430B and front belt 430F may both be formed at least in part by an elastomeric laminate 302 comprising a first substrate layer 306 and a second substrate layer 308 and a plurality of elastics disposed between the first and second substrate layers 306 and 308. One or both of the first and second substrate 306 and 308 forming at least a portion of the back belt 430B and one or both of the first and second substrate 306 and 308 forming at least a portion of the front belt 43F are separate and spaced apart from each other. Alternatively, one or both of the first and second substrate 306 and 308 forming at least a portion of the back belt 430B and one or both of the first and second substrate 306 and 308 forming at least a portion of the front belt 43F are continuous and extends from the first waist edge to the longitudinally opposing second waist edge. The elastomeric laminate may also comprise an adhesive joining the first substrate layer 306 and/or second substrate layer 308 to the plurality of elastics 316. The adhesive may be selected from the group consisting of Styrenic block copolymers, Polyolefins, Ethylene-vinyl Acetates, Polyurethanes, Ethylene-propylene copolymers, Propylene-ethylene copolymers, Polyolefin block polymers, Polyolefin homo-polymers, Polyesters, Polyamides, Silicones, Cyanoacrylics, Acrylics, butyl rubber, and combinations thereof.

In certain embodiments, one of the sections in the front belt 430F may comprise more elastics that one or more of the remaining sections of the front belt 430F and one of the sections in the back belt 430B may comprise more elastics that one or more of the remaining sections of the back belt 430B. The front belt 430F may have at least one section that comprises greater than 10 elastics and the back belt 430B may have at least two sections that comprise greater than 10 elastics. The front belt 430F may have at least two sections having an Average-Strand-Spacing of less than about 3 mm and the back belt 430B may have at least three sections having an Average-Strand-Spacing of less than about 3 mm.

In another example of an absorbent article 100, the absorbent article comprises a chassis 200 having a topsheet 124, a backsheet 125 and an absorbent core 128 disposed between the topsheet 124 and the backsheet 125. The absorbent article 100 also comprises a back belt 430B joined to the back waist region 38 of the chassis 200 and extending outboard of the back waist region 38 of the chassis 200. The article also comprising a front belt 430F joined to the front waist region 36 of the chassis 200 and extending outboard of the front waist region 36 of the chassis 200. The front belt 430F may be joined to the back belt 430B at or adjacent the laterally opposing belt side edges 437 to form leg openings 192 and a waist 190 opening to form a closed-form pant 400. The back belt 430B having a first plurality of elastics 316a comprising greater than about 40 elastic strands and the front belt 430F having a second plurality of elastics 316b comprising greater than about 40 elastics strands. The first plurality of elastics 316a having an Average-Strand-Spacing of less than about 4 mm. The second plurality of elastics 316b having an Average-Strand-Spacing of less than about 4 mm. One or both of the first plurality of elastics 316a and second plurality of elastics 316b having a portion that overlaps with the absorbent core 128. The absorbent article 100 having a Product Hip-to-Waist Silhouette from about 0.8 to about 1.1, alternatively from about 0.9 to about 1.1. The absorbent article 100 may have a Product Waist-to-Crotch Silhouette is from about 0.8 to about 2.8, alternatively from about 0.8 to about 2.5, in another embodiment the Product Waist-to-Crotch Silhouette may be from about 0.8 to about 2.0. The absorbent article may also have a Relaxed Product Waist Width from about 200 mm to about 400 mm alternatively from about 225 mm to about 375 mm and in other embodiments from about 250 mm to about 350 mm. The absorbent article may also have a Relaxed Product Hip Width from about 200 mm to about 450 mm, alternatively from about 225 mm to about 425 mm, in other embodiments the Relaxed Product Hip Width may be from about 250 mm to about 400 mm. The absorbent article may also have a Relaxed Product length from about 250 mm to about 450 mm, alternatively from about 275 to about 425, in yet another embodiment the Relaxed Product Length may be from about 300 mm to about 400 mm.

The back belt 430B may be divided into 4 equal sections, the first section, Section 1, including the distal most elastic, the fourth section, Section 4, including the proximal most elastic, the second section, Section 2, is disposed adjacent the first section and the third section, Section 3, is disposed between the second section and the fourth section, Section 4. The front belt 430F may also be divided into 4 equal sections, the first section, Section 1, including the distal most elastic, the fourth section, Section 4, including the proximal most elastic, the second section, Section 2, is disposed adjacent the first section and the third section, Section 3, is disposed between the second section and the fourth section, Section 4. One or more of the sections forming the front belt 430F may have a different Section-Modulus from the remaining sections of the front belt 430F. One or more of the sections forming the back belt 430B may have a different Section-Modulus from the remaining sections of the front belt 430B. Alternatively, one or more of the sections forming the front belt 430F may have a different Section-Modulus from one or more of the sections forming the back belt 430B The back belt 430B and front belt 430F may both be formed at least in part by an elastomeric laminate 302 comprising a first substrate layer 306 and a second substrate layer 308 and a plurality of elastics disposed between the first and second substrate layers 306 and 308. One or both of the first and second substrate 306 and 308 forming at least a portion of the back belt 430B and one or both of the first and second substrate 306 and 308 forming at least a portion of the front belt 43F are separate and spaced apart from each other. Alternatively, one or both of the first and second substrate 306 and 308 forming at least a portion of the back belt 430B and one or both of the first and second substrate 306 and 308 forming at least a portion of the front belt 43F are continuous and extends from the first waist edge to the longitudinally opposing second waist edge. The elastomeric laminate may also comprise an adhesive joining the first substrate layer 306 and/or second substrate layer 308 to the plurality of elastics 316. The adhesive may be selected from the group consisting of Styrenic block copolymers, Polyolefins, Ethylene-vinyl Acetates, Polyurethanes, Ethylene-propylene copolymers, Propylene-ethylene copolymers, Polyolefin block polymers, Polyolefin homo-polymers, Polyesters, Polyamides, Silicones, Cyanoacrylics, Acrylics, butyl rubber, and combinations thereof.

In certain embodiments, one of the sections in the front belt 430F may comprise more elastics that one or more of the remaining sections of the front belt 430F and one of the sections in the back belt 430B may comprise more elastics that one or more of the remaining sections of the back belt 430B. The front belt 430F may have at least one section that comprises greater than 20 elastics, alternatively greater than 40 elastics and the back belt 430B may have at least two sections that comprise greater than 20 elastics, alternatively greater than 40 elastics. The front belt 430F may have at least two sections having an Average-Strand-Spacing of less than about 3 mm and the back belt 430B may have at least three sections having an Average-Strand-Spacing of less than about 3 mm.

| Examples of Product Hip-to-Waist & Waist-to-Crotch Silhouette for Existing Stranded Products | | | | | |
|---|---|---|---|---|---|
| | Relaxed Product Waist Width (mm) | Relaxed Product Hip Width (mm) | Relaxed Product Crotch Width (mm) | Product Hip-to-Waist Silhouette | Product Waist-to-Crotch Silhouette |
| Moony Man Air Fit | | | | | |
| size S | 122 | 159 | 120 | 1.30 | 1.02 |
| size M | 111 | 166 | 117 | 1.50 | 0.95 |
| size LG | 129 | 170 | 114 | 1.32 | 1.13 |
| size BIG | 146 | 163 | 122 | 1.12 | 1.20 |
| size BIGGER THAN BIG | 139 | 190 | 117 | 1.37 | 1.19 |
| size SUPER | 152 | 206 | 117 | 1.35 | 1.30 |
| Goo.N Yawaraka Fit Pants | | | | | |
| size S | 93 | 166 | 127 | 1.79 | 0.73 |
| size M | 84 | 175 | 122 | 2.07 | 0.69 |
| size LG | 92 | 177 | 117 | 1.92 | 0.79 |
| size BIG | 105 | 170 | 137 | 1.61 | 0.77 |
| size BIGGER THAN BIG | 96 | 186 | 127 | 1.95 | 0.75 |
| size SUPER | 117 | 220 | 178 | 1.88 | 0.66 |
| Pampers Sara Sara Pants | | | | | |
| size S | 111 | 167 | 81 | 1.50 | 1.37 |
| size M | 89 | 168 | 85 | 1.89 | 1.04 |
| size L | 102 | 173 | 84 | 1.69 | 1.22 |
| Merries Pull-Ups | | | | | |
| size M | 125 | 173 | 122 | 1.38 | 1.03 |
| size L | 131 | 185 | 125 | 1.41 | 1.05 |
| Depend Fit-Flex Underwear for Women-Moderate | | | | | |
| size S/M | 230 | 263 | 114 | 1.14 | 2.02 |
| size L | 231 | 274 | 118 | 1.18 | 1.96 |
| size XL | 249 | 291 | 120 | 1.17 | 2.07 |
| Always Discreet Boutique | | | | | |
| size S/M | 286 | 325 | 102 | 1.14 | 2.80 |
| size L | 304 | 330 | 107 | 1.08 | 2.84 |

Examples of Product Hip-to-Waist & Waist-to-Crotch Silhouette for Inventive Stranded Products

| Inventive Beamed Product | Relaxed Product Waist Width (mm) | Relaxed Product Hip Width (mm) | Relaxed Product Crotch Width (mm) | Product Hip-to-Waist Silhouette | Product Waist-to-Crotch Silhouette |
|---|---|---|---|---|---|
| size M | 145 | 155 | 102 | 1.07 | 1.42 |
| size L | 170 | 175 | 105 | 1.03 | 1.62 |
| size S/M | 300 | 320 | 120 | 1.07 | 2.50 |
| size L | 360 | 380 | 130 | 1.06 | 2.77 |

Fastening Systems

The absorbent article 100 may also include a fastening system 179. When fastened, the fastening system 179 interconnects the front waist region 36 and the rear waist region 38 resulting in a waist circumference that may encircle the wearer during wear of the absorbent article 100. This may be accomplished by connecting the side panels 330 in one waist region with the side panels 330 in the longitudinally opposing waist region (e.g. a refastenable seam in a pant comprising side panels 300) or by connecting elastomeric ear panels 530 in one waist region with the chassis 200 in the longitudinally opposing waist region (e.g. a closure in a taped diaper 500). The fastening system 179 may comprises a fastener 175 such as tape tabs, hook and loop fastening components, interlocking fasteners such as tabs & slots, buckles, buttons, snaps, and/or hermaphroditic fastening components, although any other known fastening means are generally acceptable. Referring to FIG. 3, the fastening system may comprise an elastomeric layer 131 formed of elastic strands, elastic scrims, elastic films, elastic ribbons and/or elastic nonwovens or combinations thereof. The fasteners 175 may releasably engage with a mating fastener 178, which may comprise a woven or nonwoven substrate. The fastening system 179 may comprise a fastener 175 joined to a fastener tab which is in turn may be joined to the elastomeric side panel 330 or elastomeric ear panel 530. Alternatively, the fastener 175 may be joined directly to the elastomeric side panel 330 or elastomeric ear panel 530 of the article 100. Each elastomeric side panel 330 may be fastened to a portion of the chassis 200 by a primary fastener 175 disposed on the elastomeric side panel 330 or on a fastener tab connected to the elastomeric side panel 330 and by a mating fastener 178 disposed on the chassis 200 designed to engage with the fastener 175 on the elastomeric side panel 330. The fastener 175 and fastener tab may be substantially rectangular. Alternatively, the fastener 175 and/or fastener tab may be shaped or rounded. Some exemplary surface fastening systems 179 are disclosed in U.S. Pat. Nos. 3,848,594; 4,662,875; 4,846,815; 4,894,060; 4,946,527; 5,151,092; and 5,221,274. An exemplary interlocking fastening system is disclosed in U.S. Pat. No. 6,432,098. The fastening system 179 including a disposal tape may also provide a means for holding the article in a disposal configuration as disclosed in U.S. Pat. No. 4,963,140. The fastening system 179 may also include primary fasteners 175 and mating fasteners 178, as disclosed in U.S. Pat. No. 4,699,622. The fastening system 179 may be constructed to reduce shifting of overlapped portions or to improve fit as disclosed in U.S. Pat. Nos. 5,242,436; 5,499,978; 5,507,736; and 5,591,152.

Figure 24:
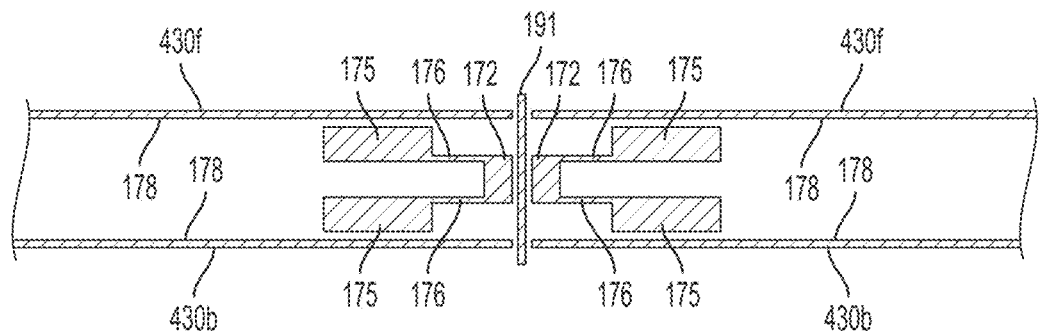
FIG. 24 is a cross section of belt pants being made, showing a configuration of a refastenable seams of a first pant (to the left of cut line 191) and a second pant (to the right of cut line 191).

As shown in FIGS. 1-3, and 22-29, the belt pant 400 may comprise a fastening system 179 having a primary fastener 175, a fastening tab 176 and a mating fastener 178. In FIG. 24 the fastening system 179 is disposed between the front and back belts 430. The mating fastener 178 forms at least a portion of the body facing surface of the belts 430 and the primary fastener 175 is disposed on a fastener tab 176. The primary fastener 175 engages with the mating fastener 178 forming a portion of the interior surface of the belts 430. The fastening system 179 forms dual refastenable seams 174, one refastenable seam 174 disposed in the front waist region 36 and one refastenable seam 174 in the back waist region 38. The fastener tabs are joined to each other by a permanent seam 172 to complete the waist opening 190. The refastenable seam is opened by disengaging the primary fastener 175 from the mating fastener 178 in one or both of the front and back waist regions 36 and 38. The refastenable seam may be reclosed by reengaging the primary fastener 175 and the mating fastener 178.

Figure 25:
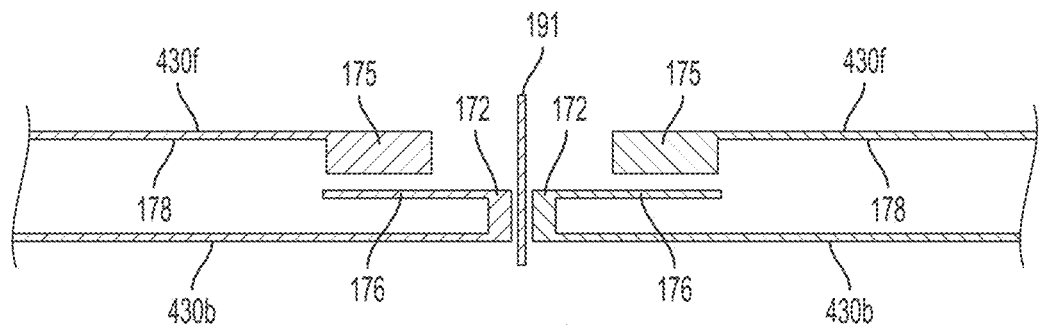
FIG. 25 is a cross section of belt pants being made, showing a configuration of a refastenable seams of a first pant (to the left of cut line 191) and a second pant (to the right of cut line 191).

In FIG. 25 the fastening system 179 is disposed between the front and back belts 430. The mating fastener 178 forms a portion of the body facing surface of the front belt 430F and the primary fastener 175 is disposed in an engaged fashion with the body facing surface of the front belt 430. The fastening system 179 also comprises a fastening tab 176 that is permanently seamed to the back belt 430B at or adjacent the side edge 437. The fastener 175 and the fastening tab 176 are joined to each other via an adhesive, cohesive, or other means known in the art to complete the waist opening 190. The refastenable seam is opened by disengaging the primary fastener 175 from the mating fastener 178. The refastenable seam may be reclosed by reengaging the primary fastener 175 and the mating fastener 178.

Figure 26:
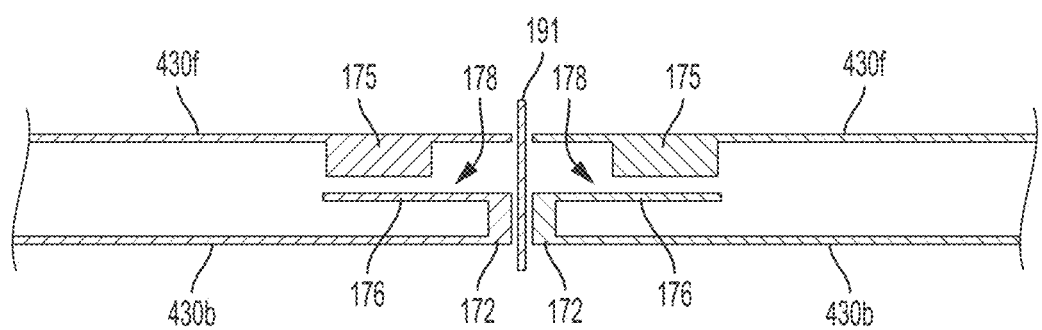
FIG. 26 is a cross section of belt pants being made, showing a configuration of a refastenable seams of a first pant (to the left of cut line 191) and a second pant (to the right of cut line 191).

In FIG. 26 the fastening system 179 is disposed between the front and back belts 430. The primary fastener 175 is permanently joined to the front belt 430F adjacent the side edge 437 of the belt 430. The mating fastener 178 forms at least a portion of the fastening tab 176. The fastening tab 176 is permanently seamed to the back belt 430B at or adjacent the side edge 437. The fastener 175 disposed on the front belt 430F is refastenably engaged with the fastening tab 176 to complete the waist opening 190. The refastenable seam is opened by disengaging the primary fastener 175 from the fastening tab 176 which is formed at least in part by the mating fastener 178. The refastenable seam may be reclosed by reengaging the primary fastener 175 and the fastening tab 176.

Figure 27:
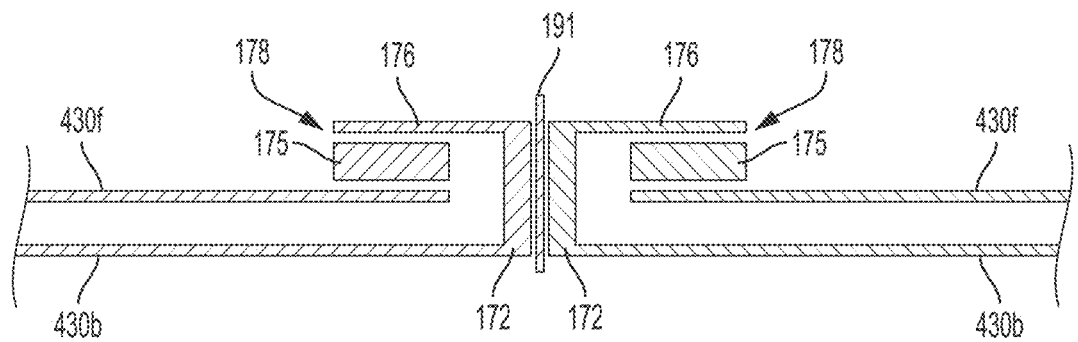
FIG. 27 is a cross section of belt pants being made, showing a configuration of a refastenable seams of a first pant (to the left of cut line 191) and a second pant (to the right of cut line 191).

In FIG. 27 the fastening system 179 is disposed on the exterior surface of the front belt 430. The primary fastener 175 is permanently joined to the front belt 430F adjacent the side edge 437 of the belt 430. The mating fastener 178 forms at least a portion of the fastening tab 176. The fastening tab 176 is permanently seamed to the back belt 430B at or adjacent the side edge 437. The fastener 175 disposed on the front belt 430F is refastenably engaged with the fastening tab 176 to complete the waist opening 190. The refastenable seam is opened by disengaging the primary fastener 175 from the fastening tab 176 which is formed at least in part by the mating fastener 178. The refastenable seam may be reclosed by reengaging the primary fastener 175 and the fastening tab 176.

Figure 28:
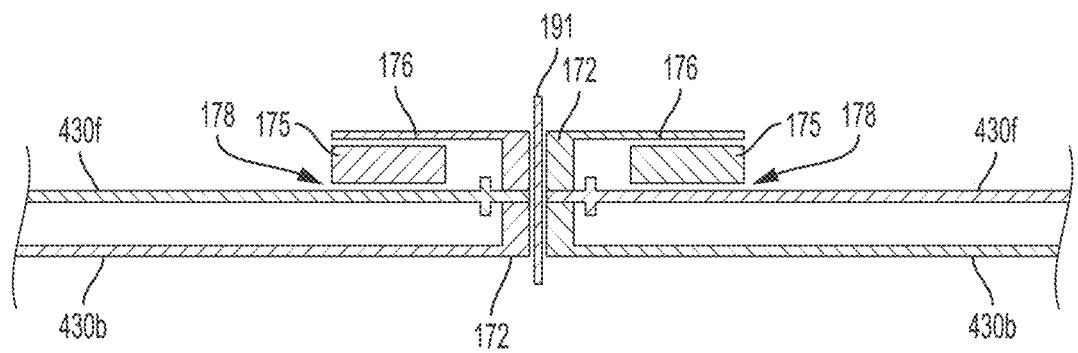
FIG. 28 is a cross section of belt pants being made, showing a configuration of a refastenable seams of a first pant (to the left of cut line 191) and a second pant (to the right of cut line 191).

In FIG. 28 the fastening system 179 is disposed on the exterior surface of the front belt 430. The primary fastener 175 is permanently joined to the fastening tab 176. The mating fastener 178 forms at least a portion of exterior surface of the front belt 430. The fastening tab 176 is permanently seamed to the front belt 430F and the back belt 430B at or adjacent the side edge 437. A perforation is disposed between the primary fastener 175 and the permanent side seam 172. The fastener 175 disposed on the fastening tab 176 is refastenably engaged with the mating fastener 178 to complete the waist opening 190. The refastenable seam is opened by disengaging the primary fastener 175 from the mating fastener 178 which forms at least a portion of the front belt 430F subsequently breaking the perforation disposed adjacent the permanent side seam 172 and opening the pant. The refastenable seam may be reclosed by engaging the primary fastener 175 to the exterior surface of the front belt 430.

Figure 29:
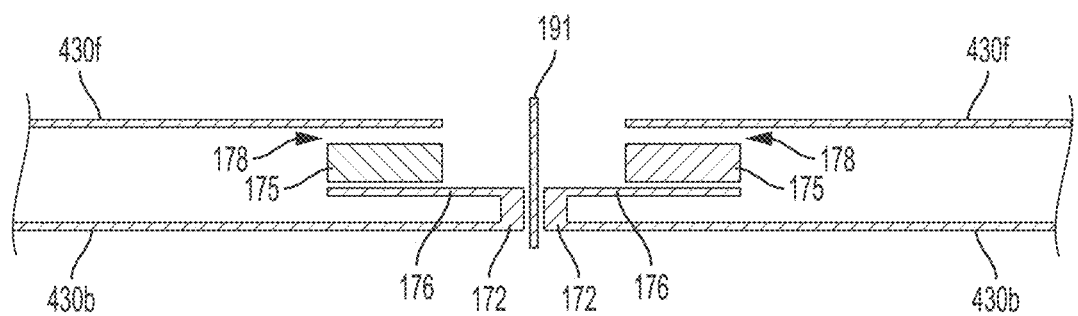
FIG. 29 is a cross section of belt pants being made, showing a configuration of a refastenable seams of a first pant (to the left of cut line 191) and a second pant (to the right of cut line 191).

In FIG. 29 the fastening system 179 is disposed between the front and back belts 430. The mating fastener 178 forms a portion of the body facing surface of the front belt 430F and the primary fastener 175 is disposed on a fastening tab 176. The fastening tab 176 is permanently seamed to the back belt 430B at or adjacent the side edge 437. The primary fastener 175 is refastenable engaged with the body facing surface of the front belt, i.e. mating fastener adjacent the side edge 437 of the belt 430 to complete the waist opening 190. The refastenable seam is opened by disengaging the primary fastener 175 from the mating fastener 178. The refastenable seam may be reclosed by reengaging the primary fastener 175 and the mating fastener 178.

For the belt refastenable executions, the references to front belt 430F and back belt 430B should be considered to be interchangeable such that a fastener 175 that is described above in the front waist region 36 may be disposed in the back waist region 38 in a similar structural configuration.

Identical or Substantially Identical Chassis

As disclosed in U.S. Pub. No. 2013/0211355, it may be desirable to offer an array of packages for fitting wearers having different needs, but comprising identical or substantially identical chassis 200. For instance, an array may comprise a first package comprising a first absorbent article 100 and a second package may comprise a second absorbent article 100, where the first and second packages comprise articles having identical or substantially identical chassis 200 as described in U.S. Pub. No. 2013/0211355. More particularly, the first package may comprise a first chassis 200 and the second package may comprise a second chassis 200, where each of the first and second chassis comprise the same dimensions of one or more of: core width at the lateral axis 44, core width at one of the front or rear core edge 26 and 28, a distance from a left outer cuff distal edge 142 to a right outer cuff distal edge 142, a distance from a left inner cuff proximal edge 152 to a left outer cuff distal edge 142, a distance from a left inner cuff proximal edge 152 to a right inner cuff proximal edge 152, a distance from a left inner cuff proximal edge 152 to a left outer cuff distal edge 142, a free height of the inner cuff, inner cuff hem fold width, inner cuff elastics length, outer cuff elastics length, core length, chassis length and backsheet width.

Further, each of the first and second chassis 200 may comprise identical chemical compositions of one or more of a topsheet 124, backsheet film 126, backsheet nonwoven 127, core super absorbent polymers, core pulp, core nonwoven, core tissue, leg cuff film, leg cuff nonwoven, super absorbent polymer adhesive, core nonwoven adhesive, leg cuff elastic adhesive, and backsheet nonwoven/film adhesive.

And, each of the first and second chassis 200 may comprise the same basis weight of one or more of the topsheet 124, backsheet film 126, backsheet nonwoven 127, core super absorbent polymers, core pulp, leg cuff nonwoven, leg cuff film, super absorbent polymer adhesive, leg cuff adhesive, and backsheet nonwoven/film adhesive.

And, each of the first and second chassis 200 may comprise compositionally identical core super absorbent polymers. The first and second chassis 200 may have identical component cross sectional order and disposition in at least one of the front waist region 36, back waist region 38, and crotch region 37. The inner leg cuffs 150 of the first and second chassis 200 may be composed of the compositionally identical materials.

Further, the inner leg cuffs 150 of the first and second chassis 200 may have identical component cross sectional order and disposition in at least one of the front waist region 36, back waist region 38, and crotch region 37. The distance from the left outer cuff distal edge 142 to a right outer cuff distal edge 142 may the same. The distance from the left inner cuff proximal edge 152 to left outer cuff distal edge 142 may be the same. The distance from the left inner cuff proximal edge 152 to the right inner cuff proximal edge 152 is the same. The lengths of the inner and outer cuffs 150 and 140 are the same.

Further one or more of the chassis 200, belt 430, side panel 330, ear panel 530, waistband 122, inner leg cuff 150, outer leg cuff 140, topsheet 124 and backsheet 125 of a first absorbent article and one or more of the chassis 200, belt 430, side panel 330, ear panel 530, waistband 122, inner leg cuff 150, outer leg cuff 140, topsheet 124 and backsheet 125 of a second absorbent article being identical or substantially identical to each other with regard to one or more of Average-Dtex, Average-Strand-Spacing, Average-Pre-Strain, nonwoven basis weight and/or nonwoven texture.

Different product offerings in an array may have identical or substantially identical chassis 200 as the side panels 330, ear panels 530 or belts 430 may be used to distinguish the absorbent article forms one from another. For example, first and second absorbent articles may have identical chassis (compositionally, dimensionally, cross-sectionally), but the first article 100 may have a different length due to disposition of the belts. As a second example, first and second absorbent articles 100 may have identical chassis (compositionally, dimensionally, cross-sectionally), but the first article may have a different length and/or width due to the size of the belts.

First and second absorbent articles 100 may have identical chassis compositionally, but not dimensionally, and not cross-sectionally. First and second absorbent articles 100 may have identical chassis dimensionally, but not compositionally, and not cross-sectionally. First and second absorbent articles 100 may have identical chassis cross-sectionally, but not dimensionally, and not compositionally. Alternatively, first and second absorbent articles 100 may have two, but not three of (1) compositionally, (2) dimensionally, and (3) cross-sectionally identical chassis.

It should be noted that for all of the above statements relating to identical or substantially identical chassis that a third package comprising a third article 100 may be added. It should also be noted that the structure and/or form of the first article 100, second article 100 and third article 100 when present can all be different in other words the first article 100 may be an open-form, taped diaper 500, the second article may be a closed-form, side panel refastenable pant 300, and the third article 100 may be a closed-form, belt pant 400.

Graphics

There is a desire to make disposable absorbent articles 100 look more like underwear. This desire is driven by the desire to address the psychological and emotional development needs of the wearer, especially infants and children. There are several factors that can affect whether an absorbent article 100 is perceived as underwear-like. These factors include, but are not limited to, the noticeability of seams 170, the existence of graphics on a larger percentage of the viewable surfaces of the absorbent article 100, the appearance of waist and leg features and graphics flowing from or over two or more absorbent article components.

There are, however, many obstacles to designing and executing an absorbent article 100 that is underwear-like. One is that absorbent articles are a compilation of separate article components and as new disposable absorbent article technologies are developed, they may result in the need for incorporation of additional, separate, article components. Because of the manner in which absorbent article components are incorporated, even the viewable surfaces of the article may have seams or areas of overlap or connection. Thus, it is challenging to place graphics on these individual components and to line them up such that the multi-component construction appears to be an integrated structure wherein the seams are de-emphasized and process variations are masked.

Further, depending on the type of article construction, it is challenging to maintain the uniform appearance of graphics that may be printed on more than one component. For example, a component with a particular graphic printed on it may eventually be incorporated into the article at a different depth than an adjacent component that also has a graphic printed on it. Depending on whether particular portions of a graphic are printed on an outermost layer, for example, or, if not, how opaque the layers may be through which the various portions of the graphic may be viewed, can have an impact on an entire article graphic that is meant to look uniform and consistent in that the various portions may have measureable differences in appearance when printed on different components or at different depths relative to the outer surface. For these and other reasons, it is challenging to create an absorbent article that comprises mainstream technologies and also that comprises graphics on multiple absorbent article components, such that the graphics flow from one absorbent article component to another article component in a manner that deemphasizes transitions from one component to another and creates a holistic underwear-like appearance.

It is a desire of the present disclosure to provide absorbent articles 100 that look like underwear, while, at the same time, incorporating multiple absorbent article components that offer the benefits and functionality of the latest technologies (e.g., high stretch components integrated with low/no stretch components, highly breathable, high air permeability components, etc.). More specifically, it is a desire of the present disclosure to provide absorbent articles 100 comprising graphics disposed on or spanning multiple viewable absorbent article components while creating a uniform appearance.

Disposable absorbent articles 100 of the present disclosure can have 2 or 4 elastomeric ear panels 530 or side panels 330 that overlap with a portion of the chassis 200 or an elastomeric belt 430 disposed in one or both of the waist regions that overlap with a portion of the chassis 200. The ear panels 530 or side panels 330 may comprise a first graphic element and the chassis 200 may comprise a second graphic element wherein the graphic elements are designed to work in concert with each other to create a composite graphic element. A first elastomeric ear panel 530 or side panel 330 may comprise a first graphic extending from a side edge of the ear or side panel 537 and 337 respectively toward the longitudinal axis 42, a second elastomeric ear panel 530 or side panel 330 comprises a second graphic extending from a side edge of the ear or side panel 537 and 337 respectively toward the longitudinal axis 42 and the center chassis 200 comprises a third graphic extending from a first side edge 237 of the chassis to the opposing side edge 237 of the chassis wherein the first, second and third graphic are substantially aligned. In general, a composite graphic is formed when two or more separate graphics are substantially aligned to form a larger continuous graphic.

As disclosed in U.S. Ser. No. 15/479,407, disposable absorbent articles comprising one or more belts 430 a first graphic may be printed on a surface of one of the layers of one of the first belt or second belts 430, a second graphic may be printed on a surface of one of the group consisting of a nonwoven layer of the first belt 430 or second belt 430, a layer of the chassis 200, a backsheet 125, and an outer cover, e.g. backsheet nonwoven 127. Additional graphics may be printed on other layers of the article, for example, any of the layers of the belts 430, the elastomeric material, the chassis 200, or of the backsheet 125 or outer cover. A first elastomeric belt 430 may comprise a first graphic element and the chassis 200 comprises a second graphic element wherein the first and second graphic elements are substantially aligned.

When the absorbent article comprises a belt 430, it is desirable that the arrangement of graphic elements cover greater than about 30% of the surface area of the belt 430 or greater than about 40% or greater than about 50%. The graphic elements may cover greater than 75% of the surface area of the belt 430. Additionally, the arrangement of graphics may when viewed from the outside appear to comprise at least 3 colors or at least 5 colors or greater than 7 colors. To provide a very underwear-like appearance the arrangement of graphic elements may be disposed within 30 mm of the waist edge 136 and 138 in one or both of the waist regions, or within 20 mm or within 10 mm of the leg opening edge. The graphics elements may be disposed at or immediately adjacent the waist edge of one or both of the belts 430. In addition, it may be desirable that the arrangement of graphic elements may also be disposed within about 10 mm of a leg edge of the belt 430.

When the absorbent article comprises discrete side panels 330 or ear panels 530, it is desirable that the arrangement of graphic elements cover greater than about 10% of the surface area of the side panel 330 or ear panel 530 or greater than about 25% or greater than about 50%. The graphic elements may cover greater than 75% of the surface area of the discrete side panel 330 or ear panel 530. Additionally, the arrangement of graphics may when viewed from the outside appear to comprise at least 3 colors or at least 5 colors or greater than 7 colors. To provide a very underwear-like appearance the arrangement of graphic elements may be disposed within 30 mm of the waist edge in one or both of the waist regions or within 20 mm or within 10 mm of the leg opening edge. The graphics elements may be disposed at or immediately adjacent the waist edge of the side panels 330 or ear panels 530. In addition, it may be desirable that the arrangement of graphic elements may also be disposed within about 10 mm of a leg opening edge of the side panel 330 or ear panel 530.

For graphics meant to be viewed from the outside of the absorbent article, it may be desirable to print on a layer that is outboard of the elastic layer, including outboard (between the elastic layer and the exterior) of elastic strands as the elastic layer may occlude the visibility of any graphics printed inboard (between the elastic layer and the wearer). As such the interior surface of the most exterior nonwoven layer of the belt, elastomeric ear panels, side panels, and chassis, may be ideal for printing graphics when combined with elastic layers as disclosed herein.

For graphics meant to be viewed from the inside of the absorbent article, it may be desirable to print on a layer that is inboard of the elastic layer, including inboard (between the elastic layer and the wearer) of elastic strands as the elastic layer may occlude the visibility of any graphics printed outboard (between the elastic layer and the exterior). As such the exterior surface of the most interior nonwoven layer of the belt, elastomeric ear panels, side panels, and chassis, may be ideal for printing graphics when combined with elastic layers as disclosed herein.

Absorbent Cores

As used herein, the term "absorbent core" 128 refers to the component of the absorbent article 100 having the most absorbent capacity and that comprises an absorbent material. Referring to FIG. 57A-C, in some instances, absorbent material (e.g., 51) may be positioned within a core bag or a core wrap 74. The absorbent material may be profiled or not profiled, depending on the specific absorbent article. The absorbent core 128 may comprise, consist essentially of, or consist of, a core wrap, absorbent material, and glue enclosed within the core wrap. The absorbent material may comprise superabsorbent polymers, a mixture of superabsorbent polymers and air felt, only air felt, and/or a high internal phase emulsion foam. In some instances, the absorbent material may comprise at least 80%, at least 85%, at least 90%, at least 95%, at least 99%, or up to 100% superabsorbent polymers, by weight of the absorbent material. In such instances, the absorbent material may free of air felt, or at least mostly free of air felt. The absorbent core periphery, which may be the periphery of the core wrap, may define any suitable shape, such as rectangular "T," "Y," "hour-glass," or "dog-bone" shaped, for example. An absorbent core periphery having a generally "dog bone" or "hour-glass" shape may taper along its width towards the crotch region 37 of the absorbent article 100.

Figure 56:
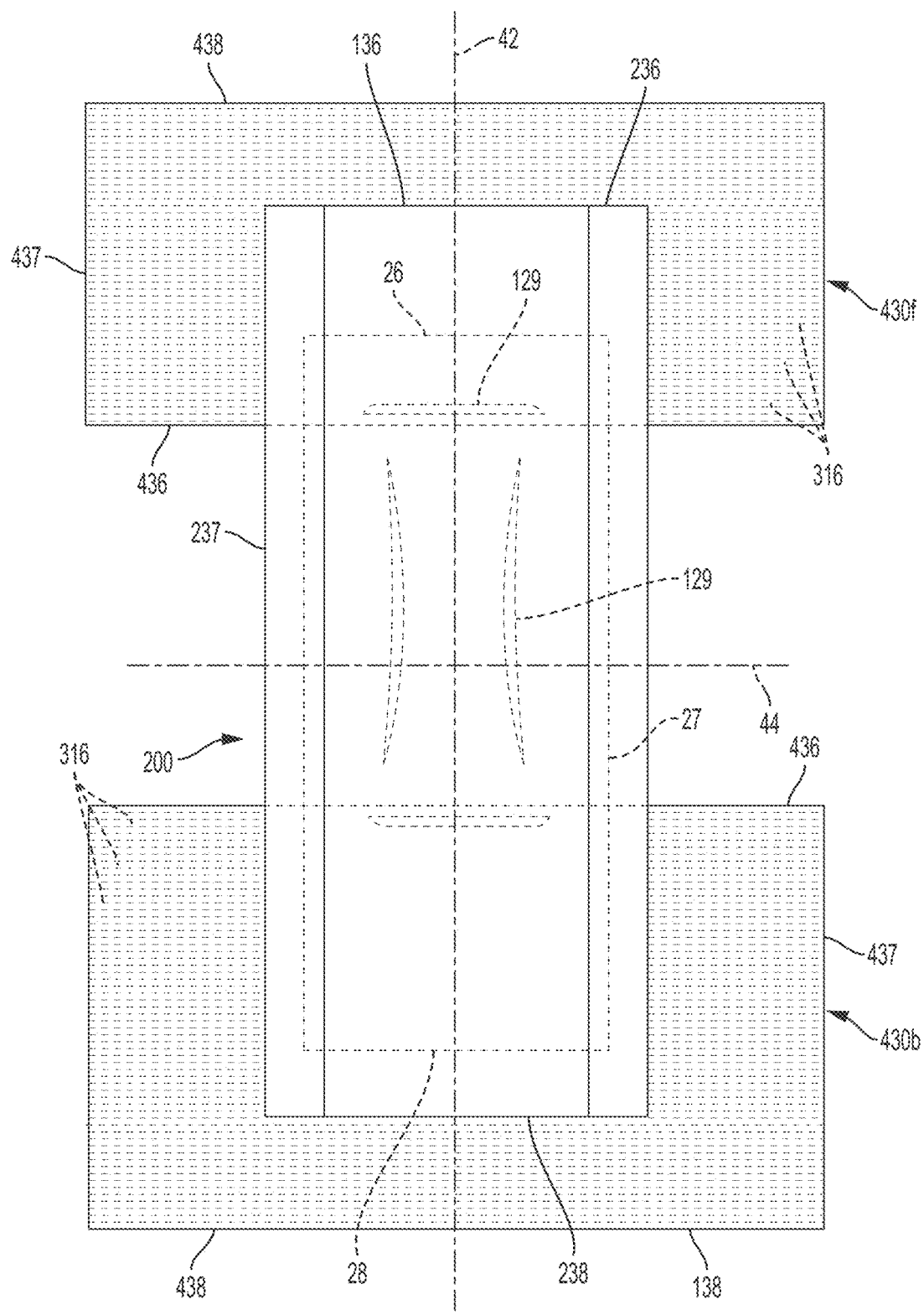
FIG. 56 is a plan view of a belt pant comprising an absorbent core comprising laterally extending core channels and longitudinally extending core channels.

Referring to FIGS. 57A, 57B and 57C, the absorbent core 128 may have areas having little or no absorbent material, where a wearer-facing surface of the core bag 74 may be joined to a garment-facing surface of the core bag 74. These areas having little or no absorbent material may be referred to as "channels" 129 as shown in FIGS. 55 and 56. These channels can embody any suitable shapes and any suitable number of channels may be provided. In other instances, the absorbent core may be embossed to create the impression of channels. The absorbent core in FIG. 57A, is merely an example absorbent core. Many other absorbent cores with or without channels are also within the scope of the present disclosure.

As used herein, a loaded absorbent core is one holding (or capable of holding) a load of at least 50, 100, or 200 milliliters (mls) for diapers, pants, and adult incontinence articles. The disposable absorbent articles of the present disclosure comprising an absorbent core are designed to fit the wearer with an empty absorbent core (i.e., one that is not loaded), as well as being capable of fitting the wear for an appreciable time (2 or more hours) even when the core is loaded.

Core Wraps

The core wrap may be made of a single substrate, material, or nonwoven folded around the absorbent material, or may comprise two (or more) substrates, materials, or nonwovens which are attached to another. Typical attachments are the so-called C-wrap and/or sandwich wrap. In a C-wrap, the longitudinal and/or transversal edges of one of the substrates may be folded over the other substrate to form flaps. These flaps are then bonded to the external surface of the other substrate, typically by gluing. Other techniques may be used to form a core wrap. For example, the longitudinal and/or transversal edges of the substrates may be bonded together and then folded underneath the absorbent core 128 and bonded in that position as illustrated in FIG. 54.

The core wrap may be at least partially sealed adjacent all of the sides of the absorbent core 128 so that substantially no absorbent material leaks out of the core. By "substantially no absorbent material" it is meant that less than 5%, less than 2%, less than 1%, or about 0% by weight of absorbent material escape the core wrap. The term "seal" is to be understood in a broad sense. The seal does not need to be continuous along the whole periphery of the core wrap but may be discontinuous along part or the whole of it, such as formed by a series of seal points spaced on a line. A seal may be formed by gluing and/or thermal bonding.

The core wrap may also be formed by a single substrate which may enclose as in a parcel wrap the absorbent material and be sealed along the front side and rear side of the core and one longitudinal seal. The core wrap may comprise one or more nonwoven layers formed of a co-form material having a pulp fiber to synthetic fiber ratio of from 1:3 to 3:1, i.e. 25%:75% pulp fiber:synthetic fiber to 75%:25% pulp fiber:synthetic fiber.

Channels

As illustrated in FIGS. 55-57C, the absorbent core 128 may comprise at least one channel 129, which is at least partially oriented in the longitudinal direction of the absorbent article 100 (i.e., has a longitudinal vector component). Other channels may be at least partially oriented in the lateral direction (i.e., has a lateral vector component) or in any other direction. In the following, the plural form "channels" will be used to mean "at least one channel". The channels 129 may be circular, oblong, or be in the shape of a variety of other closed polygons. The channels 129 may be formed in various ways. For example, the channels 129 may be formed by zones within the absorbent core 128 and may be substantially free of, or free of, absorbent material, in particular, SAP. In addition, or alternatively, the channels 129 may also be formed by continuously or discontinuously bonding the top side of the core wrap to the bottom side of the core wrap through the absorbent core in the channel area. The channels 129 may be continuous or intermittent. The liquid management system, which may comprise an acquisition layer, distribution layer or both, or another layer of the absorbent article 100, may also comprise channels 129, which may or not correspond to the channels 129 of the absorbent core, as described in more detail below.

The absorbent core 128 may comprise more than two channels, for example, at least 3, at least 4, etc. Shorter channels may also be present, for example in the rear waist region or the front waist region of the core as represented by the pair of channels 129 towards the front of the absorbent article 100. The channels 129 may comprise one or more pairs of channels symmetrically arranged, or otherwise arranged relative to the longitudinal axis 42 or the lateral axis 44.

At least some or all of the channels 129 may be permanent channels, meaning their integrity is at least partially maintained both in the dry state and in the wet state. Permanent channels may be obtained by provision of one or more adhesive materials, for example, the fibrous layer of adhesive material or construction glue that helps adhere a substrate with an absorbent material within the walls of the channel. Permanent channels may also be formed by bonding the upper side and lower side of the core wrap and/or the topsheet 124 to the backsheet 125 together through the channels. Typically, an adhesive may be used to bond both sides of the core wrap or the topsheet and the backsheet through the channels, but it is possible to bond via other known processes, such as pressure bonding, ultrasonic bonding, heat bonding, or combinations thereof. The core wrap or the topsheet 124 and the backsheet 125 may be continuously bonded or intermittently bonded along the channels 129. The channels 129 may advantageously remain or become visible at least through the topsheet 124 and/or backsheet 125 when the absorbent article 100 is fully loaded with a fluid. This may be obtained by making the channels substantially free of SAP, so they will not swell, and sufficiently large so that they will not close when wet. Furthermore, bonding the core wrap to itself or the topsheet 124 to the backsheet 125 in the channel area may be advantageous.

Absorbent cores and/or liquid management systems without any channels are also within the scope of the present disclosure. These cores may include airfelt-free cores, SAP/pulp cores, pulp cores, or other cores known to those of skill in the art.

Acquisition Layers

One or more acquisition materials (e.g., 130) may be present at least partially intermediate the topsheet 124 and the absorbent core 128. The acquisition materials are typically hydrophilic materials that provide significant wicking of bodily exudates. These materials may dewater the topsheet 124 and quickly move bodily exudates into the absorbent core 128. The acquisition materials 38 may comprise one or more nonwoven materials, foams, cellulosic materials, cross-linked cellulosic materials, air laid cellulosic nonwoven materials, spunlace materials, or combinations thereof, for example. In some instances, portions of the acquisition materials may extend through portions of the topsheet 124, portions of the topsheet 124 may extend through portions of the acquisition materials, and/or the topsheet 124 may be nested with the acquisition materials. Typically, an acquisition material or layer may have a width and length that are smaller than the width and length of the topsheet 124. The acquisition material may be a secondary topsheet in the feminine pad context. The acquisition material may have one or more channels as described in the absorbent core 128 section (including the embossed version). The channels in the acquisition material may align or not align with channels in the absorbent core 128. In an example, a first acquisition material may comprise a nonwoven material and as second acquisition material may comprise a cross-linked cellulosic material.

Absorbent Article Packaging and Package Indicia

The absorbent articles 100 of the present disclosure may be placed into packages 610 (shown in FIG. 105 as dotted lines so the absorbent articles 100 may be seen). The packages may comprise polymeric films and/or other materials. Graphics and/or indicia 1000 relating to properties of the absorbent articles may be formed on, printed on, positioned on, and/or placed on outer portions of the packages. Each package may comprise a plurality of absorbent articles 100. The absorbent articles 100 may be packed under compression so as to reduce the size of the packages, while still providing an adequate amount of absorbent articles per package. By packaging the absorbent articles under compression, caregivers can easily handle and store the packages 610, while also providing distribution savings to manufacturers owing to the size of the packages. Accordingly, packages 610 of the absorbent articles 100 of the present disclosure may have an In-Bag Stack Height as disclosed in U.S. Publication No. 2014/0052088 to Weisman, titled ABSORBENT PRODUCTS HAVING IMPROVED PACKAGING EFFICIENCY.

Desirably, the package 610 has parallel sides and a package top that is parallel to the package bottom, making the package ideal for stacking on a shelf for storage or for display in a store for purchase by consumers. Typically packages 610 of absorbent articles 100 are labeled with a recommended wearer weight range (typically for babies, infants, and toddlers) and/or by waist circumference (typically for adult absorbent article products) that the packaged article is intended to fit. As a result, the weight and/or the waist circumference information is most often placed on the package 610 as part of the indicia 1000 to identify the appropriate size of the article needed by the consumer.

Further, the indicia 1000 may illustrate the wearer wearing the article and/or a separate indicia may illustrate the article component or feature. Regarding absorbent articles for babies, descriptions of suitable stages of development indicia and methods of displaying packages comprising absorbent articles may be found in U.S. Pat. No. 7,222,732 to Ronn, titled MERCHANDISE DISPLAY SYSTEM FOR IDENTIFYING DISPOSABLE ABSORBENT ARTICLE CONFIGURATIONS FOR WEARERS. CHEMISTRY (SPANDEX vs. EXTRUDED STRANDS) AND STRUCTURE Beamed elastic uses Spandex fibers. One type of Spandex fiber is "PolyUrethane Urea" elastomer or the "high hard segment level PolyUrethane" elastomer, which must be formed into fibers using a solution (solvent) spinning process (as opposed to being processable in the molten state.) The Urea linkages in PolyUrethane Urea provides strong mutual chemical interactions crucial for providing "anchoring" that enables good stress relaxation performance at temperatures near body temperature on timescales corresponding to diaper wear, including overnight. This type of anchoring enables better force relaxation (i.e. little force decay with time when held in stretched condition at body temperature) over many thermoplastic polyurethane (PolyUrethane with hard segment melting below 200 deg. C.) or thermoplastic Styrenic block copolymers.

In contrast, extruded strands and scrims are typically made of Styrenic block copolymers or thermoplastic elastomers that can be formed in the molten state by conventional extrusion processes. Thermoplastic elastomers include compositions like polyolefin, polyurethane (PolyUrethane with hard segment melting below 200 deg. C.) elastomers, etc. Because these thermoplastic elastomers like Polyurethane (PolyUrethane with hard segment melting below 200 deg. C.) can be melted/remelted, and extruded it makes them susceptible to higher stress relaxation in use, which is a major negative. The styrenic block copolymers used in extruded strands comprise a comparatively long rubbery midblock situated between comparatively short end blocks. End blocks sufficiently short to enable good flow conventional extrusion processes often have a greater propensity to stress relax and undergo force relaxation over time see FIG. 104.

The Urea linkage present in Spandex requires it to be made by spinning process. Spandex can't be melted/remelted or extruded like Styrenic block copolymers. Spandex pre-polymer is combined with solvent and additives, and the solution is spun to make solid spandex fiber. Multiple fibers are then formed together to make one spandex strand. The Spandex strands may have surface finish to avoid blocking and wound onto spools. The one spandex fiber may have a decitex of about 15, so a 500 decitex strand may have nominally 33 fibers wound together to make one strand. Depending on the decitex we use for beam approach, we may have 15 fibers (or filaments), 8 fibers, 5 fibers, 3 fibers or even as low as 2 fibers. Spandex fiber can be mono-component or bi-component (as disclosed in WO201045637A2).

Further related to the chemistry of beamed elastics, it may be desirable to coat the beamed elastics with an oil, such as a silicone oil, including about 10%, about 7%, about 5%, about 3%, or about 1% silicone oil. Treating the beamed elastics with silicone oil helps to prevent blocking (cross-linking) when the strands are wound to a spool or a beam and it also lowers the COF for the strand in textile machinery (for weaving, knitting and warping processes).

Commercially available Spandex strands may also be known as Lycra, Creora, Roica, or Dorlastan. Spandex is often referred as Elastan fiber or Polyurethane fiber.

LYCRA HYFIT strands, a product of Invista, Wichita, Kans., are a suitable for making the strands that make up the plurality of elastics 316 that make up the elastomeric laminate 302. Some strands, for example, the aforementioned LYCRA HYFIT, may comprise a number of individual fibers wound together to form the strand. With regard to elastic strands formed of a number of individual fibers it has been discovered that the individual fibers can move relative to each other changing the cross sectional shape of the strand as well as becoming unraveled which can lead to poor control of the strands as well as poor bonding/adhering/joining of the elastic strands to one or both of the first substrate layer 306 and second substrate layer 308 of the elastomeric laminate 302. In order to minimize the negatives with regard to strands comprising a plurality of fibers it would be advantageous to minimize the number of fibers in a given strand. It would therefore be desirable to have less than about 40 fibers per strand, less than about 30 fibers per strand, less than about 20 fibers per strand, less than about 10 fibers per strand, less than about 5 fibers per strand and 1 fiber forming the strand. In the case of a single fiber forming the strand which can deliver comparable performance to the multi-fiber strands of the prior art it would be desireable for the fiber to have a fiber decitex from about 22 to about 300 and a fiber diameter from about 50 micrometers to about 185 micrometers.

Sensors

The absorbent articles of the present disclosure may comprise a sensor system for monitoring changes within the absorbent article 100. The sensor system may be discrete from or integral with the absorbent article 100. The absorbent article 100 may comprise sensors that can sense various aspects of the absorbent article 100 associated with insults of bodily exudates such as urine and/or BM (e.g., the sensor system may sense variations in temperature, humidity, presence of ammonia or urea, various vapor components of the exudates (urine and feces), changes in moisture vapor transmission through the absorbent articles garment-facing layer, changes in translucence of the garment-facing layer, color changes through the garment-facing layer, etc.). Additionally, the sensor system my sense components of urine, such as ammonia or urea and/or byproducts resulting from reactions of these components with the absorbent article 100. The sensor system may sense byproducts that are produced when urine mixes with other components of the absorbent article 100 (e.g., adhesives, AGM, etc.). The components or byproducts being sensed may be present as vapors that may pass through the garment-facing layer. It may also be desirable to place reactants in the diaper that change state (e.g. color, temperature, etc.) or create a measurable byproduct when mixed with urine or BM. The sensor system may also sense changes in pH, pressure, odor, the presence of gas, blood, a chemical marker or a biological marker or combinations thereof.

The sensor system or portions thereof may be integrated with the absorbent article 100 with hook and loops fasteners, adhesives, thermal bonds, mating fasteners like snaps or buttons, or may be disposed in pockets, recesses or void spaces built into the absorbent article 100, or combinations thereof. Many of these integration means enable removal of and/or attachment of the sensor system or portions thereof from or to the absorbent article 100. The absorbent article 100 may further comprise graphics for the purpose of properly locating the sensor system or portions thereof. In addition, in cases where an auxiliary article is present, the auxiliary article may be joined to the absorbent article 100 by similar integration means. Regarding pockets, it may be desirable to form a pocket within or adjacent to the wearer-facing layer or garment-facing layer of the article. A pocket may be formed by joining an additional material (e.g., a nonwoven strip) to the interior or exterior surface of the garment-facing layer. When joined to the interior surface of the garment-facing layer, it may be desirable to position an open edge (to be the pocket opening) of the sheet to be coterminous or adjacent to an edge of the waist opening 190 such that there is no need to make a cut in the garment-facing layer for inserting the sensor system 700 or portions thereof into the pocket opening.

As used in this application, the term "sensor system" refers not only to the elements responsible for detecting a stimulus and/or change in status of the article and signaling such detection, but also may include the housing or carrier layer or substrate around such element(s). A "sensor system" may include a carrier layer with multiple elements capable of detecting one or more stimuli; and, the multiple elements may create multiple locations capable of detecting one or more stimuli. The sensor systems of the present disclosure may be formed of multiple components capable of monitoring urine and/or fecal insults. The sensor system may take on a variety of configurations, which are determined by the means in which the presence of urine and/or feces is detected. After detection of urine and/or feces, the sensor system may inform a caregiver and/or a child by generating a notification. The notification may be an auditory signal, an olfactory signal, a tactile signal or a visual signal. It is understood that the sensor system may comprise a device for sending a wireless signal to a remote receiver which may in turn result in an auditory signal, a visual signal, a tactile signal or other sensory signal and/or combinations thereof.

Various sensors may be used as part of the sensor system, including inductive, capacitive, ultra-sonic, optical, moisture, humidity (e.g., MVTR), pH, biological, chemical, mechanical, temperature, electromagnetic and combinations thereof, as described and illustrated in U.S. Pub. Nos. 2012/0310190 and 2012/0310191.

The sensor system may include one or more transmitters. A transmitter is a device that sends electromagnetic waves carrying messages or signals, for instance, one or more of the sensor elements may comprise a transmitter. Alternatively, a transmitter may be removably fixed to the absorbent article 100 or to an auxiliary article such that it is in contact or in communication with the sensor elements.

Feminine Absorbent Article

The feminine absorbent article 801, shown in FIGS. 78-83 may comprise any known or otherwise effective topsheet 124, such as one which is compliant, soft feeling, and non-irritating to the wearer's skin. Suitable topsheet materials include a liquid pervious material that is oriented towards and contacts the body of the wearer permitting bodily discharges to rapidly penetrate through it without allowing fluid to flow back through the topsheet to the skin of the wearer. The topsheet 124, while being capable of allowing rapid transfer of fluid through it, also provides for the transfer or migration of the lotion composition onto an external or internal portion of a wearer's skin. A suitable topsheet can be made of various materials such as woven and nonwoven materials; apertured film materials including apertured formed thermoplastic films, apertured plastic films, and fiber-entangled apertured films; hydro-formed thermoplastic films; porous foams; reticulated foams; reticulated thermoplastic films; thermoplastic scrims; or combinations thereof.

Apertured film materials suitable for use as the topsheet 124 as shown in FIG. 81 include those apertured plastic films that are non-absorbent and pervious to body exudates and provide for minimal or no flow back of fluids through the topsheet. Non-limiting examples of other suitable formed films, including apertured and non-apertured formed films, are more fully described in U.S. Pat. No. 3,929,135, issued to Thompson on Dec. 30, 1975; U.S. Pat. No. 4,324,246, issued to Mullane et al. on Apr. 13, 1982; U.S. Pat. No. 4,342,314, issued to Radel et al. on Aug. 3, 1982; U.S. Pat. No. 4,463,045, issued to Ahr et al. on Jul. 31, 1984; U.S. Pat. No. 5,006,394, issued to Baird on Apr. 9, 1991; U.S. Pat. No. 4,609,518, issued to Curro et al. on Sep. 2, 1986; and U.S. Pat. No. 4,629,643, issued to Curro et al. on Dec. 16, 1986. Commercially available formed filmed topsheets include those topsheet materials marketed by the Procter & Gamble Company (Cincinnati, Ohio) under the DRI-WEAVE® tradename.

Non-limiting examples of woven and nonwoven materials suitable for use as the topsheet 124 include fibrous materials made from natural fibers, modified natural fibers, synthetic fibers, or combinations thereof. These fibrous materials can be either hydrophilic or hydrophobic, but it is preferable that the topsheet be hydrophobic or rendered hydrophobic. As an option portions of the topsheet can be rendered hydrophilic, by the use of any known method for making topsheets containing hydrophilic components. One such method include treating an apertured film component of a nonwoven/apertured thermoplastic formed film topsheet with a surfactant as described in U.S. Pat. No. 4,950,264, issued to Osborn on Aug. 21, 1990. Other suitable methods describing a process for treating the topsheet with a surfactant are disclosed in U.S. Pat. Nos. 4,988,344 and 4,988,345, both issued to Reising et al. on Jan. 29, 1991. The topsheet 124 may have hydrophilic fibers, hydrophobic fibers, or combinations thereof.

When the topsheet 124 comprises a nonwoven fibrous material in the form of a nonwoven web, the nonwoven web may be produced by any known procedure for making nonwoven webs, nonlimiting examples of which include spunbonding, carding, wet-laid, air-laid, meltblown, needle-punching, mechanical entangling, thermo-mechanical entangling, and hydroentangling. A specific example of a suitable meltblown process is disclosed in U.S. Pat. No. 3,978,185, to Buntin et al., issued Aug. 31, 1976. The nonwoven may be compression resistant as described in U.S. Pat. No. 7,785,690 entitled "Compression Resistant Nonwovens" issued on Aug. 31, 2010. The nonwoven web may have loops as described in U.S. Pat. No. 7,838,099 entitled "Looped Nonwoven Web" issued on Nov. 23, 2010.

Other suitable nonwoven materials include low basis weight nonwovens, that is, nonwovens having a basis weight of from about 18 $g/m^2$ to about 25 $g/m^2$. An example of such a nonwoven material is commercially available under the tradename P-8 from Veratec, Incorporation, a division of the International Paper Company located in Walpole, Mass. Other nonwovens are described in U.S. Pat. Nos. 5,792,404 and 5,665,452.

The topsheet 124 may comprise tufts as described in U.S. Pat. No. 8,728,049 entitled "Absorbent Article Having a Tufted Topsheet" issued on May 20, 2014, U.S. Pat. No. 7,553,532 entitled "Tufted Fibrous Web" issued on Jun. 30, 2009, U.S. Pat. No. 7,172,801 entitled "Tufted Laminate Web" issued on Feb. 6, 2007, or U.S. Pat. No. 8,440,286 entitled "Capped Tufted Laminate Web" issued on May 14, 2013. The topsheet may have an inverse textured web as described in U.S. Pat. No. 7,648,752 entitled "Inverse Textured Web" issued on Jan. 19, 2010. Tufts are also described in U.S. Pat. No. 7,410,683 entitled "Tufted Laminate Web" issued on Aug. 12, 2008.

The topsheet 124 may comprise one or more structurally modified zones as described in U.S. Pat. No. 8,614,365 entitled "Absorbent Article" issued on Dec. 24, 2013. The topsheet may have one or more out of plane deformations as described in U.S. Pat. No. 8,704,036 entitled "Sanitary Napkin for Clean Body Benefit" issued on Apr. 22, 2014. The topsheet 124 may have a masking composition as described in U.S. Pat. No. 6,025,535 entitled "Topsheet For Absorbent Articles Exhibiting Improved Masking Properties" issued on Feb. 15, 2000.

The absorbent core 128 may be any absorbent means capable of absorbing or retaining liquids (e.g., menses and/or urine). The absorbent core 128 may be manufactured in a wide variety of sizes and shapes (e.g., rectangular, oval, hourglass, dog bone, asymmetric, etc.) and from a wide variety of liquid-absorbent materials commonly used in sanitary napkins and other absorbent articles such as comminuted wood pulp which is generally referred to as airfelt. Examples of other suitable absorbent materials include creped cellulose wadding; meltblown polymers including coform; chemically stiffened, modified or cross-linked cellulosic fibers; synthetic fibers such as crimped polyester or polyolefin fibers; peat moss; tissue including tissue wraps and tissue laminates; absorbent foams; absorbent sponges; superabsorbent polymers; absorbent gelling materials; or any equivalent material or combinations of materials, or mixtures of these. The absorbent core 128 may have more than one layer wherein each layer may be identical or distinct in one or more property or composition from another layer. A particularly preferred absorbent core 128 is made of thermally bonded airlaid material having less than 50 percent synthetic fibers. Synthetic fibers are preferred due to the ease with which they fuse together to join the core and topsheet as described below. A particularly preferred synthetic fiber is a bi-component material having a polyethylene sheath and a polypropylene center.

The configuration and construction of the absorbent core 128 may also be varied (e.g., the absorbent core may have varying caliper zones (e.g., profiled so as to be thicker in the center), hydrophilic gradients, superabsorbent gradients, or lower density and lower average basis weight acquisition zones; or may comprise one or more layers or structures). The total absorbent capacity of the absorbent core should, however, be compatible with the design loading and the intended use of the sanitary napkin. Further, the size and absorbent capacity of the absorbent core 128 may be varied to accommodate different uses such as incontinence pads, panty liners, regular sanitary napkins, or overnight sanitary napkins.

The fluid absorbent material can be constructed from any of a variety of materials commonly used in disposable absorbent articles. Examples of suitable absorbent materials include creped cellulose wadding, cotton fluff, and citric acid cross-linked cellulose pulp disclosed in U.S. Pat. No. 5,190,563, issued Mar. 2, 1993, U.S. Pat. No. 5,183,707, issued Feb. 2, 1993; and U.S. Pat. No. 5,137,537, issued Aug. 11, 1992, all issued to Herron et al.; synthetic fibers disclosed in U.S. Pat. No. 4,578,414, Sawyer, issued Mar. 25, 1986; absorbent foams, absorbent sponges, superabsorbent composites, superabsorbent foam, and super absorbent polymers. A preferred fluid absorbent material is comminuted and airlaid wood pulp fibers commonly referred to as absorbent fluff. An absorbent fluff having a density of from about 0.05 g to about 0.175 g per $cm^3$ is generally acceptable.

The absorbent core structure may comprise a substrate and superabsorbent polymer layer as those described in U.S. Pat. No. 8,124,827 filed on Dec. 2, 2008 (Tamburro); U.S. application Ser. No. 12/718,244 published on Sep. 9, 2010; U.S. application Ser. No. 12/754,935 published on Oct. 14, 2010; or U.S. Pat. No. 8,674,169 issued on Mar. 18, 2014.

The backsheet 125 acts as a barrier to any absorbed bodily fluids that may pass through the absorbent core to the garment surface thereof with a resulting reduction in risk of staining undergarments or other clothing. Further, the barrier properties of the backsheet 125 permit manual removal, if a wearer so desires, of the interlabial absorbent article with reduced risk of hand soiling. A preferred material is a soft, smooth, compliant, liquid and vapor pervious material that provides for softness and conformability for comfort, and is low noise producing so that movement does not cause unwanted sound.

The backsheet 125 may comprise a wet laid fibrous assembly having a temporary wet strength resin incorporated therein as described in U.S. Pat. No. 5,885,265 (Osborn, III.) issued Mar. 23, 1999. The backsheet 125 may further be coated with a water resistant resinous material that causes the backsheet 125 to become impervious to bodily fluids without impairing the spreading of adhesive materials thereon.

Another suitable backsheet material is a polyethylene film having a thickness of from about 0.012 mm (0.5 mil) to about 0.051 mm (2.0 mils). The backsheet 125 may be embossed and/or matte finished to provide a more clothlike appearance. Further, the backsheet 125 may permit vapors to escape from the absorbent core 42 (i.e., the backsheet is breathable) while still preventing body fluids from passing through the backsheet 125. A preferred microporous polyethylene film which is available from Tredegar Corporation, Va., USA, under Code No. XBF-112W.

Suitable breathable backsheets for use herein include all breathable backsheets known in the art. In principle there are two types of breathable backsheets, single layer breathable backsheets which are breathable and impervious to liquids and backsheets having at least two layers, which in combination provide both breathability and liquid imperviousness. Suitable single layer breathable backsheets for use herein include those described for example in GB A 2184389, GB A 2184390, GB A 2184391, U.S. Pat. Nos. 4,591,523, 3,989,867, 3,156,242 and WO 97/24097.

The backsheet 125 may have two layers: a first layer comprising a gas permeable aperture formed film layer and a second layer comprising a breathable microporous film layer as described in U.S. Pat. No. 6,462,251 (Cimini) issued Oct. 8, 2002. Suitable dual or multi layer breathable backsheets for use herein include those exemplified in U.S. Pat. Nos. 3,881,489, 4,341,216, 4,713,068, 4,818,600, EP 203821, EP 710471, EP 710472, and EP 793952.

The backsheet 125 may be vapor permeable as described in U.S. Pat. No. 6,623,464 (Bewick-Sonntag) issued Sep. 23, 2003 or U.S. Pat. No. 6,664,439 (Arndt) issued Dec. 16, 2003. The backsheet 125 can be formed from any vapor permeable material known in the art. Backsheet 125 can be a microporous film, an apertured formed film, or other polymer film that is vapor permeable, or rendered to be vapor permeable, as is known in the art.

The backsheet 125 can be typically positioned adjacent the outer-facing surface of the absorbent core and can be joined thereto by any suitable attachment device known in the art. For example, the backsheet 125 may be secured to the absorbent core by a uniform continuous layer of adhesive, a patterned layer of adhesive, or an array of separate lines, spirals, or spots of adhesive.

The absorbent article may also include such other suitable features as are known in the art including, but not limited to, re-closable fastening system, lotion, acquisition layers, distribution layers, wetness indicators, sensors, elasticized waist bands and other similar additional elastic elements and the like, belts and the like, waist cap features, containment and aesthetic characteristics and combinations thereof.

Wings/Flaps

Sanitary napkins may have flaps 802 as shown in FIGS. 81-83 extending outwardly from the longitudinal side margins as are well known in the art. For example, U.S. Pat. No. 4,589,876 issued May 20, 1986, to Van Tilburg and U.S. Pat. No. 4,687,478 issued Aug. 18, 1987, to Van Tilburg disclose preferred sanitary napkins with flaps 802 and are incorporated herein by reference to illustrate particularly preferred flapped sanitary napkin constructions.

Sanitary napkins having flaps of the various types are disclosed in U.S. Pat. No. 4,687,478, entitled "Shaped Sanitary Napkin With Flaps," which issued to Van Tilburg on Aug. 18, 1987, U.S. Pat. No. 4,589,876, entitled "Sanitary Napkin," which issued to Van Tilburg on May 20, 1986 and U.S. Pat. No. 5,389,094 entitled "Absorbent Article Having Flaps and Zones of Differential Extensibility," which issued to Lavash et al. on Feb. 14, 1995.

The flaps 802 extend laterally outward beyond the longitudinal side edges of the main body portion from their proximal edges to their distal edges (or "free ends"). The flaps 802 extend outward from at least the central region of the main body portion. The flap transverse centerline may coincide with the principal transverse centerline of the absorbent article, but this is not absolutely required.

The flaps 802 can be joined to the main body portion in any suitable manner. The term "joined", as used herein, encompasses configurations in which an element is directly secured to another element by affixing the element directly to the other element; configurations in which the element is indirectly secured to the other element by affixing the element to intermediate member(s) which in turn are affixed to the other element; and configurations in which one element is integral with another element, i.e., one element is essentially part of the other element.

The flaps 802 can comprise one or more separate components that are joined to the garment-facing side of the main body portion, Preferably, in such a case, the flaps each comprise a separate component that is joined to the garment-facing side of the main body portion. In such alternative embodiments, the flaps are preferably otherwise unattached to the garment-facing side of the main body portion of the absorbent article between the points where they are attached to the main body portion and the longitudinal side edges of the main body portion. The flaps 802 in these latter embodiments can be joined to the garment-facing side of the main body portion by any suitable attachment mechanism. Suitable attachment mechanisms include, but are not limited to adhesives, and the like.

The places or regions on the absorbent article where the flaps 802 are joined to (or extend from) the main body portion, are referred to herein as "junctures". These regions will typically be longitudinally-oriented (or "longitudinal") junctures, such as lines of juncture. These regions can be any of various curved or straight lines, but they are not limited to lines. Thus, the junctures can comprise flanges, strips, intermittent lines, and the like.

Flaps 802 may have zones of extensibility (or "zones of differential extensibility") in the front half and the back half of each flap. The zones of extensibility relieve stresses which are created in flaps by the folding of the flaps around the crotch of the wearer's undergarment. The zones of extensibility thereby help eliminate bunching of flaps caused by said stresses. The zones of extensibility may comprise pre-corrugated or "ring roiled" regions of the flaps in which the corrugations define ridges and valleys that are oriented at an angle to the principal longitudinal centerline. Suitable structures for providing the flaps with zones of extensibility are described in greater detail in U.S. Pat. No. 5,389,094 issued to Lavash, et al.

The flaps 802 may be transparent as described in U.S. Pat. No. 8,491,554, "Transparent Absorbent Article" issued on Jul. 23, 2013.

The flaps 802 may be spaced apart flaps associated with the main body portion as described in U.S. Pat. No. 8,178,748 entitled "Absorbent Article" filed in the name of John Lee Hammons, issued on May 15, 2012. The article may have more than one set of flaps extending from the main body as described in U.S. Pat. No. 6,375,645 entitled "Absorbent Article Wrapper Comprising A Side Flap Fastener Cover, issued on Apr. 23, 2002.

Each flap 802 may have an adhesive patch. Preferentially, such adhesive is associated with the face of the flap which contacts the undergarment of the wearer. Also the central portion of the absorbent article intermediate the flaps may have adhesive associated with the area of the central portion of the absorbent article which contacts the undergarment of the wearer. Preferentially such adhesive is joined to the outwardly oriented face of the backsheet 125.

A feminine absorbent article 801 may comprise flaps 802 and/or cuffs 150 formed at least in part by an elastomeric laminate 302 comprising a first plurality of elastics 316 disposed between first and second substrate layers. Such an elastomeric laminate 302 may have first plurality of elastics 316 comprising from about 10 to about 400 elastic strands having an Average-Strand-Spacing from about 0.25 mm to about 5 mm and an Average-Dtex of the first plurality of elastics 316 from about 10 to about 600.

In alternative embodiments of the elastomeric laminate 302 the first plurality of elastics 316 may comprise from about 15 to about 300 elastic strands. In other embodiments, the first plurality of elastics 316 may comprise from about 20 to about 225 elastic strands. In yet other alternative embodiments, the first plurality of elastics 316 may comprise from about 25 to about 150 elastic strands.

In certain embodiments, the first plurality of elastics 316 may have an Average-Strand-Spacing from about 0.25 mm to about 3.0 mm. In other embodiments, the first plurality of elastics 316 has an Average-Strand-Spacing from about 0.5 mm to about 2.0 mm.

In some embodiments, the Average-Dtex of the first plurality of elastics 316 may be from about 30 to about 400 and in alternative embodiments, the Average-Dtex of the first plurality of elastics 316 may be from about 50 to about 250.

In certain embodiments, the feminine absorbent article 801 may comprise leg cuff like structures disposed at or adjacent the side edges of the article as shown in FIGS. 79 and 80. The leg cuff 150 may be formed by an elastomeric laminate 302 comprising a first substrate layer 306 and a second substrate layer 308 and an elastic material, for example elastic strands 316, disposed between the first and second substrate layers 306 and 308. The first substrate layer 306 and the second substrate layer 308 may be separate and discrete layers or alternatively the first substrate layer 306 and second substrate layer 308 may be formed from a single web of material that is folded to form the first substrate layer 306 and second substrate layer 308 as shown in FIG. 80. In some configurations of the leg cuffs 150, one or both of the first and second substrate layers 306 and 308 may be formed in part or whole by one or both of the backsheet 125 and topsheet 124.

The absorbent article may have one or more graphics as shown in FIG. 81. The graphics may be on the topsheet or visible via the topsheet as described in U.S. Pat. No. 8,629,315 entitled "Absorbent Article Having a Graphic Visible Through Body Contacting Surface" issued on Jan. 14, 2014. Two or more color regions may be produced in the absorbent article using the methods described in U.S. Pat. No. 8,691,041 entitled "Method of Producing a Composite Multi-Layered Printed Absorbent Article" issued on Apr. 8, 2014. The graphics may be on different layers as described in U.S. Pat. No. 8,292,864 entitled "Absorbent Article Having a Multilayer Visual Signal" issued on Oct. 23, 2012. The article may have a multi-component visual signal as described in U.S. Pat. No. 8,262,633 entitled "Absorbent Article Having a Multi-Component Visual Signal" issued on Sep. 11, 2012.

Process

Referring to FIGS. 49A-51, absorbent articles 100 comprising elastomeric laminates 302 that may be used in a variety of components of the absorbent articles 100. The elastomeric laminates 302 may include a first substrate 306, a second substrate 308, and an elastic material located between the first substrate 306 and second substrate 308. During the process of making the elastomeric laminate 302, the elastic material may be advanced and stretched in a machine direction and may be joined with either or both the first and second substrates, 306 and/or 308 advancing in the machine direction.

The elastomeric laminates 302 made according to the processes and apparatuses 301 discussed herein may be used as to construct various types of components used in the manufacture of different types of absorbent articles 100, such as diaper pants and taped diapers. To help provide additional context to the subsequent discussion of the absorbent article embodiments, the following provides a general description of absorbent articles 100 in the form of diapers and/or pants that include components comprising the elastomeric laminates 302 disclosed herein.

In some assembly processes, stretched elastic strands 316 may be advanced in a machine direction and may be adhered between two advancing substrates, wherein the stretched elastic strands 316 are spaced apart from each other in a cross direction. Some assembly processes are also configured with several elastic strands 316 that are very closely spaced apart from each other in the cross direction. In some configurations, close cross directional spacing between elastic strands 316 can be achieved by drawing elastic strands 316 from windings that have been stacked in the cross direction on a beam 314 (e.g., a warp beam). For example, various textile manufacturers may utilize beam elastics and associated handling equipment, such as available from Karl Mayer Corporation. It may be desirable to treat the elastic strands of the beam(s) with silicone oil because it avoids blocking (cross-linking) when the strands are wound to a spool or a beam and because it also lowers the COF for the strand in textile machinery (for weaving, knitting and warping processes).

As illustrated herein, the apparatuses 301 and processes may be configured such that elastic strands 316 may be advanced from the beams 314 and directly to the assembly process without having to touch additional machine components, such as for example, guide rollers. It is also to be appreciated that in some configurations, elastic strands 316 may be advanced from the beams 314 and may be redirected and/or otherwise touched by and/or redirected before advancing to the assembly process. For example, the process may have a first beam 314a with a rotation axis in a first cross direction CD1. As the first beam 314a rotates, the first plurality of elastic strands 316a advance from the first beam 314a in a first machine direction MD1 with the first elastic strands 316a being spaced apart from each other in the first cross direction CD1. The elastic strands 316 may then be redirected by rollers from the first machine direction MD1 to a second machine direction MD2, wherein the elastic strands 316 may remain separated from each other in a second cross direction CD2. From the rollers, the elastic strands 316 may advance in the second machine direction MD2 to be combined with the first and second substrates, 306, 308 to form the elastomeric laminate 302. It is to be appreciated that for processes comprising multiple beams, the first and/or second beams 314a, 314b may be arranged and/or oriented such that the beam rotation axis 346 may be parallel, perpendicular, or otherwise angularly offset with respect to the machine direction advancement of the elastomeric laminate 302 and/or the first and/or second substrates 306, 308. It should also be appreciated that the elastomeric laminate 302 may comprise more than a first substrate 306 and a second substrate 308, i.e. a third substrate and/or a fourth substrate. In such embodiments, a first set of elastic strands 316a from a first beam 314a may be disposed between a first substrate 306 and a second substrate 308 and a second set of elastic strands 316b from a second beam 314b may be disposed between a second substrate 308 and a third substrate providing an elastomeric laminate 302 with elastic strands 316 disposed in multiple, separate, layers of the laminate.

Figure 49B:
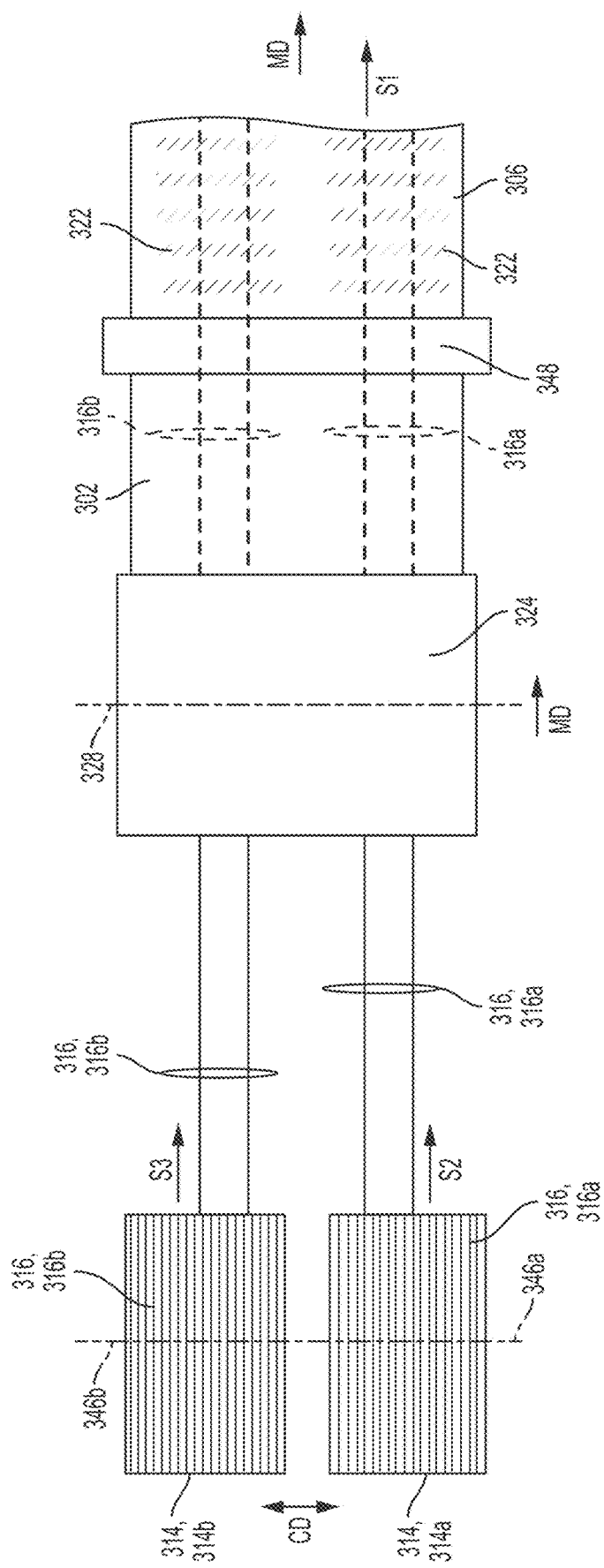
FIG. 49B is a view of the converting apparatus of FIG. 49A taken along line 49B-49B.

It is to be appreciated that the apparatuses 301 herein may be configured in various ways with various features described herein to assemble elastomeric laminates 302 having various stretch characteristics. For example, FIGS. 49A and 49B illustrate the apparatus 301 configured to assemble elastomeric laminates 302 with elastic strands 316 unwound from more than one beam 314. In particular, the apparatus 301 may include a first beam 314a with first elastic strands 316a wound thereon and a second beam 314b with second elastic strands 316b wound thereon. The first beam 314a is rotatable about a first beam rotation axis 346a, and the second beam 314b is rotatable about a second beam rotation axis 346b. During operation, as the first beam 314a rotates, the first elastic strands 316a advance in the machine direction MD from the first beam 314a at a speed S2 with the first elastic strands 316a being spaced apart from each other in the cross-direction CD. From the first beam 314a, the first elastic strands 316a advance in the machine direction MD and are joined with the first substrate 306 and the second substrate 308. Similarly, as the second beam 314b rotates, the second elastic strands 316b advance in the machine direction MD from the second beam 314b at a speed S3 with the second elastic strands 316b being spaced apart from each other in the cross-direction CD. From the second beam 314b, the second elastic strands 316b advance in the machine direction MD and are joined with the first substrate 306 and the second substrate 308. It is also to be appreciated that the apparatus configuration shown in FIGS. 49A and 49B may also include the bond applicator 348 arranged to apply the bonds 322. The bond applicator 348 is generically represented by a dashed-line rectangle in FIG. 49A.

With continued reference to FIGS. 49A and 49B, the elastic strands 316a, 316b may be joined with the first and second substrates 306, 308 such that the elastomeric laminate 302 may have different stretch characteristics in different regions along the cross-direction CD. For example, when the elastomeric laminate 302 is elongated, the first elastic strands 316a may exert contraction forces in the machine direction MD that are different from contraction forces exerted by the second elastic strands 316b. Such differential stretch characteristics can be achieved by stretching the first elastic strands 316a more or less than the second elastic strands 316b before joining the elastic strands 316a, 316b with the first and second substrates 306, 308. For example, as previously discussed, the first substrate 306 and the second substrate 308 may each advance at a speed S1. In some configurations, the first elastic strands 316a may advance from the first beam 314a at speed S2 that is less than the speed S1, and second elastic strands 316b may advance from the second beam 314b at the speed S3 that is less than the speed S1. As such, the first elastic strands 316a and the second elastic strands 316b are stretched in the machine direction MD when combined with the first and second substrates 306, 308. In addition, the speed S2 may be less than or greater than different than the speed S3. Thus, the first elastic strands 316a may be stretched more or less than the second elastic strands 316b when combined with the first and second substrates 306, 308. It is also appreciated that the first and second elastic strands 316a, 316b may have various different material constructions and/or decitex values to create elastomeric laminates 302 different stretch characteristics. As previously mentioned, in some configurations, the elastic strands 316 may be supplied on the beam 314 in a stretched state, and as such, may not require additional stretching (or may require relatively less additional stretching) before being combined with the first substrate 306 and/or the second substrate 308. Thus, in some configurations, the first elastic strands 316a may be supplied on the first beam 314a at a first tension, and the second elastic strands 316b may be supplied on the second beam 314b at a second tension, wherein the first tension is not equal to the second tension.

Figure 51:
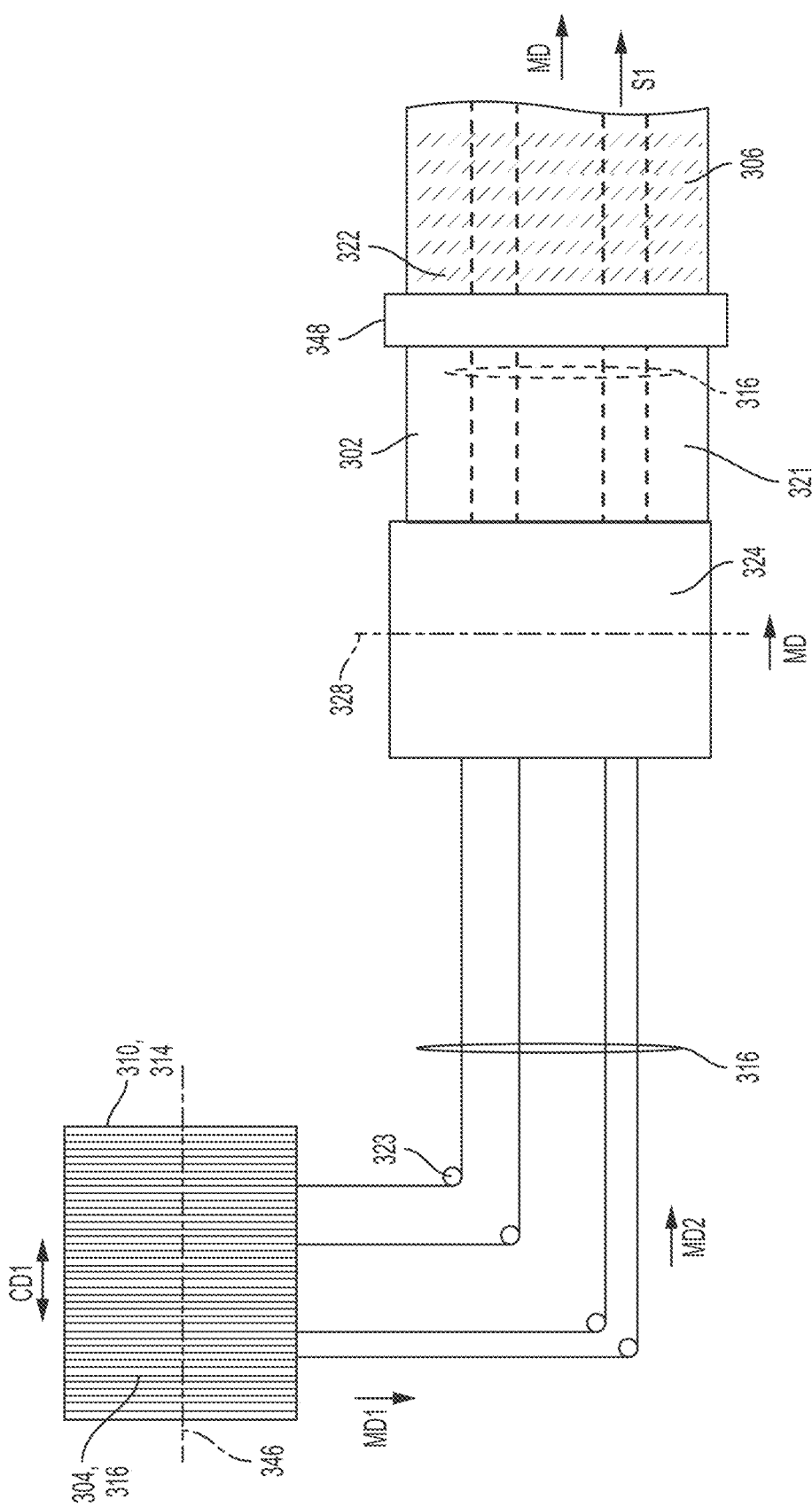
FIG. 51 is a schematic side view of an alternative configuration of a converting apparatus adapted to manufacture an elastomeric laminate.

As illustrated herein, the apparatuses and processes may be configured such that elastic strands may be advanced from the beams and directly to the assembly process without having to touch additional machine components, such as for example, guide rollers. It is also to be appreciated that in some configurations, elastic strands may be advanced from beams and may be redirected and/or otherwise touched by and/or redirected before advancing to the assembly process. For example, FIG. 51 shows a configuration where the beam rotation axis 346 may extend in a first cross direction CD1. As the beam 314 rotates, the elastic strands 316 advance from the beam 314 in a first machine direction MD1 with the elastic strands 316 being spaced apart from each other in the first cross direction CD1. The elastic strands 316 may then be redirected by rollers 323 from the first machine direction MD1 to a second machine direction MD2, wherein the elastic strands 316 may remain separated from each other in a second cross direction CD2. From the rollers 323, the elastic strands 316 may advance in the second machine direction MD2 to be combined with the first and second substrates 306, 308 to form the elastomeric laminate 302. Thus, it is to be appreciated that the beam 314 may be arranged and/or oriented such that the beam rotation axis 346 may be parallel, perpendicular, or otherwise angularly offset with respect to the machine direction advancement of the elastomeric laminate 302 and/or the substrates 306, 308.

Figure 50A:
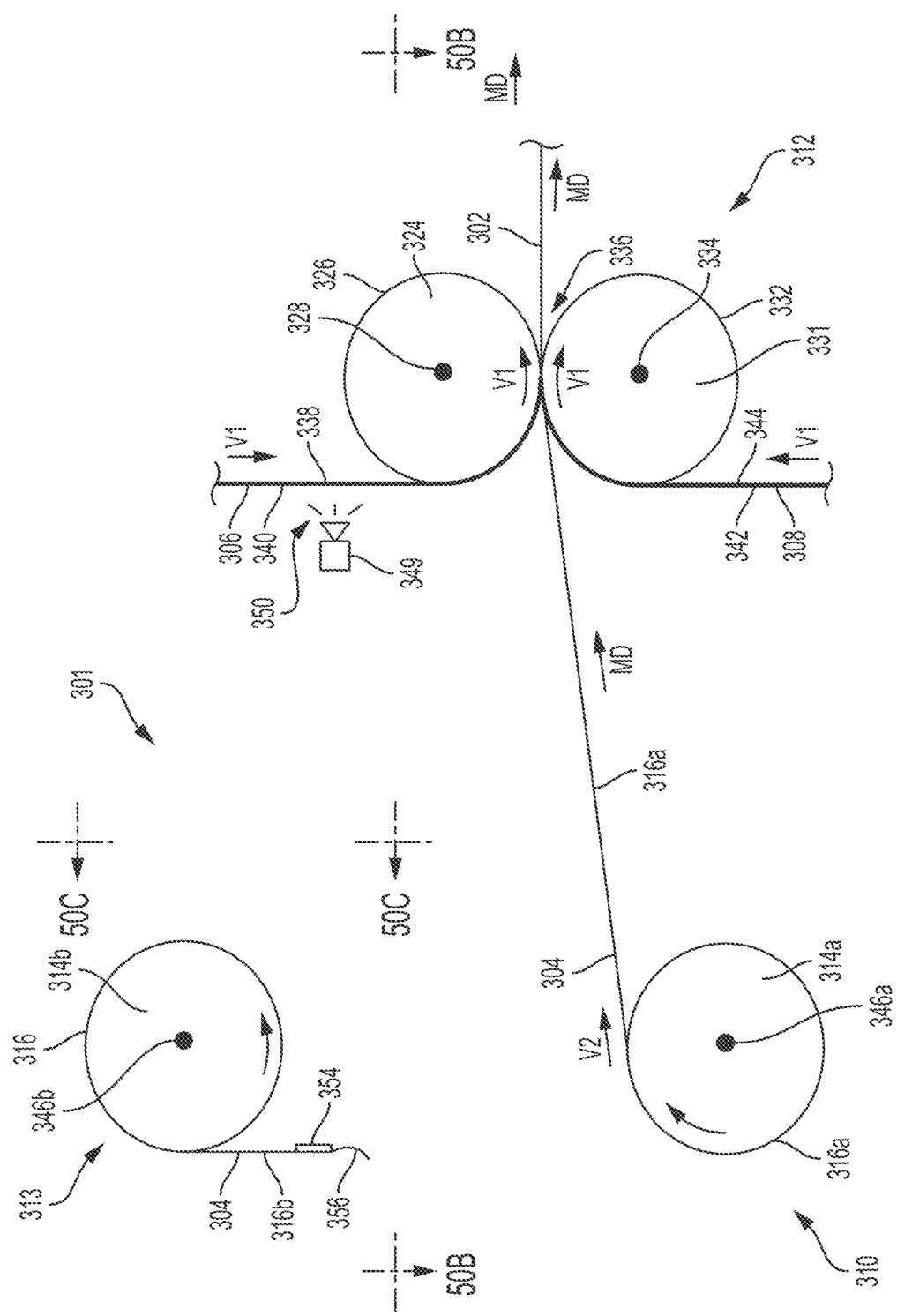
FIG. 50A is a schematic side view of a converting apparatus adapted to manufacture an elastomeric laminate including a first plurality of elastic strands positioned between a first substrate and a second substrate.

As shown in FIGS. 50A and 50B, a converting apparatus 301 for producing an elastomeric laminate 302 may include a first metering device 310, a second metering device 312, and a third metering device 313. The first metering device may be configured as a first beam 314a with a first plurality of elastic strands 316a wound thereon, and the third metering device is configured as a second beam 314b with a second plurality of elastics 316b wound thereon. It is to be appreciated that beams of various sizes and technical specifications may be utilized in accordance with the methods and apparatuses herein, such as for example, beams that are available from ALUCOLOR Textilmaschinen, GmbH. During operation, the first plurality of elastics 316a advance in the machine direction MD from the first beam 314a to the second metering device 312. In addition, the first plurality of elastics 316a may be stretched along the machine direction MD between the first beam 314a and the second metering device 312. The stretched first elastic strands 316a are also joined with a first substrate 306 and a second substrate 308 at the second metering device 312 to produce an elastomeric laminate 302. As discussed in more detail below, once the first beam 314a is empty or nearly depleted of first elastic strands 316a, the second plurality of elastics 316b can be introduced into the assembly operation as replacements for the first plurality of elastics 316a without having to stop the assembly operation.

As shown in FIG. 50A, the second metering device 312 includes: a first roller 324 having an outer circumferential surface 326 and rotates about a first axis of rotation 328, and a second roller 331 having an outer circumferential surface 332 and rotates about a second axis of rotation 334. The first roller 324 and the second roller 331 rotate in opposite directions, and the first roller 324 is adjacent the second roller 331 to define a nip 336 between the first roller 324 and the second roller 331. The first roller 324 rotates such that the outer circumferential surface 326 has a surface speed V1, and the second roller 331 may rotate such that the outer circumferential surface 332 has the same, or substantially the same, surface speed V1.

As shown in FIGS. 50A-50C, the first substrate 306 includes a first surface 338 and an opposing second surface 340, and the first substrate 306 advances to the first roller 324. In particular, the first substrate 306 advances at speed V1 to the first roller 324 where the first substrate 306 partially wraps around the outer circumferential surface 326 of the first roller 324 and advances through the nip 336. As such, the first surface 338 of the first substrate 306 travels in the same direction as and in contact with the outer circumferential surface 326 of the first roller 324. In addition, the second substrate 308 includes a first surface 342 and an opposing second surface 344, and the second substrate 308 advances to the second roller 331. In particular, the second substrate 308 advances at speed V1 to the second roller 331 where the second substrate 308 partially wraps around the outer circumferential surface 332 of the second roller 331 and advances through the nip 336. As such, the second surface 344 of the second substrate 308 travels in the same direction as and in contact with the outer circumferential surface 332 of the second roller 331.

With continued reference to FIGS. 50A and 50B, the first beam 314a includes the first plurality of elastics 316a wound thereon, and the first beam 314a is rotatable about a first beam rotation axis 346. In some configurations, the first beam rotation axis 346 may extend in the cross-direction CD. As the first beam 314a rotates, the first plurality of elastics 316a advance from the first beam 314a at a speed V2 with the first elastics 316a being spaced apart from each other in the cross-direction CD. From the first beam 314a, the first plurality of elastics 316a advances in the machine direction MD to the nip 336. In some configurations, the speed V2 is less than the speed V1, and as such, the first plurality of elastics 316a are stretched in the machine direction MD. In turn, the stretched first elastics 316a advance through the nip 336 between the first and second substrates 306, 308 such that the first elastics 316a are joined with the second surface 340 of the first substrate 306 and the first surface 342 of the second substrate 308 to produce a continuous length of elastomeric laminate 302. The first substrate 306 may advance past an adhesive applicator device 349 that applies adhesive 350 to the second surface 340 of the first substrate 306 before advancing to the nip 336. It is to be appreciated that the adhesive 350 may be applied to the first substrate 306 upstream of the first roller 324 and/or while the first substrate 306 is partially wrapped around the outer circumferential surface 326 of the first roller 324. It is to be appreciated that adhesive may be applied to the first elastics 316a before and/or while being joined with first substrate 306 and second substrate 308. In addition, it is to be appreciated that adhesive may be applied to the first surface 342 of the second substrate 308 before or while being joined with the first elastics 316a and the first substrate 306.

As previously discussed, the apparatus 301 includes the second plurality of elastic strands 316b configured to replace the first plurality of elastics 316a once the first beam 314a is completely depleted or nearly depleted of first elastics 316a. As shown in FIGS. 50A and 50B, the second beam 320 includes the second plurality of elastics 316b wound thereon, and the second beam 314b is rotatable about a second beam rotation axis 352. In some configurations, the second beam rotation axis 352 may extend in the cross-direction CD. As the second beam 314b rotates, the second plurality of elastic strands 316b advance from the second beam 314b at a speed V2 with the second elastic strands 316b being spaced apart from each other in the cross-direction CD. When introducing the second elastic strands 316b into the assembly operation, the second plurality of elastic strands 316b may first be connected with a splicer member 354. As shown in FIG. 50B, the splicer member 354 may be connected adjacent leading ends 356 of the second elastics 316b. In turn, the splicer member 354 and the second elastics 316b may be connected with the first plurality of elastics 316a that are advancing from the first beam 314a to the nip 336.

As previously mentioned, the elastomeric laminate 302 may also be subject to additional converting processes. Such additional converting processes may incorporate the elastomeric laminate 302 into discrete absorbent articles 100. As such, an inspection system may be configured to detect and/or track a defective length of the elastomeric laminate 302. A defective length of elastomeric laminate 302 may be defined by a length of elastomeric laminate 302 that includes both the first elastic strands 316a and the second elastics 316b positioned together between the first and second substrates 306, 308. A defective length of elastomeric laminate 302 may also be defined by a length of elastomeric laminate 302 that includes the splicer member 354, leading ends 356 of the second elastics 316b, and/or the trailing ends 358 of the first elastics 316a. The inspection system may also correlate inspection results and measurements from the defect length of the elastomeric laminate 302 with absorbent articles 100 made therefrom. In turn, the inspection system may be used to control a reject system on a converting process of absorbent articles, wherein absorbent articles manufactured with portions of the defective length of elastomeric laminate 302 are rejected. In some configurations, defective articles may be subject to the rejection system and removed from the assembly process. Absorbent articles 100 that are not deemed to be defective may be subject to further processing steps, such as folding and packaging. It is to be appreciated that such an inspection system may be configured in various ways, such as disclosed in U.S. Patent Publication No. 2013/0199696 A1.

As previously mentioned, absorbent articles according to the present disclosure may comprise elastomeric laminates that may be used to construct various components of taped and/or pant diapers, such as a pair of laterally opposing inner leg cuffs, a pair of laterally opposing outer leg cuffs, a back belt, a front belt, a pair of laterally opposing side panels, a pair of laterally opposing ear panels, a back waistband, a front waistband, front and/or back waist caps, and discrete expansion panels disposed in areas overlapping the center chassis and the like.

It is to be appreciated that different components may be used to construct the elastomeric laminates 302 in accordance with the methods and apparatuses herein. For example, the first and/or second substrates 306, 308 may include nonwovens and/or films. In addition, the first and/or second elastics 316a, 316b may be configured in various ways and having various decitex values. In some configurations, the first and/or second plurality of elastics 316a, 316b may be configured with decitex values ranging from about 10 decitex to about 500 decitex, specifically reciting all 1 decitex increments within the above-recited range and all ranges formed therein or thereby. It is also to be appreciated the first beam 314a and the second beam 314b may be configured in various ways and with various quantities of elastic strands, types of elastic strands and/or colors of elastic strands. Example beams, also referred to as warp beams, that may be used with the apparatus and methods herein are disclosed in U.S. Pat. Nos. 4,525,905; 5,060,881; and 5,775,308; and U.S. Patent Publication No. 2004/0219854 A1. Although FIG. 50b shows nine elastics 316 advancing from the first beam 314a, it is to be appreciated that the apparatuses herein may be configured such that more or less than nine elastic strands 316 advance from the first beam 314a. In some configurations, the first elastics 316a advancing from the first beam 314a and/or the second elastics 316b advancing from the second beam 314b may include from about 10 to about 1000 strands, specifically reciting all 1 strand increments within the above-recited range and all ranges formed therein or thereby. In some configurations, the first elastics 316a and/or the second elastics 316b may be separated from each other by about 0.5 mm to about 5 mm in the cross direction, specifically reciting all 0.1 mm increments within the above-recited range and all ranges formed therein or thereby. It is also to be appreciated that one or more beams of elastics may be arranged along the cross direction CD of a converting process and/or arranged along a machine direction MD in various different portions of a converting process. It is also to be appreciated that the first beam 314a and the second beam 314b can be connected with one or more motors, such as servo motors, to drive and control the rotation of the beams 314a, 314b.

Furthermore, the plurality of elastics 316 may be joined to one or both of the first substrate 306 and second substrate 308 by means of adhesive bonding, mechanical bonding, thermal bonding, ultrasonic bonding or other lamination means known in the art, including elastics that have been treated with silicone oil. The first and second substrates 306 and 308 may be melted around the elastic strands (by, for example, ultrasonic bonding the first and second substrates), filed on Sep. 1, 2017, first-named inventor Uwe Schneider, assigned to The Procter & Gamble Company. Melting the first and second substrates 306 and 308 together may be desirable for overcoming the anti-stick properties of the elastics of silicone oil placed on the strands. Alternatively, the first and second substrates 306 and 308 may be bonded in between elastic strands comprising silicone oil. Further, lines of adhesives may also be used between first and second substrates 306 and 308 as described in (U.S. Ser. No. 62/553,149), filed on Sep. 1, 2017, first-named inventor Uwe Schneider, assigned to The Procter & Gamble Company. Still further, silicone oil may be removed from the elastic strands to allow for better bonding of the elastic strands to the first and second substrates 306 and 308 as disclosed in (62/483,965), filed on Apr. 11, 2017, first-named inventor Uwe Schneider, assigned to The Procter & Gamble Company. One or more of the bonding methods described and referenced in this paragraph may be used with elastic strands comprising from about 10%, about 7%, about 5%, about 3%, or about 1% silicone oil.

In addition, the first substrate 306 and/or second substrate 308 may have a material basis weight of from about 6 grams per square meter to about 30 grams per square meter. It should also be understood that the elastomeric laminates 302 described herein may have a uniform elastic pattern, decitex, spacing and pre-strain or may alternatively have multiple zones that may be supplied via multiple beams 314 having comprising varying compositions of elastic type, decitex, spacing or pre-strain.

It is the process disclosed in this PROCESS section of the present application that forms the elastomeric laminate 302 of the present disclosure and that may be further incorporated into the various absorbent article components such as the belts, ear panels, side panels, transverse barriers, topsheets, backsheets, cuffs, waistbands, waistcaps, and/or chassis to offer the benefits described in this patent application. Further details of the process of creating beamed elastomeric laminate(s) for use in disposable absorbent articles are disclosed in U.S. Publication No. 62/436,589, titled "METHODS AND APPARATUSES FOR MAKING ELASTOMERIC LAMINATES WITH ELASTIC STRANDS UNWOUND FROM BEAMS," first-named inventor being Schneider, filed on Dec. 20, 2016. The elastomeric laminate 302 may be produced as part of the absorbent article manufacturing line, or may be produced offline, and unwound as an elastomeric laminate that is fed into the absorbent article manufacturing line.

Elastomeric Laminate(s) of the Present Disclosure

An "elastomeric laminate 302" of the present disclosure may comprise a plurality of elastics 316 between a first substrate 306 and a second substrate layer 308, where the plurality of elastics 316 (often referred to as a "first plurality of elastics," a "second plurality of elastics," etc.) has an Average-Strand-Spacing from about 0.25 mm to about 4 mm, an Average-Dtex from about 10 to about 500, and a Pressure-Under-Strand from about 0.1 to about 1 psi. Ultimately, "plurality of elastics" is a term of context, where certain properties, arrangements, attributes, characteristics, etc. define what a certain "plurality of elastics" is. Said elastomeric laminate 302 may be used to form at least a portion of various absorbent article components. When the elastomeric laminate 302 forms at least a portion of at least one of the group consisting of a belt, a chassis, a side panel, a topsheet, a backsheet, an ear panel, and combinations thereof, the plurality of elastics 316 of the elastomeric laminate 302 may comprise from about 40 to about 1000 elastic strands. And, when the elastomeric laminate 302 forms at least a portion of at least one of the group consisting of a waistband, a waistcap, an inner leg cuff, an outer leg cuff, a transverse barrier, and combinations thereof, the first plurality of elastics 316 of the elastomeric laminate 302 may comprise from about 10 to about 400 elastic strands. Ultimately, "plurality of elastics" is a term of context, where certain properties (e.g., Average-Dtex, Average-Strand-Spacing, Pressure-Under-Strand, etc.), arrangements, attributes, characteristics, disposition, etc. of the elastics are referenced to define what a certain "plurality of elastics" is.

Further, the elastomeric laminate 302 may form at least a portion of one or more of the group of article components including a belt 430, a side panel 330, chassis 200, a topsheet 124, backsheet 125, and an ear panel 530, the elastomeric laminate 302 may comprise a plurality of elastics 316 having from about 40 to about 1000 elastic strands with an Average-Strand-Spacing from about 0.25 mm to about 4 mm, Average-Dtex from about 10 to about 500, an Average-Pre-Strain from about 50% to about 400%; and a first substrate 306 and a second substrate 308 each having a basis weight from about 6 grams per square meter to about 30 grams per square meter.

When the elastomeric laminate 302 may form at least a portion of one or more of the group of article components including a belt 430, a side panel 330, chassis 200, a topsheet 124, backsheet 125, and an ear panel 530, the elastomeric laminate 302 may comprise a plurality of elastics 316 having from about 50 to about 825 elastic strands. Further, the plurality of elastics 316 may comprise from about 100 to about 650 elastic strands. Still further, the plurality of elastics 316 may comprise from about 150 to about 475 elastic strands.

When the elastomeric laminate 302 may form at least a portion of one or more of the group of article components including a belt 430, a side panel 330, chassis 200, a topsheet 124, backsheet 125, and an ear panel 530, the elastomeric laminate 302 may comprise a plurality of elastics 316 having an Average-Strand-Spacing from about 0.5 mm to about 3.5 mm. Further, the plurality of elastics 316 may have an Average-Strand-Spacing from about 1.0 mm to about 2.5 mm.

When the elastomeric laminate 302 may form at least a portion of one or more of the group of article components including a belt 430, a side panel 330, chassis 200, a topsheet 124, backsheet 125, and an ear panel 530, the elastomeric laminate 302 may comprise a plurality of elastics 316 having an Average-Dtex from about 30 to about 400. Further, the elastomeric laminate 302 may have an Average-Dtex of the plurality of elastics 316 from about 50 to about 250.

When the elastomeric laminate 302 may form at least a portion of one or more of the group of article components including a belt 430, a side panel 330, chassis 200, a topsheet 124, backsheet 125, and an ear panel 530, the elastomeric laminate 302 may comprise a plurality of elastics 316 having an Average-Pre-Strain which may be from about 75% to about 300%. Further, the elastomeric laminate may comprise a plurality of elastics 316 with an Average-Pre-Strain of from about 100% to about 250%

The elastomeric laminate 302 may form at least a portion of one or more of the group of article components including a waistband 122, waistcap 123, inner leg cuff 150, outer leg cuff 140 and a transverse barrier 16, and may comprise a plurality of elastics 316 having from about 10 to about 400 elastic strands with an Average-Strand-Spacing from about 0.25 mm to about 4 mm, Average-Dtex from about 10 to about 500, an Average-Pre-Strain from about 50% to about 400% and a first substrate 306 and/or second substrate 308 each having a basis weight from about 6 grams per square meter to about 30 grams per square meter.

The elastomeric laminate 302 may form at least a portion of one or more of the group of article components including a waistband 122, waistcap 123, inner leg cuff 150, outer leg cuff 140 and a transverse barrier 16, and may comprise a plurality of elastics 316 having from about 15 to about 300 elastic strands. Further, the plurality of elastics 316 may comprise from about 20 to about 225 elastic strands. Further, the plurality of elastics may 316 comprise from about 25 to about 150 elastic strands.

The elastomeric laminate 302 may form at least a portion of one or more of the group of article components including a waistband 122, waistcap 123, inner leg cuff 150, outer leg cuff 140 and a transverse barrier 16, and may comprise a plurality of elastics 316 having an Average-Strand-Spacing from about 0.5 mm to about 3.0 mm. Further, the plurality of elastics 316 may have an Average-Strand-Spacing from about 0.75 mm to about 2.5 mm.

The elastomeric laminate 302 may form at least a portion of one or more of the group of article components including a waistband 122, waistcap 123, inner leg cuff 150, outer leg cuff 140 and a transverse barrier 16, and may comprise a plurality of elastics 316 having an Average-Dtex from about 30 to about 400. Alternatively, the plurality of elastics 316 of the elastomeric laminate 302 may have an Average-Dtex from about 50 to about 250.

The elastomeric laminate 302 may form at least a portion of one or more of the group of article components including a waistband 122, waistcap 123, inner leg cuff 150, outer leg cuff 140 and a transverse barrier 16, and may comprise a plurality of elastics 316 having an Average-Pre-Strain from about 75% to about 300%. Alternatively, the elastomeric laminate may comprise elastic elements with an Average-Pre-Strain of from about 100% to about 250%.

Any one of the belt 430, side panel 330, ear panel 530, chassis 200, topsheet 124, backsheet 125, waistband 122, waistcap 123, inner leg cuff 150, outer leg cuff 140 or transverse barrier may comprise an elastomeric laminate 302 comprising a plurality of elastics 316 having Pressure-Under-Strand from about 0.1 psi to about 1 psi, or from about 0.2 psi to about 0.8 psi.

Any one of the belt 430, side panel 330, ear panel 530, chassis 200, topsheet 124, backsheet 125, waistband 122, waistcap 123, inner leg cuff 150, outer leg cuff 140 or transverse barrier may comprise an elastomeric laminate comprising an Air Permeability at 0 gf/mm (no extension) of greater than about 40 cubic meters/square meter/minute and/or a level of Air Permeability at 3 gf/mm (slight extension) of greater than about 60 cubic meters/square meter/ minute and/or a level of Air Permeability at 7 gf/mm (moderate extension) of greater than about 80 cubic meters/square meter/minute.

Any one of the belt 430, side panel 330, ear panel 530, chassis 200, topsheet 124, backsheet 125, waistband 122, waistcap 123, inner leg cuff 150, outer leg cuff 140 or transverse barrier may comprise an elastomeric laminate comprising a Water Vapor Transmission Rate of greater than 2000 g/m2/24 hrs, greater than 4000 g/m2/24 hrs or greater than 6000 g/m2/24 hrs.

Any one of the belt 430, side panel 330, ear panel 530, chassis 200, topsheet 124, backsheet 125, waistband 122, waistcap 123, inner leg cuff 150, outer leg cuff 140 or transverse barrier may comprise an elastomeric laminate comprising an Open Area greater than about 70%, greater than about 80%, greater than about 90%.

Any one of the belt 430, side panel 330, ear panel 530, chassis 200, topsheet 124, backsheet 125, waistband 122, waistcap 123, inner leg cuff 150, outer leg cuff 140 or transverse barrier may comprise an elastomeric laminate having a Caliper at 0 gf/mm (no extension) of from about 0.5 mm to about 4 mm and/or a Caliper Retention Value at 3 gf/mm (slight extension) of from about 60% to about 95% and/or a Caliper Retention Value at 7 gf/mm (moderate extension) of from about 40% to about 90%

Any one of the belt 430, side panel 330, ear panel 530, chassis 200, topsheet 124, backsheet 125, waistband 122, waistcap 123, inner leg cuff 150, outer leg cuff 140 or transverse barrier may comprise an elastomeric laminate comprising a Cantilever Bending of less than about 40 mm or alternatively less than about 35 mm in other embodiments the Cantilever Bending may be less than 30 mm or alternatively less than 25 mm. The elastomeric laminate 302 of the present disclosure may have Cantilever Bending of from about 15 mm to about 30 mm.

Any one of the belt 430, side panel 330, ear panel 530, chassis 200, topsheet 124, backsheet 125, waistband 122, waistcap 123, inner leg cuff 150, outer leg cuff 140 or transverse barrier may comprise an elastomeric laminate comprising a Percent Contact Area of greater than about 13% at 100 um and/or greater than about 27% at 200 um and/or greater than about 39% at 300 um and/or a 2%-98% Height Value of <1.6 mm. Alternatively, any one of the belt 430, side panel 330, ear panel 530, chassis 200, topsheet 124, backsheet 125, waistband 122, waistcap 123, inner leg cuff 150, outer leg cuff 140 or transverse barrier may comprise an elastomeric laminate comprising a Percent Contact Area of greater than about 10% at 100 um and/or greater than about 20% at 200 um and/or greater than about 30% at 300 um and/or a 2%-98% Height Value of <2.2 mm. Comparative difference in Percent Contact Area are show in FIGS. 100, 100A for elastomeric laminates 302 of the present disclosure and FIGS. 101 and 101A for elastic laminates of the prior art, currently marketed products. The elastomeric laminate 302 of the present disclosure may have a 2-98% Height Value of between 0.3 to about 3.0.

Any one of the belt 430, side panel 330, ear panel 530, chassis 200, topsheet 124, backsheet 125, waistband 122, waistcap 123, inner leg cuff 150, outer leg cuff 140 or transverse barrier may comprise an elastomeric laminate comprising a Rugosity Frequency of from about 0.2 mm$^{-1}$ to about 1 mm$^{-1}$ and a Rugosity Wavelength of from about 0.5 mm to about 5 mm.

It is also to be appreciated that any one of the belt 430, side panel 330, ear panel 530, chassis 200, topsheet 124, backsheet 125, waistband 122, waistcap 123, inner leg cuff 150, outer leg cuff 140 or transverse barrier may comprise an elastomeric laminate comprising one or more of the parametric values and ranges cited herein above.

An absorbent article of the present disclosure may have an elastomeric laminate 302 forming at least a portion of one or more of a belt 430, side panel 330, ear panel 530, waistband 122, chassis 200, topsheet 124 and backsheet 125. The elastomeric laminate 302 may comprise a plurality of elastics 316 having a specific Average-Dtex, nonwoven type, nonwoven basis weight, Average-Strand-Spacing and Average-Pre-Strain. And, the article may comprise two or more absorbent article components (including a belt 430, side panel 330, ear panel 530, waistband 122, chassis 200, topsheet 124 and backsheet 125) comprising an elastomeric laminate 302 having one or more identical or substantially identical laminate elements (including Average-Dtex, nonwoven type, nonwoven basis weight, Average-Strand-Spacing and Average-Pre-Strain).

Beyond the beamed elastic strands 316 that may be used in each of the absorbent article components, other elastic components such as elastic nonwovens, elastomeric films, elastomeric foams, elastomeric scrims, and elastomeric ribbons, or combinations thereof, may be used with the beamed elastics 316.

In one embodiment, an absorbent article comprising an elastomeric laminate 302 and the elastomeric laminate may form at least a portion of one or more of the group of article components including a belt 430, a side panel 330, chassis 200, a topsheet 124, backsheet 125, and an ear panel 530. The elastomeric laminate 302 may comprise a plurality of elastics 316 having from about 40 to about 1000 elastic strands or from about 100 to about 650 elastic strands or from about 150 to about 475 elastic strands. The plurality of elastics 316 may have an Average-Strand-Spacing from about 0.25 mm to about 4 mm or from about 0.5 mm to about 3.5 mm or from about 0.75 mm to about 2.5 mm. The plurality of elastics 316 may comprise elastic having an Average-Dtex from about 10 to about 500 or from about 30 to about 400 or from about 50 to about 250. The plurality of elastic 316 may also have an Average-Pre-Strain from about 50% to about 400% or from about 75% to about 300% or from about 100% to about 250%. The elastomeric laminate may also comprise a first substrate layer 306 and/or a second substrate layer 308 wherein each may have a basis weight from about 6 grams per square meter to about 30 grams per square meter. The elastomeric laminate 302 comprising the plurality of elastics 316 may have Pressure-Under-Strand from about 0.1 psi to about 1 psi, or from about 0.2 psi to about 0.8 psi. The elastomeric laminate may comprise an Air Permeability at 0 gf/mm (no extension) of greater than about 40 cubic meters/square meter/minute and/or a level of Air Permeability at 3 gf/mm (slight extension) of greater than about 60 cubic meters/square meter/minute and/or a level of Air Permeability at 7 gf/mm (moderate extension) of greater than about 80 cubic meters/square meter/minute. The elastomeric laminate may comprise a Water Vapor Transmission Rate of greater than 2000 g/m2/24 hrs, greater than 4000 g/m2/24 hrs or greater than 6000 g/m2/24 hrs. The elastomeric laminate having a Caliper at 0 gf/mm (no extension) of from about 0.5 mm to about 4 mm and/or a Caliper Retention Value at 3 gf/mm (slight extension) of from about 60% to about 95% and/or a Caliper Retention Value at 7 gf/mm (moderate extension) of from about 40% to about 90%. The elastomeric laminate may comprise a Cantilever Bending of less than about 40 mm, alternatively less than about 35 mm. The elastomeric laminate may also comprise a Percent Contact Area of greater than about 10% at 100 um and/or greater than about 20% at 200 um and/or greater than about 28% at 300 um and/or a 2%-98% Height Value of <1.8 mm. Alternatively, the elastomeric laminate may comprise a Percent Contact Area of greater than about 11% at 100 um and/or greater than about 28% at 200 um and/or greater than about 51% at 300 um and/or a 2%-98% Height Value of <1.6 mm. The elastomeric laminate having a Rugosity Frequency of from about 0.2 mm$^{-1}$ to about 1 mm$^{-1}$ and a Rugosity Wavelength of from about 0.5 mm to about 5 mm. In alternative embodiments, the elastomeric laminate may comprise a Rugosity Frequency from about 0.2 mm$^{-1}$ to about 0.85 mm$^{-1}$ and Rugosity Wavelengths of from about 1.2 mm to about 5 mm. The elastomeric laminate may also have a Section-Modulus of from about 2 gf/mm to about 15 gf/mm, alternatively from about 3 gf/mm to about 12 gf/mm, in alternative embodiments from about 4 gf/mm to about 10 gf/mm. The elastomeric laminate may also have an Open Area of greater than about 60%, alternatively greater than about 75% or greater than about 90%.

In another embodiment, an absorbent article comprising an elastomeric laminate 302 and the elastomeric laminate may form at least a portion of one or more of the group of article components including a waistband 122, waistcap 123, inner leg cuff 150, outer leg cuff 140 and a transverse barrier 16. The elastomeric laminate 302 may comprise a plurality of elastics 316 having from about 10 to about 400 elastic strands or from about 15 to about 300 elastic strands or from about 20 to about 225 elastic strands or from about 25 to about 150 elastic strands. The plurality of elastics 316 may have an Average-Strand-Spacing from about 0.25 mm to about 4 mm or from about 0.5 mm to about 3.5 mm or from about 0.75 mm to about 2.5 mm. The plurality of elastics 316 may comprise elastic having an Average-Dtex from about 10 to about 500 or from about 30 to about 400 or from about 50 to about 250. The plurality of elastic 316 may also have an Average-Pre-Strain from about 50% to about 400% or from about 75% to about 300% or from about 100% to about 250%. The elastomeric laminate may also comprise a first substrate layer 306 and/or a second substrate layer 308 wherein each may have a basis weight from about 6 grams per square meter to about 30 grams per square meter. The elastomeric laminate 302 comprising the plurality of elastics 316 may have Pressure-Under-Strand from about 0.1 psi to about 1 psi, or from about 0.2 psi to about 0.8 psi. The elastomeric laminate may comprise an Air Permeability at 0 gf/mm (no extension) of greater than about 40 cubic meters/square meter/minute and/or a level of Air Permeability at 3 gf/mm (slight extension) of greater than about 60 cubic meters/square meter/minute and/or a level of Air Permeability at 7 gf/mm (moderate extension) of greater than about 80 cubic meters/square meter/minute. The elastomeric laminate may comprise a Water Vapor Transmission Rate of greater than 2000 g/m2/24 hrs, greater than 4000 g/m2/24 hrs or greater than 6000 g/m2/24 hrs. The elastomeric laminate having a Caliper at 0 gf/mm (no extension) of from about 0.5 mm to about 4 mm and/or a Caliper Retention Value at 3 gf/mm (slight extension) of from about 60% to about 95% and/or a Caliper Retention Value at 7 gf/mm (moderate extension) of from about 40% to about 90%. The elastomeric laminate may comprise a Cantilever Bending of less than about 40 mm, alternatively less than about 35 mm. The elastomeric laminate may also comprise a Percent Contact Area of greater than about 10% at 100 um and/or greater than about 20% at 200 um and/or greater than about 28% at 300 um and/or a 2%-98% Height Value of <1.8 mm. Alternatively, the elastomeric laminate may comprise a Percent Contact Area of greater than about 11% at 100 um and/or greater than about 28% at 200 um and/or greater than about 51% at 300 um and/or a 2%-98% Height Value of <1.6 mm. The elastomeric laminate having a Rugosity Frequency of from about 0.2 mm$^{-1}$ to about 1 mm$^{-1}$ and a Rugosity Wavelength of from about 0.5 mm to about 5 mm. In alternative embodiments, the elastomeric laminate may comprise a Rugosity Frequency from about 0.2 mm$^{-1}$ to about 0.85 mm$^{-1}$ and Rugosity Wavelengths of from about 1.2 mm to about 5 mm. The elastomeric laminate may also have a Section-Modulus of from about 2 gf/mm to about 15 gf/mm, alternatively from about 3 gf/mm to about 12 gf/mm, in alternative embodiments from about 4 gf/mm to about 10 gf/mm. The elastomeric laminate may also have an Open Area of greater than about 60%, alternatively greater than about 75% or greater than about 90%.

In another embodiment, an absorbent article 100 comprising a chassis 200 having a topsheet 124, a backsheet 125 and an absorbent core 128 disposed between the topsheet 124 and the backsheet 125 and an elastomeric laminate 302 joined to the chassis 200 whereby the elastomeric laminate 302 comprises a first plurality of elastics 316 disposed between first and second substrate layers 306 and 308. The elastomeric laminate 302 may form at least a portion of at least one of the group consisting of a chassis 200, belt 430, a side panel 330, topsheet 124, backsheet 125 and an ear panel 530. The first plurality of elastics 316 of the elastomeric laminate 302 may comprise from about 40 to about 1000 elastic strands disposed at an Average-Strand-Spacing from about 0.25 mm to about 4 mm having an Average-Dtex from about 10 to about 600 thereby providing an Pressure-Under-Strand from about 0.1 to about 1 psi. The elastomeric laminate 302 may also have an Air Permeability at 0 gf/mm of from about 40 to about 120 m3/m2/min.

In an alternative embodiment, the absorbent article 100 comprising a chassis 200 having a topsheet 124, a backsheet 125 and an absorbent core 128 disposed between the topsheet 124 and the backsheet 125 and an elastomeric laminate 302 joined to the chassis 200 whereby the elastomeric laminate 302 comprises a first plurality of elastics 316 disposed between first and second substrate layers 306 and 308. The elastomeric laminate 302 may form at least a portion of at least one of the group consisting of a chassis 200, belt 430, a side panel 330, topsheet 124, backsheet 125 and an ear panel 530. The first plurality of elastics 316 of the elastomeric laminate 302 may comprise from about 100 to about 600 elastic strands disposed at an Average-Strand-Spacing from about 0.5 mm to about 2.5 mm having an Average-Dtex from about 25 to about 250 thereby providing an Pressure-Under-Strand from about 0.2 to about 0.8 psi. The elastomeric laminate 302 may also have an Air Permeability at 3 gf/mm of from about 50 to about 150 m3/m2/min.

In another embodiment, an absorbent article 100 comprising a chassis 200 having a topsheet 124, a backsheet 125 and an absorbent core 128 disposed between the topsheet 124 and the backsheet 125 and an elastomeric laminate 302 joined to the chassis 200 whereby the elastomeric laminate 302 comprise a first plurality of elastics 316 disposed between first and second substrate layers 306 and 308. The elastomeric laminate 302 may form at least a portion of at least one of the group consisting of a waistband 122, a waistcap 123, an inner leg cuff 150, an outer leg cuff 140, and a transverse barrier 165. The first plurality of elastics 316 of the elastomeric laminate 302 may comprise from about 10 to about 400 elastic strands disposed at an Average-Strand-Spacing from about 0.25 mm to about 5 mm having an Average-Dtex from about 10 to about 600 thereby providing a Pres sure-Under-Strand from about 0.1 to about 1 psi. The elastomeric laminate 302 may also have an Air Permeability at 0 gf/mm of from about 40 to about 120 m3/m2/min.

In an alternative embodiment, the absorbent article 100 comprising a chassis 200 having a topsheet 124, a backsheet 125 and an absorbent core 128 disposed between the topsheet 124 and the backsheet 125 and an elastomeric laminate 302 joined to the chassis 200 whereby the elastomeric laminate 302 comprise a first plurality of elastics 316 disposed between first and second substrate layers 306 and 308. The elastomeric laminate 302 may form at least a portion of at least one of the group consisting of a waistband 122, a waistcap 123, an inner leg cuff 150, an outer leg cuff 140, and a transverse barrier 165. The first plurality of elastics 316 of the elastomeric laminate 302 may comprise from about 20 to about 225 elastic strands disposed at an Average-Strand-Spacing from about 0.5 mm to about 2.0 mm having an Average-Dtex from about 50 to about 250 thereby providing an Pressure-Under-Strand from about 0.1 to about 1 psi. The elastomeric laminate 302 may also have an Air Permeability at 0 gf/mm of from about 50 to about 150 m3/m2/min.

In another embodiment, an absorbent article 100 comprising a chassis 200 having a topsheet 124, a backsheet 125 and an absorbent core 128 disposed between the topsheet 124 and the backsheet 125, the chassis further comprises a front waist region and a back waist region. The absorbent article 100 may comprise a back belt 430 joined to the back waist region 38 of the chassis 200. The back belt 430 extending outboard of the back waist region 38 of the chassis 200. The back belt 430 is formed at least in part by an elastomeric laminate 302 comprising a first plurality of elastics 316 disposed between a first substrate layer 306 and a second substrate layer 308 the first plurality of elastics 316 comprising greater than about 40 elastic strands having an Average-Strand-Spacing of less than 4 mm. The first plurality of elastics 316 of the belt is disposed between first and second substrate layers, wherein the substrate layers may have differences in composition, polymer type, fiber diameter, fiber shape, bond pattern, color, nonwoven type (e.g. spunbond, carded, etc.) and/or basis weight. The back belt 430 may be joined at or adjacent the side edges of the belt 437 to another portion of the absorbent article 100 to form a closed-form pant. Alternatively, the back belt 430 at or adjacent the end edges 437 may remain unattached, e.g. unfastened, to other parts of the absorbent article 100 and thus may be packaged in an open-form.

In another embodiment, an absorbent article 100 may comprise a chassis 200 having a topsheet 124, a backsheet 125 and an absorbent core 128 disposed between the topsheet 124 and the backsheet 125, the chassis further comprising a front waist region and a back waist region. The absorbent article 100 may comprise a front belt 430F joined to the front waist region and a back belt 430B joined to the back waist region 38 of the chassis 200. The front belt 430F extending outboard of the front waist region 36 of the chassis 200 and the back belt 430B extending outboard of the back waist region 38 of the chassis 200. The back belt 430B may be formed at least in part by an elastomeric laminate 302 comprising a first plurality of elastics 316a disposed between a first substrate layer 306 and a second substrate layer 308 the first plurality of elastics 316a comprising greater than about 40 elastic strands having an Average-Strand-Spacing of less than 4 mm and Average-Pre-Strain from about 75% to about 300%. The first plurality of elastics 316a of the back belt 430B is disposed between first and second substrate layers 306 and 308, wherein the substrate layers may have differences in composition, polymer type, fiber diameter, fiber shape, bond pattern, color, nonwoven type (e.g. spunbond, carded, etc.) and/or basis weight. The front belt 430F may be formed at least in part by an elastomeric laminate 302 comprising a second plurality of elastics 316b disposed between a first substrate layer 306 and a second substrate layer 308 the second plurality of elastics 316b comprising greater than about 40 elastic strands having an Average-Strand-Spacing of less than 4 mm and Average-Pre-Strain from about 75% to about 300%. The second plurality of elastics 316b of the front belt 430F is disposed between first and second substrate layers 306 and 308, wherein the substrate layers may have differences in composition, polymer type, fiber diameter, fiber shape, bond pattern, color, nonwoven type (e.g. spunbond, carded, etc.) and/or basis weight. The front belt 430F and back belt 430B may be joined to each other at or adjacent the respective side edges of the belt 437 to form a closed-form pant. Alternatively, the front belt 430F and back belt 430B may remain unattached, e.g. unfastened, at or adjacent the end edges 437 and thus may be packaged in an open-form. The first plurality of elastics 316a and the second plurality of elastics 316b may have one or more of substantially the same number of elastics, substantially the same Average-Strand-Spacing, substantially the same Average-Pre-Strain and/or Average-Dtex. Alternatively, the first plurality of elastics 316a and the second plurality of elastics 316b may have one or more of a different number of elastics, different Average-Strand-Spacing, different Average-Pre-Strain and/or different Average-Dtex.

In another embodiment, an absorbent article 100, comprising a chassis 200 having a topsheet 124, a backsheet 125 and an absorbent core 128 disposed between the topsheet 124 and the backsheet 125. The absorbent article having first and second side panels 330 wherein the proximal side edges of the side panels 330 are joined to the chassis 200 at or adjacent the laterally opposing side edges 237 of the chassis 200 in the back waist region 38. The first and second side panels 330 may comprise an elastomeric laminate 302 having a first plurality of elastics 316 disposed between a first substrate layer 306 and a second substrate layer 308. The first plurality of elastics 316 comprising greater than about 40 elastic strands and an Average-Strand-Spacing of less than 4 mm. The absorbent article 100 may also comprise a waistband 122 disposed in the back waist region 38 of the center chassis 200 between but not overlapping with the first and second side panels 330. Alternatively, the waistband 122 may overlap with a portion of the first and second side panels 330. The waistband 122 may comprise an elastomeric laminate 302 having a plurality of elastics 316 comprising greater than about 10 elastic strands having an Average-Strand-Spacing of less than 4 mm and an Average-Pre-Strain from about 75% to about 300%. 19. The first and second substrate layers 306 and 308 may each have a basis weight from about 6 grams per square meter to about 30 grams per square meter. The absorbent article 100 may also comprise a waistband 122 disposed in the back waist region 38 of the center chassis 200 between but not overlapping with the first and second side panels 330. Alternatively, the waistband 122 may overlap with a portion of the first and second side panels 330. The waistband 122 may comprise an elastomeric laminate 302 having a plurality of elastics 316 comprising greater than about 10 elastic strands having an Average-Strand-Spacing of less than 4 mm and Average-Pre-Strain from about 75% to about 300%. 19. The first and second substrate layers 306 and 308 may each have a basis weight from about 6 grams per square meter to about 30 grams per square meter. The first and second side panels 330 may be joined to a portion of the absorbent article 100 at or adjacent the respective distal side edges of the of the side panel 330 to form a closed-form pant. Alternatively, the side panels 330 may remain unattached, e.g. unfastened, at or adjacent the distal side edges of the side panel and thus may be packaged in an open-form.

In another embodiment, an absorbent article 100, comprising a chassis 200 having a topsheet 124, a backsheet 125 and an absorbent core 128 disposed between the topsheet 124 and the backsheet 125. The absorbent article having first and second side panels 330 wherein the proximal side edges of the first and second side panels 330 are joined to the chassis 200 at or adjacent the laterally opposing side edges 237 of the chassis 200 in the back waist region 38. The first and second side panels 330 may comprise an elastomeric laminate 302 having a first plurality of elastics 316 disposed between a first substrate layer 306 and a second substrate layer 308. The first plurality of elastics 316 comprising greater than about 50 elastic strands and an Average-Strand-Spacing of less than 2.5 mm and an Average-Pre-Strain from about 75% to about 300%. The absorbent article also having third and fourth side panels 330 wherein the proximal side edges of the third and fourth side panels 330 are joined to the chassis 200 at or adjacent the laterally opposing side edges 237 of the chassis 200 in the front waist region 36. The third and fourth side panels 330 may comprise an elastomeric laminate 302 having a second plurality of elastics 316 disposed between a first substrate layer 306 and a second substrate layer 308. The second plurality of elastics 316 comprising greater than about 50 elastic strands and an Average-Strand-Spacing of less than 2.5 mm and an Average-Pre-Strain from about 75% to about 300%. The absorbent article 100 may also comprise a waistband 122 disposed in one or both of the front waist region 36 and the back waist region 38 of the center chassis 200 and the waistband 122 may be disposed between but not overlapping with the first, second, third or fourth side panels 330. Alternatively, the waistband 122 may overlap with a portion of one or more of the first, second, third and fourth side panels 330. The waistband 122 may comprise an elastomeric laminate 302 having a plurality of elastics 316 comprising greater than about 10 elastic strands having an Average-Strand-Spacing of less than 5 mm and Average-Pre-Strain from about 75% to about 300%. 19. The first and second substrate layers 306 and 308 may each have a basis weight from about 6 grams per square meter to about 30 grams per square meter. The first and second side panels 330 in the back waist region 38 may be joined to the third and fourth side panels 330 in the front waist region 36 at or adjacent their respective distal side edges to form a closed-form pant. Alternatively, the first and second side panels 330 may remain unattached, e.g. unfastened, to the third and fourth side panels 330 and thus may be packaged in an open-form.

In another embodiment, an absorbent article 100 comprising a chassis 200 having a topsheet 124, a backsheet 125 and an absorbent core 128 disposed between the topsheet 124 and the backsheet 125 and one or more elastomeric laminates 302 joined to or forming a portion of the chassis 200. The elastomeric laminate 302 comprising a first plurality of elastics 316 disposed between a first substrate layer 306 and a second substrate layer 308 wherein the first plurality of elastics 316 comprises greater than 40 elastic strands having an Average-Strand-Spacing of less than about 3 mm, an Average-Dtex of less than about 600, an Average-Pre-Strain of less than about 350%. The elastomeric laminate 302 may form at least a portion of at least one of the group consisting of a belt 430, a side panel 330, a topsheet 124, backsheet 125 and an ear panel 530. The elastomeric laminate 302 may comprise one or more sections having a Section-Modulus of less than about 15 gf/mm, alternatively from about 3 gf/mm to about 12 gf/mm. The elastomeric laminate 302 having an Open Area greater than about 70%, alternatively from about 75% to about 90%. The elastomeric laminate 302 having a Pressure-Under-Strand of less than about 1.0 psi alternatively from about 0.2 psi to about 0.8 psi.

In another embodiment, an absorbent article 100 comprising a chassis 200 having a topsheet 124, a backsheet 125 and an absorbent core 128 disposed between the topsheet 124 and the backsheet 125 and one or more elastomeric laminates 302 joined to or forming a portion of the chassis 200. The elastomeric laminate 302 comprising a first plurality of elastics 316 disposed between a first substrate layer 306 and a second substrate layer 308 wherein the first plurality of elastics 316 comprises from about 42 to about 1000 elastic strands having an Average-Strand-Spacing from about 0.125 mm to about 2.9 mm, an Average-Dtex from about 10 to about 500 and an Average-Pre-Strain of less than about 150%. The elastomeric laminate 302 may form at least a portion of at least one of the group consisting of a belt 430, a side panel 330, a topsheet 124, backsheet 125 and an ear panel 530. The elastomeric laminate 302 may comprise one or more sections having a Section-Modulus of less than about 15 gf/mm, alternatively from about 3 gf/mm to about 12 gf/mm. The elastomeric laminate 302 having an Open Area greater than about 70%, alternatively from about 75% to about 90%. The elastomeric laminate 302 having a Pressure-Under-Strand of less than about 1.0 psi alternatively from about 0.2 psi to about 0.8 psi.

In another embodiment, an absorbent article 100 comprising a chassis 200 having a topsheet 124, a backsheet 125 and an absorbent core 128 disposed between the topsheet 124 and the backsheet 125 and one or more elastomeric laminates 302 joined to or forming a portion of the chassis 200. The elastomeric laminate 302 comprising a first plurality of elastics 316 disposed between a first substrate layer 306 and a second substrate layer 308 wherein the first plurality of elastics 316 comprises from about 125 to about 625 elastic strands having an Average-Strand-Spacing of less than about 1.0 mm, an Average-Dtex from about 20 to about 350 and an Average-Pre-Strain from about 75% to about 300%. The elastomeric laminate 302 may form at least a portion of at least one of the group consisting of a belt 430, a side panel 330, a topsheet 124, backsheet 125 and an ear panel 530. The elastomeric laminate 302 may comprise one or more sections having a Section-Modulus of less than about 15 gf/mm, alternatively from about 3 gf/mm to about 12 gf/mm. The elastomeric laminate 302 having an Open Area greater than about 70%, alternatively from about 75% to about 90%. The elastomeric laminate 302 having a Pressure-Under-Strand of less than about 1.0 psi alternatively from about 0.2 psi to about 0.8 psi.

In another embodiment, an absorbent article 100 comprising a chassis 200 having a topsheet 124, a backsheet 125 and an absorbent core 128 disposed between the topsheet 124 and the backsheet 125 and one or more elastomeric laminates 302 joined to or forming a portion of the chassis 200. The elastomeric laminate 302 comprising a first plurality of elastics 316 disposed between a first substrate layer 306 and a second substrate layer 308 wherein the first plurality of elastics 316 comprises from about 44 to about 350 elastic strands having an Average-Strand-Spacing from about 0.375 mm to about 2.7 mm, an Average-Dtex of less than about 155 and an Average-Pre-Strain from about 75% to about 300%. The elastomeric laminate 302 may form at least a portion of at least one of the group consisting of a belt 430, a side panel 330, a topsheet 124, backsheet 125 and an ear panel 530. The elastomeric laminate 302 may comprise one or more sections having a Section-Modulus of less than about 15 gf/mm, alternatively from about 3 gf/mm to about 12 gf/mm. The elastomeric laminate 302 having an Open Area greater than about 70%, alternatively from about 75% to about 90%. The elastomeric laminate 302 having a Pressure-Under-Strand of less than about 1.0 psi alternatively from about 0.2 psi to about 0.8 psi.

In another embodiment, an absorbent article 100 comprising a chassis 200 having a topsheet 124, a backsheet 125 and an absorbent core 128 disposed between the topsheet 124 and the backsheet 125 and one or more elastomeric laminates 302 joined to or forming a portion of the chassis 200. The elastomeric laminate 302 comprising a first plurality of elastics 316 disposed between a first substrate layer 306 and a second substrate layer 308 wherein the first plurality of elastics 316 comprises from about 10 to about 200 elastic strands having an Average-Strand-Spacing from about 0.25 mm to about 5 mm, an Average-Dtex from about 25 to about 500 and an Average-Pre-Strain from about 75% to about 300%. The elastomeric laminate 302 may form at least a portion of at least one of the group consisting of a waistband 122, a waistcap 123, an inner leg cuff 150, an outer leg cuff 140, and a transverse barrier 165. The elastomeric laminate 302 may comprise one or more sections having a Section-Modulus of less than about 15 gf/mm, alternatively from about 3 gf/mm to about 12 gf/mm. The elastomeric laminate 302 having an Open Area greater than about 70%, alternatively from about 75% to about 90%. The elastomeric laminate 302 having a Pressure-Under-Strand of less than about 1.0 psi alternatively from about 0.2 psi to about 0.8 psi.

Surface Topography

In the Surface Topography Method, an elastic laminate specimen is removed from an absorbent article and extended across and in contact with the convex surface of a transparent horizontal cylindrical tubing segment, allowing the areal surface topology of the body facing side of the laminate to be measured through the transparent tubing segment using optical profilometry. The 3D surface data are then sampled and processed to extract several parameters that describe the Percent Contact Area and 2-98% Height of the elastic laminate specimen surface as well as the Rugosity frequency and Rugosity Wavelength.

The epidermis is the outermost layer of the skin. Categorized into five horizontal layers, the epidermis actually consists of anywhere between 50 cell layers (in thin areas) to 100 cell layers (in thick areas). The average epidermal thickness is 0.1 millimeters or 100 micrometers, which is about the thickness of one sheet of paper. The dermis which is the layer immediately below the epidermis can have a thickness of between 1.0 mm and 1.5 mm. For comparison, we have selected a first setting to determine the Percent Contact Area corresponding with the thickness of the epidermis, 100 micrometers, a second setting at 2X the epidermis or 200 micrometers and a third setting at 3X the epidermis of 300 micrometers.

It is apparent from the surface topography measurements that the inventive elastomeric laminate 302 examples have significantly greater Percent Contact Area at 100 um (1.5× to 1.9×), 200 um (1.8× to 2.5×) and 300 um (1.9× to 2.7×) compared to the prior art structures in table 8 for both waistband 122 applications as well as belt 430 applications (see FIGS. 100, 100A, 101 and 101A). In addition, the 2%-98% Height Value which is derived from the surface topography data also shows a significant difference is surface smoothness for the inventive elastomeric laminate 302 examples versus the prior art structures. These differences in increased surface contact as well as surface smoothness will have a direct and significant impact on minimizing or eliminating skin marking of the various structures that can me created from the inventive elastomeric laminates 302, such as belts 430, side panels 330, ear panels 530, waistbands 122, waistcaps 123, topsheets 124, backsheets, 125, inner leg cuffs 150, outer leg cuffs 140 and transverse barriers 165. In contrast, the data above 2% to 98% Height Value shows that the prior art product have a much rougher surface due in part to their larger decitex elastic and larger spacing which results in larger uncontrolled rugosities. Combine the larger uncontrolled rugosities with the significantly lower surface contact and one can see that the pressure on the skin and skin marking is likely to be significantly greater for the prior art product executions.

In addition to surface topography, it is also important to ensure the skin maintains the proper level of hydration and does not become overly hydrated such as by occlusion. Overly hydrated skin such as skin that has been occluded especially in warmer climates can be more prone to skin marking and damage. Thus, it is also an objective of such inventive elastomeric laminate 302 to provide adequate breathability, Air Permeability through the structure, to help maintain the skin at the proper hydration level working collaboratively with the smooth surface of the inventive elastomeric laminate to provide optimum skin condition with no skin marking or damage. Therefore, it is desirable for the inventive elastomeric laminate 302 to have a level of Air Permeability at 0 gf/mm (no extension) of greater than about 40 cubic meters/square meter/minute and/or a level of Air Permeability at 3 gf/mm (slight extension) of greater than about 60 cubic meters/square meter/minute and/or a level of Air Permeability at 7 gf/mm (moderate extension) of greater than about 80 cubic meters/square meter/minute.

Therefore, it would be beneficial to have an absorbent article 100 comprising a chassis 200 having a topsheet 124, a backsheet 125 and an absorbent core 128 disposed between the topsheet 124 and the backsheet 125 and an elastomeric laminate 302 joined to the chassis 200 whereby the elastomeric laminate 302 comprises a first plurality of elastics 316 disposed between first and second substrate layers 306 and 308. The elastomeric laminate 302 may form at least a portion of at least one of the group consisting of a belt 430, a side panel 330, topsheet 124, and an ear panel 530. The elastomeric laminate 302 may have a percent surface contact at 100 um of greater than about 10% and/or a percent surface contact at 200 um of greater than about 20% and/or a percent surface contact at 300 um or greater than about 28%. In addition, the elastomeric laminate 302 may have a 2%-98% Height Value of less than about 1.6. The elastomeric laminate 302 may have a level of Air Permeability at 0 gf/mm (no extension) of from about 40 cubic meters/square meter/minute to about 80 cubic meters/square meter/minute and/or a level of Air Permeability at 3 gf/mm (slight extension) of from about 60 cubic meters/square meter/minute to about 120 cubic meters/square meter/minute and/or a level of Air Permeability at 7 gf/mm (moderate extension) of from about 80 cubic meters/square meter/minute to about 160 cubic meters/square meter/minute. The elastomeric laminate 302 may also have an Air Permeability at 0 gf/mm of from about 40 to about 120 m3/m2/min.

It would also be beneficial to have an absorbent article 100 comprising a chassis 200 having a topsheet 124, a backsheet 125 and an absorbent core 128 disposed between the topsheet 124 and the backsheet 125 and an elastomeric laminate 302 joined to the chassis 200 whereby the elastomeric laminate 302 comprises a first plurality of elastics 316 disposed between first and second substrate layers 306 and 308. The elastomeric laminate 302 may form at least a portion of at least one of the group consisting of a waistband 122, a waistcap 123, an inner leg cuff 150, an outer leg cuff 140, and a transverse barrier 165. The elastomeric laminate 302 may have a percent surface contact at 100 um of greater than about 13% and/or a percent surface contact at 200 um of greater than about 27% and/or a percent surface contact at 300 um of greater than about 39%. In addition, the elastomeric laminate 302 may have a 2%-98% Height Value of less than about 1.6. The elastomeric laminate 302 may have a level of Air Permeability at 0 gf/mm (no extension) of greater than about 40 cubic meters/square meter/minute and/or a level of Air Permeability at 3 gf/mm (slight extension) of greater than about 60 cubic meters/square meter/minute and/or a level of Air Permeability at 7 gf/mm (moderate extension) of greater than about 80 cubic meters/square meter/minute. The elastomeric laminate 302 may also have an Air Permeability at 0 gf/mm of from about 40 to about 120 m3/m2/min.

In addition to the skin health and skin marking benefits associated with the smooth textures enabled by the elastomeric laminate 302 as illustrated above by the profilometry data the structure of the elastomeric laminate 302 also delivers a significant improvement in graphics clarity and control. Many absorbent articles, taped diapers and pants, intended for use on infants and young children comprise a large number of graphical elements disposed on the outer surface of the article as well as the inner surface. Many elastomeric structures such as the belts 430 of the prior art have structures that are course with large rugosities and undulating surfaces which distort the graphics on the surface of the article. The surface of the elastomeric laminate 302 of the present invention is significantly smoother and as a result does not distort or mask the graphics on the surface. The magnitude of the difference is captured in Table 6 below.

The measurement involves stretching the article to its full width and scribing a line on the outer surface of the article extending from the upper left corner of the belt at or adjacent the intersection of the side seam and the waist edge to the lower right corner of the belt at or adjacent the intersection of the side seam and the leg edge. For the examples in Table 6, a 6 mm wide line was scribed on the surface. The article is then allowed to return to its relaxed state. A rectangular box is created based on the dimensions of the contracted line. The width of the box if measured and reported above. A distortion factor is then calculated by taking the final box dimension and dividing it by the original width of the line. I can be seen from the data above that the inventive elastomeric laminate 302 has a distortion factor of 1 meaning it demonstrated little or no distortion from the fully extended state to the contracted state. The elastic belt 430 products of the prior art have significantly higher distortion factors with all of the samples having a distortion factor of 4 or greater, 4 to 5 time higher than the distortion factor of the inventive elastomeric laminate 302.

Therefore, it would be beneficial to have an absorbent article 100 comprising a chassis 200 having a topsheet 124, a backsheet 125 and an absorbent core 128 disposed between the topsheet 124 and the backsheet 125 and an elastomeric laminate 302 joined to the chassis 200 whereby the elastomeric laminate 302 comprises a first plurality of elastics 316 disposed between first and second substrate layers 306 and 308. The elastomeric laminate 302 may form at least a portion of at least one of the group consisting of a belt 430, a side panel 330, topsheet 124, and an ear panel 530. The elastomeric laminate 302 may have a percent surface contact at 100 um of greater than about 10% and/or a percent surface contact at 200 um of greater than about 20% and/or a percent surface contact at 300 um or greater than about 28%. In addition, the elastomeric laminate 302 may have a 2%-98% Height Value of less than about 1.6. The elastomeric laminate 302 may also have a Graphic Distortion Ratio (illustrated in FIGS. 102, 102A, 103 and 103A) of less than about 4, less than about 3 or less than about 2 or from about 1 to about 3. Contracted graphics (symbolized by scribed lines 1001' and 1002') are less distorted when placed on the inventive elastomeric laminates 302 of the present disclosure versus currently marketed stranded laminates.

Absorbent Article Sections

Components of absorbent articles comprising elastomeric laminates 302 may be sectioned to enable measurement and detailed characterization of the structure. Waistband 122 (see FIGS. 7 and 46), waistcap 123 (see FIG. 39), inner leg cuff 150, outer leg cuff 140, and transverse barrier 165 all comprise 1 section. With regard to the waistband 122, waistcap 123, inner leg cuff 150, outer leg cuff 140 and transverse barrier 165 the section is defined as the region disposed between and including the distal most elastic and the proximal most elastic.

Other components such as the chassis 200, topsheet 124 (see FIG. 57C), backsheet 125 (see FIGS. 57C and 57D), side panel 330 (see FIG. 2), ear panel 530 (FIGS. 39, 45, and 46), and belt panel 430 (see FIG. 55) all comprise multiple sections as described herein. With regard to the side panel 330, ear panel 530 and belt panel 430 the portion of the component to be sectioned is defined as the region disposed between and including the distal most elastic of the elastomeric laminate 302 and the proximal most elastic of the elastomeric laminate 302. The region is defined by a first line extending parallel to the lateral axis 44 and passing through the distal most point of the distal most elastic and a second line extending parallel to the lateral axis and passing through the proximal most point of the proximal most elastic. For each of these elements, the region is then divided into 4 equal sections, defined by three lines disposed parallel to the lateral axis 44 and disposed at 25%, 50% and 75% of the distance between the first line and second line. The region comprises a first section which includes the distal most elastic, a fourth section which includes the proximal most elastic, a second section disposed adjacent the first section and a third section disposed between the second section and the fourth section.

With regard to the chassis 200, topsheet 124 (see FIG. 57C), and backsheet 125 (see FIG. 57C) wherein the elastics 316 of the elastomeric laminate 302 extend in a substantially longitudinal orientation, the portion of the component to be sectioned is defined as the region disposed between and including the distal most elastic of the elastomeric laminate 302 on a first side of the longitudinal axis 42 and the distal most elastic of the elastomeric laminate 302 on a second side of the longitudinal axis 42. The region is defined by a first line extending parallel to the longitudinal axis 42 and passing through the distal most point of the distal most elastic on a first side of the longitudinal axis 42 and a second line extending parallel to the longitudinal axis 42 and passing through the distal most point of the distal most elastic on a second side of the longitudinal axis 42. For each of these elements, the region is then divided into 4 equal sections, defined by three lines disposed parallel to the longitudinal axis 42 and disposed at 25%, 50% and 75% of the distance between the first line and second line. The region comprises a first section which includes the distal most elastic on the first side of the longitudinal axis, a fourth section which includes the distal most elastic on the second side of the longitudinal axis, a second section disposed adjacent the first section and a third section disposed between the second section and the fourth section.

With regard to the chassis 200, topsheet 124, and backsheet 125 (see FIG. 57D) wherein the elastics 316 of the elastomeric laminate 302 extend in a substantially lateral orientation, the portion of the component to be sectioned is defined as the region disposed between and including the distal most elastic of the elastomeric laminate 302 on a first side of the lateral axis 44 and the distal most elastic of the elastomeric laminate 302 on a second side of the lateral axis 44. The region is defined by a first line extending parallel to the lateral axis 44 and passing through the distal most point of the distal most elastic on a first side of the lateral axis 44 and a second line extending parallel to the lateral axis 44 and passing through the distal most point of the distal most elastic on a second side of the lateral axis 44. For each of these elements, the region is then divided into 4 equal sections, defined by three lines disposed parallel to the lateral axis 44 and disposed at 25%, 50% and 75% of the distance between the first line and second line. The region comprises a first section which includes the distal most elastic on the first side of the lateral axis, a fourth section which includes the distal most elastic on the second side of the lateral axis, a second section disposed adjacent the first section and a third section disposed between the second section and the fourth section.

TABLE 1

Inventive Belt Elastic Profiles

| Section | Number of Elastics | Average-Dtex | Average-Pre-Strain | Average-Strand-Spacing (mm) | Open Area (%) | Section-Modulus (gf/mm) | Pressure-Under-Strand (psi) |
|---|---|---|---|---|---|---|---|
| A Front Belt | | | | | | | |
| 1 | 40 | 140 | 100% | 0.6 | 79.2% | 10.9 | 0.328 |
| 2 | 40 | 70 | 150% | 0.6 | 85.3% | 5.5 | 0.463 |
| 3 | 40 | 70 | 150% | 0.6 | 85.3% | 5.5 | 0.463 |
| 4 | 40 | 140 | 100% | 0.6 | 79.2% | 10.9 | 0.328 |
| Back Belt | | | | | | | |
| 4 | 40 | 140 | 100% | 0.6 | 79.2% | 10.9 | 0.328 |
| 3 | 40 | 70 | 150% | 0.6 | 85.3% | 5.5 | 0.463 |
| 2 | 40 | 70 | 150% | 0.6 | 85.3% | 5.5 | 0.463 |
| 1 | 40 | 140 | 100% | 0.6 | 79.2% | 10.9 | 0.328 |
| B Front Belt | | | | | | | |
| 1 | 50 | 70 | 175% | 0.5 | 82.4% | 6.6 | 0.386 |
| 2 | 50 | 70 | 175% | 0.5 | 82.4% | 6.6 | 0.386 |
| 3 | 50 | 70 | 175% | 0.5 | 82.4% | 6.6 | 0.386 |
| 4 | 50 | 70 | 175% | 0.5 | 82.4% | 6.6 | 0.386 |
| Back Belt | | | | | | | |
| 4 | 50 | 70 | 175% | 0.5 | 82.4% | 6.6 | 0.386 |
| 3 | 50 | 70 | 175% | 0.5 | 82.4% | 6.6 | 0.386 |
| 2 | 50 | 70 | 175% | 0.5 | 82.4% | 6.6 | 0.386 |
| 1 | 50 | 70 | 175% | 0.5 | 82.4% | 6.6 | 0.386 |
| C Front Belt | | | | | | | |
| 1 | 30 | 70 | 200% | 0.8 | 89.0% | 4.1 | 0.618 |
| 2 | 20 | 210 | 150% | 1.1 | 86.1% | 8.9 | 0.490 |
| 3 | 30 | 70 | 200% | 0.8 | 89.0% | 4.1 | 0.618 |
| 4 | 30 | 70 | 200% | 0.8 | 89.0% | 4.1 | 0.618 |
| Back Belt | | | | | | | |
| 4 | 30 | 70 | 200% | 0.8 | 89.0% | 4.1 | 0.618 |
| 3 | 30 | 70 | 200% | 0.8 | 89.0% | 4.1 | 0.618 |
| 2 | 30 | 70 | 200% | 0.8 | 89.0% | 4.1 | 0.618 |
| 1 | 30 | 210 | 150% | 1.1 | 86.1% | 8.9 | 0.490 |

TABLE 2

Inventive Ear/Side Panel Elastic Profiles

| Section | Number of Elastics | Average-Dtex | Average-Pre-Strain | Average-Strand-Spacing (mm) | Open Area (%) | Section-Modulus (gf/mm) | Pressure-Under-Strand (psi) |
|---|---|---|---|---|---|---|---|
| A | | | | | | | |
| 1 | 30 | 140 | 125% | 1.0 | 87.5% | 6.6 | 0.546 |
| 2 | 30 | 140 | 125% | 0.8 | 84.4% | 8.2 | 0.437 |
| 3 | 30 | 140 | 125% | 1.0 | 87.5% | 6.6 | 0.546 |
| 4 | 30 | 140 | 125% | 1.0 | 87.5% | 6.6 | 0.546 |
| B | | | | | | | |
| 1 | 60 | 70 | 125% | 0.5 | 82.4% | 6.6 | 0.386 |
| 2 | 60 | 70 | 125% | 0.5 | 82.4% | 6.6 | 0.386 |
| 3 | 60 | 70 | 125% | 0.5 | 82.4% | 6.6 | 0.386 |
| 4 | 60 | 70 | 125% | 0.5 | 82.4% | 6.6 | 0.386 |
| C | | | | | | | |
| 1 | 15 | 210 | 165% | 2.0 | 92.4% | 4.9 | 0.892 |
| 2 | 15 | 210 | 165% | 1.1 | 86.1% | 8.9 | 0.490 |
| 3 | 15 | 210 | 165% | 2.0 | 92.4% | 4.9 | 0.892 |
| 4 | 15 | 210 | 165% | 2.0 | 92.4% | 4.9 | 0.892 |

TABLE 3

Inventive Waistband Elastic Profiles

| Section | Number of Elastics | Average-Dtex | Average-Pre-Strain | Average Strand-Spacing (mm) | Open Area (%) | Section-Modulus (gf/mm) | Pressure-Under-Strand (psi) |
|---|---|---|---|---|---|---|---|
| A | | | | | | | |
| 1 | 40 | 111 | 100% | 0.6 | 81.5% | 8.7 | 0.368 |
| B | | | | | | | |
| 1 | 50 | 90 | 110% | 0.5 | 80.0% | 8.4 | 0.341 |
| C | | | | | | | |
| 1 | 35 | 120 | 200% | 0.7 | 83.5% | 8.0 | 0.413 |

TABLE 4

Inventive Cuff Elastic Profiles

| Section | Number of Elastics | Average-Dtex | Average-Pre-Strain | Average Strand-Spacing (mm) | Open Area (%) | Section-Modulus (gf/mm) | Pressure-Under-Strand (psi) |
|---|---|---|---|---|---|---|---|
| A | | | | | | | |
| Inner | 50 | 30 | 200% | 0.5 | 88.5% | 2.8 | 0.590 |
| Outer | 50 | 70 | 200% | 0.5 | 82.4% | 6.6 | 0.386 |
| B | | | | | | | |
| Inner | 25 | 70 | 170% | 0.5 | 82.4% | 6.6 | 0.386 |
| Outer | 25 | 140 | 200% | 1.0 | 87.5% | 6.6 | 0.546 |
| C | | | | | | | |
| Inner | 25 | 140 | 85% | 0.5 | 75.1% | 13.1 | 0.273 |
| Outer | 25 | 140 | 200% | 1.0 | 87.5% | 6.6 | 0.546 |

TABLE 5

Performance Characteristics of Existing and Inventive Belt Sections

| Example Belt Sections | Average-Dtex | Average-Strand-Spacing (mm) | Open Area (%) | Section-Modulus (gf/mm) | Pressure-Under-Strand (psi) |
|---|---|---|---|---|---|
| Currently Marketed Product A (example section 1 of 4) | 1100 | 9.0 | 96.1% | 5.7 | 1.753 |
| Currently Marketed Product A (example section 2 of 4) | 940 | 9.0 | 96.4% | 7.3 | 1.897 |
| Currently Marketed Product A (example section 3 of 4) | 680 | 9.0 | 97.0% | 3.5 | 2.230 |
| Currently Marketed Product B (example section 1 of 4) | 800 | 7.0 | 95.7% | 5.4 | 1.599 |
| Currently Marketed Product B (example section 2 of 4) | 680 | 7.0 | 96.1% | 4.6 | 1.734 |
| Currently Marketed Product C (example section 1 of 4) | 470 | 4.0 | 94.3% | 5.5 | 1.192 |
| Currently Marketed Product C (example section 2 of 4) | 680 | 4.0 | 93.1% | 8.0 | 0.991 |
| Inventive Example (example section 1 of 4) | 160 | 0.5 | 73.4% | 15.0 | 0.255 |
| Inventive Example (example section 2 of 4) | 140 | 0.5 | 75.1% | 13.1 | 0.273 |
| Inventive Example (example section 3 of 4) | 250 | 0.8 | 79.2% | 14.6 | 0.327 |

TABLE 6

Inventive Elastomeric Laminate and Prior Art Comparison

| Product | Average-Strand-Spacing (mm) | Section-Modulus (gf/mm) | Cantilever Bend (mm) | Graphic Distortion Ratio | Estimated Avg. Dtex | Avg. Fibers/Strand |
|---|---|---|---|---|---|---|
| Currently Marketed Product 1 (Baby) | 8.5 | 6.7 | 28.96 | 5.0 | 940 | 56 |
| Currently Marketed Product 2 (Baby) | 5.2 | 5.6 | 38.06 | 4.7 | 625 | 55 |
| Currently Marketed Product 3 (Baby) | 5.3 | 3.9 | 35.27 | 4.0 | 450 | 56 |
| Currently Marketed Product 4 (Baby) | 4.8 | 5.4 | 29.15 | 5.0 | 550 | 56 |
| Currently Marketed Product 5 (Adult) | 6.8 | 3.4 | 36.87 | | 490 | 43 |
| Currently Marketed Product 6 (Adult) | 3.6 | 6.9 | 25.95 | | 525 | 43 |
| Inventive Elastomeric Laminate 120 | 0.5 | 7.9 | 24.67 | 1.0 | 85 | 5 |
| Inventive Elastomeric Laminate 150 | 0.5 | 7.9 | 23.13 | | 85 | 5 |
| Inventive Elastomeric Laminate UB | 0.5 | 7.9 | | | 85 | 5 |
| Currently Marketed Product 7 (Baby) | 5.6 | 5.2 | | | 620 | 42 |
| Currently Marketed Product 8 (Baby) | 8.3 | 2.9 | | | 510 | 43 |

TABLE 7

Inventive Elastomeric Laminate and Prior Art Comparison

| Product | Caliper @ 0 gf/mm (mm) | Caliper @ 3 gf/mm (mm) | Caliper Retention Value @ 3 gf/mm (%) | Caliper @ 7 gf/mm (mm) | Caliper Retention Value @ 7 gf/mm (%) |
|---|---|---|---|---|---|
| Currently Marketed Product 1 (Baby) | 2.8 | 2.4 | 84 | 1.8 | 65 |
| Currently Marketed Product 2 (Baby) | 4.5 | 2.4 | 54 | 1.1 | 23 |
| Currently Marketed Product 3 (Baby) | 3.4 | 3.0 | 89 | 2.5 | 75 |
| Currently Marketed Product 4 (Baby) | 2.4 | 2.2 | 92 | 1.9 | 80 |
| Currently Marketed Product 5 (Adult) | 2.4 | 1.9 | 81 | 1.0 | 40 |
| Currently Marketed Product 6 (Adult) | 1.4 | 1.3 | 90 | 0.9 | 65 |
| Inventive Elastomeric Laminate 120 | 1.2 | 1.1 | 90 | 1.1 | 86 |
| Currently Marketed Product 7 (Baby) | 1.9 | 1.7 | 89 | 1.1 | 58 |
| Currently Marketed Product 8 (Baby) | 0.9 | 0.3 | 38 | 0.3 | 32 |

TABLE 8

Inventive Elastomeric Laminate and Prior Art Comparison

| Product | Rugosity Frequency (1/mm) | Rugosity Wavelength (mm) | Percent Contact Area 100 um (%) | Percent Contact Area 200 um (%) | Percent Contact Area 300 um (%) | 2-98% Height (mm) |
|---|---|---|---|---|---|---|
| Currently Marketed Product 1 (Baby) | 0.288 | 3.47 | 9.8 | 19.1 | 27.3 | 2.667 |
| Currently Marketed Product 2 (Baby) | 0.210 | 4.77 | 7 | 15.8 | 24.6 | 3.092 |
| Currently Marketed Product 3 (Baby) | 0.210 | 4.77 | 6.5 | 16.1 | 24.7 | 2.292 |
| Currently Marketed Product 4 (Baby) | 0.459 | 2.18 | 5.3 | 11.6 | 19 | 2.260 |
| Currently Marketed Product 5 (Adult) | 0.249 | 4.02 | 6.2 | 14.9 | 24.4 | 1.841 |
| Currently Marketed Product 6 (Adult) | 0.524 | 1.91 | 7.3 | 16.2 | 26.9 | 1.619 |
| Inventive Elastomeric Laminate 120 | 0.616 | 1.62 | 19.7 | 53.1 | 80.5 | 0.614 |
| Inventive Elastomeric Laminate 150 | 0.721 | 1.39 | 17.1 | 43 | 67.9 | 0.503 |
| Inventive Elastomeric Laminate UB | 0.367 | 2.73 | 20.6 | 32.7 | 40.8 | 1.286 |
| Currently Marketed Product 7 (Baby) | 0.315 | 3.18 | 12.2 | 26.2 | 38.6 | 1.714 |
| Currently Marketed Product 8 (Baby) | 0.341 | 2.93 | 9.4 | 18.9 | 26.9 | 1.661 |

TABLE 9

Inventive Elastomeric Laminate and Prior Art Comparison

| Product | Pressure-Under-Strand (psi) | Air Permeability 0 gf/mm (m3/m2/min) | Air Permeability 3 gf/mm (m3/m2/min) | Air Permeability 7 gf/mm (m3/m2/min) | Water Vapor Transmission Rate (g/m$^2$/24 hrs) | Open Area (%) |
|---|---|---|---|---|---|---|
| Currently Marketed Product 1 (Baby) | 1.578 | 75 | 104 | 109 | 5279 | 95.7% |
| Currently Marketed Product 2 (Baby) | 1.344 | 43 | 64 | 70 | 5021 | 94.9% |
| Currently Marketed Product 3 (Baby) | 1.626 | 48 | 68 | 70 | 4568 | 95.8% |
| Currently Marketed Product 4 (Baby) | 1.323 | 69 | 121 | 110 | 4616 | 94.9% |
| Currently Marketed Product 5 (Adult) | 1.987 | 55 | 83 | 86 | 4654 | 96.6% |
| Currently Marketed Product 6 (Adult) | 1.001 | 111 | 146 | 146 | 5234 | 93.2% |
| Inventive Elastomeric Laminate 120 | 0.351 | 40 | 58 | 58 | 4684 | 80.6% |
| Inventive Elastomeric Laminate 150 | 0.351 | | | | 4670 | |
| Inventive Elastomeric Laminate UB | 0.351 | 88 | 105 | 91 | 4586 | 80.6% |
| Currently Marketed Product 7 (Baby) | 1.451 | 120 | 100 | 92 | | 95.3% |
| Currently Marketed Product 8 (Baby) | 2.368 | 91 | 92 | 85 | | 97.1% |

Tables 6-9 illustrate combinations of structural parameters enabled by the inventive elastomeric laminates of the present disclosure that cannot be realized by elastic structures of the prior art or currently marketed products. For example, although the inventive elastomeric laminate of the present invention in the tables have a Section-Modulus of 7.9 gf/mm, higher than any of the prior art references and the inventive elastomeric laminate also has the lowest Pressure-Under-Strand 0.35 psi. The inventive elastomeric laminates also have a very smooth surface delivering higher Percent Contact Area than any other prior art product in the tables above and the highest Rugosity Frequency all while delivering the unique combination of low Caliper (thinness) and high Caliper Retention Value. All of these inventive elastomeric laminate benefits are derived from Average-Dtex lower than any of the prior art references, combined with Average-Strand-Spacing lower than any of the prior art references.

Example 1—Belt Pant Article (See, for Example, FIG. 11)

Figure 73B:
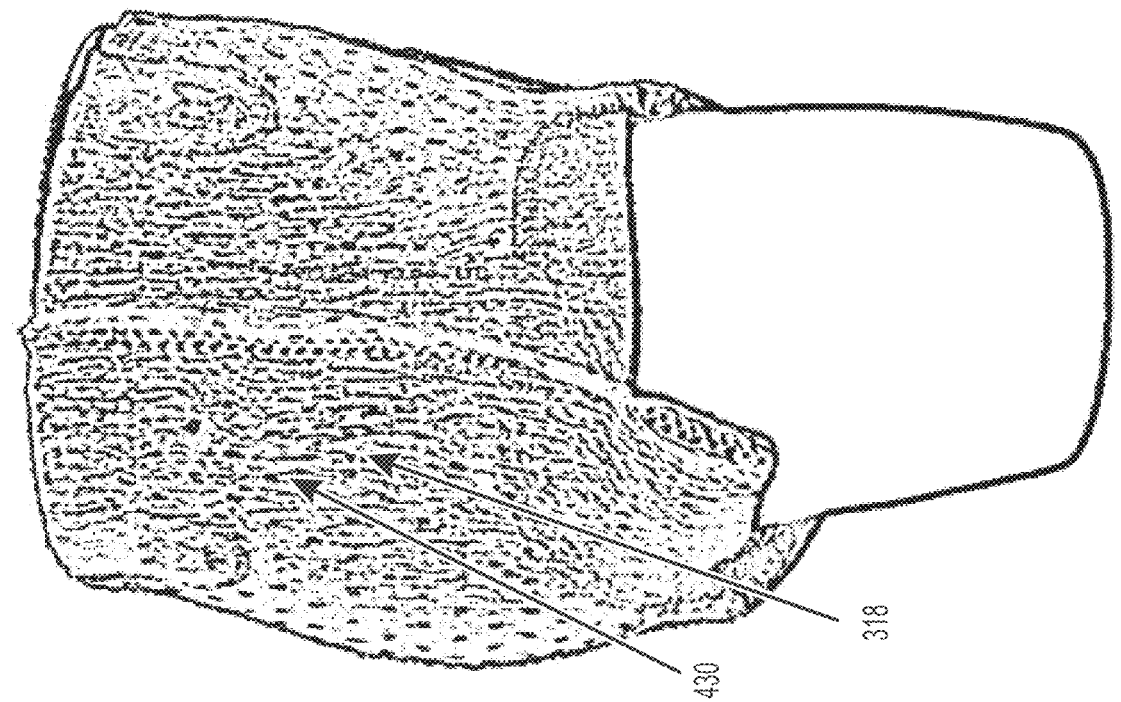
FIG. 73B is a side view of an inventive absorbent article fitted onto a mannequin, the absorbent article comprising an inventive belt 430 comprising an inventive elastomeric laminate 302. The inventive texture zone 318 of the belt 430 in FIG. 73B is meant to be directly compared to same areas of the belt 430 in FIG. 73A.
Figure 73A:
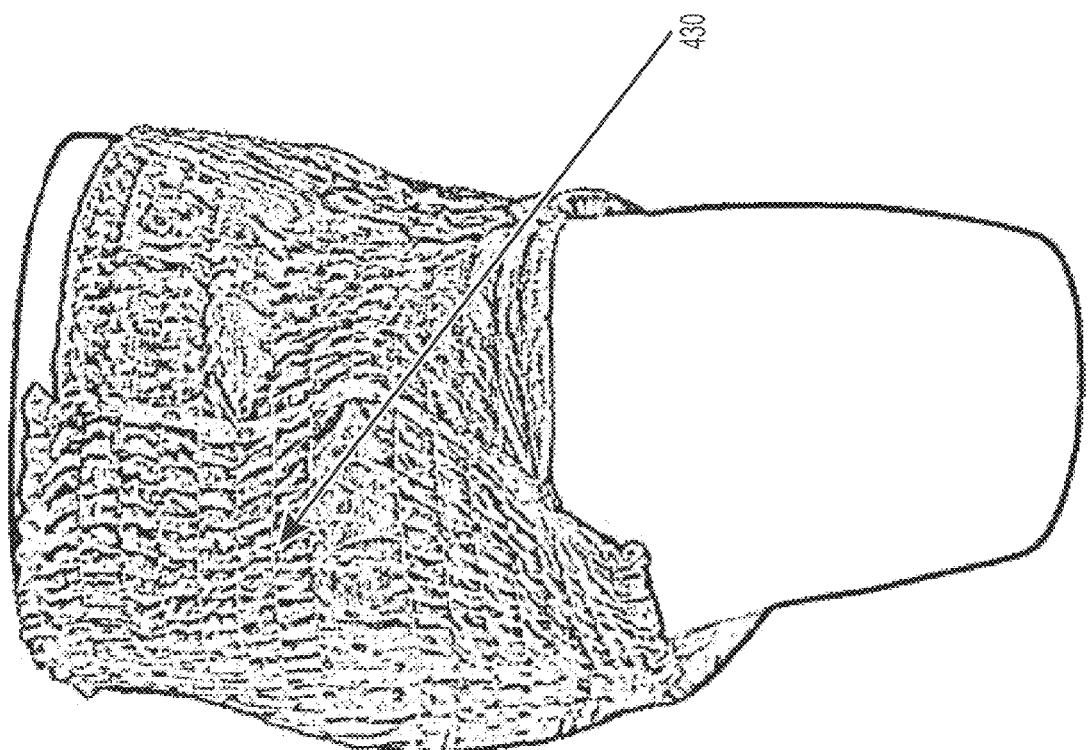
FIG. 73A is a side view of a comparative absorbent article fitted onto a mannequin, the absorbent article comprising a comparative belt 430 comprising an existing elastic profile of strands. The belt 430 of FIG. 73A shows oversized groupings of large uncontrolled gathers indicative of less uniform and higher elastic stress that will result in higher pressure on the wearer's skin (versus the belt 430 of FIG. 73B).
Figure 76A:
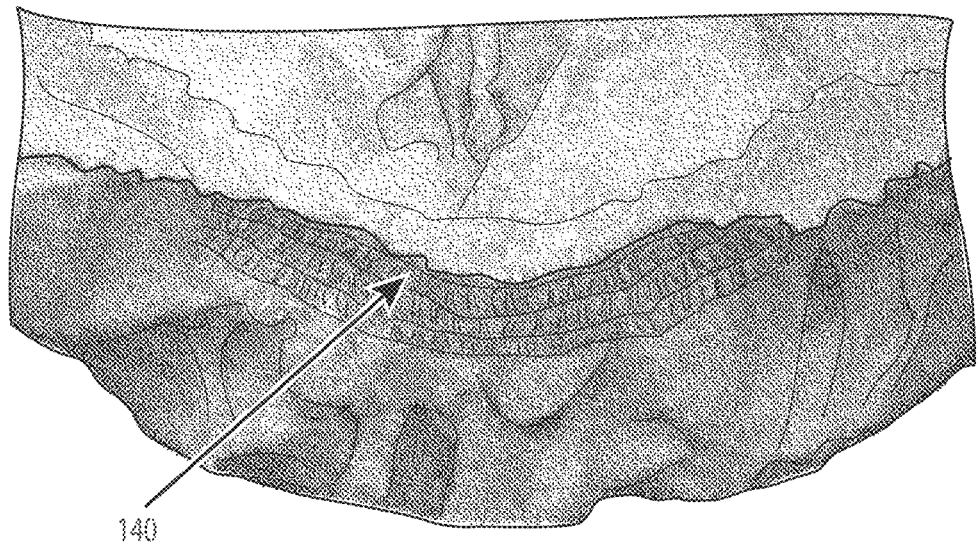
FIG. 76A is a perspective side view of a comparative outer leg cuff 140 comprising an existing elastic profile of strands showing a grouping of large irregular and uncontrolled gathers indicative of less uniform and higher elastic stress that will result in higher pressure on the wearer's skin (versus the outer leg cuff of FIG. 76B).
Figure 76B:
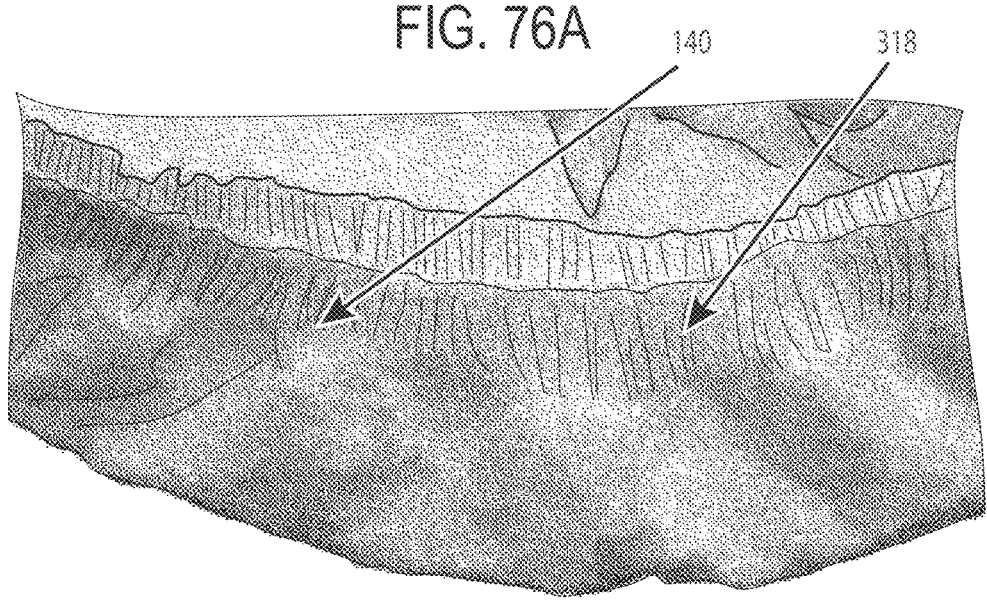
FIG. 76B is a perspective side view of an inventive outer leg cuff 140 comprising an inventive elastomeric laminate 302. The inventive texture zone 318 of the outer leg cuff in FIG. 76B is meant to be directly compared to same areas of the outer leg cuff in FIG. 76A.

Example 1 is a belted pant absorbent article. The pant comprises a belt laminate disposed in both the waist regions and the following materials and construction.
Outer Belt Layer (first substrate layer 306): 13 gsm spunbond nonwoven
Inner Belt Layer (second substrate layer 308): 13 gsm spunbond nonwoven
Backsheet Film 126: 12 gsm liquid impermeable polyethylene film
Core Wrap: 10 gsm hydrophilic spunbond nonwoven
AGM: absorbent gelling material
Distribution Layer: crosslinked cellulosic fiber
Acquisition Layer: 43 gsm synthetic acquisition layer
Topsheet 124: 12 gsm hydrophilic spunbond nonwoven
Belt Elastic Profile: Table 1, group B
Cuff Elastic Profile: Table 4, group C
The belt 430 of Example 1 may present on a wearer consistent with the images of FIGS. 72B, and 73B. Further, the cuffs 52 of Example 1 may present consistent with the images of FIGS. 76B, and 77B.

Example 2—Taped Article (See, for Example, FIG. 46)

Figure 70B:
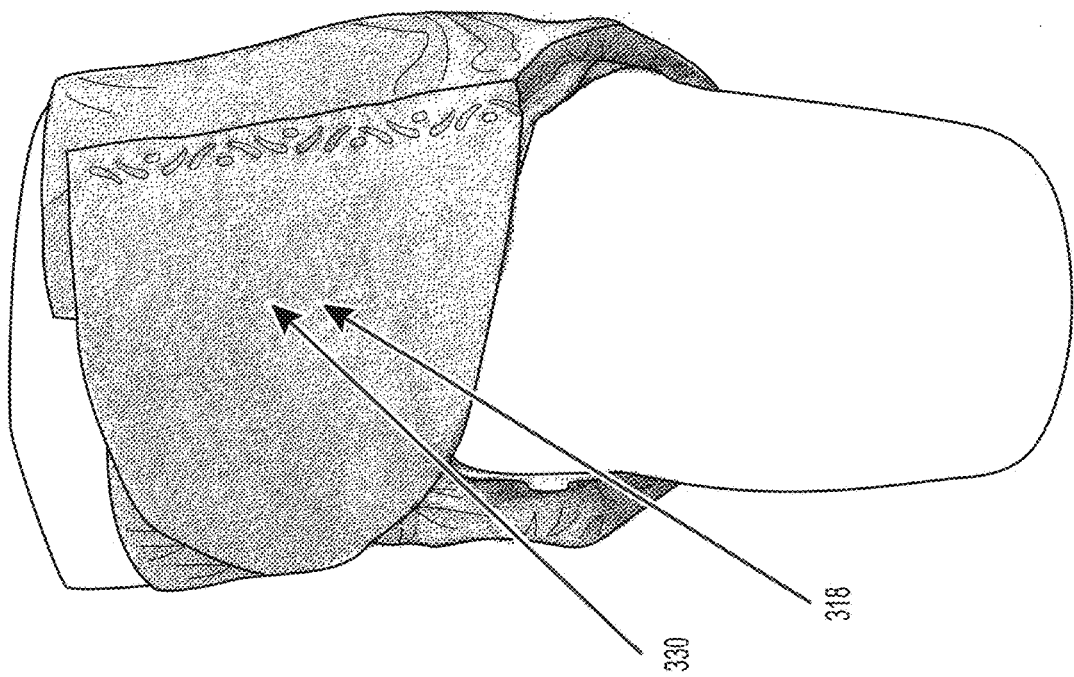
FIG. 70B is a side view of an inventive absorbent article fitted onto a mannequin, the absorbent article comprising an inventive discrete side panel 330 comprising an inventive elastomeric laminate 302. The inventive texture zone 318 of the discrete side panel 330 in FIG. 70B is meant to be directly compared to same areas of the discrete side panel 330 in FIG. 70A.
Figure 70A:
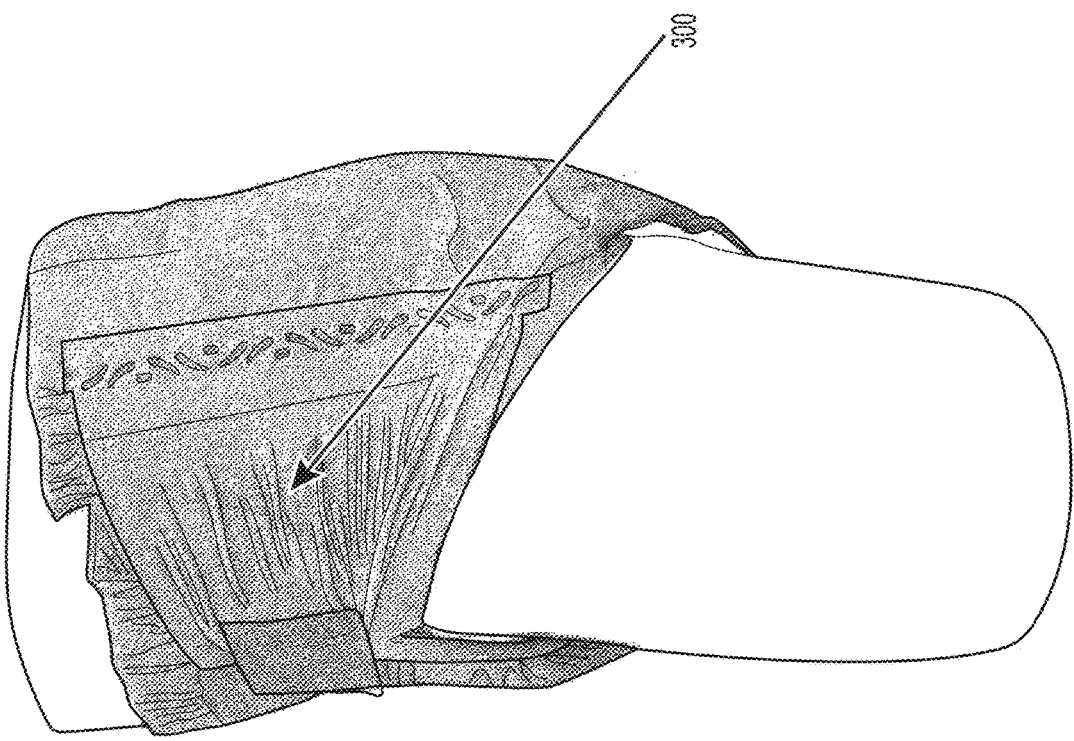
FIG. 70A is a side view of a comparative absorbent article fitted onto a mannequin, the absorbent article comprising a comparative discrete side panel 330. The discrete side panel 330 of FIG. 70A shows stress lines indicative of less even and higher elastic stress that will result in higher pressure on the wearer's skin (versus the discrete side panel 330 of FIG. 70B).
Figure 71B:
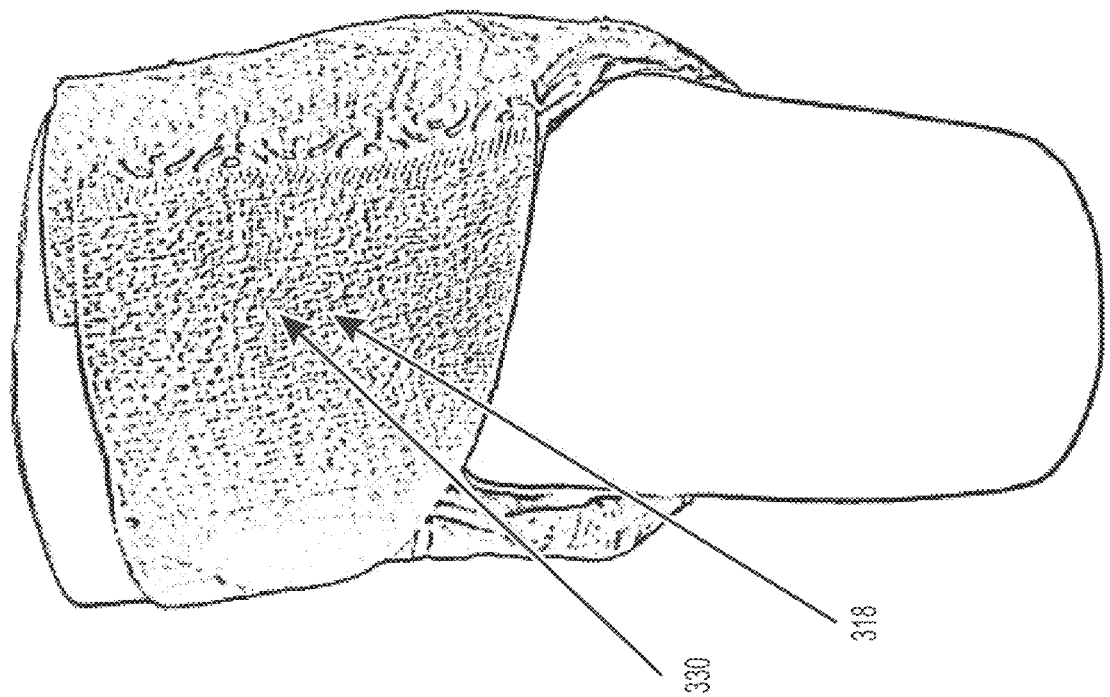
FIG. 71B is a side view of an inventive absorbent article fitted onto a mannequin, the absorbent article comprising an inventive discrete side panel 330 comprising an inventive elastomeric laminate 302. The inventive texture zone 318 of the discrete side panel 330 in FIG. 71B is meant to be directly compared to same areas of the discrete side panel 330 in FIG. 71A.
Figure 71A:
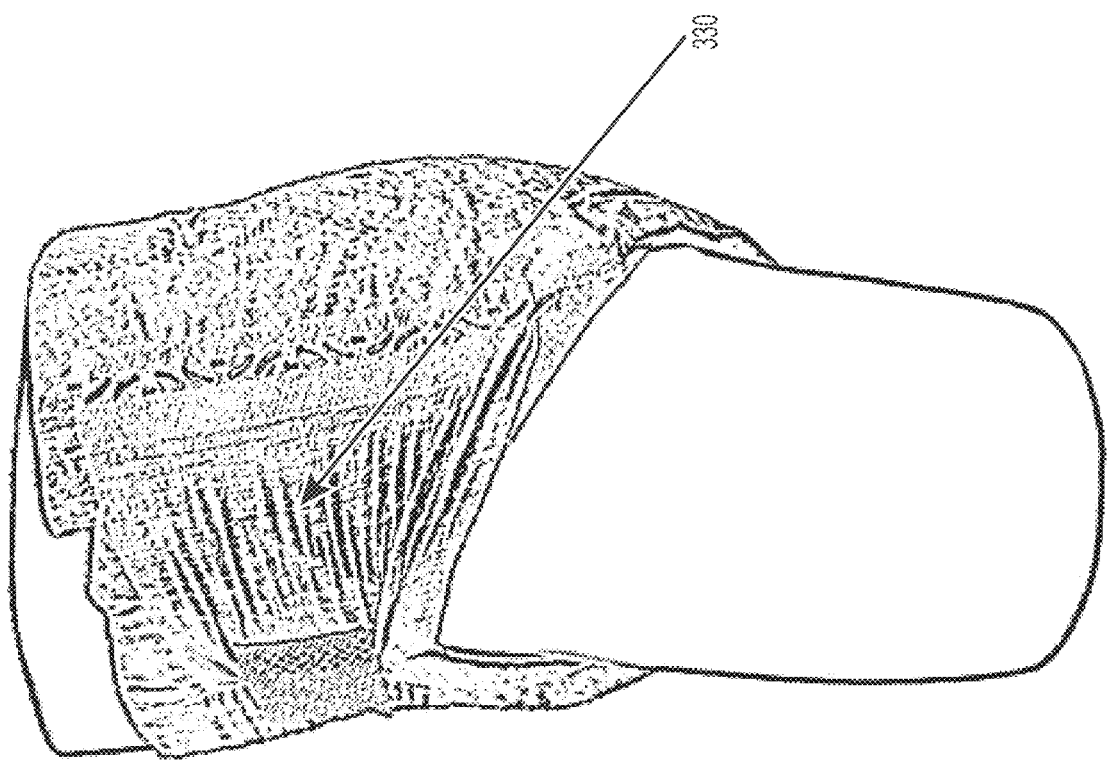
FIG. 71A is a side view of a comparative absorbent article fitted onto a mannequin, the absorbent article comprising a comparative discrete side panel 330. The discrete side panel 330 of FIG. 71A shows stress lines indicative of less even and higher elastic stress that will result in higher pressure on the wearer's skin (versus the discrete side panel 330 of FIG. 71B).
Figure 74A:
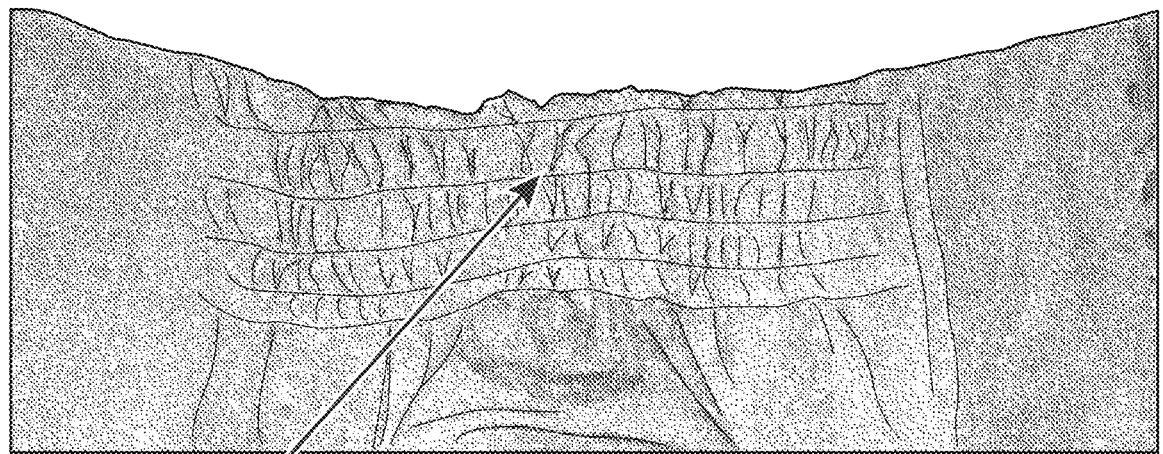
FIG. 74A is a front view of a comparative waistband 122 comprising an existing elastic profile of strands showing a grouping of large irregular and uncontrolled gathers indicative of less uniform and higher elastic stress that will result in higher pressure on the wearer's skin (versus the waistband 122 of FIG. 74B).
Figure 74B:
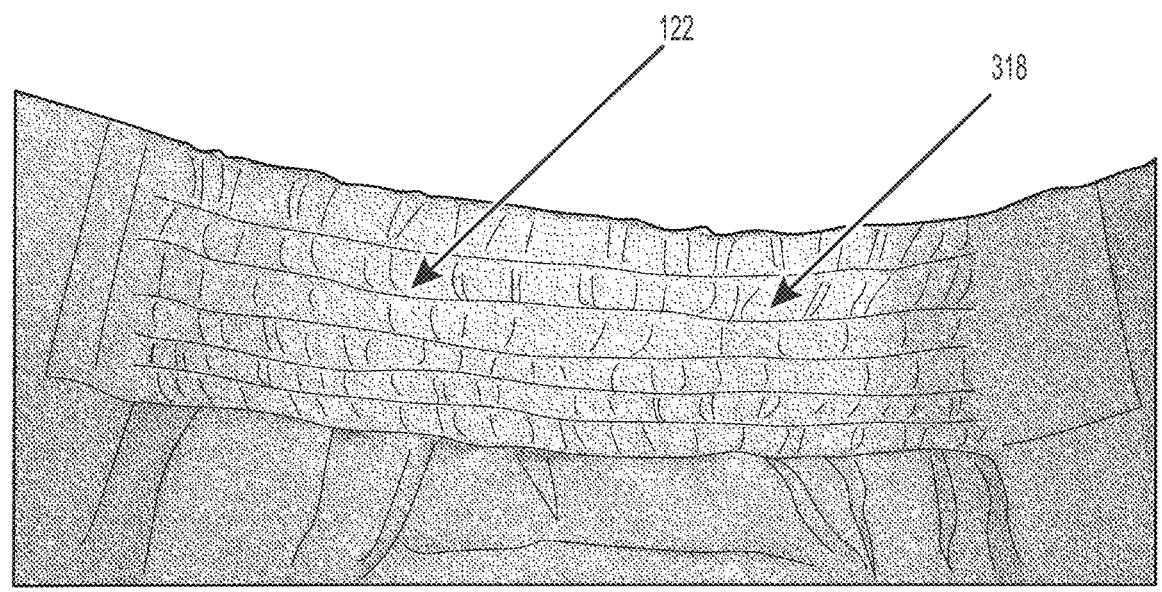
FIG. 74B is a front view of an inventive waistband 122 comprising an inventive elastomeric laminate 302. The inventive texture zone 318 of the waistband 122 in FIG. 74B is meant to be directly compared to same areas of the waistband 122 in FIG. 74A.
Figure 75A:
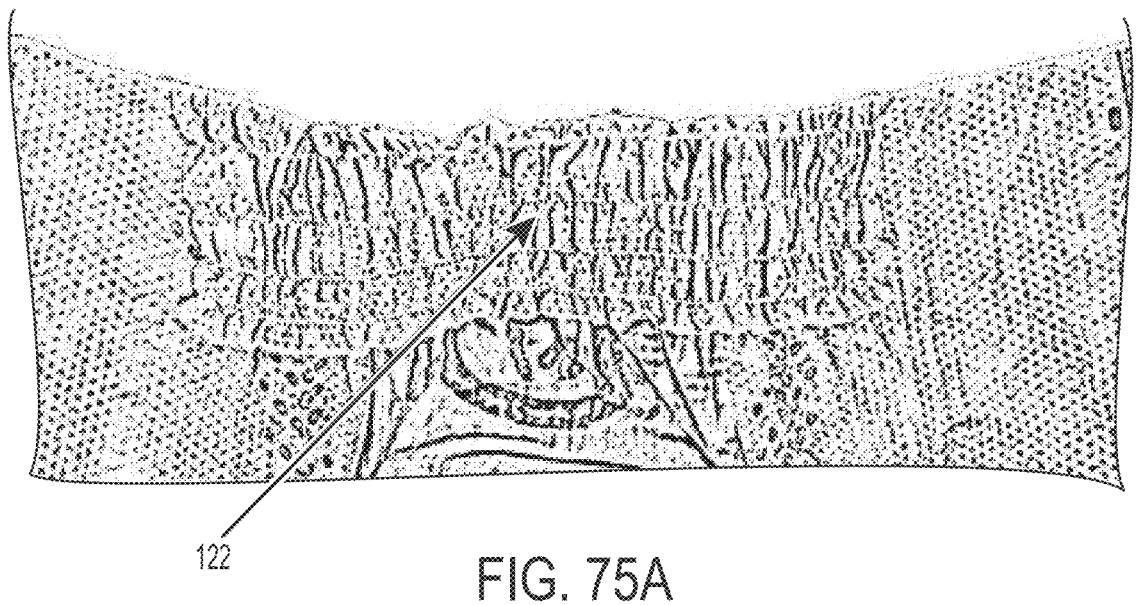
FIG. 75A is a front view of a comparative waistband 122 comprising an existing elastic profile of strands showing a grouping of large irregular and uncontrolled gathers indicative of less uniform and higher elastic stress that will result in higher pressure on the wearer's skin (versus the waistband 122 of FIG. 75B).
Figure 75B:
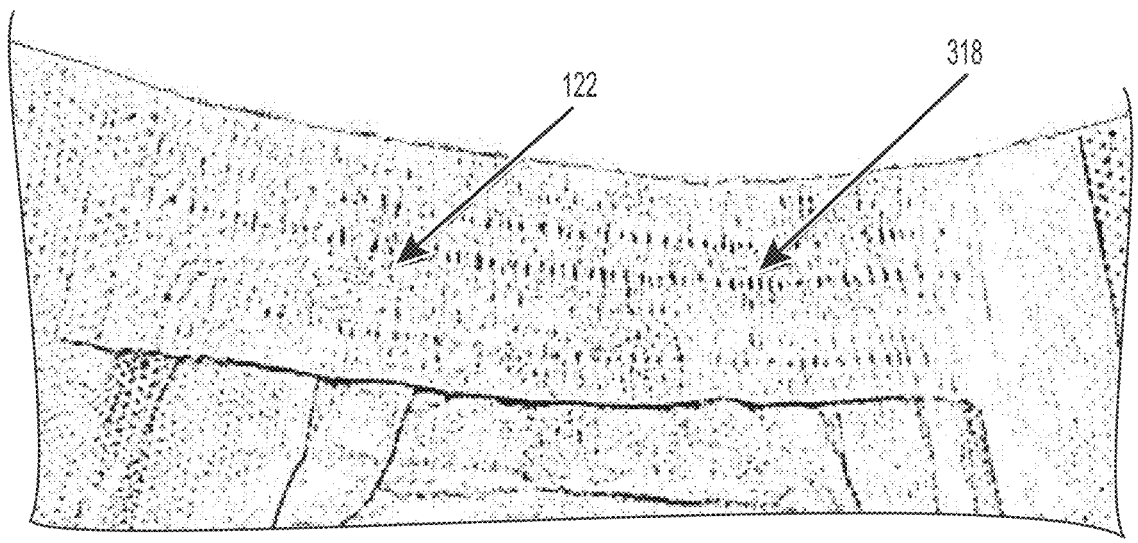
FIG. 75B is a front view of an inventive waistband 122 comprising an inventive elastomeric laminate 302. The inventive texture zone 318 of the waistband 122 in FIG. 75B is meant to be directly compared to same areas of the waistband 122 in FIG. 75A.

Example 2 is a side panel taped absorbent article. The taped article comprises a pair of side panels disposed in a first waist region and the following materials and construction.
Elastomeric Ear Panel Outer Layer (first substrate layer 306): 17 gsm carded nonwoven
Elastomeric Ear Panel Inner Layer (second substrate layer 308): 17 gsm spunbond nonwoven Backsheet Film 126: 12 gsm liquid impermeable polyethylene film
Core Wrap: 10 gsm hydrophilic spunbond nonwoven
AGM: absorbent gelling material
Distribution Layer: crosslinked cellulosic fiber
Acquisition Layer: 43 gsm synthetic acquisition layer
Topsheet 124: 12 gsm hydrophilic spunbond nonwoven
Side Panel Elastic Profile: Table 2, group A
Cuff Elastic Profile: Table 4, group B
Front Waistband: Table 3, group A
Back Waistband: Table 3, group A
The elastomeric ear panels 530 of Example 2 may present on a wearer consistent with the images in FIGS. 70B, and 71B. Further, the cuffs 52 of Example 2 may present consistent with the images of FIGS. 76B, and 77B. Still further, the front and back waistbands 122 of Example 2 may present consistent with the images of FIGS. 74B, and 75B.

Example 3—Taped Article with Belt (See, for Example, FIG. 43)

Example 3 is a belted taped absorbent article. The taped article comprises a belt disposed in a first waist region and the following materials and construction.
Outer Belt Layer (first substrate layer 306): 15 gsm spunbond nonwoven
Inner Belt Layer (second substrate layer 308): 10 gsm spunbond nonwoven
Backsheet Film 126: 12 gsm liquid impermeable polyethylene film
Core Wrap: 10 gsm hydrophilic spunbond nonwoven
AGM: absorbent gelling material
Distribution Layer: crosslinked cellulosic fiber
Acquisition Layer: 43 gsm synthetic acquisition layer
Topsheet 124: 12 gsm hydrophilic spunbond nonwoven
Belt Elastic Profile: Table 1, group B
Cuff Elastic Profile: Table 4, group A
Front Waistband: Table 3, group B
The belt 430 of Example 3 may present on a wearer consistent with the images of FIGS. 72B, and 73B. Further, the cuffs 52 of Example 3 may present consistent with the images of FIGS. 76B, and 77B. Still further, the front waistband 122 of Example 3 may present consistent with the images of FIGS. 74B, and 75B.

Example 4—Side Panel Pant Article (See, for Example, FIG. 2)

Example 4 is a side panel pant absorbent article. The pant article has a pair of side panels disposed in each waist region and comprises the following materials and construction.
Side Panel Outer Layer (first substrate layer 306): 17 gsm carded nonwoven
Side Panel Inner Layer (second substrate layer 308): 17 gsm spunbond nonwoven
Backsheet Film 126: 12 gsm liquid impermeable polyethylene film
Core Wrap: 10 gsm hydrophilic spunbond nonwoven
AGM: absorbent gelling material
Distribution Layer: crosslinked cellulosic fiber
Acquisition Layer: 43 gsm synthetic acquisition layer
Topsheet 124: 12 gsm hydrophilic spunbond nonwoven
Front Side Panel Elastic Profile: Table 2, group B
BackSide Panel Elastic Profile: Table 2, group B
Cuff Elastic Profile: Table 4, group A
Front Waistband: Table 3, group C
Back Waistband: Table 3, group C
The side panels 330 of Example 4 may present on a wearer consistent with the images in FIGS. 70B, and 71B. Further, the cuffs 52 of Example 4 may present consistent with the images of FIGS. 76B, and 77B. Still further, the front and back waistbands 122 of Example 4 may present consistent with the images of FIGS. 74B, and 75B.

Figure 17:
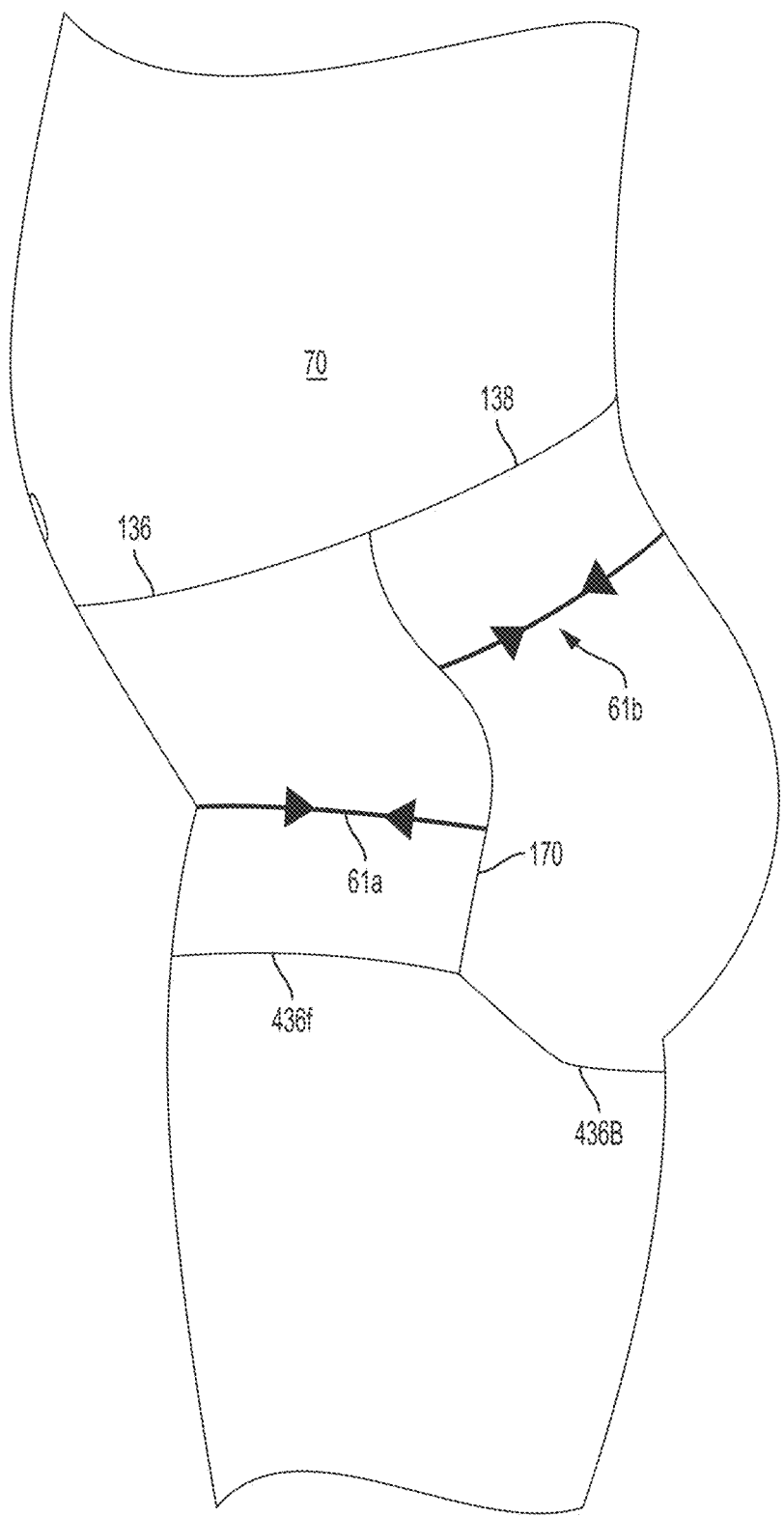
FIG. 17 is a side view of a pant donned on a wearer showing low motion zone anchoring zones 61a and 61b.
Figure 18:
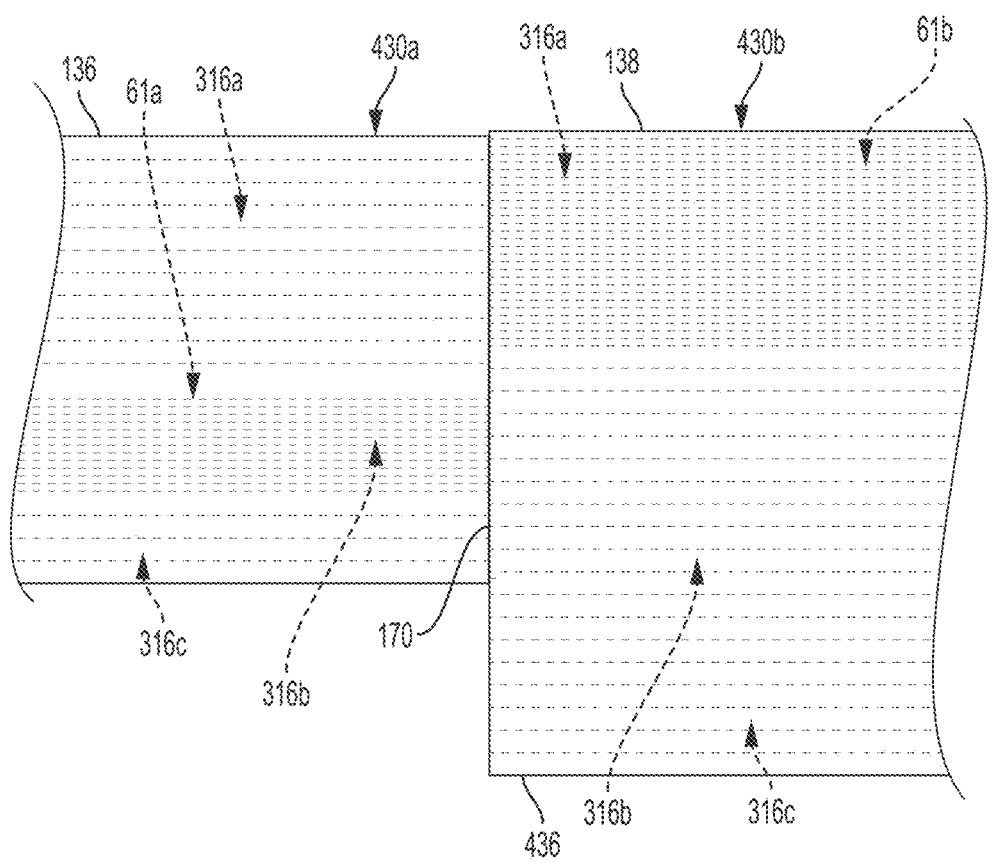
FIG. 18 is a partial side view of a pant showing low motion zone anchoring zones 61a and 61b.
Figure 19:
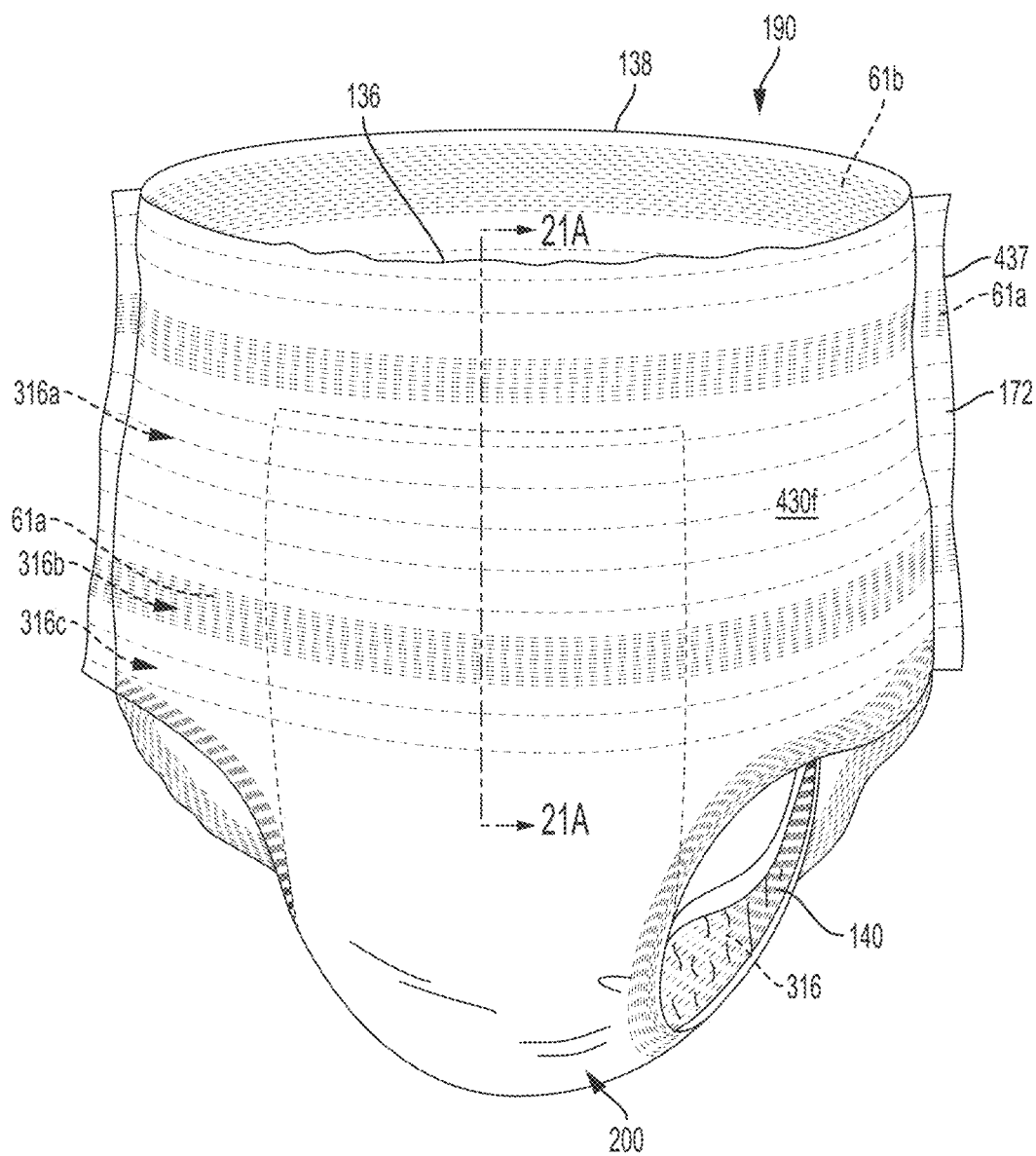
FIG. 19 is a perspective front view of pant with multiple beam zones disposed in the low motion zones of a potential wearer, showing the elastics responsible for anchoring forces 61a and b.

Example 5—Targeted Force Belt Pant Article (See, for Example, FIG. 17)

Example 5 is a belted pant absorbent article. The pant comprises a belt laminate disposed in both the waist regions and the following materials and construction.
Outer Belt Flap Layer (first substrate layer 306): 13 gsm spunbond nonwoven
Inner Belt Flap Layer (second substrate layer 308): 13 gsm spunbond nonwoven
Backsheet Film 126: 12 gsm liquid impermeable polyethylene film
Core Wrap: 10 gsm hydrophilic spunbond nonwoven
AGM: absorbent gelling material
Distribution Layer: crosslinked cellulosic fiber
Acquisition Layer: 43 gsm synthetic acquisition layer
Topsheet 124: 12 gsm hydrophilic spunbond nonwoven
Belt Elastic Profile: Table 1, group C
Cuff Elastic Profile: Table 4, group B
The belt 430 of Example 5 may present on a wearer consistent with the images of FIGS. 72B, and 73B. Further, the cuffs 52 of Example 5 may present consistent with the images of FIGS. 76B, and 77B.

EXAMPLE CLAIM COMBINATIONS

Example Claim Set 1

1. An absorbent article, comprising:
a chassis comprising a topsheet, a backsheet and an absorbent core disposed between the topsheet and the backsheet;
a first belt;
a longitudinal centerline extending from the midpoint of a front waist edge of the absorbent article to a midpoint of a back waist edge of the absorbent article;
a lateral centerline extending perpendicular to the longitudinal centerline through a midpoint of the longitudinal centerline;
wherein the first belt is formed at least in part by an elastomeric laminate comprising a first substrate layer, a second substrate layer and a first plurality of elastics disposed between the first and second substrate layers;
wherein the first plurality of elastics comprises greater than about 40 elastic strands disposed at an Average-Strand-Spacing of less than 4 mm, having an Average-Dtex of less than 600, and having an Average-Pre-Strain of less than 400%; and
wherein a basis weight of each of the first and second substrate layers is from about 6 grams per square meter to about 30 grams per square meter.

2. The absorbent article of claim 1, wherein the first plurality of elastics comprises greater than about 100 strands.

3. The absorbent article according to any of the preceding claims, wherein the first plurality of elastics is disposed at an Average-Strand-Spacing of less than 3 mm.

4. The absorbent article according to any of the preceding claims, wherein the first plurality of elastics has an Average-Dtex of less than 400.

5. The absorbent article according to any of the preceding claims, wherein the first plurality of elastics has an Average-Pre-Strain of less than 350%.

6. The absorbent article according to any of the preceding claims, wherein the first plurality of elastics is disposed at an Average-Strand-Spacing of less than 2 mm.

7. The absorbent article according to any of the preceding claims, wherein the first plurality of elastics has an Average-Dtex of less than 300.

8. The absorbent article according to any of the preceding claims, wherein the first plurality of elastics has an Average-Pre-Strain of less than 300%.

9. The absorbent article according to any of the preceding claims, wherein the elastomeric laminate comprising the first plurality of elastics has an Pressure-Under-Strand of less than about 1 psi.

10. The absorbent article according to any of the preceding claims, wherein the first plurality of elastics comprises greater than about 150 strands.

11. The absorbent article according to any of the preceding claims, wherein the first plurality of elastics is disposed at an Average-Strand-Spacing of less than 1.5 mm.

12. The absorbent article according to any of the preceding claims, wherein the first plurality of elastics has an Average-Dtex of less than 250.

13. The absorbent article according to any of the preceding claims, wherein the first plurality of elastics has an Average-Pre-Strain of less than 300%.

14. The absorbent article according to any of the preceding claims, wherein the first plurality of elastics comprises greater than about 200 strands.

15. The absorbent article according to any of the preceding claims, wherein the first plurality of elastics is disposed at an Average-Strand-Spacing of less than 1 mm.

16. The absorbent article according to any of the preceding claims, wherein the first plurality of elastics has an Average-Dtex of less than 200.

17. The absorbent article according to any of the preceding claims, wherein the first plurality of elastics has an Average-Pre-Strain of less than 250%.

18. The absorbent article according to any of the preceding claims, wherein the first plurality of elastics comprises greater than about 250 strands.

19. The absorbent article according to any of the preceding claims, wherein the first plurality of elastics is disposed at an Average-Strand-Spacing of less than 0.75 mm.

20. The absorbent article according to any of the preceding claims, wherein the first plurality of elastics has an Average-Dtex of less than 150.

21. The absorbent article according to any of the preceding claims, wherein the first plurality of elastics has an Average-Pre-Strain of less than 200%.

22. The absorbent article according to any of the preceding claims, wherein the first plurality of elastics comprises greater than about 500 strands.

23. The absorbent article according to any of the preceding claims, wherein the first plurality of elastics is disposed at an Average-Strand-Spacing of less than 0.5 mm.

24. The absorbent article according to any of the preceding claims, wherein the first plurality of elastics has an Average-Dtex of less than 125.

25. The absorbent article according to any of the preceding claims, wherein the first plurality of elastics has an Average-Pre-Strain of less than 175%.

26. The absorbent article according to any of the preceding claims, wherein the elastomeric laminate comprising the first plurality of elastics has a Pressure-Under-Strand of less than about 0.75 psi.

27. The absorbent article according to any of the preceding claims, wherein the first plurality of elastics, the second plurality of elastics, and the third plurality of elastics each comprise PolyUrethane Urea.

28. The absorbent article according to any of the preceding claims, wherein the first plurality of elastics, the second plurality of elastics, and the third plurality of elastics each comprise a silicone oil coating.

29. The absorbent article according to any of the preceding claims, wherein the first plurality of elastics, the second plurality of elastics, and the third plurality of elastics each are joined to the inner and outer nonwoven layers via an adhesive.

30. The absorbent article according to any one of claims 29, wherein the adhesive is selected from the group consisting of Styrenic block copolymers, Polyolefins, Ethylene-vinyl Acetates, Polyurethanes, Ethylene-propylene copolymers, Propylene-ethylene copolymers, Polyolefin block polymers, Polyolefin homo-polymers, Polyesters, Polyamides, Silicones, Cyano acrylics, Acrylics, butyl rubber, and combinations thereof.

31. The absorbent article according to any of the preceding claims, wherein the first plurality of elastics, the second plurality of elastics, and the third plurality of elastics each consists essentially of PolyUrethane Urea.

32. The absorbent article according to any of the preceding claims, wherein the first plurality of elastics, the second plurality of elastics, and the third plurality of elastics each consists of PolyUrethane Urea.

33. The absorbent article according to any one of claims 29, wherein the adhesive is selected from the group consisting of thermoplastic, thermoset, hot-melt, pressure sensitive, solvent-based, and reactive thermoset.

34. A method for producing the disposable absorbent article of any of the preceding claims, comprising the step of unwinding the first plurality of elastics are unwound from a single beam to form the elastomeric laminate.

Example Claim Set 2

1. An absorbent article, comprising:
a chassis comprising a topsheet, a backsheet and an absorbent core disposed between the topsheet and the backsheet;
a first panel that may be a first side panel or an a first ear panel;
a second panel that may be a second side panel or a second ear panel;
a longitudinal centerline extending from a midpoint of a front waist edge of the absorbent article to a midpoint of a back waist edge of the absorbent article;
a lateral centerline extending perpendicular to the longitudinal centerline through the midpoint of the longitudinal centerline;
wherein the first and second panels are formed at least in part by an elastomeric laminate comprising a first substrate layer, a second substrate layer, and a first plurality of elastics disposed between the first and second substrate layers;
wherein the first plurality of elastics comprises greater than about 10 elastic strands disposed at an Average-Strand-Spacing of less than 4 mm, and having an Average-Dtex of less than 600 and an Average-Pre-Strain of less than 400%; and wherein a basis weight of each of the first and second substrate layers is from about 6 grams per square meter to about 30 grams per square meter.

2. The absorbent article of claim 1, wherein the first plurality of elastics comprises greater than about 20 strands.

3. The absorbent article according to any of the preceding claims, wherein the first plurality of elastics is disposed at an Average-Strand-Spacing of less than 3 mm.

4. The absorbent article according to any of the preceding claims, wherein the first plurality of elastics has an Average-Dtex of less than 400.

5. The absorbent article according to any of the preceding claims, wherein the first plurality of elastics has an Average-Pre-Strain of less than 350%.

6. The absorbent article according to any of the preceding claims, wherein the first plurality of elastics is disposed at an Average-Strand-Spacing of less than 2 mm.

7. The absorbent article according to any of the preceding claims, wherein the first plurality of elastics has an Average-Dtex of less than 300.

8. The absorbent article according to any of the preceding claims, wherein the first plurality of elastics has an Average-Pre-Strain of less than 300%.

9. The absorbent article according to any of the preceding claims, wherein the elastomeric laminate comprising the first plurality of elastics has an Pressure-Under-Strand of less than about 1 psi.

10. The absorbent article according to any of the preceding claims, wherein the first plurality of elastics comprises greater than about 40 strands.

11. The absorbent article according to any of the preceding claims, wherein the first plurality of elastics is disposed at an Average-Strand-Spacing of less than 1.5 mm.

12. The absorbent article according to any of the preceding claims, wherein the first plurality of elastics has an Average-Dtex of less than 250.

13. The absorbent article according to any of the preceding claims, wherein the first plurality of elastics has an Average-Pre-Strain of less than 300%.

14. The absorbent article according to any of the preceding claims, wherein the first plurality of elastics comprises greater than about 80 strands.

15. The absorbent article according to any of the preceding claims, wherein the first plurality of elastics is disposed at an Average-Strand-Spacing of less than 1 mm.

16. The absorbent article according to any of the preceding claims, wherein the first plurality of elastics has an Average-Dtex of less than 200.

17. The absorbent article according to any of the preceding claims, wherein the first plurality of elastics has an Average-Pre-Strain of less than 250%.

18. The absorbent article according to any of the preceding claims, wherein the first plurality of elastics comprises greater than about 115 strands.

19. The absorbent article according to any of the preceding claims, wherein the first plurality of elastics is disposed at an Average-Strand-Spacing of less than 0.75 mm.

20. The absorbent article according to any of the preceding claims, wherein the first plurality of elastics has an Average-Dtex of less than 150.

21. The absorbent article according to any of the preceding claims, wherein the first plurality of elastics has an Average-Pre-Strain of less than 200%.

22. The absorbent article according to any of the preceding claims, wherein the first plurality of elastics comprises greater than about 150 strands.

23. The absorbent article according to any of the preceding claims, wherein the first plurality of elastics is disposed at an Average-Strand-Spacing of less than 0.5 mm.

24. The absorbent article according to any of the preceding claims, wherein the first plurality of elastics has an Average-Dtex of less than 125.

25. The absorbent article according to any of the preceding claims, wherein the first plurality of elastics has an Average-Pre-Strain of less than 175%.

26. The absorbent article according to any of the preceding claims, wherein the elastomeric laminate comprising the first plurality of elastics has an Pressure-Under-Strand of less than about 0.75 psi.

27. The absorbent article according to any of the preceding claims, wherein the first plurality of elastics, the second plurality of elastics, and the third plurality of elastics each comprise PolyUrethane Urea.

28. The absorbent article according to any of the preceding claims, wherein the first plurality of elastics, the second plurality of elastics, and the third plurality of elastics each comprise a silicone oil coating.

29. The absorbent article according to any of the preceding claims, wherein the first plurality of elastics, the second plurality of elastics, and the third plurality of elastics each are joined to the inner and outer nonwoven layers via an adhesive.

30. The absorbent article according to any one of claims 29, wherein the adhesive is selected from the group consisting of Styrenic block copolymers, Polyolefins, Ethylene-vinyl Acetates, Polyurethanes, Ethylene-propylene copolymers, Propylene-ethylene copolymers, Polyolefin block polymers, Polyolefin homo-polymers, Polyesters, Polyamides, Silicones, Cyanoacrylics, Acrylics, butyl rubber, and combinations thereof.

31. The absorbent article according to any of the preceding claims, wherein the first plurality of elastics, the second plurality of elastics, and the third plurality of elastics each consists essentially of PolyUrethane Urea.

32. The absorbent article according to any of the preceding claims, wherein the first plurality of elastics, the second plurality of elastics, and the third plurality of elastics each consists of PolyUrethane Urea.

33. The absorbent article according to any one of claims 29, wherein the adhesive is selected from the group consisting of thermoplastic, thermoset, hot-melt, pressure sensitive, solvent-based, and reactive thermoset.

34. A method for producing the disposable absorbent article of any of the preceding claims, comprising the step of unwinding the first plurality of elastics are unwound from a single beam to form the elastomeric laminate.

Example Claim Set 3

1. An absorbent article, comprising:
a chassis comprising a topsheet, a backsheet and an absorbent core disposed between the topsheet and the backsheet;
an elastomeric laminate forming at least a portion of one or more absorbent article components selected from the group consisting of a waistband, a waistcap, an inner leg cuff, an outer leg cuff, and a transverse barrier;
a longitudinal centerline extending from a midpoint of a front waist edge of the absorbent article to a midpoint of a back waist edge of the absorbent article;
a lateral centerline extending perpendicular to the longitudinal centerline through a midpoint of the longitudinal centerline;

wherein the elastomeric laminate comprises a first substrate layer, a second substrate layer and a first plurality of elastics disposed between the first and second substrate layers;

wherein the first plurality of elastics comprises from about 10 to about 200 elastic strands disposed at an Average-Strand-Spacing of from about 0.25 to about 5 mm, and having an Average-Dtex from about 10 to about 600 and an Average-Pre-Strain of from about 75% to about 400%; and wherein a basis weight of each of the first and second substrate layers is from about 6 grams per square meter to about 30 grams per square meter.

2. The absorbent article of claim 1, wherein the first plurality of elastics comprises from about 15 to about 175 elastic strands.

3. The absorbent article according to any of the preceding claims, wherein the first plurality of elastics is disposed at an Average-Strand-Spacing of less than 3 mm.

4. The absorbent article according to any of the preceding claims, wherein the first plurality of elastics has an Average-Dtex of less than 400.

5. The absorbent article according to any of the preceding claims, wherein the first plurality of elastics has an Average-Pre-Strain of less than 350%.

6. The absorbent article according to any of the preceding claims, wherein the first plurality of elastics is disposed at an Average-Strand-Spacing of less than 2 mm.

7. The absorbent article according to any of the preceding claims, wherein the first plurality of elastics has an Average-Dtex of less than 300.

8. The absorbent article according to any of the preceding claims, wherein the first plurality of elastics has an Average-Pre-Strain of less than 300%.

9. The absorbent article according to any of the preceding claims, wherein the elastomeric laminate comprising the first plurality of elastics has an Pressure-Under-Strand of less than about 1 psi.

10. The absorbent article according to any of the preceding claims, wherein the first plurality of elastics comprises from about 20 to about 160 elastic strands.

11. The absorbent article according to any of the preceding claims, wherein the first plurality of elastics is disposed at an Average-Strand-Spacing of less than 1.5 mm.

12. The absorbent article according to any of the preceding claims, wherein the first plurality of elastics has an Average-Dtex of less than 250.

13. The absorbent article according to any of the preceding claims, wherein the first plurality of elastics has an Average-Pre-Strain of less than 300%.

14. The absorbent article according to any of the preceding claims, wherein the first plurality of elastics comprises from about 25 to about 140 elastic strands.

15. The absorbent article according to any of the preceding claims, wherein the first plurality of elastics is disposed at an Average-Strand-Spacing of less than 1 mm.

16. The absorbent article according to any of the preceding claims, wherein the first plurality of elastics has an Average-Dtex of less than 200.

17. The absorbent article according to any of the preceding claims, wherein the first plurality of elastics has an Average-Pre-Strain of less than 250%.

18. The absorbent article according to any of the preceding claims, wherein the first plurality of elastics comprises from about 35 to about 120 elastic strands.

19. The absorbent article according to any of the preceding claims, wherein the first plurality of elastics is disposed at an Average-Strand-Spacing of less than 0.75 mm.

20. The absorbent article according to any of the preceding claims, wherein the first plurality of elastics has an Average-Dtex of less than 150.

21. The absorbent article according to any of the preceding claims, wherein the first plurality of elastics has an Average-Pre-Strain of less than 200%.

22. The absorbent article according to any of the preceding claims, wherein the first plurality of elastics comprises from about 45 to about 100 elastic strands.

23. The absorbent article according to any of the preceding claims, wherein the first plurality of elastics is disposed at an Average-Strand-Spacing of less than 0.5 mm.

24. The absorbent article according to any of the preceding claims, wherein the first plurality of elastics has an Average-Dtex of less than 125.

25. The absorbent article according to any of the preceding claims, wherein the first plurality of elastics has an Average-Pre-Strain of less than 175%.

26. The absorbent article according to any of the preceding claims, wherein the elastomeric laminate comprising the first plurality of elastics has an Pressure-Under-Strand of less than about 0.75 psi.

27. The absorbent article according to any of the preceding claims, wherein the first plurality of elastics, the second plurality of elastics, and the third plurality of elastics each comprise PolyUrethane Urea.

28. The absorbent article according to any of the preceding claims, wherein the first plurality of elastics, the second plurality of elastics, and the third plurality of elastics each comprise a silicone oil coating.

29. The absorbent article according to any of the preceding claims, wherein the first plurality of elastics, the second plurality of elastics, and the third plurality of elastics each are joined to the inner and outer nonwoven layers via an adhesive.

30. The absorbent article according to any one of claims 29, wherein the adhesive is selected from the group consisting of Styrenic block copolymers, Polyolefins, Ethylene-vinyl Acetates, Polyurethanes, Ethylene-propylene copolymers, Propylene-ethylene copolymers, Polyolefin block polymers, Polyolefin homo-polymers, Polyesters, Polyamides, Silicones, Cyanoacrylics, Acrylics, butyl rubber, and combinations thereof.

31. The absorbent article according to any of the preceding claims, wherein the first plurality of elastics, the second plurality of elastics, and the third plurality of elastics each consists essentially of PolyUrethane Urea.

32. The absorbent article according to any of the preceding claims, wherein the first plurality of elastics, the second plurality of elastics, and the third plurality of elastics each consists of PolyUrethane Urea.

33. The absorbent article according to any one of claims 29, wherein the adhesive is selected from the group consisting of thermoplastic, thermoset, hot-melt, pressure sensitive, solvent-based, and reactive thermoset.

34. A method for producing the disposable absorbent article of any of the preceding claims, comprising the step of unwinding the first plurality of elastics are unwound from a single beam to form the elastomeric laminate.

Methods

General Sample Preparation

The General Sample Preparation is intended to be used for methods that do not have specific sample preparation instructions within the method itself.

The When collecting a specimen for testing, the specimen must contain a plurality of elastic strands and/or an elastic material; film, elastic scrim, elastic foam, elastic ribbons, elastic strips, etc. In situations where the elastic material and/or elastic strands is not fully secured within the sample, the test specimen must be obtained in a way that elastic material and/or elastic strands within the test region of the specimen are as they were intended and not altered as a result of collection of the specimen. If the elastic material or any elastic strands release, creep or become separated within or from the laminate, the specimen is discarded and a new specimen prepared.

For pants, remove the side panels where they are attached to the chassis and separate the side panels at the side seams. Identify the elastic material that transverses the entire width of the panel. Identify the longitudinally distal most edge of the elastic material or elastic strand (closest to the waist edge) and the longitudinally proximal most edge of the elastic material or elastic strand (closest to the leg edge) determine the midpoint between the distal most elastic strand or elastic material edge and the proximal most elastic strand or elastic material edge. Cut a 40 mm wide strip laterally across the entire panel centered at the midpoint. Repeat for each front and rear side panel that contains elastic material and/or elastic strands.

For taped, remove ear panels where they are attached to the chassis. Identify the elastic material that transverses the entire width of the panel. Identify the distal most elastic material edge or elastic strand (closest to the waist edge) and the proximal most elastic material edge or elastic strand (closest to the leg edge) determine the midpoint between the distal most elastic strand or elastic material edge and the proximal most elastic strand or elastic material edge. Cut a 40 mm wide strip laterally across the entire ear panel centered at the midpoint. Repeat for each front and rear ear panel that contains elastic material and/or elastic strands.

For a belted article, mark the product on the front and back by extending a line from along the side of the core to the waist edge. Remove the belt from the article, using an appropriate means (e.g. freeze spray), taking care not to delaminate the belt or release the elastics. Separate the front belt from the back belt along any seams. Identify the distal most elastic material edge or elastic strand (closest to the waist edge) and the proximal most elastic material edge or strand (closest to the leg edge) determine the midpoint between the distal most elastic strand or elastic material edge and the proximal most elastic strand or elastic material edge. Cut a 40 mm wide strip parallel to the waist edge if linear or to the elastic strands if linear and centered at the midpoint, across the entire belt portion. If the strip has a region that does not contain elastic strands or elastic material (e.g., a portion that overlapped the core, etc.) cut along the ends of the elastic strands/elastic material, to remove the non-elastic region and treat as two specimens.

For waistbands, they are tested as a single piece of material. Remove the belt from the article, using an appropriate means (e.g. freeze spray), taking care not to delaminate the belt or release the elastics.

For the leg cuffs, each of the leg cuffs are tested as a single piece of material. The inner leg cuff sample is considered to be the portion of the inner leg cuff that extends from the proximal most edge of the inner leg cuff to and including the distal most elastic of the inner leg cuff and extending longitudinally to the front and back waist edges of the chassis. The outer leg cuff sample is considered to be the portion of the outer leg cuff that extends from the distal most edge of the outer leg cuff to and including the proximal most elastic of the outer leg cuff and extending longitudinally to the front and back waist edges of the chassis.

For all specimen strips calculate a Span Corrected Width (SCW) is calculated as:

$$\text{Span Corrected Width} = d\left(\frac{n}{n-1}\right)$$

where d is the distance (mm) between the two distal strands, and n is the number of strands, when n>1. Clamp the strip at each end and measure the length between the clamps to the nearest 1 mm. Apply a weight equal to 3 g/mm SCW. After 10 seconds measure the final weight to the nearest 1 mm. Calculate the elongation as (Final Length—Initial Length)/Initial length.

Product Measurement Preparation for Donning-Ratio, Product Length-to-Waist Silhouette and Product Hip-to-Waist Silhouette All measurements are conducted at 22° C.+/−2° and 50% RH+/−20%.

Purpose

This method is used to prepare pant type products for subsequent dimensional measurement. The method provides a consistent means of opening a product that has been removed from a bag. This method is applicable to all forms of pant products. A constant rate of extension tensile testing machine with computer interface is used.

A load cell is chosen so that the load cell capacity ensures accuracy of a 5N load to within 0.1N.

Sample Holder Apparatus

Figure 30A:
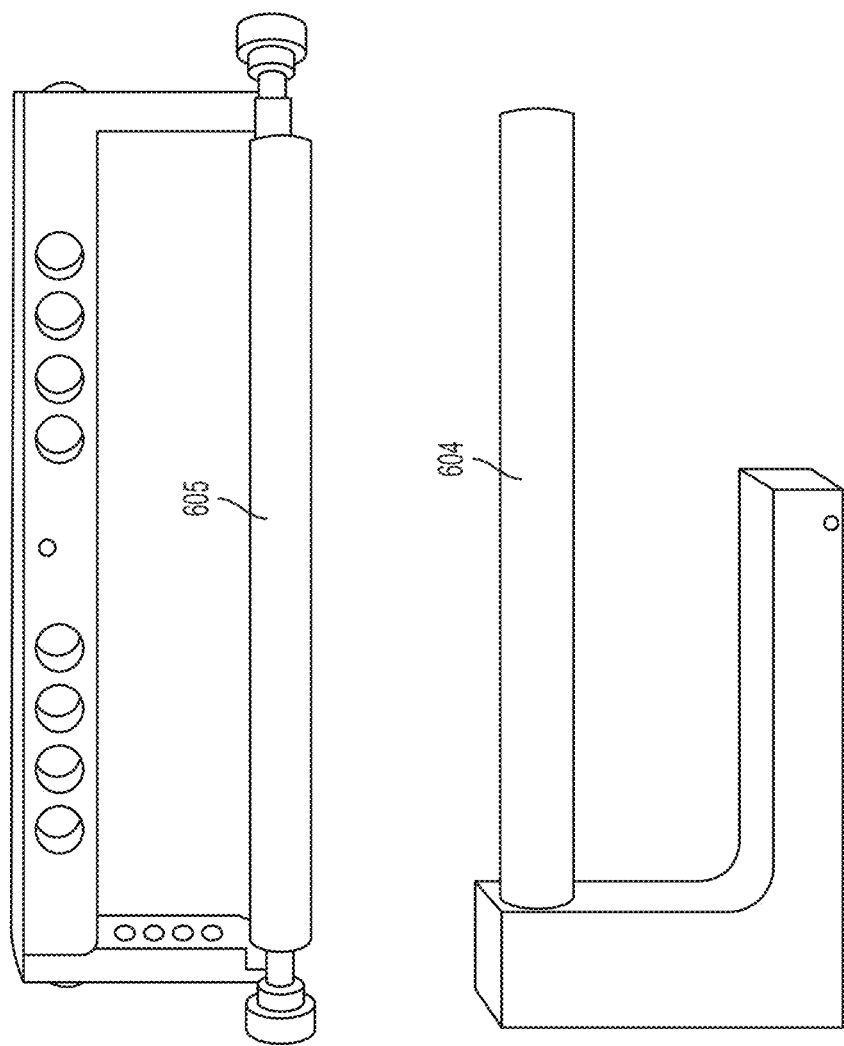
FIG. 30A is a simplified view of the apparatus for measuring the belt hoop force.
Figure 31:
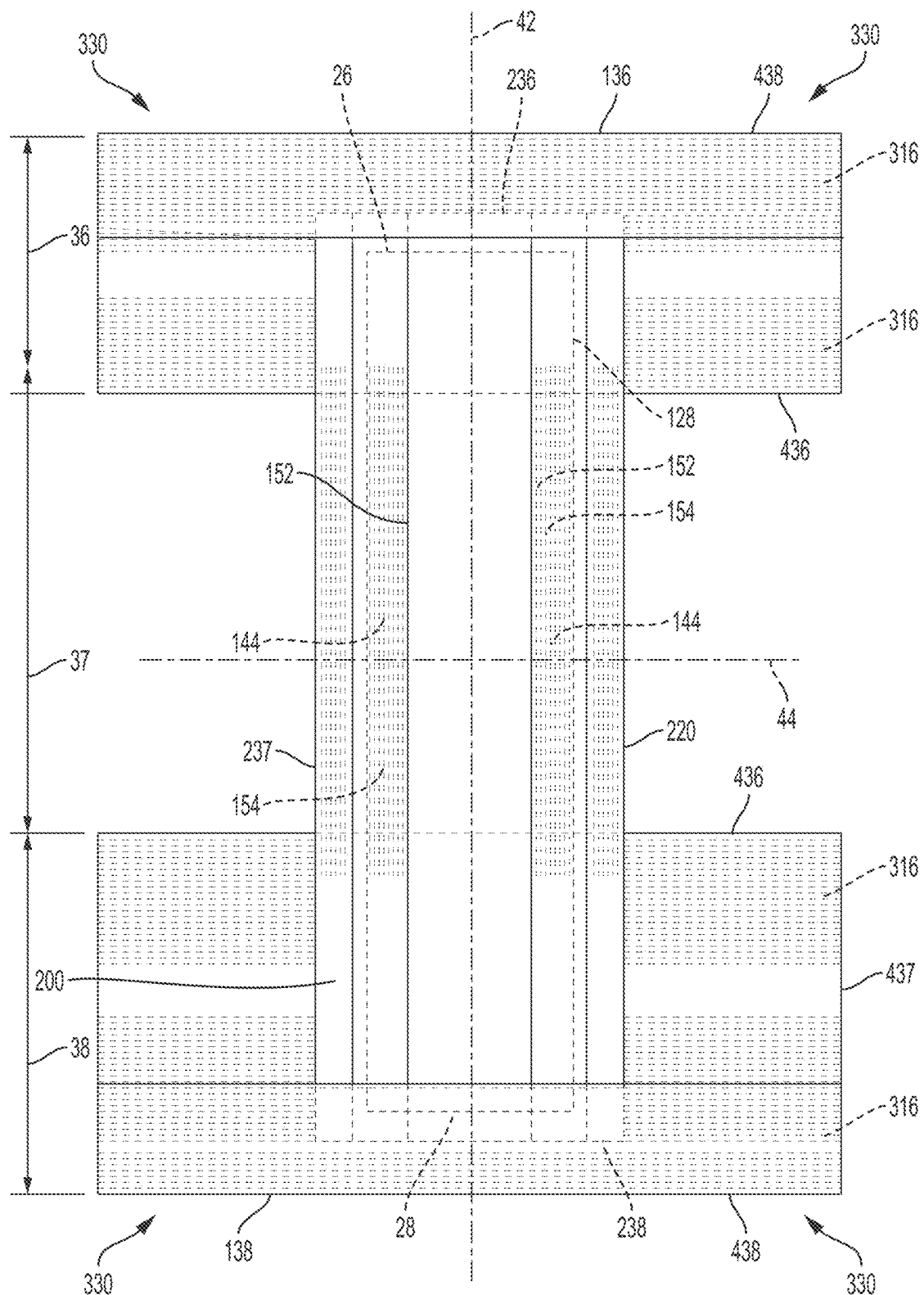
FIG. 31 is a plan view of the belt pant of FIG. 32.
Figure 32:
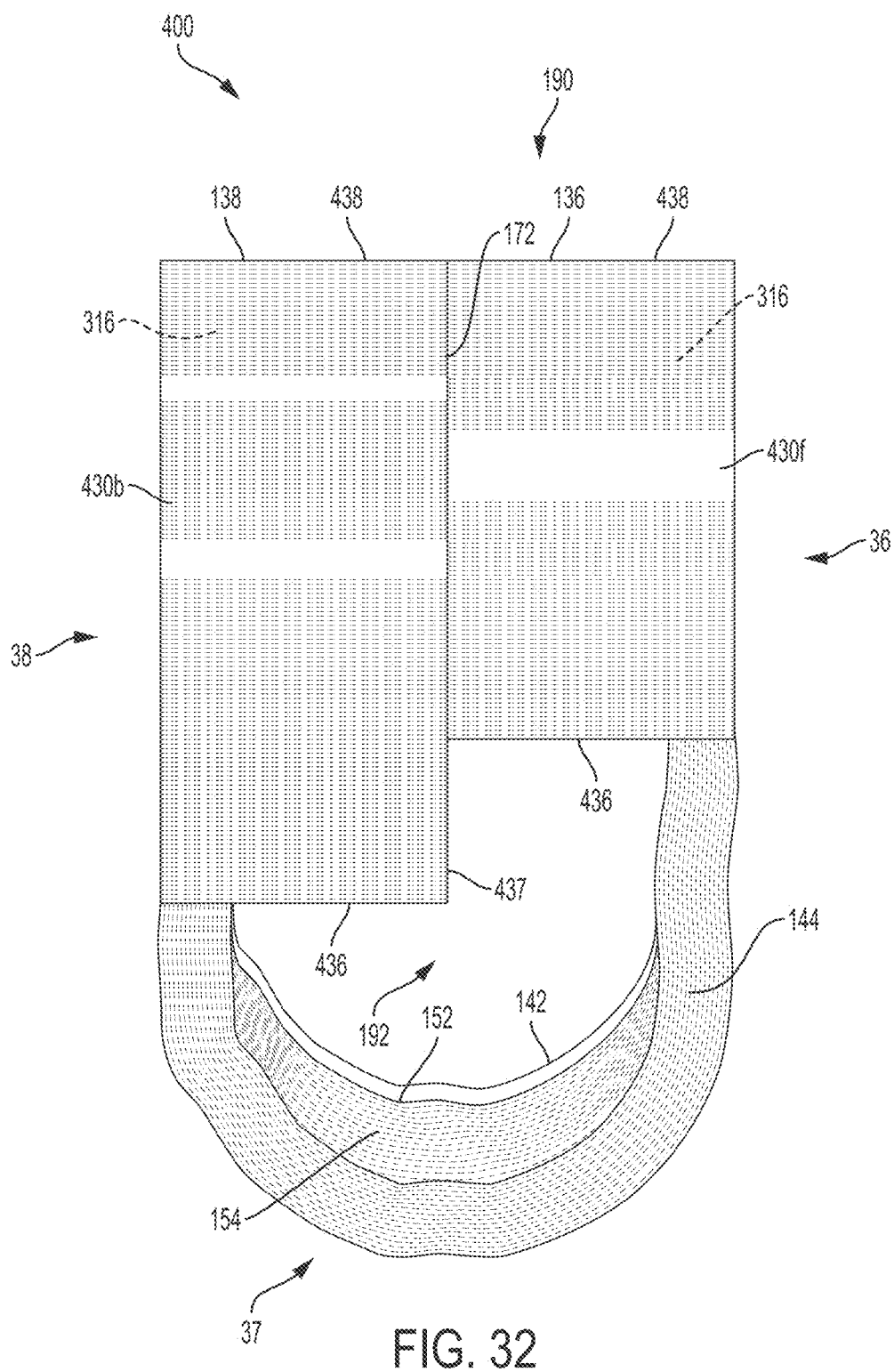
FIG. 32 is a perspective side view of a belt pant showing differing longitudinal lengths of a front belt and a back belt at a side seam 172.
Figure 33:
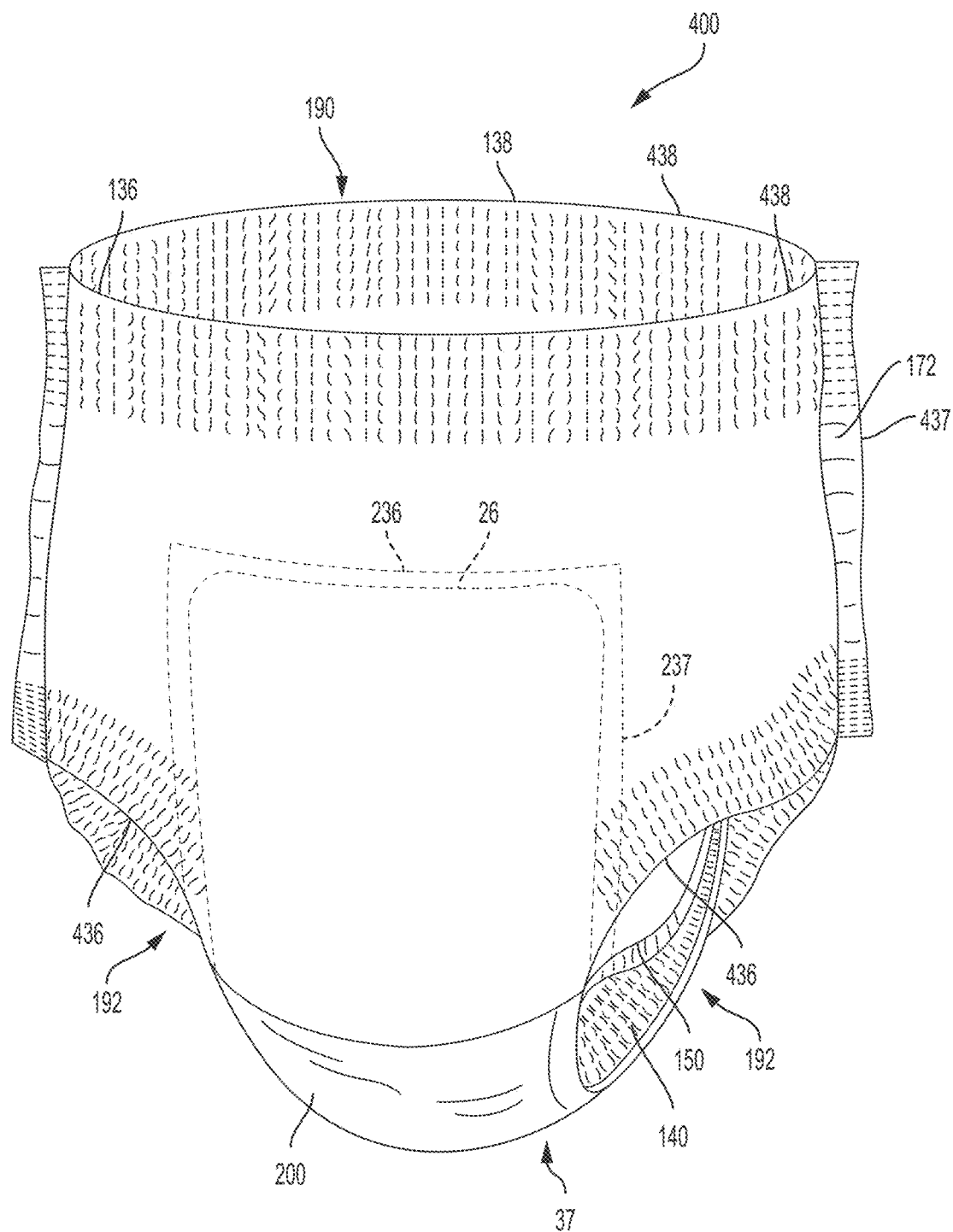
FIG. 33 is a perspective front view of a belt pant showing a concentration of elastic gathers at the waist and leg openings.

"C" (604) and "O" (605) Bar attachments each with a rod radius of 9.50 mm that extend longer than the length of the longest side seam. Refer to FIG. 30A. The bars are mounted horizontally in the tensile tester with their longitudinal axes in the same vertical plane and with upper bar mounted directly above the lower bar.

Equipment Set Up

Calibrate tensile tester equipment according to the instrument manufacturer's recommendations.

The initial gauge length is determined by removing 10 sample products from the bag, unfolding the pant products (607) and laying them flat as illustrated in FIG. 90, below and measuring the distance between the sides of the pant at the waist as shown (606). The average of the waist measurement will be used as the initial gauge length for the specific set of specimens. The initial gauge length is the distance from the uppermost edge of the upper bar to the lowermost edge of the lower bar.

Apply the whole product (607) to the bars as shown in FIG. 30B while minimizing manipulation of the specimen. Pull Sample to 5N Force then hold for 10 seconds. Return to initial gauge length.

Crosshead Speed=254.0 mm/min, Data acquisition rate=50 Hz.

Cycles=1

Remove the specimen from the bars while minimizing manipulation. Lay the specimen flat with the front side facing upward as shown in FIG. 90.

Repeat for all 10 specimens

Physical Measurements

Each of the measurements below is to be conducted on 10 separate like specimens and the average of the 10 separate like specimens is considered to be the measurement for that specific specimen set.

Relaxed Product Length (600)

Relaxed Product Length is the longitudinal distance between the longitudinally distal most point in the crotch region and the longitudinally distal most point along the front waist edge. The longitudinal distance is measured parallel to the longitudinal axis of the product. Refer to FIG. 90.

Relaxed Product Hip Width (601)

Relaxed Product Hip Width is the lateral distance from the laterally distal most point of the left side edge of the product at the upper edge of the left leg opening to the laterally distal most point of the right side edge of the product at the upper edge of the right leg opening. Refer to FIG. 90. The lateral distance is measured perpendicular to the longitudinal axis of the product.

Relaxed Product Waist Width (602)

Relaxed Product Waist Width is the lateral distance from the distal most point at the right side of the front waist edge to the distal most point at the left side of the front waist edge. The lateral distance is measured perpendicular to the longitudinal axis of the product. Refer to FIG. 90.

Relaxed Product Crotch Width (608)

Relaxed Product Crotch Width is the lateral distance from the laterally distal most point of the left side edge of the product at the lower edge of the left leg opening to the laterally distal most point of the right side edge of the product at the lower edge of the right leg opening. Refer to FIG. 90. The lateral distance is measured perpendicular to the longitudinal axis of the product.

Cantilever Bending

The Bending Length and Flexural Rigidity at the waist is measured as the cantilever bending value as determined using ASTM Method D1388, Option A Cantilever Test with the modifications described below. The test apparatus described in the D1388 is used without modification. Articles are conditioned at 23° C.±2 C.° and 50%±2% relative humidity for 2 hr prior to analysis and then tested under the same environmental conditions.

The method is applied to a dry nonwoven laminate specimen dissected from an absorbent article rather than a fabric. For a belted article cut the belt at the side seams and remove the belt from the rest of the article using for example a cryogenic spay (e.g. Quick-Freeze, Miller-Stephenson Company, Danbury, Conn.). For pants, remove the side panel from the chassis and separate/cut along the side seam. The specimen is cut as a 25.4 mm strip parallel to the longitudinal axis of the product, starting at the waist and extending toward the crotch of the product. The length of the specimen can be less than the 200 mm cited in D1388, but must be at least 10 mm longer than the overhang length determined during testing. If the waist of the specimen is folded over, leave the fold intact for testing.

The specimen is placed on the platform with the garment facing side down and the end proximal to the waist as the leading edge. The bend is performed as described in D1388. Record the overhang length (OL) to the nearest 1 mm. Calculate the Bending Length (BL) as the Overhang Length divided by 2 and report to the nearest 1 mm. Take the specimen and measure the overhang length from the leading edge and cut across the strip. Measure and record the mass of the overhang piece and record to the nearest 0.001 g. From the mass and the dimensions of the overhang piece calculate the basis weight (BW) and record to the nearest 0.01 g/m².

Water Vapor Transmission Rate

Water Vapor Transmission Rate (WVTR) is measured using the wet cup approach to determine the rate for a stretch laminate under strain. A cylindrical cup is filled with water, maintaining a constant headspace between the water surface and a specimen sealed over the cup's upper opening. The vapor loss is measured gravimetrically after heating the assembled cup for a specified time in an oven. Glass straight walled, cylindrical vials, 95 mm tall with a 17.8 mm internal diameter at the opening are used as WVTR test cup. Articles are preconditioned at 23° C.±2 C.° and 50%±2% relative humidity for two hours prior to testing and all testing is performed under the same environmental conditions.

The test is intended for use with stretch laminate of the sample article such as belts, side panels, ears, waist bands, cuffs etc. tested in their relaxed state. Specimens are prepared as describe in General Sample Preparation force 3 articles for each test set.

One edge of laminate that is perpendicular to the machine direction (MD) of the laminate is secured to a lab bench. The specimen is then extended in the machine direction to a length equivalent to 3 gf per mm width and secured. A circle is marked on the laminate with a diameter corresponding to the diameter of the test cup. A test cup is filled with distilled water accurately to a level 25.0 mm±0.1 mm from the upper lip of the cup's opening. The specimen is placed, body-facing surface of the laminate downward, over the cup's opening. The specimen is extended such that the marked circle aligns with the cup's opening and secured around the vial's circumference with an elastic band. The specimen is further sealed by wrapping 0.25" wide Teflon tape around the cup's circumference. The Teflon tape is applied up to the top edge of the vial but should not cover any portion of the vial's opening. The mass of the cup assembly is weighed to the nearest 0.0001 gram. This is the starting mass (SM). The cup assemblies are placed upright in a mechanical convection oven (e.g. Lindberg/BlueM oven available from Thermo Scientific or equivalent) maintained at 38° C.±2 C.° for 12 hours, taking care to avoid contact between the water in the cups and the specimens. After 24 hours has elapsed, the cup assemblies are removed from the oven and allowed to come to room temperature. The mass of each cup assembly is measured to the nearest 0.0001 gram. This is the final mass (FM). The WVTR is calculated using the following equation:

$$\text{WVTR (g/m}^2\text{/24 hrs)} = ([\text{SM (g)} - \text{FM (g)}]/\text{surface area (m}^2))/24 \text{ hrs}$$

In like fashion, analyze a total of 3 replicates for each stretch laminate and record their WVTR result. Calculate the arithmetic mean WVTR for each stretch laminate set and reported to the nearest 1 g/m²/24 hrs.

Air Permeability

Air permeability is tested using a TexTest FX3300 Air Permeability Tester (available from Advanced Testing Instruments, Greer, S.C.) with a custom made 1 cm² aperture (also available from Advanced Testing Instruments). Standardize the instrument according to the manufacturer's procedures. Precondition the articles at about 23° C.±2 C.° and about 50%±2% relative humidity for two hours prior to testing. Articles are preconditioned at 23° C.±2 C.° and 50%±2% relative humidity for two hours prior to testing and all testing is performed under the same environmental conditions.

The test is intended for use with stretch laminate of the sample article such as belts, side panels, ears, waist bands, etc. Stretch components are removed from the article using, for example, cryogenic spay (e.g. Quick-Freeze, Miller-Stephenson Company, Danbury, Conn.) or cutting. Specimens are dissected from the laminate avoiding material seams or other structures not integral to the stretch. Stretch laminates are harvested from 3 articles for each test set.

Cut a specimen from the stretch region of the laminate that is 25 mm by 25 mm. For a specimen with unevenly spaced strands, a Span Corrected Width (SCW) is calculated as:

$$\text{Span Corrected Width} = d\left(\frac{n}{n-1}\right)$$

where d is the distance (mm) between the two distal strands, and n is the number of strands, when n>1. Using the Span Corrected Width determine the elongation need to achieve 3 g/mm SCW and 7 g/mm SCW by hanging weights on a substantially similar specimen and measuring the elongation.

The on the instrument's air pressure is set for 125 Pa. Place a specimen in its relaxed state with the body-facing side downward on the port plate. The stretch region must completely cover the instruments port. Close the sample ring and adjust the measuring range until it is within specification. Record the air permeability for the un-extended specimen to the nearest 0.1 m³/m²/min.

Select one of the edges of laminate that is perpendicular to the machine direction (MD) and secure it to the port plate of the instrument using adhesive tape. The specimen is then extended in the machine direction to a length equivalent to 3 gf/mm and secured. The stretch region must completely cover the port. Close the sample ring and adjust the measuring range until the it is within specification. Record the air permeability for the 3 g/mm to the nearest 0.1 m³/m²/min. Repeat in like fashion for the 7 g/mm extension and record the air permeability for the 3 g/mm to the nearest 0.1 m³/m²/min.

A total of five measures are made on replicate specimens for each stretch laminate. Calculate and report the arithmetic average for air permeability at the 0 gf/mm, 3 gf/mm, and 7 gf/mm elongation and report each to the nearest 0.1 m3/m2/min.

Caliper (Caliper Retention Value)

Caliper is measured using a foot and anvil type digital caliper such as an Ono Sokki GS 503/DG 3610 caliper gage or equivalent. The instrument is operated and calibrated as per the manufacturer's instructions. A circular 25.4 mm diameter foot that applies a confining pressure of 0.69 kPa.

The test is intended for use with stretch laminate of the sample article such as belts, side panels, ears, waist bands, cuffs etc. tested in their relaxed state. Specimens are prepared as describe in General Sample Preparation force 3 articles for each test set.

Place the specimen, with the body-facing side downward on the anvil. The middle of the test strip is centered underneath the foot. Lower the foot at approximately 0.5 mm sec, and read the value after 5.0 sec. Record as the caliper for 0 gf/mm elongation to the nearest 0.01 mm.

Select one of the edges of laminate that is perpendicular to the prominent stretch direction and secure it to the anvil using adhesive tape. The specimen is then extended in the machine direction to a length equivalent to 3 gf/mm and secured. The equivalent target site is centered under the foot. Lower the foot at approximately 0.5 mm sec, and read the value after 5.0 sec. Record as the caliper for 3 gf/mm elongation to the nearest 0.01 mm. Repeat in like fashion for the 7 g/mm extension and record the caliper for the 7 g/mm to the nearest 0.01 mm.

A total of five measures are made on replicate specimens for each stretch laminate. Calculate and report the arithmetic average for caliper at the 0 gf/mm, 3 gf/mm, and 7 gf/mm elongation and report each to the nearest 0.01 mm. The percentage at 3 gf/mm and 7 gf/mm is considered to be the Caliper Retention Value.

Average-Strand-Spacing

Using a ruler calibrated against a certified NIST ruler and accurate to 0.5 mm, measure the distance between the two distal strands within a section to the nearest 0.5 mm, and then divide by the number of strands in that section−1

Average-Strand-Spacing=$d/(n-1)$ where $n>1$ report to the nearest 0.1 mm.

Pressure-Under-Strand (Also Referred to as Average Pressure-Under-Strand)

Defined as the average pressure imparted by each individual elastic strand of a section under specific conditions. These conditions are defined as (refer to FIG. 92):

The section is pulled to a Stress of 7 gf/mm (within a consumer preferred range of stresses as determined experimentally)

The section is pulled over a cylinder whose circumference is defined as a Representative-Circumference Where:

Pressure-Under-Strand (psi)=1.422*Strand-Force/(2*Representative-Radius*Average-Strand-Diameter)

Representative-Radius (mm)=Representative-Circumference/(2*pi)

Representative-Circumference (mm)=460 mm

Stress (gf/mm)=(Summation of Strand-Forces within a section)/(Section-Width)

Section-Width (mm)=(Number of Elastics in the section) *Average-Strand-Spacing (mm)

Strand-Force (gf)=Strand-Strain (%)*0.046875*Average-Dtex

Strand-Strain (%)=strain in each elastic strand within a section

Average-Strand-Diameter (mm)=2*sqrt (Strand-Cross-Sectional-Area/pi)

Strand-Cross-Sectional-Area (mm²)=Average-Dtex/Strand-Density/10,000

Strand-Density (g/cc)=1.15 g/cc (industry standard for PolyUrethaneUrea based spandex elastics)

Dtex (g/10,000 m)=Standard textile unit of measure. Dtex is weight in grams for 10,000 m of the material Average-Pre-Strain=Amount of stretch in elastic strands in a section prior to combining with substrate layer(s).

Maximum-Strain=Average-Pre-Strain. This is the maximum amount of strain each section can be pulled to. It cannot exceed the Average-Pre-Strain.

Maximum-Section-Force=Summation of each strand in the section pulled to the Maximum-Strain.

Section-Modulus

Defined as the modulus of a given section. Section-Modulus (also referred to as modulus) is the linear slope of the stress vs strain data of the section between 3 gf/mm and 7 gf/mm (refer to FIG. 93). Section-Modulus is calculated as:

Section-Modulus=[7 gf/mm−3 gf/mm]/[(section strain at 7 gf/mm)−(section strain at 3 gf/mm)]

Where:

section strain at 7 gf/mm=7 gf/mm*(Average-Strand-Spacing)/DTEX-FACTOR section strain at 3 gf/mm=3 gf/mm*(Average-Strand-Spacing)/DTEX-FACTOR Average-Strand-Spacing (mm)=d/(n−1)

d is the distance (mm) between the two distal strands of the section n is the number of strands, when n>1

DTEX-FACTOR=37.5*Average-Dtex/800 (dtex as measured, specified)

Section-Modulus is reported in units of (gf/mm)

Average Decitex (Average-Dtex)

The Average Decitex Method is used to calculate the Average-Dtex on a length-weighted basis for elastic fibers present in an entire article, or in a specimen of interest extracted from an article. The decitex value is the mass in grams of a fiber present in 10,000 meters of that material in the relaxed state. The decitex value of elastic fibers or elastic laminates containing elastic fibers is often reported by manufacturers as part of a specification for an elastic fiber or an elastic laminate including elastic fibers. The Average-Dtex is to be calculated from these specifications if available. Alternatively, if these specified values are not known, the decitex value of an individual elastic fiber is measured by determining the cross-sectional area of a fiber in a relaxed state via a suitable microscopy technique such as scanning electron microscopy (SEM), determining the composition of the fiber via Fourier Transform Infrared (FT-IR) spectroscopy, and then using a literature value for density of the composition to calculate the mass in grams of the fiber present in 10,000 meters of the fiber. The manufacturer-provided or experimentally measured decitex values for the individual elastic fibers removed from an entire article, or specimen extracted from an article, are used in the expression below in which the length-weighted average of decitex value among elastic fibers present is determined.

The lengths of elastic fibers present in an article or specimen extracted from an article is calculated from overall dimensions of and the elastic fiber pre-strain ratio associated with components of the article with these or the specimen, respectively, if known. Alternatively, dimensions and/or elastic fiber pre-strain ratios are not known, an absorbent article or specimen extracted from an absorbent article is disassembled and all elastic fibers are removed. This disassembly can be done, for example, with gentle heating to soften adhesives, with a cryogenic spray (e.g. Quick-Freeze, Miller-Stephenson Company, Danbury, Conn.), or with an appropriate solvent that will remove adhesive but not swell, alter, or destroy elastic fibers. The length of each elastic fiber in its relaxed state is measured and recorded in millimeters (mm) to the nearest mm.

Calculation of Average-Dtex

For each of the individual elastic fibers $f_i$ of relaxed length $L_i$ and fiber decitex value $d_i$ (obtained either from the manufacturer's specifications or measured experimentally) present in an absorbent article, or specimen extracted from an absorbent article, the Average-Dtex for that absorbent article or specimen extracted from an absorbent article is defined as:

$$\text{Average-Dtex} = \frac{\sum_{i=1}^{n}(L_i \times d_i)}{\sum_{i=1}^{n} L_i}$$

where n is the total number of elastic fibers present in an absorbent article or specimen extracted from an absorbent article. The Average-Dtex is reported to the nearest integer value of decitex (grams per 10000 m).

If the decitex value of any individual fiber is not known from specifications, it is experimentally determined as described below, and the resulting fiber decitex value(s) are used in the above equation to determine Average-Dtex.

Experimental Determination of Decitex Value for a Fiber

For each of the elastic fibers removed from an absorbent article or specimen extracted from an absorbent article according to the procedure described above, the length of each elastic fiber $L_k$ in its relaxed state is measured and recorded in millimeters (mm) to the nearest mm. Each elastic fiber is analyzed via FT-IR spectroscopy to determine its composition, and its density $\rho_k$ is determined from available literature values. Finally, each fiber is analyzed via SEM. The fiber is cut in three approximately equal locations perpendicularly along its length with a sharp blade to create a clean cross-section for SEM analysis. Three fiber segments with these cross sections exposed are mounted on an SEM sample holder in a relaxed state, sputter coated with gold, introduced into an SEM for analysis, and imaged at a resolution sufficient to clearly elucidate fiber cross sections. Fiber cross sections are oriented as perpendicular as possible to the detector to minimize any oblique distortion in the measured cross sections. Fiber cross sections may vary in shape, and some fibers may consist of a plurality of individual filaments. Regardless, the area of each of the three fiber cross sections is determined (for example, using diameters for round fibers, major and minor axes for elliptical fibers, and image analysis for more complicated shapes), and the average of the three areas $a_k$ for the elastic fiber, in units of micrometers squared (m²), is recorded to the nearest 0.1 μm². The decitex $d_k$ of the kth elastic fiber measured is calculated by:

$$d_k = 10000 \text{ m} \times a_k \times \rho_k \times 10^{-6}$$

where $d_k$ is in units of grams (per calculated 10,000 meter length), $a_k$ is in units of μm², and $\rho_k$ is in units of grams per cubic centimeter (g/cm³). For any elastic fiber analyzed, the experimentally determined $L_k$ and $d_k$ values are subsequently used in the expression above for Average-Dtex.

Surface Topography (Percent Contact Area, Rugosity Frequency, Rugosity Wavelength and 2-98% Height Value)

In the Surface Topography Method, an elastic laminate specimen is removed from an absorbent article and extended across and in contact with the convex surface of a transparent horizontal cylindrical tubing segment, allowing the areal surface topology of the body facing side of the laminate to be measured through the transparent tubing segment using optical profilometry. The 3D surface data are then sampled and processed to extract several parameters that describe the percent contact area and height of the elastic laminate specimen surface as well as the frequency and wavelength of its associated rugosities. All sample preparation and testing is performed in a conditioned room maintained at about 23±2° C. and about 50±2% relative humidity, and samples are equilibrated in this environment for at least 24 hours prior to testing.

Sample Preparation

Specimen Prep Description

Each elastic laminate specimen extracted from an article is mounted on a horizontal tubing segment as described below. The tubing segment is cut from a sufficient length of optically clear, colorless cast acrylic cylindrical tubing having an outer diameter of 8.0 inches (203 mm) and a wall thickness of 0.1875 inches (4.76 mm). The segment has a dimension of 4.0 inches (102 mm) along an axis parallel to the central cylindrical axis of the parent tubing and a circumferential outer arc length of 5.5 inches (140 mm).

The elastic laminate specimen is extended in its primary stretch direction to a ratio corresponding to its extension at 3 g/mm (mass per linear width), where its width is determined by the Span Corrected Width metric as defined in the Caliper Test Method, and in which the extension is the average ratio measured under static load for the first ten seconds during which it is applied. In this extended state, the extended elastic laminate specimen is oriented such that its body-facing surface is in contact with the convex surface of the tubing segment and that the axis of extension is oriented around the circumference of the tubing segment. The extended laminate is secured at both ends to the transparent tubing segment such that the body-facing surface of the laminate is viewable through the concave side of the transparent tubing segment.

Five replicate elastic laminate specimens are isolated and prepared in this way from five equivalent absorbent articles for analysis.

3D Surface Image Acquisition

A three-dimensional (3D) surface topography image of the body facing surface of the extended elastic laminate specimen is obtained using a DLP-based, structured-light 3D surface topography measurement system (a suitable surface topography measurement system is the MikroCAD Premium instrument commercially available from LMI Technologies Inc., Vancouver, Canada, or equivalent). The system includes the following main components: a) a Digital Light Processing (DLP) projector with direct digital controlled micro-mirrors; b) a CCD camera with at least a 1600×1200 pixel resolution; c) projection optics adapted to a measuring area of at least 60 mm×45 mm; d) recording optics adapted to a measuring area of 60 mm×45 mm; e) a table tripod based on a small hard stone plate; f) a blue LED light source; g) a measuring, control, and evaluation computer running surface texture analysis software (a suitable software is MikroCAD software with Mountains Map technology, or equivalent); and h) calibration plates for lateral (XY) and vertical (Z) calibration available from the vendor.

The optical 3D surface topography measurement system measures the surface height of a sample using the digital micro-mirror pattern fringe projection technique. The nature of this pattern projection technique allows the surface topography of a specimen to be interrogated through a transparent material. The result of the measurement is a 3D data set of surface height (defined as the Z-axis) versus displacement in the horizontal (XY) plane. This 3D data set can also be thought of as an image in which every pixel in the image there is associated an XY displacement, and the value of the pixel is the recorded Z-axis height value. The system has a field of view of 60×45 mm with an XY pixel resolution of approximately 37 microns, and a height resolution of 0.5 microns, with a total possible height range of 32 mm.

The instrument is calibrated according to manufacturer's specifications using the calibration plates for lateral (XY plane) and vertical (Z-axis) available from the vendor.

The elastic laminate specimen mounted on the transparent tubing segment is positioned with the concave surface of the tubing segment surface facing upward so that the body facing surface is facing upward and visible through the transparent material. The tubing segment is placed on a stand such that the convex (downward-facing) specimen surface in the region to be analyzed is suspended freely and not resting on a surface. The tubing segment is oriented such that its circumferential direction (that direction or axis along which the laminate is stretched) is centered and perpendicular relative to the long axis of the camera's field of view (or either of the central axes if the field of view is square). A 3D surface topology image of the elastic laminate specimen is collected by following the instrument manufacturer's recommended measurement procedures, which may include focusing the measurement system and performing a brightness adjustment. No pre-filtering options are used. The collected height image file is saved to the evaluation computer running the surface texture analysis software.

If the field of view of the 3D surface topography measurement system exceeds the evaluation region on the elastic laminate specimen the image may be cropped to remove extraneous areas and retain a rectangular field of view of the relevant portion, while maintaining the XY resolution, prior to performing the analysis.

3D Surface Image Analysis

The 3D surface topography image is opened in the surface texture analysis software. The following filtering procedure is then performed on each image: 1) removal of invalid or non-measured points; 2) a 5×5 pixel median filter to remove noise; 3) a 5×5 pixel mean filter to smooth the surface; and 4) subtraction of a two-dimensional, second-order polynomial (determined via least-squares fit of the surface topology image) to remove the general form and flatten the surface. The second-order polynomial is defined by the following equation:

$$f(x,y)=c_1+c_2x+c_3y+c_4x^2+c_5y^2+c_6xy$$

Each data set that has been processed to this point as described above is referred to as a "preprocessed specimen data set." The highest points of the resulting topology image correspond to those areas in contact with the convex surface of the tubing segment, and the lowest points are those points most distal below the convex surface of the tubing segment.

Contact Surface Areas and 2-98% Height Value

For each of the 3D surface topography images of the five replicate specimens, the following analysis is performed on preprocessed specimen data sets. The Percent Surface Contact Area and 2-98% Height measurements are derived from the Areal Material Ratio (Abbott-Firestone) curve described in the ISO 13565-2:1996 standard extrapolated to surfaces. This curve is the cumulative curve of the surface height distribution histogram versus the range of surface heights measured. A material ratio is the ratio, expressed as a percent, of the area corresponding to points with heights equal to or above an intersecting plane passing through the surface at a given height, or cut depth, to the cross-sectional area of the evaluation region (field of view area). The height at a material ratio of 2% is initially identified. A cut depth of 100 μm below this height is then identified, and the material ratio at this depth is recorded as the Percent Surface Contact Area at 100 p.m. This procedure is repeated at a cut depth of 200 μm and 300 μm below the identified height at a material ratio of 2%, and the material ratio at these depths are recorded as the Percent Surface Contact Area at 200 μm and the Percent Surface Contact Area at 300 μm respectively. All of the Percent Contact Area values are recorded to the nearest 0.1%.

The 2-98% Height of the specimen surface is defined as the difference in heights between two material ratios that exclude a small percentage of the highest peaks and lowest valleys. The 2-98% Height of the specimen surface is the height between the two cutting depths corresponding to a material ratio value of 2% to the material ratio of 98%, and is recorded to the nearest 0.01 mm.

Rugosity Frequency and Rugosity Wavelength

The preprocessed 3D surface topology images for each specimen are subjected to Fourier transform spatial frequency analysis to determine Rugosity Frequency and Rugosity Wavelength.

Each 3D surface topology image is deconstructed into individual line profiles by isolating each entire row of single data points that run in the dimension parallel to the elastic strands (if present and evident) of the elastic laminate, or, more generally, perpendicular to the rugosity exhibited by the elastic laminate in the relaxed state. These line profiles are therefore data sets in the form of height (in millimeters) versus distance (in millimeters).

For each replicate 3D surface topology image deconstructed, each line profile is mean centered, and a fast Fourier transform (FFT) is applied to calculate the frequency amplitude spectrum of each line profile. The Fourier transform amplitude versus spatial frequency spectra of all extracted line profiles are averaged, and the resulting average amplitude versus spatial frequency spectrum is defined as $F(1/d)$, where $1/d$ is reciprocal distance in units of $mm^{-1}$. Finally, the function $P(1/d)=d \times F^2(1/d)$, the spatial frequency power spectral density with a prefactor of distance d to correct for the expected $1/d$ noise, is plotted versus $1/d$. The value of reciprocal distance $1/d$ at which $P(1/d)$ is at a maximum is defined as the Rugosity Frequency and is recorded in units of $mm^{-1}$ to the nearest $0.001\ mm^{-1}$. The reciprocal of the Rugosity Frequency is defined as the Rugosity Wavelength and is recorded in units of mm to the nearest 0.01 mm.

Reporting of Method Parameters

After the 3D surface image analysis described above is performed on 3D surface topology images of all five specimen replicates, the following output parameters are defined and reported. The arithmetic mean of all five Percent Surface Contact Area at 100 μm measurements is defined as the Average Percent Surface Contact Area at 100 μm and is reported to the nearest 0.1%. The arithmetic mean of all five Percent Surface Contact Area at 200 μm measurements is defined as the Average Percent Surface Contact Area at 200 μm and is reported to the nearest 0.1%. The arithmetic mean of all five Percent Surface Contact Area at 300 μm measurements is defined as the Average Percent Surface Contact Area at 300 μm and is reported to the nearest 0.1%. The arithmetic mean of all five 2-98% Height measurements is defined as the Average 2-98% Height and is reported in units of mm to the nearest 0.01 mm. The arithmetic mean of all five Rugosity Frequency measurements is defined as the Average Rugosity Frequency and is reported in units of mm to the nearest $0.001\ mm^{-1}$. The arithmetic mean of all five Rugosity Wavelength measurements is defined as the Average Rugosity Wavelength and is reported in units of mm to the nearest 0.01 mm.

Open Area

Defined as the percentage of a Section not occluded by elastic strands. Un-apertured films have an Open Area 0%. Apertured film Open Area=(area occupied by apertures)/(total film area). None of today's marketed disposable absorbent articles comprising a film in one or more of a belt, sided panel, or ear panel, waistband, cuff, wing are believed to have and Open Area above 50%. Open Area is defined as:

Open Area (%)=(Average-Strand-Diameter)/Average-Strand-Spacing

Average-Pre-Strain

The Average-Pre-Strain of a specimen are measured on a constant rate of extension tensile tester (a suitable instrument is the MTS Insight using Testworks 4.0 Software, as available from MTS Systems Corp., Eden Prairie, Minn.) using a load cell for which the forces measured are within 1% to 90% of the limit of the cell. Articles are conditioned at 23° C.±2 C.° and 50%±2% relative humidity for 2 hours prior to analysis and then tested under the same environmental conditions.

Program the tensile tester to perform an elongation to break after an initial gage length adjustment. First raise the cross head at 10 mm/min up to a force of 0.05N. Set the current gage to the adjusted gage length. Raise the crosshead at a rate of 100 mm/min until the specimen breaks (force drops 20% after maximum peak force). Return the cross head to its original position. Force and extension data is acquired at a rate of 100 Hz throughout the experiment.

Set the nominal gage length to 40 mm using a calibrated caliper block and zero the crosshead. Insert the specimen into the upper grip such that the middle of the test strip is positioned 20 mm below the grip. The specimen may be folded perpendicular to the pull axis, and placed in the grip to achieve this position. After the grip is closed the excess material can be trimmed. Insert the specimen into the lower grips and close. Once again, the strip can be folded, and then trimmed after the grip is closed. Zero the load cell. The specimen should have a minimal slack but less than 0.05 N of force on the load cell. Start the test program.

From the data construct a Force (N) verses Extension (mm). The Average-Pre-Strain is calculated from the bend in the curve corresponding to the extension at which the nonwovens in the elastic are engaged. Plot two lines, corresponding to the region of the curve before the bend (primarily the elastics), and the region after the bend (primarily the nonwovens). Read the extension at which these two lines intersect, and calculate the % Pre-Strain from the extension and the corrected gage length. Record as % Pre-strain 0.1%. Calculate the arithmetic mean of three replicate samples for each elastomeric laminate and Average-Pre-Strain to the nearest 0.1%.

Force Relaxation Over Time

The Force Relaxation over Time of a specimen is measured on a constant rate of extension tensile tester (a suitable instrument is the MTS Insight using Testworks 4.0 Software, as available from MTS Systems Corp., Eden Prairie, Minn.) using a load cell for which the forces measured are within 1% to 90% of the limit of the cell. Articles are conditioned at 23° C.±2 C.° and 50%±2% relative humidity for 2 hours prior to analysis and then tested under the same environmental conditions. Prepare a sample size such that it enables a gauge length of 25.4 mm (parallel to the elastic stretch) at a width of 12.7 mm.

Program the tensile tester to perform an elongation to determine the engineering strain at which the tensile force reaches 0.0294 N/mm.

Prepare and condition a second sample as described above for the Force Relaxation over time test. The test is performed on the same equipment as described above. It is performed at a temperature of 37.8° C. Extend the sample to the strain as determined above. Hold the sample for 10 hours and record the force at a rate of 100 Hz throughout the experiment a chart showing the data for an extruded strand prior art product and an inventive elastomeric laminate comprising beam elastic as described herein is show in FIG. 104.

Graphic Distortion Ratio

The influence of the gathering of the belt or waist band of an absorbent article on the potential integrity of a Graphic on the front and back of and absorbent article is measured by extending the article, applying a marker stripe and measuring the change in the area the stripe occupies once the tension is removed from the absorbent article. Articles are conditioned at 23° C.±2 C.° and 50%±2% relative humidity for 2 hr prior to analysis and then tested under the same environmental conditions.

Place the product on a bench with the front of the article facing upward. Secure the left side seam of the article to the bench and elongate the product to a force of 10 gf/mm of belt width and secure the right side seam to the bench. Using a black marker (e.g. A Sharpie chisel tip permanent marker, or equivalent) apply a continuous 6 mm wide linear stripe from the left hand upper corner to the right hand lower corner of the belt, side panel, ear panel or waistband. Measure the dimensions of a bounding box around the marked stripe and record the length (L1) and width (W1) of the bounding box to the nearest 1 mm. Sample preparation and measurement in the extended state should be performed in less than 2 mins.

Unsecure the article and let the article retract to the untensioned state (5 min.). Measure the dimensions of a bounding box applied around the marked stripe the length (L2) and width (W2) of the bounding box and record to the nearest 1 mm.

Calculate the differences in the area of the figure as (L1×W1)–(L2×W2) and record to the nearest 1 mm². Repeat the measurement on 5 products and record the average. Calculate the arithmetic average of the Lengths L1 and L2 and widths W1 and W2 and the differences in the areas for the replicates and report the linear measures to the nearest 1 mm and the areas to the nearest mm². The Graphic Distortion Ratio is determined by dividing the final width W2 by the original width W1. Illustrations of the Graphic Distortion Ratio can be found in FIGS. 102, 102A, 103 and 103A where 102 and 102A are illustrations of an article comprising an elastomeric laminate of the present invention and 103 and 103A are illustrations of an article of the prior art.

CONCLUSION

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present disclosure have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article, comprising:
a chassis comprising a topsheet, a backsheet and an absorbent core disposed a first belt;
between the topsheet and the backsheet;
a longitudinal centerline extending from the midpoint of a front waist edge of the absorbent article to a midpoint of a back waist edge of the absorbent article;
a lateral centerline extending perpendicular to the longitudinal centerline through a midpoint of the longitudinal centerline;
wherein the first belt is formed at least in part by an elastomeric laminate comprising a first substrate layer, a second substrate layer and a first plurality of elastics disposed between the first and second substrate layers, wherein the first substrate layer is bonded directly with the second substrate layer in elastic regions of the elastomeric laminate;
wherein the first plurality of elastics comprises greater than about 40 elastic strands disposed at an Average-Strand-Spacing of less than 4 mm, having an Average-Dtex of less than 600; and
wherein the elastomeric laminate comprising the first plurality of elastics has a Pressure-Under-Strand of less than about 1.0 psi.

* * * * *